US011813304B2

(12) United States Patent
Charmot et al.

(10) Patent No.: US 11,813,304 B2
(45) Date of Patent: Nov. 14, 2023

(54) COMPOUNDS AND METHODS FOR INHIBITING PHOSPHATE TRANSPORT

(71) Applicant: Ardelyx, Inc., Fremont, CA (US)

(72) Inventors: Dominique Charmot, Fremont, CA (US); Jason G. Lewis, Fremont, CA (US); Jeffrey W. Jacobs, Fremont, CA (US); Ingrid Langsetmo, Fremont, CA (US); Christopher Carreras, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 280 days.

(21) Appl. No.: 16/512,210

(22) Filed: Jul. 15, 2019

(65) Prior Publication Data

US 2020/0038475 A1 Feb. 6, 2020

Related U.S. Application Data

(63) Continuation of application No. 14/911,225, filed as application No. PCT/US2014/050290 on Aug. 8, 2014, now abandoned.

(60) Provisional application No. 61/936,715, filed on Feb. 6, 2014, provisional application No. 61/864,215, filed on Aug. 9, 2013.

(51) Int. Cl.

| | | |
|---|---|---|
| *A61K 38/10* | (2006.01) | |
| *A61K 31/00* | (2006.01) | |
| *A61K 38/16* | (2006.01) | |
| *A61K 31/195* | (2006.01) | |
| *A61K 31/27* | (2006.01) | |
| *A61K 31/352* | (2006.01) | |
| *A61K 31/353* | (2006.01) | |
| *A61K 31/382* | (2006.01) | |
| *A61K 31/4045* | (2006.01) | |
| *A61K 31/421* | (2006.01) | |
| *A61K 31/4418* | (2006.01) | |
| *A61K 31/4439* | (2006.01) | |
| *A61K 31/4525* | (2006.01) | |
| *A61K 31/475* | (2006.01) | |
| *A61K 31/506* | (2006.01) | |
| *A61K 31/7072* | (2006.01) | |
| *A61K 33/26* | (2006.01) | |
| *A61K 45/06* | (2006.01) | |
| *G01N 33/50* | (2006.01) | |
| *G01N 33/84* | (2006.01) | |

(52) U.S. Cl.
CPC .............. *A61K 38/10* (2013.01); *A61K 31/00* (2013.01); *A61K 31/195* (2013.01); *A61K 31/27* (2013.01); *A61K 31/352* (2013.01); *A61K 31/353* (2013.01); *A61K 31/382* (2013.01); *A61K 31/4045* (2013.01); *A61K 31/421* (2013.01); *A61K 31/4418* (2013.01); *A61K 31/4439* (2013.01); *A61K 31/4525* (2013.01); *A61K 31/475* (2013.01); *A61K 31/506* (2013.01); *A61K 31/7072* (2013.01); *A61K 33/26* (2013.01); *A61K 38/16* (2013.01); *A61K 45/06* (2013.01); *G01N 33/5038* (2013.01); *G01N 33/5044* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 4,954,642 A | 9/1990 | Tatee et al. | |
| 7,704,947 B2 | 4/2010 | Currie et al. | |
| 8,916,569 B2 * | 12/2014 | Lewis | ............ C07D 213/81 514/256 |
| 2009/0048175 A1 | 2/2009 | Shailubhai et al. | |
| 2009/0305993 A1 | 12/2009 | Currie | |
| 2010/0016305 A1 * | 1/2010 | Krahn | ............ A61K 31/197 514/234.2 |
| 2010/0152118 A1 | 6/2010 | Shailubhai | |
| 2010/0215779 A1 | 8/2010 | Currie et al. | |
| 2013/0336920 A1 * | 12/2013 | Lewis | ............ C07D 213/81 424/78.38 |
| 2016/0067242 A1 * | 3/2016 | Carreras | ............ A61K 31/472 514/308 |
| 2016/0184387 A1 * | 6/2016 | Charmot | ............ A61K 38/10 424/78.1 |

FOREIGN PATENT DOCUMENTS

| | | | |
|---|---|---|---|
| WO | 2005087797 A1 | | 9/2005 |
| WO | 2007009607 A1 | | 1/2007 |
| WO | WO2007009607 | * | 1/2008 |
| WO | 2009149278 A1 | | 12/2009 |
| WO | 2011156453 A2 | | 12/2011 |
| WO | 2012006475 A1 | | 1/2012 |

(Continued)

OTHER PUBLICATIONS

Bryant, A , et al., "Linaclotide is a potent and selective guanylate cyclase C agonist that elicits pharmacological effects locally in the gastrointestinal tract", Life Sciences 86(19-20), 760-765 (2010).

(Continued)

*Primary Examiner* — Maury A Audet
(74) *Attorney, Agent, or Firm* — Viksnins Harris Padys Malen LLP

(57) ABSTRACT

Provided are non-NHE3-binding agents having activity as phosphate transport/uptake inhibitors in the gastrointestinal tract, including in the small intestine, methods for their use as therapeutic or prophylactic agents, and related methods of drug discovery.

14 Claims, 55 Drawing Sheets

Specification includes a Sequence Listing.

(56) References Cited

FOREIGN PATENT DOCUMENTS

| WO | 2012006477 | A1 | | 1/2012 |
|---|---|---|---|---|
| WO | 2012054110 | A2 | | 4/2012 |
| WO | WO2012054110 | | * | 4/2012 |
| WO | 2013025969 | A1 | | 2/2013 |
| WO | 2014169094 | A2 | | 10/2014 |

OTHER PUBLICATIONS

Dominique, C , "Non-systemic drugs: a critical review", Current Pharmaceutical Design 18 (10), 1434-1445 (2012).

Grenader, A , et al., "A68930 is a potent, full agonist at dopaminel (D1) receptors in renal epithelial LLC-PK1 cells", Br J Pharmacol 106, 229-230 (1992).

Hector, G , et al., "NHE3 regulatory factor 1 (NHERF1) modulates intestinal sodium-dependent phosphate transporter (NaPi-2b) expression in apical microvilli", Journal of Biological Chemistry 287(42), 35047-35056 (2012).

Malberti, F , "Hyperphosphataemia: treatment options", Drugs 73, 673-688 (2013).

Havre, M , et al., "Novel Non-Systemic NaP2b Inhibitors Block Instestinal Phosphate Uptake", Proceedings of ASN meeting 2011, Philadelphia, p. 6, 2011.

Patent Cooperation Treaty , International Search Report from corresponding International Application No. PCT/US2014/050290, dated Apr. 1, 2015.

Rao, S , et al., "A role for guanylate cyclase C in acid-stimulated duodenal mucosal bicarbonate secretion", Am J Physiol Gastrointest Liver Physiol 286, 95-101 (2004).

Salmi, P , et al., "Dihydrexidine—The First Full Dopamine D1 Receptor Agonist", CNS Drug Reviews 10(3), 230-242 (2004).

Shailubhai, K , et al., "Plecanatide, an Oral Guanylate Cyclase C Agonist Acting Locally in the Gastrointestinal Tract, Is Safe and Well-Tolerated in Single Doses", Digestive Diseases and Sciences 58(9), 2580-2586 (2013).

Chernova, M , et al., "Acute regulation of the SLC26A3 congenital chloride diarrhoea anion exchanger (DRA) expressed in Xenopus oocytes", The Journal of Physiology 549(1), 3-19 (2003).

Liu, L , et al., "Involvement of Alpha-2 Adrenoceptors in the Effects of Moxonidine on Intestinal Motility and Fluid Transport", Journal of Pharmacology and Experimental Therapeutics 283(3), 1367-1374 (1997).

Mochly-Rosen, D , et al., "Protein kinase C, an elusive therapeutic target?", Nature Reviews Drug Discovery 11(12), 937-957 (2012).

Takeuchi, K , et al., "PACAPs stimulate duodenal bicarbonate secretion at PACAP receptors in the rat", Gastrointestinal and Liver Physiology 272(3), G401-G687 (1997).

Tanahashi, M , et al., "Effects of NKH477 on renal functions and cyclic AMP production in anesthetized dogs", European Journal of Pharmacology 372(3), 253-259 (1999).

Zadori, Z , et al., "Imidazoline versus alpha2-adrenoceptors in the control of gastric motility in mice", European Journal of Pharmacology 705(1-3), 61-67 (2013).

Head, G , et al., "Imidazoline Receptors, Novel Agents and Therapeutic Potential", Cardiovascular & Hematological Agents in Medicinal Chemistry 4, 17-32 (2006).

Reddy, A , et al., "Polypharmacology: drug discovery for the future", Expert Rev Clin Pharmacol 6(1), doi:10.1586/ecp.12.74, 13 pages (2013).

De Souza, N , et al., "Forskolin: A Labdane Diterpenoid with Antihypertensive, Positive Inotropic, Platelet Aggregation Inhibitory, and Adenylate Cyclase Activating Properties", Medicinal Research Reviews 3(2), 201-219 (1983).

Hosono, M , et al., "Cardiovascular and adenylate cyclase stimulant properties of NKH477, a novel water-soluble forskolin derivative", J Cardiovasc Pharmacol 19 (4), p. 625, Summary (1992).

Satake, K , et al., "Relaxant effects of NKH477, a new water-soluble forskolin derivative, on guinea-pig tracheal smooth muscle: the role of Ca2+-activated K+ channels", Br J Pharmacol 123 (4), 753-761 (1998).

* cited by examiner

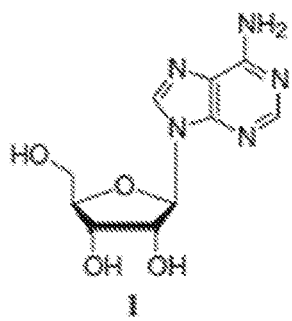
1
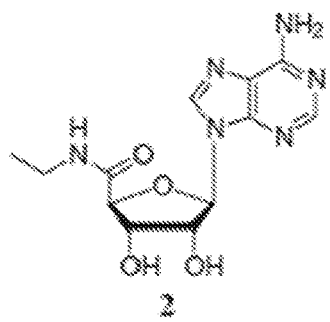
2
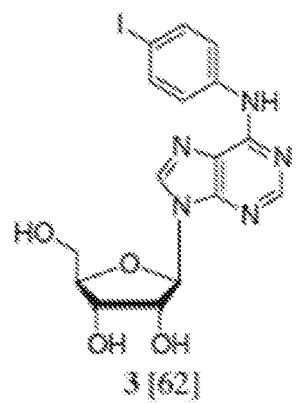
3 [62]
rA$_1$ (K$_i$) = 20.0 nM
rA$_{2A}$ (K$_i$) = 710 nM
hA$_{2B}$ (EC$_{50}$) = 370 nM
hA$_3$ (K$_i$) = 31.0 nM
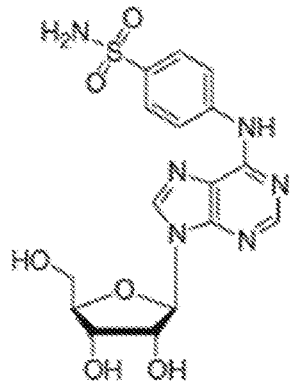
4 [62]
rA$_1$ (K$_i$) = 30.0 nM
rA$_{2A}$ (K$_i$) = 50% at 1μM
hA$_{2B}$ (EC$_{50}$) = 440 nM
hA$_3$ (K$_i$) = 37.0 nM
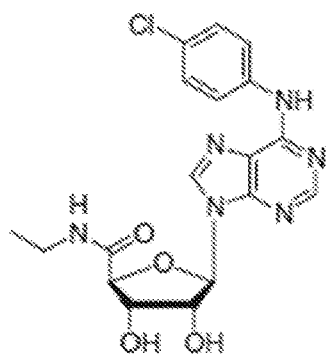
5 [62]
rA$_1$ (K$_i$) = 30.0 nM
rA$_{2A}$ (K$_i$) = 183 nM
hA$_{2B}$ (EC$_{50}$) = 730 nM
hA$_3$ (K$_i$) = 64.0 nM
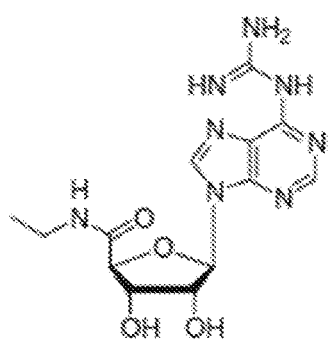
MRS3218 (6) [68]
hA$_1$ (K$_i$) = 7.0 nM
hA$_{2A}$ (K$_i$) = 628 nM
hA$_{2B}$ (EC$_{50}$) = 54.5 nM
hA$_3$ (K$_i$) = 5.1 nM
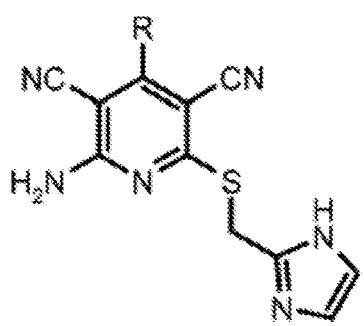
R:
phenyl
p-OH phenyl
m-OH phenyl
p-OCH$_3$ phenyl
m-OCH$_3$ phenyl
*FIG. 6A*

EP4 receptor-selective agonists.

| Name | Dose, concentration, affinity | Model, species | References |
|---|---|---|---|
| ACT295203 | Ki = 81 nM | HEK-EP4, human | Jiang et al. 2007 |
| | 3 mg/kg | Colitis, mouse | El-Naggar et al. 2005 |
| APS-999 Na | 50 μg/animal | Ovarian follicle growth, rat | Biber et al. 2003 |
| Cay10598 (10a) | Ki = 1.2 nM | HEK-EP4, human | Vukicevic et al. 2006 |
| CP-044,519-02 | 10 mg/kg/day | Acute and chronic kidney failure, rat | Hoshikawa et al. 2009 |
| EP4RAG | 1–3 mg/kg | Myocardial dysfunction, rat | Hoshikawa et al. 2009 |
| | 10–50–100 nM | THP-1 monocyte migration | |
| L-902688 | 10 nM–10 μM | Bronchi, human | Benyahia et al. 2012 |
| | 10 nM–10 μM | Pulmonary vein, human | Foudi et al. (2008) |
| Lubiprostone | 50–500 nM | Short circuit current in tracheal epithelium and submucosal gland secretion, sheep | Cuthbert, 2011 |
| ONO-4819CD | 36 ng/g | Ulcerative colitis, human | Nakase et al. 2010 |
| | 300 μg/kg | Cardiac ischemia, mouse | Maruyama et al. 2002 |
| | 1–30 μg/kg 3× a day | Inhibition of bone loss, de novo bone formation, rat | Yoshida et al. 2002 |
| ONO AE1-329 | 25–100 nM | Colitis, mouse | Nitta et al. 2002 |
| | 10 nM–10 μM | Bronchi, human | Benyahia et al. 2012 |
| | 30 nM | Eosinophil inhibition, human | Konya et al. 2011 and Luschnig-Schratl et al. 2011 |
| | 100 nM | Aortic rings, mouse | Hristovska et al. 2007 |
| | 10 nM–10 μM | Pulmonary vein, human | Foudi et al. 2008 |
| | 1 μM | Ductus arteriosus smooth muscle cells, rat | Maruyama et al. 2002 and Yokoyama et al. 2006 |
| | 300 μg/kg | Cardiac ischemia, mouse | Maruyama et al. 2002 |
| | 30–100 μg/kg | Hepatic ischemia, mouse | Kuzumoto et al. 2005 |
| | 30–300 μg/kg | Cerebral ischemia, mouse | Liang et al. 2011 |
| | 30 nM | Human pulmonary endothelial barrier | Konya et al. 2013 |
| | 3–30 nM | Human platelet aggregation | Philipose et al. 2010 |
| | 880 nM/kg/day | Bone formation, mouse | Yoshida et al. 2002 |
| ONO AE1-734 | 0.1 mg/kg/day | Colitis, mouse | Kabashima et al. 2002 |
| PGE₁-OH | 10–1000 nM | Human dermal microvascular endothelial angiogenesis | Zhang and Daaka, 2011 |
| TCS 2510 | 1 μM | Renal epithelial cell proliferation, mouse | Liu et al. 2012 |
| | 10 μM | GLP-1 release, mouse GLUTag cells | Coskun et al. 2013 |
| γ-Lactam PGE analog 3 | 30–300 μg/kg | Bone fracture healing, rat | Kanbe et al. 2012 |

FIG. 7

| indicator | $\lambda_{max,abs}$ (nm) | $\lambda_{max,em}$ (nm) | $pK_a$ | dual excitation or emission | φ | refs |
|---|---|---|---|---|---|---|
| BCECF, 4 | 503 | 525 | 7.0 | excitation | 0.84 (0.1 M NaOH) | 43, 49, 55 |
| BCPCF, 11 | 505 | 527 | 7.0 | excitation | 0.83 (0.1 M NaOH) | 55, 57 |
| C.fluorescein | 492 | 516 | 6.3 | excitation | 0.93 (0.1 M NaOH) | 58, 158 |
| C.SNARF-1, 37[b] | 544 | 573 | 7.5 | both | 0.03 (pH 5–6) | 5, 42, 94, 159 |
| C.SNARF-1, 37[c] | 583 | 631 | | | 0.09 (pH 10–12) | |
| C.SNARF-4F, 38[b] | 520 | 592 | 6.4 | both | na | 88, 96 |
| C.SNARF-4F, 38[c] | 582 | 661 | | | | |
| C.SNARF-5F, 39[b] | 560 | 580 | 7.2 | both | na | 88, 97 |
| C.SNARF-5F, 39[c] | 575 | 628 | 7.8 | both | | 42 |
| C.SNAFL-1, 40[b] | 510 | 539 | 7.0 | both | 0.32 (pH 5–6) | 98 |
| C.SNAFL-1, 40[c] | 542 | 623 | | | 0.08 (pH 10–12) | |
| SNAFL-calcein, 41[b] | 492 | 540 | 7.3 | na | na | 102, 103 |
| SNAFL-calcein, 41[c] | 535 | 623 | 7.1 | na | na | 102 |
| 45 and 46 | 645 | 665 | 7.1 | na | na | 102 |
| 47 | 653 | 660 | 7.1 | na | na | 100 |
| 48 | 640 | 670 | 7.0 | both | | 108 |
| 50 | 648 | 750 | 8.0 | both | 0.13 (N-protonated form) | 108 |
| 55 | 341 | 391 | ~7.3 | na | 0.21 (pH 4 buffer) | 110, 111 |
| 55 | 382 | ~580 | | | 0.56 (pH 10 buffer) | |
| 1,4-DHPN, 57[b] | 342 | 402 | 6.5 | excitation | 1.0 (pH 5.5) | 114, 115, 160 |
| 1,4-DHPN, 57[c] | 453 | 483 | | | 1.0 (pH 9.0) | |
| HPTS, 58[b] | 405 | 514 | | excitation | 0.18 (pH 4.1 buffer) | 38 |
| HPTS, 58[c] | 465 | 514 | | emission | 0.15 (pH 8.8 buffer) | |
| 60[b] | 480/576 | 607 | | | | |
| 60[c] | 499/576 | 525 | | | | |

*FIG. 8A*

| indicator | $\lambda_{max,ex}$ (nm) | $\lambda_{max,em}$ (nm) | $pK_a$ | dual excitation or emission | $\phi$ | refs |
|---|---|---|---|---|---|---|
| Oregon Green 488, 22 | 490 | 514 | 4.8 | excitation | 0.97 (pH 9 buffer) | 61 |
| 6-carboxyl Oregon Green 488, 23 | 492 | 514 | 4.8 | excitation | 0.92 (pH 9 buffer) | 61 |
| Oregon Green 514, 24 | 506 | 529 | 4.8 | excitation | 0.22, 0.65* | 76 |
| CDCF, 25 | 503 | 525 | 4.7 | excitation | na | 77, 161 |
| 26 | 494 | 520 | 5.6 | emission | 0.89 (pH 8–9) | 82, 83 |
| C.SNARF-4F, 38* | 520 | 582 | 6.4 | both | na | 88, 96 |
| C.SNARF-4F, 38* | 592 | 661 | | | | |
| 51 | 655 | 665 | 6.1 | na | na | 102 |
| 52 | 650 | 665 | 6.4 | na | na | 102 |
| 53 (Ap-Cy) | 558 | 615 | 5.1 | na | na | 105 |
| HPTS, 58* | 405 | 514 | 7.3 | excitation | 1.0 (pH 5.5) | 114, 115, 160 |
| HPTS, 58* | 465 | 514 | | | 1.0 (pH 9.0) | |
| DND-160 (PDMPO), 59* | 385 | 542 | 4.5 | both | 0.31 (pH 3.0) | 124 |
| DND-160 (PDMPO), 59* | 329 | 464 | | | 0.41 (pH 7.7) | |
| Blue DND-167, 60 | 373 | 425 | 5.1 | na | 0.80 (pH 3.0) | 120, 123, 124 |
| Green DND-189, 61 | 443 | 505 | 5.2 | na | 0.48 (pH 4.4) | 124 |
| Green DND-153, 62 | 442 | 505 | 7.5 | na | 0.34 (pH 4.0) | 124 |
| Blue DND-192, 63 | 374 | 424 | 7.5 | na | 0.88 (pH 4.0) | 124 |
| Acridine Orange, 65* | 495 | 530 | na | emission | 0.46 EtOH (0.01 M HCl) | 127–129 |
| Acridine Orange, 65* | 465 | 655 | | | | |
| ACMA, 66 | 419 | 484 | 8.6 | na | 0.66 (pH 7.2) | 130–132, 162 |
| Green DND-26, 67 | 504 | 511 | na | na | na | 125 |
| 68 | ~506 | ~516 | 3.8–6.0 | na | 0.55–0.60 (protonated) | 163 |
| 69* | 489/570 | 607 | 6.5 | emission | 0.18 (pH 4.1) | 38 |
| 69* | 490/576 | 525 | | | 0.15 (pH 8.8) | |
| pHrodot | 560 | 585 | 6.5 | na | na | 18 |

FIG. 8B

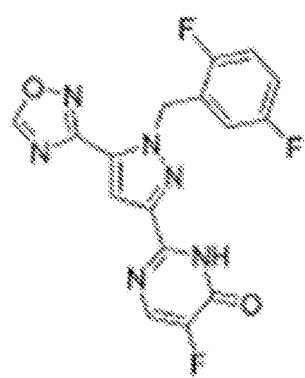
Compound 75
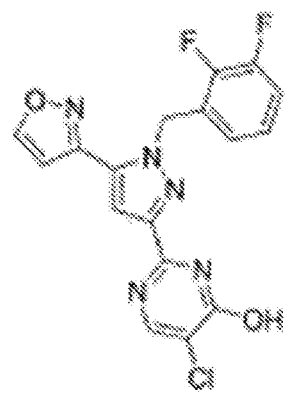
Compound 76
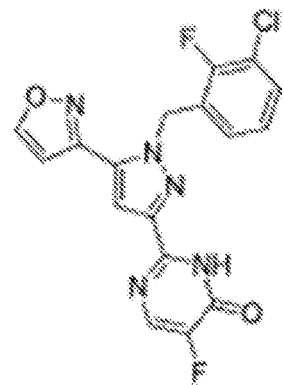
Compound 77
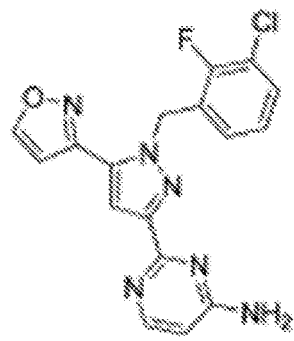
Compound 78
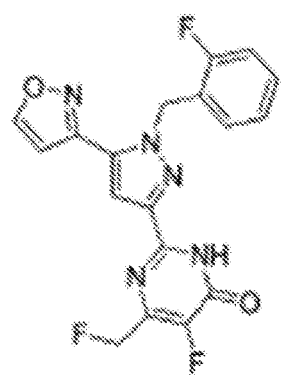
Compound 79
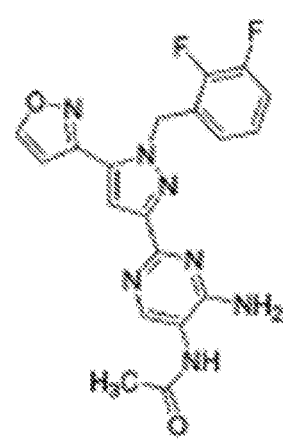
Compound 80
*FIG. 9H (Continued)*

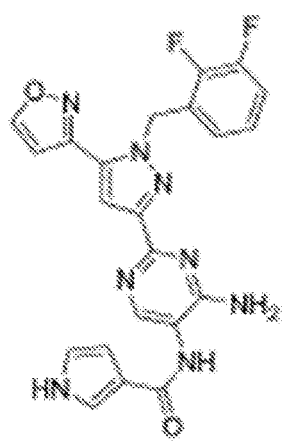
Compound 105
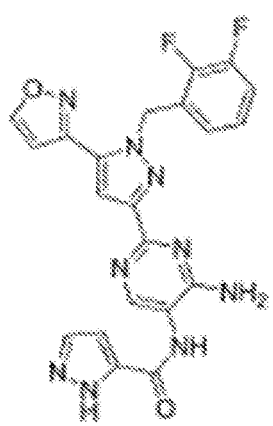
Compound 106
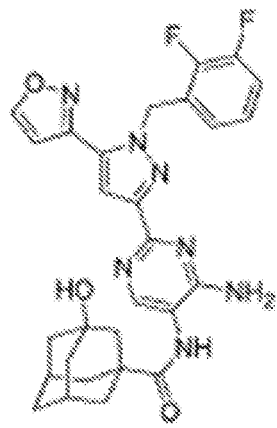
Compound 107
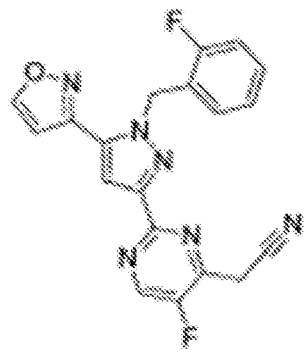
Compound 108
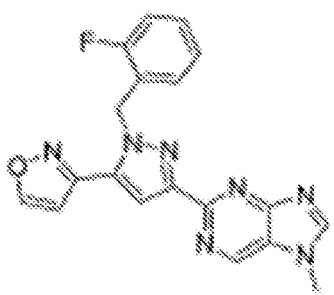
Compound 109
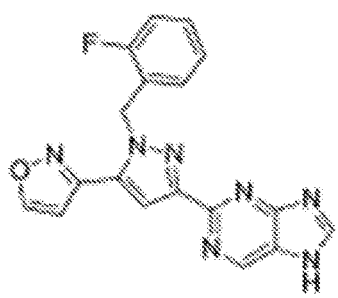
Compound 110
*FIG. 9K*

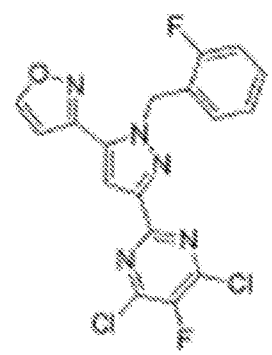
Compound 117
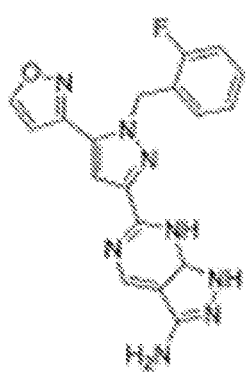
Compound 118
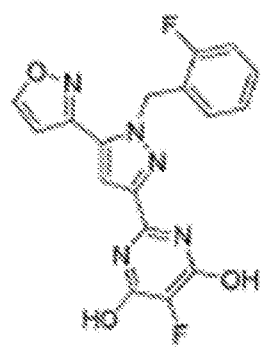
Compound 119
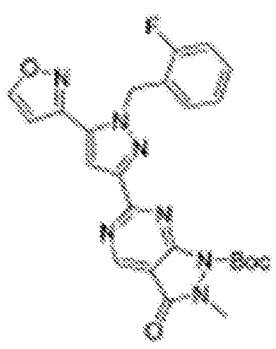
Compound 120
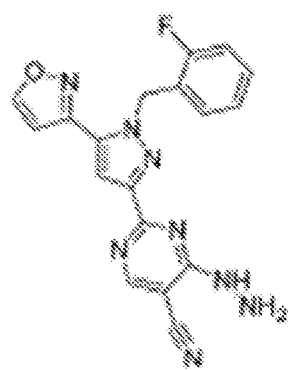
Compound 121
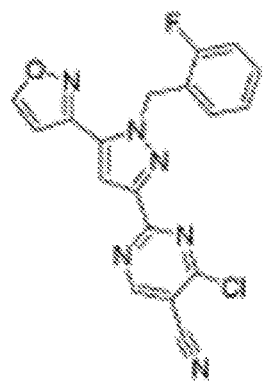
Compound 122
*FIG. 9L*

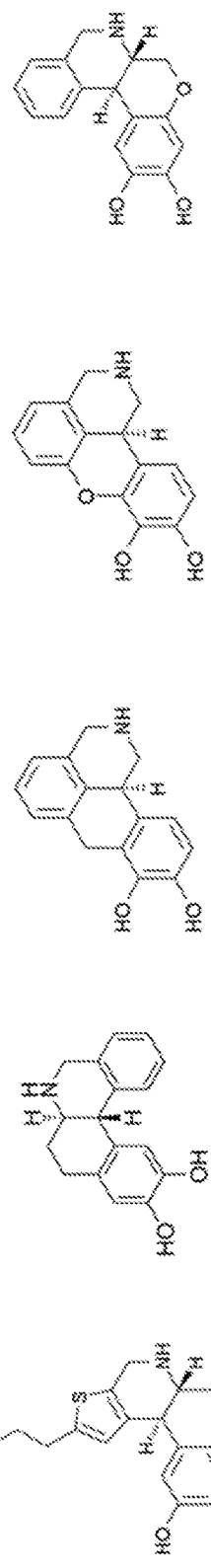
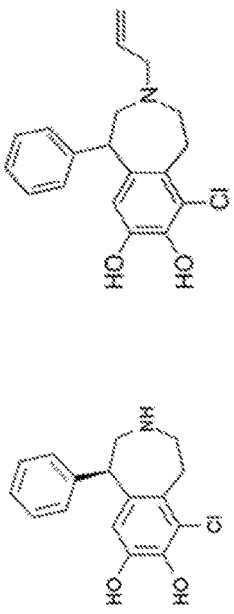
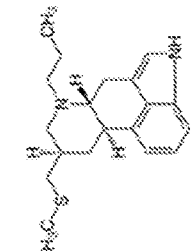
FIG. 14

Hypothetical change in pH profile across the epithelial cell membrane upon inhibition of outward proton flux and stimulation of outward bicarbonate flux upon treatment

| Drug name | Structure and description | Selectivity | Isozyme selectivity | Refs |
|---|---|---|---|---|
| Balanol, N-tosyl derivative | | An inhibitor of PKC and PKA (ATP-binding site) | PKCβII> PKCβI> PKCη>PKCδ> PKCα> PKCε>>PKA | 76,245 |
| Riluzole | | Likely to inhibit other serine/threonine kinases (ATP-binding site) | Preferential inhibitor of PKCα | 77 |
| Staurosporine | | ATP-binding site | Non-selective PKC inhibitor | 246 |
| Enzastaurin | | ATP-binding site | Three-to-fivefold selectivity for PKCβ inhibition | 247 |
| δV1-1 (KAI-9803 or delcasertib)* | SFNSYELGSL-carrier* (SEQ ID NO: 757) | PKCδ inhibitor (RACK-binding site) | >1,000-fold selectivity over other isozymes | 28 |
| εV1-2 (KAI-1678)* | EAVSLKPT-carrier* (SEQ ID NO: 758) | PKCε inhibitor (RACK-binding site) | >100-fold selectivity over other isozymes | 248 |

FIG. 21A

| | | | | |
|---|---|---|---|---|
| ψεRACK (KAI-1455) | HDAPIGYD-carrier* (SEQ ID NO: 760) | | PKCε activator (intramolecular interaction in PKC) | >100-fold selectivity over other isozymes | — |
| Aprinocarsen | Antisense oligonucleotide that targets PKCα mRNA | | PKCα inhibitor (expression) | Selectivity for PKCα | 249 |
| Midostaurin (PKC412) | | | ATP-binding site | Inhibitor of various protein kinases, including PKC | 152,250 |
| UCN-01 (7-hydroxystaurosporine) | | | ATP-binding site | Inhibitor of various protein kinases, including tyrosine kinases and classical PKC, at a similar IC$_{50}$ (25-50nM) | 251 |
| Rottlerin (5,7-dihydroxy-2,2-dimethyl-6-(2,4,6-trihydroxy-3-methyl-5-acetylbenzyl)-8-cinnamoyl-1,2-chromene) | | | PKCδ inhibitor (ATP-binding site) | Selective for PKCδ, but also targets calcium/calmodulin-dependent protein kinase VI at a similar IC$_{50}$ (5μM) | 72,250 |
| Bryostatin 1 | | | C1 domain of PKC | Twofold selectivity for PKCα over PKCα and PKCδ | 84,252 |

(SEQ ID NO: 759)

FIG. 21B

COMPOUNDS AND METHODS FOR
INHIBITING PHOSPHATE TRANSPORT

CROSS-REFERENCE TO RELATED APPLICATIONS

This application is a continuation of U.S. application Ser. No. 14/911,225 that was filed on Feb. 9, 2016, which is a 35 U.S.C. § 371 application of International Application Number PCT/US2014/050290 that was filed on Aug. 8, 2014, which claims priority to U.S. Provisional Application No. 61/864,215 that was filed Aug. 9, 2013, and claims priority to U.S. Provisional Application No. 61/936,715 that was filed on Feb. 6, 2014. The entire content of the applications referenced above is hereby incorporated by reference herein.

STATEMENT REGARDING SEQUENCE LISTING

The instant application contains a Sequence Listing which has been submitted in ASCII format via EFS-Web and is hereby incorporated by reference in its entirety. The name of the text file containing the Sequence Listing is 00888_017US2_SL.txt. The text file is 197,667, was created on Sep. 26, 2018, and is being submitted electronically via EFS-Web.

BACKGROUND

Technical Field

The present invention relates to non-NHE3-binding agents having activity as phosphate transport inhibitors in the gastrointestinal tract, including in the small intestine, methods for their use as therapeutic or prophylactic agents, and related methods of drug discovery.

Description of the Related Art

Patients with inadequate renal function, hypoparathyroidism, or certain other medical conditions (such as hereditary hyperphosphatemia, Albright hereditary osteodystrophy, amyloidosis, etc.) often have hyperphosphatemia, or elevated serum phosphorus levels (where the level, for example, is more than about 6 mg/dL). Hyperphosphatemia, especially if present over extended periods of time, leads to severe abnormalities in calcium and phosphorus metabolism, often manifested by secondary hyperparathyroidism, bone disease and ectopic calcification in the cardiovascular system, joints, lungs, eyes and other soft tissues. Higher serum phosphorus levels are strongly associated with the progression of renal failure, cardiovascular calcification and mortality in end-stage renal disease (ESRD) patients. High-normal serum phosphorus levels have been associated with cardiovascular events and mortality among individuals who have chronic kidney disease (CKD) and among those who have normal kidney function (see, e.g., Joy et al., *J. Manag. Care Pharm.*, 13:397-411, 2007) The progression of kidney disease can be slowed by reducing phosphate retention. Thus, for renal failure patients who are hyperphosphatemic and for chronic kidney disease patients who have serum phosphorus levels within the normal range or only slightly elevated, therapy to reduce phosphate retention is beneficial.

For patients who experience hyperphosphatemia, calcium salts have been widely used to bind intestinal phosphate and prevent its absorption. Different types of calcium salts, including calcium carbonate, acetate, citrate, alginate, and ketoacid salts have been utilized for phosphate binding. However, these therapies often cause hypercalcemia, a condition which results from absorption of high amounts of ingested calcium. Hypercalcemia causes serious side effects such as cardiac arrhythmias, renal failure, and skin and vascular calcification. Frequent monitoring of serum calcium levels is required during therapy with calcium-based phosphate binders. Other calcium and aluminum-free phosphate binders, such as sevelamer, a crosslinked polyamine polymer, have drawbacks that include the amount and frequency of dosing required to be therapeutically active. The relatively modest phosphate binding capacity of those drugs in vivo obliges patients to escalate the dose (up to 7 grams per day or more). Such quantities have been shown to produce gastrointestinal discomfort, such as dyspepsia, abdominal pain and, in some extreme cases, bowel perforation.

An alternative approach to the prevention of phosphate absorption from the intestine in patients with elevated phosphate serum levels is through inhibition of the intestinal transport system which mediates phosphate uptake in the intestine. It is understood that phosphate absorption in the upper intestine is mediated at least in part by a carrier-mediated mechanism which couples the absorption of phosphate to that of sodium. Inhibition of intestinal phosphate transport will reduce body phosphorus overload. In patients with advanced kidney disease (e.g. stage 4 and 5), the body phosphorus overload manifests itself by serum phosphorus concentration above normal levels, i.e., hyperphosphatemia. Hyperphosphatemia is directly related to mortality and morbidity. Inhibition of intestinal phosphate transport will reduce serum phosphorus concentration and therefore improve outcome in those patients. In chronic kidney disease patients at stage 2 or 3, the body phosphorus overload does not necessarily lead to hyperphosphatemia, i.e., some patients remain normophosphatemic, but there is a need to reduce or prevent body phosphorus overload even at those early stages to avoid associated bone and vascular disorders, and ultimately improve mortality rate. Similarly, inhibition of intestinal phosphate transport would be particularly advantageous in patients that have a disease that is treatable by inhibiting the uptake of phosphate from the intestines. Furthermore, inhibition of phosphate transport may slow the progression of renal failure and reduce risk of cardiovascular events.

The luminal pole of the intestinal epithelia comprises a so-called unstirred water layer (UWL) where transport is essentially of diffusive nature because of the viscosity of the mucus layer. This unstirred layer is defined as a stagnant layer adjacent to the membrane on the apical side acting as a diffusion barrier so that rapidly permeating substances could actually be rate-limited by diffusion. This limited diffusion applies to $H^+$ and therefore the UWL contributes to establishing a pH microclimate due to the outward flux of proton and the diffusion limit imposed by the mucus layer. The acidic environment at the vicinity of the cell surface maintains a relatively large electrochemical gradient across the epithelial membrane—a cross epithelial pH gradient, or CEPG.

Strong evidence exists for the involvement of this CEPG in the transport of nutrients via proton co-transporters and —OH— antiporters, such as PEPT1, folate/OH— antiporter, and 3-alanine/H+ cotransporter. See, e.g., Ikuma, *J Med Chem.* 50:1166-1176, 1996. The disturbance of the pH microclimate, for example, a decrease of the CEPG, can alter the absorption of nutrients. This has been shown in the case of proton-mediated absorption of peptide via PEPT1.

See, e.g., Thwaites et al., *Gastroenterology*. 122:1322-1333, 2002; and Thwaites and Anderson, *Exp. Physiol.* 92:603-619, 2007. However, no role for the CEPG has been established in the absorption of phosphate ions across the intestinal membrane.

Evidence also exists for the involvement of water absorption in the transport of ions across the epithelia of the small intestine particularly the jejenum. Juan et al., *J Clin Endocrinol Metab.* 43:517-22, 1976. But such mechanisms have been little-explored in the area of phosphate-lowering therapeutics.

BRIEF SUMMARY

The present invention relates generally to non-NHE3-binding compounds having activity as phosphate transport inhibitors in the gastrointestinal tract, especially in the small intestine, including stereoisomers, pharmaceutically acceptable salts and prodrugs thereof, and the use of such compounds to inhibit phosphate uptake and to thereby treat any of a variety of conditions or diseases in which modulation of phosphate uptake provides a therapeutic benefit.

Embodiments of the present invention thus include methods for inhibiting phosphate uptake in the gastrointestinal tract of a patient in need of phosphate lowering, comprising administering to the patient a compound that does not bind NHE3, where the compound is substantially active in the gastrointestinal tract to inhibit transport of phosphate ions (Pi) therein upon administration to the patient in need thereof.

In specific embodiments, the compound is a guanylate cyclase C receptor (GC-C) agonist compound.

In certain embodiments, the compounds are pH-modulatory agents. These and related embodiments include methods for inhibiting phosphate uptake in the gastrointestinal tract of a patient in need of phosphate lowering, comprising administering to the patient a compound that decreases the cross-epithelial pH gradient (CEPG) in the small intestine, where the CEPG is defined as the difference in pH between (i) the cytoplasm of the epithelial cells of the surface of the small intestine, optionally at the subapical surface of the epithelial cell, and (ii) the unstirred layer at the apical surface of the small intestine, where the compound is substantially active in the gastrointestinal tract to inhibit transport of phosphate ions (Pi) therein upon administration to the patient in need thereof, and where the compound does not bind NHE3.

In some embodiments, the compounds reduce water absorption in the small intestine, optionally the jejunum. These and related embodiments include methods for inhibiting phosphate uptake in the gastrointestinal tract of a patient in need of phosphate lowering, comprising administering to the patient a compound that decreases water absorption in the small intestine, optionally the jejunum, where the compound does not bind NHE3, and where the compound is substantially active in the gastrointestinal tract to inhibit transport of phosphate ions (Pi) therein upon administration to the patient in need thereof.

In some embodiments, the compound decreases the CEPG in the small intestine and also decreases water absorption in the small intestine. In some embodiments, the compound decreases the CEPG in the small intestine without significantly decreasing water absorption in the small intestine. In other embodiments, the compound decreases water absorption in the small intestine without significantly decreasing the CEPG in the small intestine (e.g., without significantly stimulating bicarbonate secretion and/or inhibiting acid secretion).

In some embodiments, the method results in a method selected from one or more of:

(a) a method for treating hyperphosphatemia, optionally postprandial hyperphosphatemia;

(b) a method for treating a renal disease, optionally chronic kidney disease (CKD) or end-stage renal disease (ESRD);

(c) a method for reducing serum creatinine levels;

(d) a method for treating proteinuria;

(e) a method for delaying time to renal replacement therapy (RRT), optionally dialysis;

(f) a method for reducing FGF23 levels;

(g) a method for reducing the hyperphosphatemic effect of active vitamin D;

(h) a method for attenuating hyperparathyroidism, optionally secondary hyperparathyroidism;

(i) a method for reducing serum parathyroid hormone (PTH)

(j) a method for improving endothelial dysfunction, optionally induced by postprandial serum phosphorus;

(k) a method for reducing vascular calcification, optionally intima-localized vascular calcification;

(l) a method for reducing urinary phosphorous;

(m) a method for normalizing serum phosphorus levels;

(n) a method for reducing phosphate burden in an elderly patient;

(o) a method for decreasing dietary phosphate uptake;

(p) a method for reducing renal hypertrophy; and (q) a method for reducing heart hypertrophy.

In certain embodiments, the compound decreases the intracellular pH of the epithelial cells of the surface of the small intestine, optionally at the subapical surface of the epithelial cell. In certain embodiments, the compound increases the pH of the unstirred layer at the apical surface of the small intestine. In some embodiments, the compound (a) stimulates bicarbonate secretion in the small intestine, or (b) inhibits acid secretion in the small intestine, or (c) stimulates bicarbonate secretion and inhibits acid secretion in the small intestine.

In certain embodiments, the compound increases one or more intracellular secondary messengers of epithelial cells of the surface of the small intestine. In some embodiments, the one or more intracellular secondary messengers are selected from $Ca^{++}$, cyclic adenosine monophosphate (cAMP), and cyclic guanosine monophosphate (cGMP).

In certain embodiments, the compound is substantially systemically non-bioavailable upon enteral administration to the patient. In particular embodiments, the compound is substantially impermeable to the epithelium of the gastrointestinal tract. In some embodiments, the compound is substantially permeable to the epithelium of the gastrointestinal tract.

In certain embodiments, administration to the patient in need thereof (a) reduces serum phosphorus concentrations or levels to about 150% or less of normal serum phosphorus levels, and/or (b) reduces uptake of dietary phosphorous by at least about 10% relative to an untreated state. In some embodiments, administration to the patient in need thereof increases phosphate levels in fecal excretion by at least about 10% relative to an untreated state. In some embodiments, administration to the patient in need thereof reduces urinary phosphate concentrations or levels by at least about 10% relative to an untreated state.

In some embodiments, the patient in need thereof has ESRD, and administration to the patient reduces serum phosphorus concentrations or levels by at least about 10% relative to an untreated state.

In some embodiments, the patient in need thereof has CKD, and administration to the patient reduces FGF23 levels and serum intact parathyroid hormone (iPTH) levels by at least about 10% relative to an untreated state.

In certain embodiments, the compound is selected from one or more of a guanylate cyclase C receptor (GC-C) agonist, a P2Y agonist, an adenosine A2b receptor agonist, a soluble guanylate cyclase agonist, an adenylate cyclase receptor agonist, an imidazoline-1 receptor agonist, a cholinergic agonist, a prostaglandin EP4 receptor agonist, a dopamine D1 agonist, a melatonin receptor agonist, a 5HT4 agonist, an atrial natriuretic peptide receptor agonist, a carbonic anhydrase inhibitor, a phosphodiesterase inhibitor, and a Down-Regulated in Adenoma (DRA or SLC26A3) agonist.

In some embodiments, the GC-C agonist is a peptide, optionally a bacterial heat stable enterotoxin, guanylin, proguanylin, uroguanylin, prouroguanylin, lymphoguanylin, or a variant or analog of any of the foregoing.

In some embodiments, the GC-C agonist peptide comprises the amino acid sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO: 1) where: $Xaa_1$ $Xaa_2$ $Xaa_3$ $Xaa_4$ $Xaa_5$ is Asn Ser Ser Asn Tyr (SEQ ID NO:2) or is missing or $Xaa_1$ $Xaa_2$ $Xaa_3$ $Xaa_4$ is missing.

In certain embodiments, $Xaa_5$ is Asn, Trp, Tyr, Asp, or Phe.

In certain embodiments, $Xaa_5$ is Thr or Ile.

In certain embodiments, $Xaa_5$ is Tyr, Asp, or Trp.

In certain embodiments, $Xaa_8$ is Glu, Asp, Gln, Gly, or Pro.

In certain embodiments, $Xaa_9$ is Leu, Ile, Val, Ala, Lys, Arg, Trp, Tyr, or Phe.

In certain embodiments, $Xaa_9$ is Leu, Ile, Val, Lys, Arg, Trp, Tyr, or Phe.

In certain embodiments, $Xaa_{12}$ is Asn, Tyr, Asp, or Ala.

In certain embodiments, $Xaa_{13}$ is Ala, Pro, or Gly.

In certain embodiments, $Xaa_{14}$ is Ala, Leu, Ser, Gly, Val, Glu, Gln, Ile, Leu, Lys, Arg, or Asp.

In certain embodiments, $Xaa_{16}$ is Thr, Ala, Asn, Lys, Arg, or Trp.

In certain embodiments, $Xaa_{17}$ is Gly, Pro, or Ala.

In certain embodiments, $Xaa_{19}$ is Trp, Tyr, Phe, Asn, or Leu.

In certain embodiments, $Xaa_{19}$ is Lys or Arg.

In certain embodiments, $Xaa_{20}$ $Xaa_{21}$ is AspPhe or $Xaa_{20}$ is Asn or Glu and $Xaa_{21}$ is missing. In certain embodiments, $Xaa_{19}$ $Xaa_{20}$ $Xaa_{21}$ is missing.

In specific embodiments, the GC-C agonist peptide comprises the amino acid sequence: Asn Ser Ser Asn Tyr Cys Cys Glu Tyr Cys Cys Asn Pro Ala Cys Thr Gly Cys Tyr (SEQ ID NO:3), or a variant thereof having 1, 2, 3, 4, or 5 deletions, insertions, and/or substitutions. In particular embodiments, the peptide comprises the amino acid sequence: Cys Cys Glu Tyr Cys Cys Asn Pro Ala Cys Thr Gly Cys Tyr (SEQ ID NO:4), or a variant thereof having 1, 2, 3, 4, or 5 deletions, insertions, and/or substitutions.

In certain embodiments, the GC-C agonist peptide comprises the amino acid sequence (III): $Xaa_1$ $Xaa_2$ $Xaa_3$ $Cys_4$ $Xaa_5$ $Xaa_6$ $Xaa_7$ $Xaa_8$ $Xaa_9$ $Xaa_{10}$ $Xaa_{11}$ $Cys_{12}$ $Xaa_{13}$ $Xaa_{14}$ $Xaa_{15}$ $Xaa_{16}$ (SEQ ID NO:5), where $Xaa_1$ is: Ser, Asn, Tyr, Ala, Gln, Pro, Lys, Gly, or Thr, or is missing; $Xaa_2$ is His, Asp, Glu, Ala, Ser, Asn, Gly, or is missing; $Xaa_3$ is Thr, Asp, Ser, Glu, Pro, Val or Leu; $Xaa_5$ is Asp, Ile or Glu; $Xaa_6$ is Ile, Trp or Leu; $Xaa_7$ is Cys, Ser, or Tyr; $Xaa_8$ is Ala, Val, Thr, Ile, Met or is missing; $Xaa_9$ is Phe, Tyr, Asn, or Trp; $Xaa_{10}$ is Ala, Val, Met, Thr or Ile; $Xaa_{11}$ is Ala or Val; $Xaa_{13}$ is Thr or Ala; $Xaa_{14}$ is Gly, Ala or Ser; $Xaa_{15}$ is Cys, Tyr or is missing; and $Xaa_{16}$ is His, Leu or Ser.

In some embodiments, the peptide comprises the amino acid sequence: Asn Asp Glu Cys Glu Leu Cys Val Asn Val Ala Cys Thr Gly Cys Leu (SEQ ID NO:6), or a variant thereof having 1, 2, 3, 4, or 5 deletions, insertions, and/or substitutions.

In certain embodiments, the P2Y agonist is selected from a compound in FIG. 4 or FIGS. 5A-5C. In certain embodiments, the adenosine A2b receptor agonist is selected from a compound in FIGS. 6A-6C. In some embodiments, the soluble guanylate cyclase agonist is selected from a compound in FIGS. 9A-9L. In certain embodiments, the adenylate cyclase receptor agonist is selected from a compound in FIG. 10. In some embodiments, the imidazoline-1 receptor agonist is selected from moxonidine and a compound in FIG. 11. In certain embodiments, the cholinergic agonist is selected from a compound in FIG. 12. In particular embodiments, the prostaglandin EP4 receptor agonist is selected from $PGE_2$ or its analogs/derivatives and a compound in FIG. 7 or FIG. 13. In certain embodiments, the dopamine D1 agonist is selected from a compound in FIG. 14. In some embodiments, the melatonin receptor agonist is selected from melatonin and a compound in FIG. 15. In some embodiments, the 5HT4 agonist is selected from serotonin and its analogs, prucalopride, metoclopramide, cleobopride, mosapride, prucalopride, renzapride, tegaserod, zacopride, norcisapride, naronopride, and velusetrag.

In some embodiments, the atrial natriuretic peptide receptor agonist comprises or consists of an amino acid sequence selected from: Ser Leu Arg Arg Ser Ser Cys Phe Gly Gly Arg Ile Asp Arg Ile Gly Ala Gln Ser Gly Leu Gly Cys Asn Ser Phe Arg Tyr (SEQ ID NO:7), Cys Phe Gly Gly Arg Ile Asp Arg Ile Gly Ala Gln Ser Gly Leu Gly Cys (SEQ ID NO:8) and Ser Ser Cys Phe Gly Gly Arg Ile Asp Arg Ile Gly Ala Gln Ser Gly Leu Gly Cys Asn Ser Phe Arg (SEQ ID NO:9), including variants thereof having 1, 2, 3, 4, or 5 deletions, insertions, and/or substitutions.

In certain embodiments, the carbonic anhydrase inhibitor is selected from a compound in FIG. 17. In certain embodiments, the phosphodiesterase inhibitor is selected from a compound in FIG. 18. In some embodiments, the DRA agonist is selected from FIGS. 21A-B.

In some embodiments, the compound is substantially systemically non-bioavailable upon enteral administration to the patient and has (i) a tPSA of at least about 200 Å$^2$. In certain embodiments, the compound has a tPSA of at least about 250 Å$^2$, a tPSA of at least about 270 Å$^2$, a tPSA of at least about 300 Å$^2$, a tPSA of at least about 350 Å$^2$, a tPSA of at least about 400 Å$^2$, or a tPSA of at least about 500 Å$^2$. In particular embodiments, the compound has a molecular weight of at least about 500 Da, at least about 1000 Da, at least about 2500 Da, or at least about 5000 Da or more. In some embodiments, the compound has (i) a total number of NH and/or OH and/or other potential hydrogen bond donor moieties greater than about 5; (ii) a total number of O atoms and/or N atoms and/or other potential hydrogen bond acceptors greater than about 10; and/or (iii) a Moriguchi partition coefficient greater than about $10^5$ or less than about 10. In some embodiments, the compound has a permeability coefficient, $P_{app}$, of less than about $100\times10^{-6}$ cm/s, or less than about $10\times10^{-6}$ cm/s, or less than about $1\times10^{-6}$ cm/s, or less than about $0.1\times10^{-6}$ cm/s.

Certain methods further comprise administering one or more additional biologically active agents. In some embodiments, the compound and the one or more additional biologically active agents are administered as part of a single pharmaceutical composition. In certain embodiments, the compound and the one or more additional biologically active agents are administered as individual pharmaceutical compositions. In some embodiments, the individual pharmaceutical compositions are administered sequentially. In some embodiments, the individual pharmaceutical compositions are administered simultaneously.

In certain embodiments, the additional biologically active agent is selected from vitamin $D_2$ (ergocalciferol), vitamin $D_3$ (cholecalciferol), active vitamin D (calcitriol) and active vitamin D analogs (e.g. doxercalciferol, paricalcitol).

In certain embodiments, the additional biologically active agent is a phosphate binder. In some embodiments, the phosphate binder is selected from the group consisting of sevelamer (e.g., Renvela® (sevelamer carbonate), Renagel® (sevelamer hydrochloride)), lanthanum carbonate (e.g., Fosrenol®), calcium carbonate (e.g., Calcichew®, Titralac®), calcium acetate (e.g. PhosLo®, Phosex®), calcium acetate/magnesium carbonate (e.g., Renepho®, OsvaRen®), MCI-196, ferric citrate (e.g., Zerenex™), magnesium iron hydroxycarbonate (e.g., Fermagate™), aluminum hydroxide (e.g., Alucaps®, Basaljel®), APS1585, SBR-759, and PA-21.

In certain embodiments, the additional biologically active agent is a NaPi2b inhibitor. In some embodiments, the additional biologically active agent is niacin or nicotinamide.

In certain embodiments, the subject has CKD and the additionally active biological agent is selected from one or more of ACE inhibitors, antiogensin II receptor blockers, beta-blockers, calcium channel blockers, direct renin inhibitors, diuretics, vasodilators, erythropoietin therapy, iron replacement therapy, inhibitors of advanced glycation end products, vitamin D, and statins.

In certain embodiments, the compound or composition is administered orally, optionally where the compound or composition is administered orally once-a-day.

Also included are methods of screening for an inhibitor of phosphate uptake, comprising (a) culturing intestinal cells, (b) contacting the cultured intestinal cells with a test compound, and (c) measuring (i) the pH at the apical surface of the intestinal cells, (ii) the intracellular pH of the intestinal cells, and/or (iii) phosphate uptake by the intestinal cells, and (d) identifying the test compound as an inhibitor of phosphate uptake where the pH from (c)(i) increases relative to a control, the intracellular pH from (c)(ii) decreases relative to a control, and/or phosphate uptake from (c)(iii) decreases relative to a control.

In some embodiments, step (a) comprise culturing intestinal cells to monolayers. In certain embodiments, step (a) comprises isolating the cells from intestinal crypts and culturing under conditions sufficient to form enteroids. In certain embodiments, step (a) comprises culturing isolated embryonic stem cells, endoderm cells, or pluripotent stem cells under conditions sufficient to form organoids. In some embodiments, step (a) comprises culturing intestinal section(s) in a Ussing chamber.

In certain embodiments, step (c)(i) comprises contacting the cells with a pH-sensitive fluorescent dye and measuring fluorescence of the dye. In some embodiments, step (c)(ii) comprises contacting the cells with $^{33}P$-labeled phosphate ions and measuring uptake of the labeled phosphate ions.

In some embodiments, the increase and/or decrease of (d) is statistically significant.

In certain embodiments, the test compound is a small molecule or peptide that is known or suspected to stimulate bicarbonate secretion and/or inhibit acid secretion in the small intestine.

In certain embodiments, the test compound is selected from one or more of a P2Y agonist, an adenosine A2b receptor agonist, a guanylate cyclase C receptor agonist, a soluble guanylate cyclase agonist, an adenylate cyclase receptor agonist, an imidazoline-1 receptor agonist, a cholinergic agonist, a prostaglandin EP4 receptor agonist, a dopamine D1 agonist, a melatonin receptor agonist, a 5HT4 agonist, an atrial natriuretic peptide receptor agonist, a carbonic anhydrase inhibitor, a phosphodiesterase inhibitor, and a Down-Regulated in Adenoma (DRA or SLC26A3) agonist, as described herein and/or known in the art.

These and other aspects of the invention will be apparent upon reference to the following detailed description.

BRIEF DESCRIPTION OF THE DRAWINGS

FIG. 7 shows a list of exemplary prostaglandin EP4 receptor agonists.

FIGS. 8A-8B show the photophysical properties of exemplary near-neutral pH indicators (8A) and acidic pH indicators (8B).

FIGS. 9A-9L show exemplary soluble guanylate cyclase (sGC) agonists, including heme-dependent and heme-independent agonists (9A).

FIG. 14 shows exemplary dopamine D1 receptor agonists.

FIGS. 21A-21B depict representative examples of sub-type selective PKC inhibitors.

DETAILED DESCRIPTION

Figure 1B:
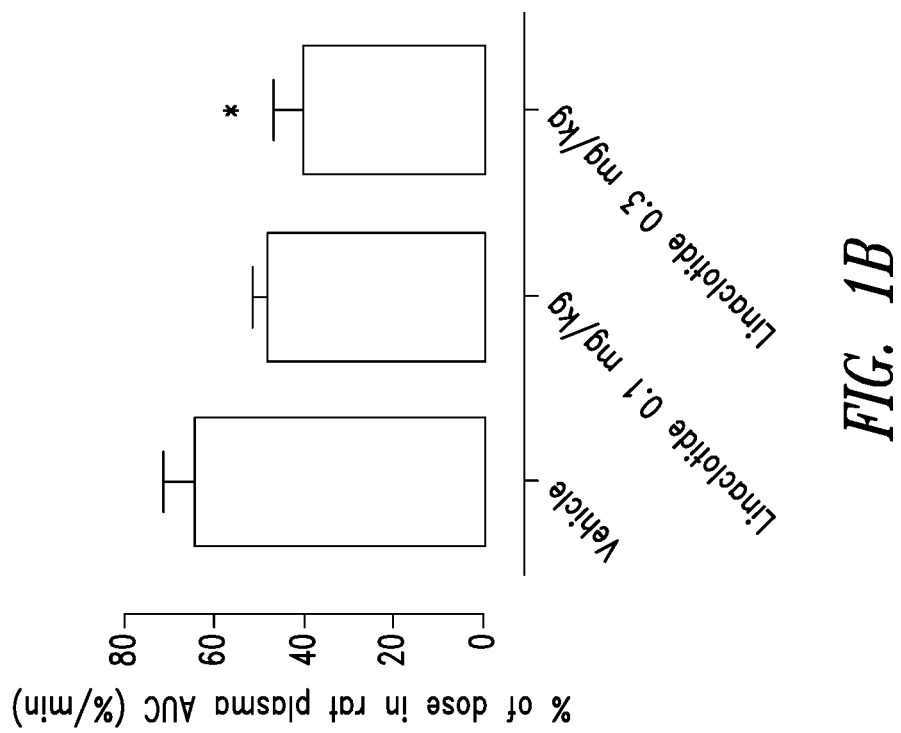
FIGS. 1A-1B shows that linaclotide (a GC-C receptor agonist) reduces the uptake of phosphate uptake in the gastrointestinal tract of rats.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of the present invention relate generally to the discovery that non-NHE3-binding compounds, such as guanylate cyclase agonist compounds, are able to inhibit phosphate uptake in the gastrointestinal tract, for example, in the small intestine.

According to one non-limiting theory, the cellular uptake of phosphate ions (Pi) can be influenced by changes to intracellular pH and/or the pH of the adjacent extracellular environment. For instance, as shown in the accompanying Examples, acidification of the cell interior of Human Embryonic Kidney (HEK-293) cells (while maintaining the extracellular pH at about 7.4) led to a significant reduction in phosphate uptake, as measured by uptake of $^{33}P$ labeled Pi.

In related experiments, where the phosphate transporter NaPi2b (SLC34A2) was transiently expressed in HEK-293 cells, the same phenomenon was observed. Because the endogenous Pi transporters, Pit-1 and/or Pit-2 (SLC20A2) are responsible for Pi uptake in non-transformed HEK-293 cells (to satisfy cell metabolic demands), it was concluded that the effect of a decrease in intracellular pH on Pi uptake is a general phenomenon not necessarily linked to a specific phosphate transporter. Pit-1 and Pit-2 transport the monobasic form of phosphate $NaH_2PO_3^-$ whereas NaPi2b transports the dibasic form $NaHPO_3^{2-}$. The observation that the cell acidification affects phosphate uptake with both transporters is inconsistent with a mechanism based on a change in the $H^+$ electrochemical gradient alone.

These observations are counterintuitive in the least because an increase in Pi uptake could have been expected. For example, a decrease in intracellular pH (e.g., without any corresponding change in the extracellular pH) could have been expected to create a driving force for the uptake of basic anions such as the dibasic form of phosphate $(NaPO_3^{2-})$.

Nonetheless, a reduction in phosphate uptake was observed, presenting the potential of using direct or indirect pH-modulatory agents, particularly those having activity as pH-modulatory agents in the gastrointestinal tract (e.g., small intestine), to reduce phosphate uptake in a patient in need of phosphate lowering. This potential is supported by the observation that a variety of pH-modulatory agents are capable of reducing phosphate uptake in the mammalian gastrointestinal tract (see the accompanying Examples). The term "pH-modulatory" agents, as used herein, includes agents or compounds that are capable of directly or indirectly increasing bicarbonate $(HCO_3^-)$ secretion and/or decreasing acid/proton (e.g., $H^+$) secretion into the lumen of the gastrointestinal tract, for example, the small intestine or duodenum. Some pH-modulatory compounds may act, for example, by modulating (e.g., increasing) certain intracellular secondary messengers of epithelial cells of the gastrointestinal tract, such as $Ca^{++}$, cAMP, cGMP, and others. Some exemplary compounds thus either directly or indirectly stimulate bicarbonate secretion into the lumen of the small intestine, inhibit acid secretion into the lumen of the small intestine, or stimulate bicarbonate secretion and inhibit acid secretion into the lumen of the small intestine. In some aspects, the compound decreases the cytoplasmic or intracellular pH of the epithelial cells of the surface of the small intestine, optionally at the subapical surface of the epithelial cell, without or without modulating the pH of the adjacent extracellular environment. In certain embodiments, the compound does not bind to and inhibit the sodium-hydrogen antiporter 3 (NHE3).

Figure 19:
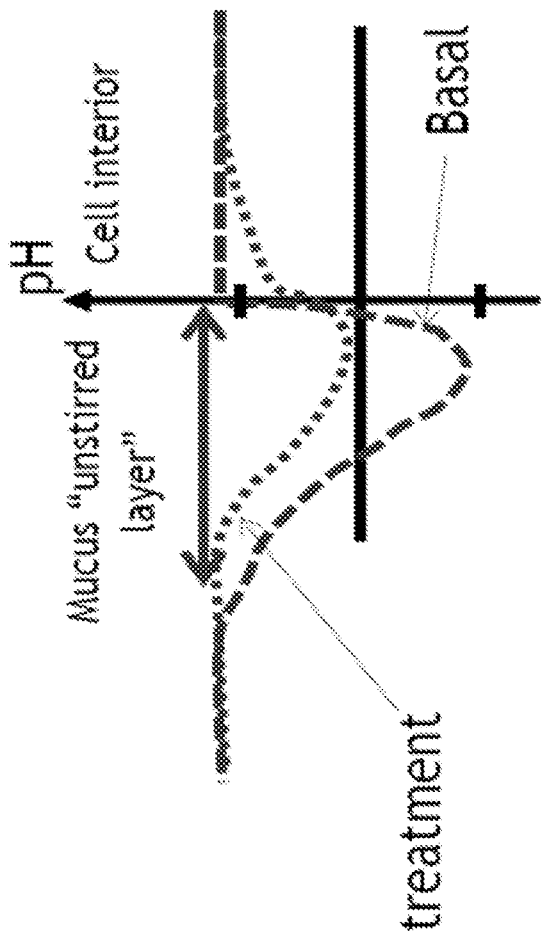
FIG. 19 illustrates the pH gradients found in the intestine, including the pH gradient across the cell membrane, and the pH gradient at the immediate vicinity of the epithelial membrane and the gut lumen.

In some aspects, the compound decreases the pH of the "unstirred layer" at the apical surface of the small intestine. The "unstirred layer" refers to a stagnant layer adjacent to the membrane on the apical side (e.g., about 600 urn deep) which acts as a diffusion barrier so that rapidly permeating substances (e.g., $^1H^+$) can be rate-limited by diffusion. Without wishing to be bound to theory, such an approach would elicit a flux of bicarbonate across the epithelial cells of the gastrointestinal tract, increase the pH in immediate vicinity of the cell exterior (UWL), and therefore decrease the pH gradient at the mucosal surface. Because of the continuous exchange of proton and bicarbonate ions at the apical surface of the intestinal cells via co-transporters, antiporters and channels, a pH gradient is maintained across the cell membrane. As a result of the unstirred layer, another pH gradient is established between the immediate vicinity of the epithelial membrane and the gut lumen. The two pH gradients are represented schematically in FIG. 19.

Accordingly, in some aspects, a compound decreases the cross-epithelial pH gradient (CEPG) in the gastrointestinal tract. The term "CEPG" includes the difference in pH between (i) the cytoplasm of the epithelial cells of the surface of the small intestine (i.e., the intracellular pH), optionally at the subapical surface of the epithelial cell, and (ii) the unstirred layer at the apical surface of the small intestine. Certain embodiments exclude compounds (e.g., antacids) that merely increase the luminal pH of the gastrointestinal tract without modulating bicarbonate and/or acid secretion or without altering the pH in the unstirred layer or UWL.

Figure 20:
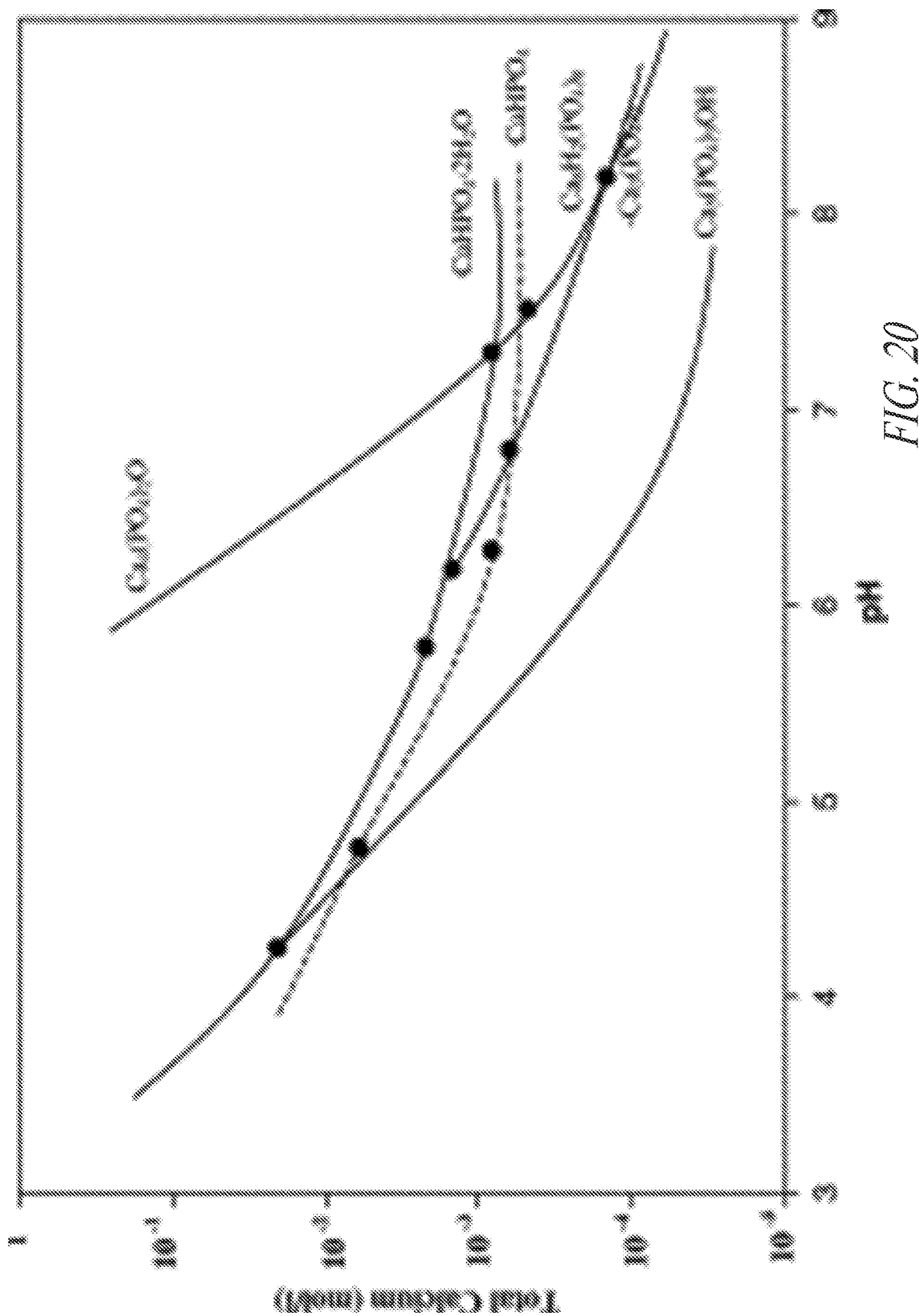
FIG. 20 shows a phase diagram of the solubility calciumn and phosphate ions in an aqueous environment (at RT) over a range of pH values.

In some embodiments, and without wishing to be bound by any one theory, intraluminal free calcium ions may contribute to the inhibition of Pi uptake induced by a decrease in the CEPG. A phase diagram of calcium and phosphate ions in an aqueous environment at room temperature shows that the solubility of calcium (and therefore phosphate) is pH dependent, that is, phosphate solubility decreases as pH increases. See FIG. 20. This phenomenon would suggest that, all things being equal, a drug-induced pH increase in the microenvironment of the mucosal surface would minimize free Pi availability, thus reducing its cellular uptake in the gastrointestinal tract.

According to another non-limiting theory, the uptake of phosphate ions can be influenced by the absorption of water in the small intestine, primarily in the jejunum. Specifically, increased water absorption in the small intestine associates with increased phosphate uptake, and vice versa. In such instances, non-NHE3-binding compounds that reduce water absorption in the small intestine can be used to inhibit phosphate uptake. Certain embodiments thus relate to methods for inhibiting phosphate uptake in the gastrointestinal tract of a patient in need of phosphate lowering, comprising administering to the patient a compound that decreases water absorption in the small intestine, where the compound does not bind NHE3, and where the compound is substantially active in the gastrointestinal tract to inhibit transport of phosphate ions (Pi) therein upon administration to the patient in need thereof. In certain embodiments, the compound decreases "net" water absorption, for instance, by modulating the balance between secretion and absorption, e.g., by decreasing absorption, increasing secretion, or both. In some embodiments, the compound decreases water absorption in the jejunum.

In some aspects, inhibition of phosphate uptake in the gastrointestinal tract may be achieved by the administration of certain compounds, and/or pharmaceutical compositions comprising them, which may advantageously be designed such that little, or substantially none, of the compound is absorbed into the blood stream (that is, it is designed to be non-systemic or substantially non-systemic). In this regard, the compounds have features that give rise to little or substantially no systemic availability upon enteral administration, including oral administration. In other words, the compounds are not absorbed into the bloodstream at meaningful levels and therefore have no activity there, but instead have their activity localized substantially within the GI tract.

Therefore, in certain illustrative embodiments as further described herein, the compounds of the invention generally require a combination of structural and/or functional features relating or contributing to their activity in the GI tract and/or their substantial non-systemic bioavailability. Such features may include, for example, one or more of (i) specific tPSA and/or MW values (e.g., at least about 190 Å$^2$ and/or at least about 736 Daltons, respectively), (ii) specific levels of fecal recovery of the compound and/or its metabolites after administration (e.g., greater than 50% at 72 hours); (iii) specific numbers of NH and/or OH and/or potentially hydrogen bond donor moieties (e.g., greater than about five); (iv) specific numbers of rotatable bonds (e.g., greater than about five); (iv) specific permeability features (e.g., $P_{app}$ less than about $100 \times 10^{-6}$ cm/s); and/or any of a number of other features and characteristics as described herein.

In patients with advanced kidney disease (e.g. stage 4 and 5), the body phosphorus overload manifests itself by serum phosphorus concentration above normal levels, i.e., hyperphosphatemia. Hyperphosphatemia is directly related to mortality and morbidity. Inhibition of intestinal phosphate transport will reduce serum phosphorus concentration and therefore improve outcome in those patients. In stage 2 and 3 chronic kidney disease patients, the body phosphorus overload does not necessarily lead to hyperphosphatemia, i.e., patients remain normophosphatemic, but it does trigger an increase in FGF-23, a risk factor in mortality and morbidity in those patients. Therefore, there is a need to reduce body phosphorus overload even at those early stages to avoid associated bone and vascular disorders, and ultimately improve mortality rate.

Inhibition of intestinal phosphate transport will be particularly advantageous in patients that have a disease that is treatable by inhibiting the uptake of phosphate from the intestines. Furthermore, inhibition of phosphate transport may slow the progression of renal failure and reduce the risk of cardiovascular events, among other diseases or conditions associated with the need for phosphate lowering.

I. Compounds that Inhibit Phosphate Transport

Embodiments of the present invention relate to compounds that are able to inhibit or reduce phosphate transport/uptake in the gastrointestinal tract, for instance, by modulating the pH within or adjacent to the epithelial membrane of the gastrointestinal lumen, by decreasing water absorption in the small intestine, or both. Examples of pH-modulatory compounds include those that stimulate bicarbonate secretion in the small intestine (i.e., duodenal bicarbonate secretion or DBS), inhibit acid/proton secretion in the small intestine, or both.

The compounds provided herein can include small molecules of synthetic or biologic origin and peptides or polypeptides. The terms "peptide" and "polypeptide" are used interchangeably herein; however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids. Antibodies are also included as polypeptides.

In some embodiments, the compound is selected from one or more of a P2Y receptor agonist, an adenosine A2b receptor agonist, a guanylate cyclase C receptor agonist, a soluble guanylate cyclase agonist, an adenylate cyclase receptor agonist, an imidazoline-1 receptor agonist, a cholinergic agonist, a prostaglandin EP4 receptor agonist, a dopamine D1 agonist, a melatonin receptor agonist, a 5HT4 agonist, an atrial natriuretic peptide receptor agonist, a carbonic anhydrase inhibitor, a phosphodiesterase inhibitor, or a Down-Regulated in Adenoma (DRA or SLC26A3) agonist. In some aspects, as noted above, such agonist compounds induce bicarbonate secretion and/or inhibit acid secretion in the upper gastrointestinal tract, including the duodenum and the proximal jejunum. In some aspects, the mechanism of action directly or indirectly modulates apical proton and bicarbonate transporters to produce a decrease in CEPG or a relatively basic microenvironment at the mucosal surface, which thereby reduces phosphate uptake/ab sorption.

In specific aspects, the compound directly or indirectly stimulates duodenal bicarbonate secretion (DBS). DBS is a natural defense of the mucosa which operates in the duodenal and proximal jejunum segments of the gut to neutralize acidic gastric fluid. DBS can be stimulated by a number of biological pathways, including those which regulate the activity of chloride/bicarbonate antiporters such as SLC26A3 (DRA) and SLC26A3 (PAT-1), chloride and bicarbonate channels via CFTR, and calcium-activated chloride channels, among others. In some aspects, these pathways are stimulated by an increase in one or more secondary messengers, such as intracellular $Ca^{++}$, cAMP, and/or cGMP.

In some aspects, the compound directly or indirectly decreases water absorption in the small intestine. In particular aspects, the compound decreases water absorption in the jejunum. The specific aspects, the compound decreases water absorption in the small intestine by about or at least about 10%, 20%, 30%, 40%, 50%, 60%, 70%, 80%, 90%, or 100% relative to a control compound or no compound.

The term "agonist" includes a compound that binds to a target molecule such as a receptor and triggers or stimulates a cellular response by that target molecule. Included are super agonists, full agonists, partial agonists, and selective agonists. Super agonists produce a greater maximal response than the endogenous agonist(s) for the target molecule, full agonists produce a comparable response relative to the endogenous agonist(s) for the target molecule, and partial agonists produce a significantly lesser (e.g., 10%, 20%, 30%, 40%, 50%, 60%, 70%, 80%) maximal response than the endogenous agonist(s) for the target molecule.

Further to its activity as an agonist, in certain embodiments a compound can also be characterized by its "specific binding" to a target. For instance, in some embodiments a compound (e.g., a direct-acting compound) can specifically bind to a target described herein with a binding affinity ($K_d$) of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In particular embodiments, the target is selected from one or more of a P2Y receptor, an adenosine A2b receptor, a guanylate cyclase C receptor, an adenylate cyclase receptor, an imidazoline-1 receptor, an acetylcholine receptor, a prostaglandin EP4 receptor, a dopamine D1 receptor, a melatonin receptor, 5HT4, an atrial natriuretic peptide receptor, a carbonic anhydrase, a phosphodiesterase, and Down-Regulated in Adenoma (DRA or SLC26A3), as described herein.

A. P2Y Agonists

In certain embodiments, the compound is a P2Y agonist (or P2Y receptor agonist). P2Y receptors refer to a family of purinergic G protein-coupled receptors. Examples of human P2Y receptors include $P2Y_1$, $P2Y_2$, $P2Y_4$, $P2Y_5$, $P2Y_6$, $P2Y_8$, $P2Y_9$, $P2Y_{10}$, $P2Y_{11}$, $P2Y_{12}$, $P2Y_{13}$, and $P2Y_{14}$. The main native or endogenous ligands of the P2Y receptors are adenosine 5'-triphosphate (ATP), adenosine 5'-diphosphate (ADP), uridine 5'-triphosphate (UTP), uridine 5'-diphosphate (UDP), and UDP-glucose (or other UDP sugars). Dinucleotides such as $Ap_4U$ are also naturally-occurring P2Y agonists.

P2Y receptors have been shown to mediate $Ca^{++}$ signaling in duodenocytes and contribute to duodenal mucosal bicarbonate secretion. See, e.g., Dong et al., *Am J Physiol Gastrointest Liver Physiol* 296:G424-G432, 2009. Without being bound by any one mechanism, in certain aspects a P2Y receptor agonist inhibits or reduces phosphate uptake in the gastrointestinal tract by stimulating bicarbonate secretion into the small intestine (also referred to as duodenal bicarbonate secretion; DBS).

In some embodiments, and without being bound by any one mechanism, a P2Y receptor agonist inhibits or reduces phosphate uptake in the gastrointestinal tract by decreasing water absorption in the small intestine.

Some P2Y receptors are selectively activated, for example, by adenine nucleotides such as ATP and ADP, and others are by uracil nucleotides or UDP-glucose. The $P2Y_1$ receptor accounts for the functionality of the defined P2Y-purinoreceptor. It operates in a variety of tissues including smooth muscle, endothelium and neuronal tissues as well as in blood platelets. The $P2Y_1$ receptor is selective for adenine nucleotides. ADP is the most potent physiological agonist. In some embodiments, the compound is a $P2Y_1$ receptor agonist, optionally a selective $P2Y_1$ receptor agonist relative to other P2Y receptors. One example of a $P2Y_1$ receptor agonist is 2-methylthio-ADP.

In particular embodiments, the compound is a $P2Y_2$ and/or $P2Y_4$ receptor agonist, optionally a selective $P2Y_2$ receptor agonist relative to other P2Y receptors. These two receptors display the highest identity in the sequences of their TM domains (66.8%) of all the P2Y receptor subtypes. The $P2Y_2$ receptor can be activated, for instance, by uracil nucleotides, UDP-sugar derivatives, and adenine nucleotides such as ATP. $P2Y_2$ receptors are expressed in many tissues including lung, heart, skeletal muscle, spleen, kidney, liver and epithelia. These receptors play an important role in regulating ion transport in epithelial cells. Triphosphate nucleotides including UTP, ATP, UTPγS and ATPγS act as full agonists of the $P2Y_2$ receptor. In addition to the above-mentioned agonists, the $P2Y_2$ receptor also responds to diadenosine-tetraphosphate (AP4A) and Up4U (diquafosol, INS365, used for the treatment for dry eye disease). The analogue P-(uridine 5')-P4-(2'-deoxycytidine 5') tetraphosphate (INS37217 is a potent agonist at the $P2Y_2$ receptor with some agonist effects on the $P2Y_4$ receptor. Denufosol ((3S,5R)-5-(4-amino-2-oxopyrimidin-1-yl)-3-hydroxyoxolan-2-yl]methoxy-hydroxyphosphoryl] [[[(2R,3 S,4R,5R)-5-(2,4-dioxopyrimidin-1-yl)-3,4-dihydroxyoxolan-2-yl] methoxy-hydroxyphosphoryl] oxy-hydroxyphosphoryl] hydrogen phosphate; including its tetrasodium salt) is also an exemplary $P2Y_2$ receptor agonist. Also included is PSB1114.

For ribose and uracil modifications, both 2'-deoxy-2'-amino-UTP and 2-thio-UTP preserve the agonist potency of UTP at the $P2Y_2$ receptor. The combination of these two modifications yields 2'-amino-2-thio-UTP, which synergizes to enhance both potency (8 nM $EC_{50}$) and selectivity (300-fold P2Y2-selective versus $P2Y_4$). Modifications at position 5, such as 5-bromo-UTP ($EC_{50}$=0.75 μM) and 5-iodo-UTP ($EC_{50}$=0.83 μM), suggest that introducing a small hydrophobic group might be beneficial at the $P2Y_2$ receptor.

The P2Y receptor agonists provided herein include mononucleotides, dinucleotides, and nucleotide-sugars, among other agonists known in the art. See, e.g., U.S. Pat. No. 6,624,150; EP 1196396; WO 2008/060632; Cosyn et al., *BioorgMed Chem Lett.* 19:3002-5, 2009 (describing uridine 5'-(phospho)phosphonate and a 5'-methylenephosphonate equivalent of UMP); Ko et al., *Bioorg Med Chem.* 16:6319-32, 2008 (describing, for example, alpha,beta-methylene-UDP, a $P2Y_6$ receptor agonist; Up(4)-phenyl ester and Up(4)-[1]glucose, selective $P2Y_2$ receptor agonists; dihalomethylene phosphonate analogues, selective $P2Y_2$ receptor agonists; a 2-thio analogue of INS37217 (P(1)-(uridine-5')-P(4)-(2'-deoxycytidine-5')tetraphosphate), a potent and selective $P2Y_2$ receptor agonist; Ivanov et al., *J Med Chem.* 50:1166-76, 2007; Brookings et al., *BioorgMed Chem Lett.* 17:562-5, 2007 (describing the synthesis and $P2Y_2$ agonist activities of a series of nucleoside triphosphates); and Jacobson et al., *Purinergic Signal.* 5:75-89, 2009; each of which is incorporated by reference in its entirety.

Additional examples of P2Y receptor agonists include those described in WO 1999/09998 and U.S. Application Nos. 2002/0052336 and 2003/0027785, including $P_1,P_4$-diadenosinetetraphosphate ($A_2P_4$); uridine-5'-diphosphate (UDP); uridine-5'-O-(2-thiodiphosphate) (UDPβS); 5-bromouridine-5'-triphosphate (5-BrUTP); 5-(1-phenylethynyl)-uridine-5'-triphosphate (5-(1-phenylethynyl)UTP); 5-methyluridine-5'-diphosphate (5-methylUDP); 4-hexylthiouridine-5'-triphosphate (4-hexylthioUTP); 4-thiouridine-5'-triphosphate (4-thioUTP); 2-methoxyuridine-5'-triphosphate (2-methoxyUTP); 4-(1-morpholino)uridine-5'-tetraphosphate (4-(1-morpholino))UP$_4$; 4-hexyloxyuridine-5'-diphosphate (4-hexyloxyUDP); 4-(N, N-dimethyl) cytidine-5'-triphosphate (N, N-dimethylCTP); 4-(N-hexyl) cytidine-5'-triphosphate (N-hexylCTP); P$^1$-(cytidine-5')-P$^4$-(uridine-5'-)tetraphosphate (CP$_4$U); P$^1$—O-(methyl)-P$^4$-(uridine-5'-)tetraphosphate (MeP$_4$U) and 4-(N-cyclopentyl) thymidine-5'-triphosphate (N-cyclopentylCTP).

Also included are 5'-adenosine-triphosphate (ATP), 5'-uridine-triphosphate (UTP), uridine-5'-O-(3-thiotriphosphate) (UTPγS), P$_1$-(uridine-5')-P.sup.4-(uridine-5'-)tetraphosphate (U$_2$P$_4$), 5'-[4-(thiouridine)]-triphosphate (4-thioUTP), and Pi-(cytidine-5')-P$_4$-(uridine-5'-) tetraphosphate (CP$_4$U). The identification and preparation of certain thiophosphate analogues of nucleoside diphosphates (such as UDP-13-S) are described in U.S. Pat. No. 3,846,402 and Goody and Eckstein (J. Am. Chem. Soc. 93: 6252-6257. 1971). Alternatively, UTP and other analogs thereof are also commercially available from vendors such as Sigma (St. Louis, Mo.) and Pharmacia (Uppsala, Sweden). Exemplary methods of identifying P2Y receptor agonists are described, for example, in U.S. Application No. 2003/0175810.

In some embodiments, the P2Y receptor agonist is a non-endogenous small molecule agonist. Additional examples of P2Y receptor agonists are shown in FIGS. 4 and 5A-5C.

B. Adenosine A2b Receptor Agonists

In certain embodiments, the compound is an adenosine A2b receptor agonist, optionally a selective agonist. Adenosine exerts most of its physiological functions by acting as a local modulator at four receptor subtypes named A1, A2A, A2B and A3 adenosine receptors (ARs). The adenosine A2b receptor (or ADORA2B) is a G-protein coupled adenosine receptor integral membrane protein that stimulates adenylate cyclase activity in the presence of adenosine.

The A2b receptor is expressed in a variety of tissues, and high concentrations have been suggested in the caecum and large intestine on both the mucosal and basolateral aspect of colonic epithelial cells. See Baraldi et al., *Purinergic Signal.* 5:3-19, 2009. Activation at either site results in Cl— secretion via direct activation of the cAMP-activated Cl— channel cystic fibrosis transmembrane conductance regulator (CFTR). CFTR modulates the secretion of both chloride and bicarbonate. For example, in rats the A2B receptor has been immuno-localized to the brush border membrane of duodenal villi, where luminal adenosine has been shown to stimulate bicarbonate secretion via A2B receptors and CFTR. See, e.g., Ham et al., *J Pharmacol Exp Ther.* 335:607-13, 2010. Without being bound by any one mechanism, in certain aspects an adenosine A2b receptor agonist inhibits or reduces phosphate uptake in the gastrointestinal tract by stimulating bicarbonate secretion into the small intestine, e.g., by decreasing the CEPG.

In some embodiments, and without being bound by any one mechanism, an adenosine A2b receptor agonist inhibits or reduces phosphate uptake in the gastrointestinal tract by decreasing water absorption in the small intestine.

General examples of adenosine A2b receptor agonists include adenosine, adenosine-like compounds, and non-adenosine compounds. In some embodiments, nucleoside-based adenosine A2b receptor agonists include modified adenosine compounds, such as adenosine compounds substituted at the N (6)-position of the purine heterocycle, the C(2)-position of the purine heterocycle, the 5'-position of the ribose moiety, and any combination of the foregoing. Also included are non-ribose ligands such as substituted dicarbonitrilepyridines, among which 2-[6-amino-3,5-dicyano-4-[4-(cyclopropylmethoxy)phenyl]pyridin-2-ylsulfanyl]acetamide is an example. See, e.g., Baraldi et al., *Purinergic Signal.* 4:287-303, 2008; and Baraldi et al., *Purinergic Signal.* 5:3-19, 2009; each of which is incorporated by reference in its entirety.

Additional non-limiting examples of adenosine A2b receptor agonists include BAY 60-6583, CV 1808, AMP579, NECA (N-ethylcarboxamidoadenosine), (S)-PHPNECA, LUF-5835, 6-guanyl NECA, and LUF-584. See also Beukers et al., *J. Med. Chem.* 47:3707-3709, 2004 (describing, for example, non-adenosine agonists such as LUF5834 (2-amino-4-(4-hydroxyphenyl)-6-(1H-imidazol-2-ylmethylsulfanyl)pyridine-3,5-dicarbonitrile) and LUF5835 (a 3-hydroxyphenyl analogue)); Beukers et al., *Med Res Rev.* 26:667-98, 2006 (describing, for example, (S)PHPNECA and certain non-ribose ligands as adenosine A2b receptor agonists); and Liu et al., *Basic Res Cardiol.* 105:129-37, 2010. Also included are the A2b receptor agonists described in U.S. Application No. 2002/0156076. These references are incorporated by reference in their entireties.

Figure 6A:
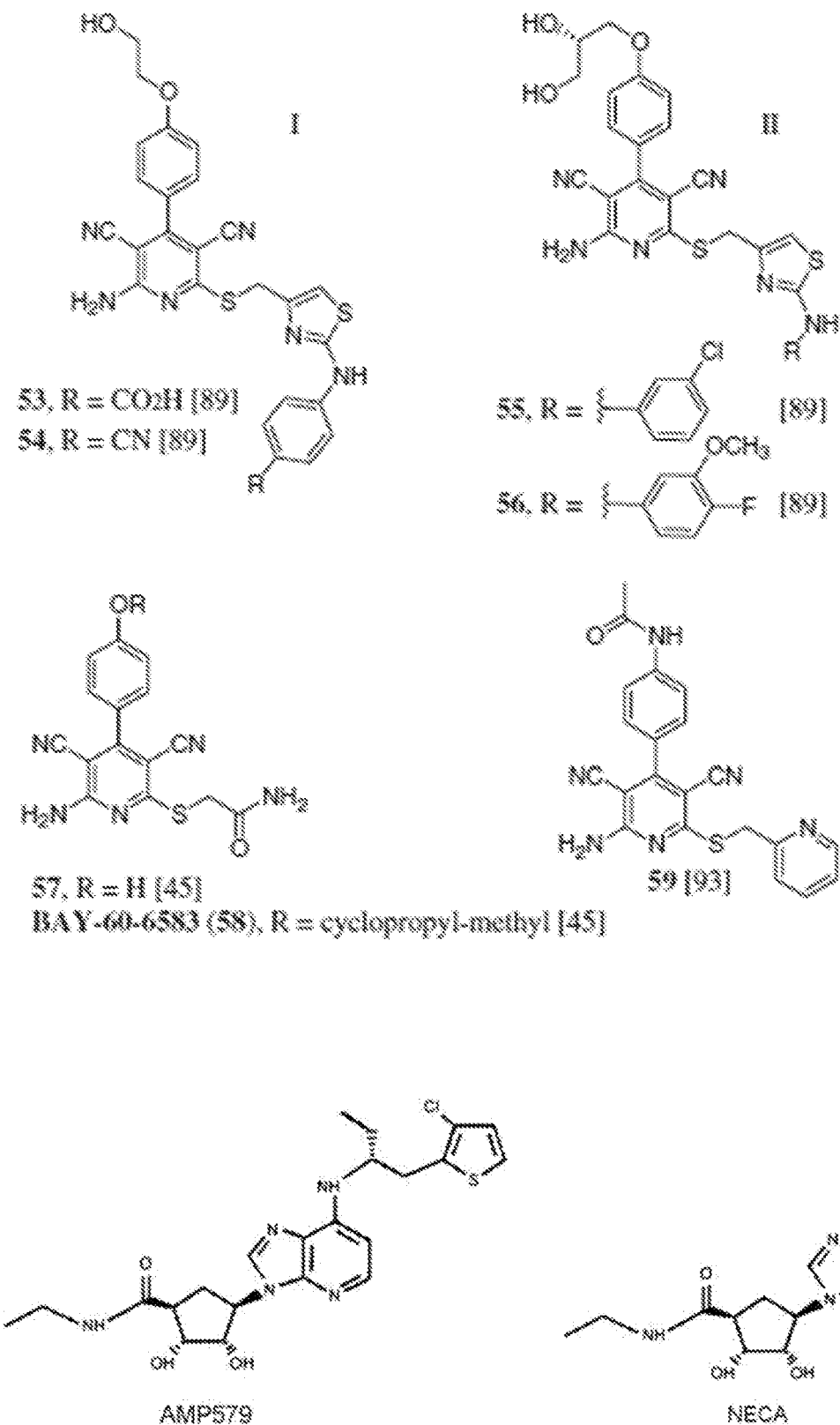
FIGS. 6A-6C show exemplary small molecule adenosine A2b receptor agonist, including representative adenosine-like A2b agonists (6B) and representative dicyanopyridine A2b agonists (6C).
Figure 6B:
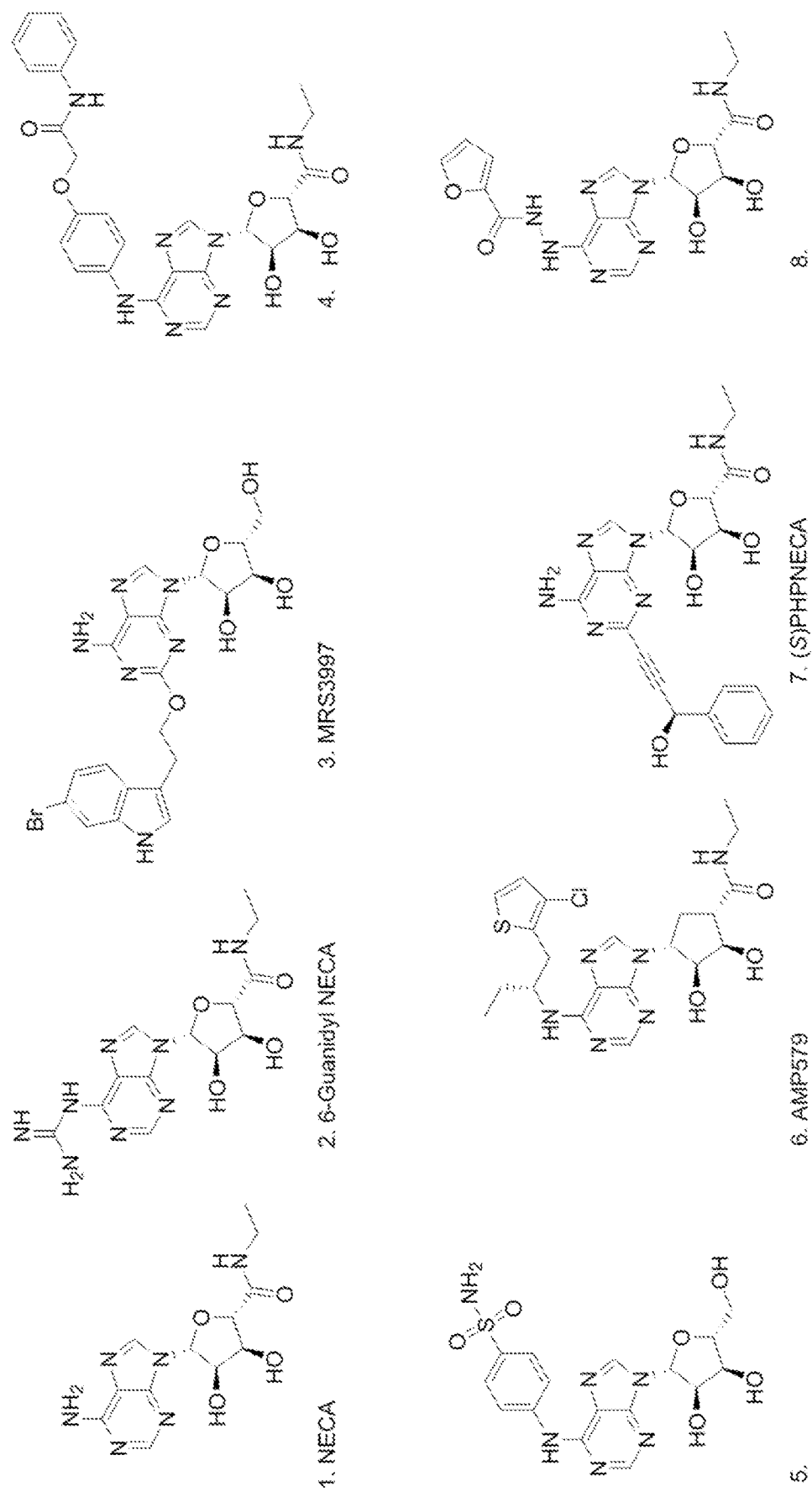
Figure 6C:
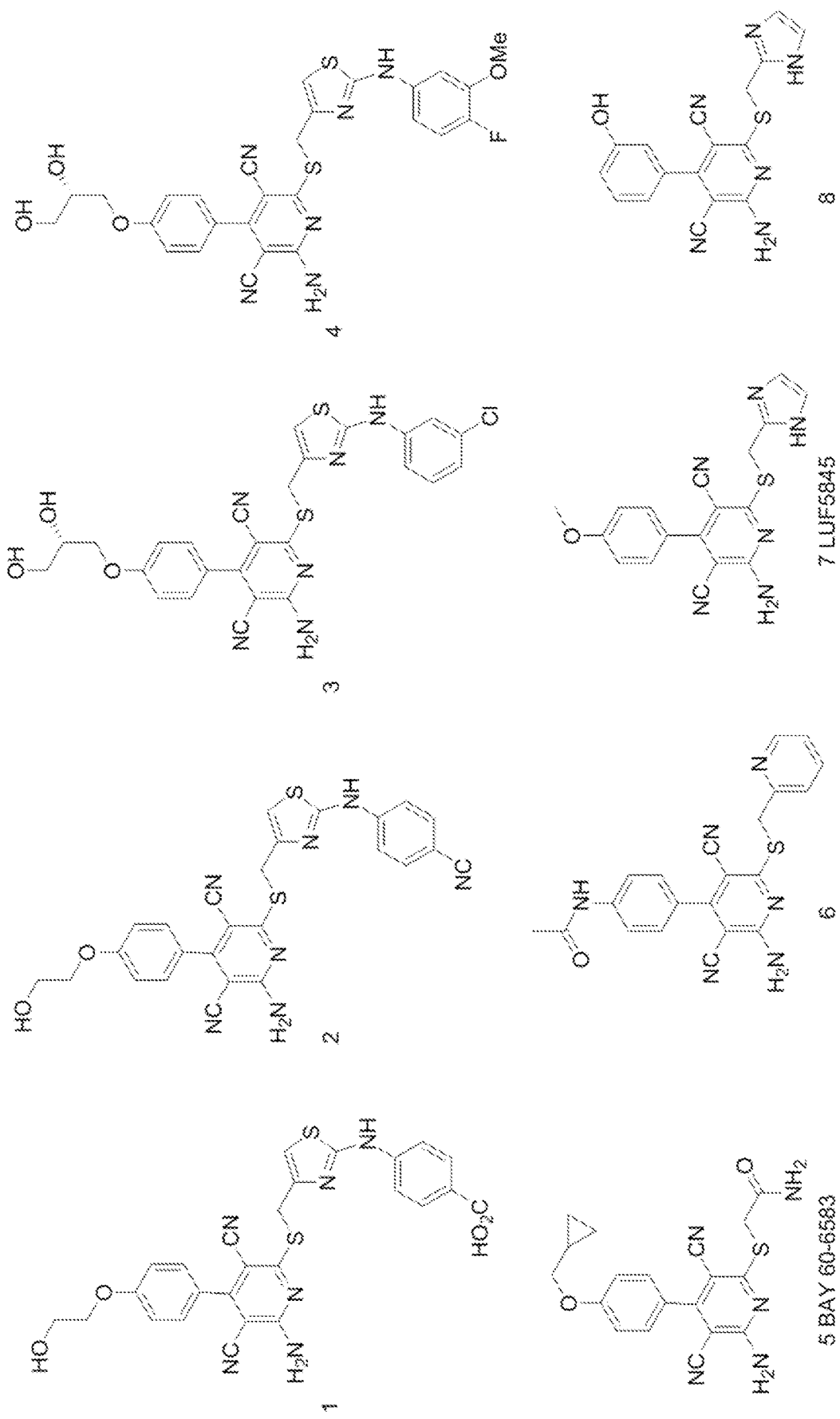
Figure 9A:
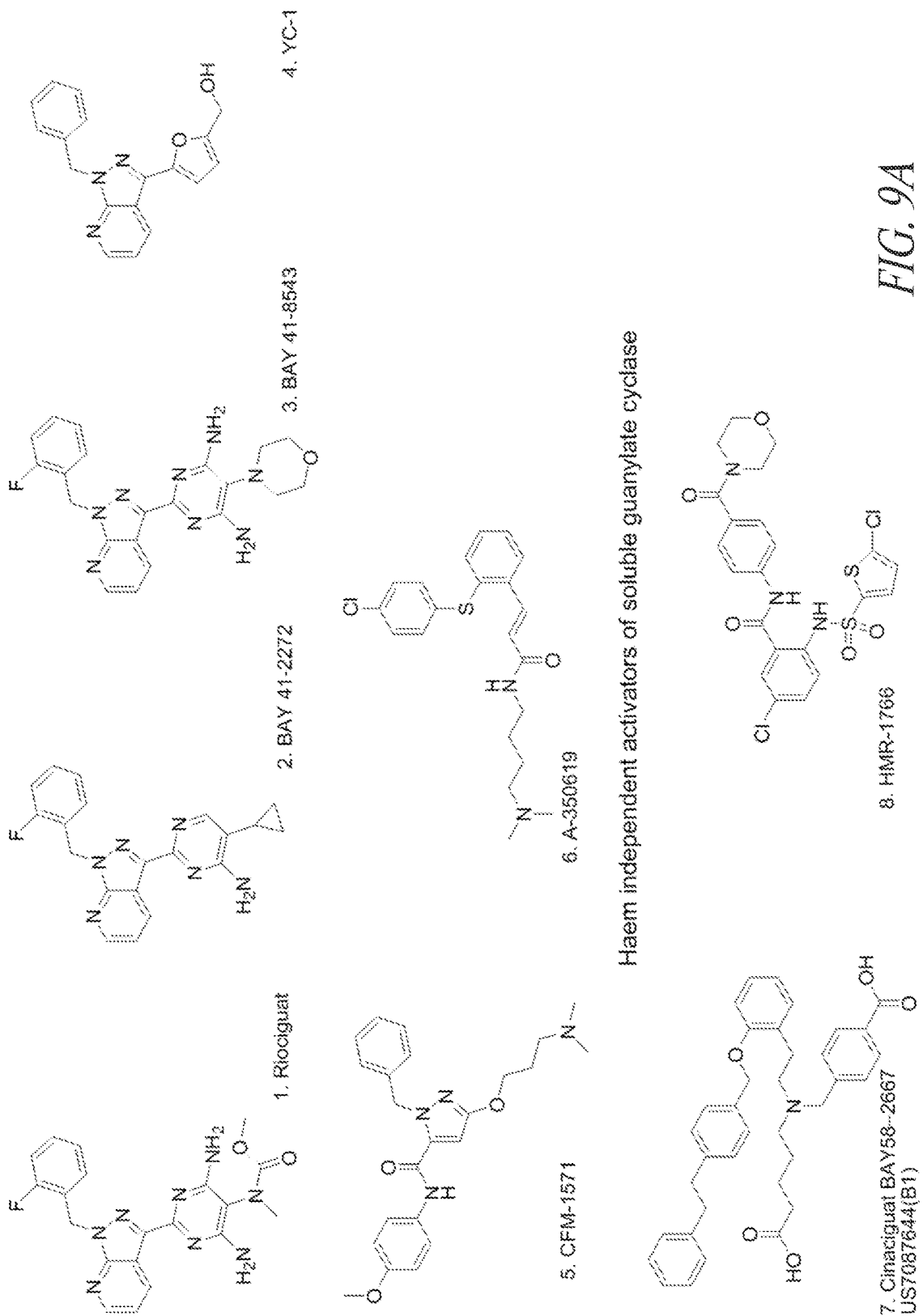
Figure 9B:
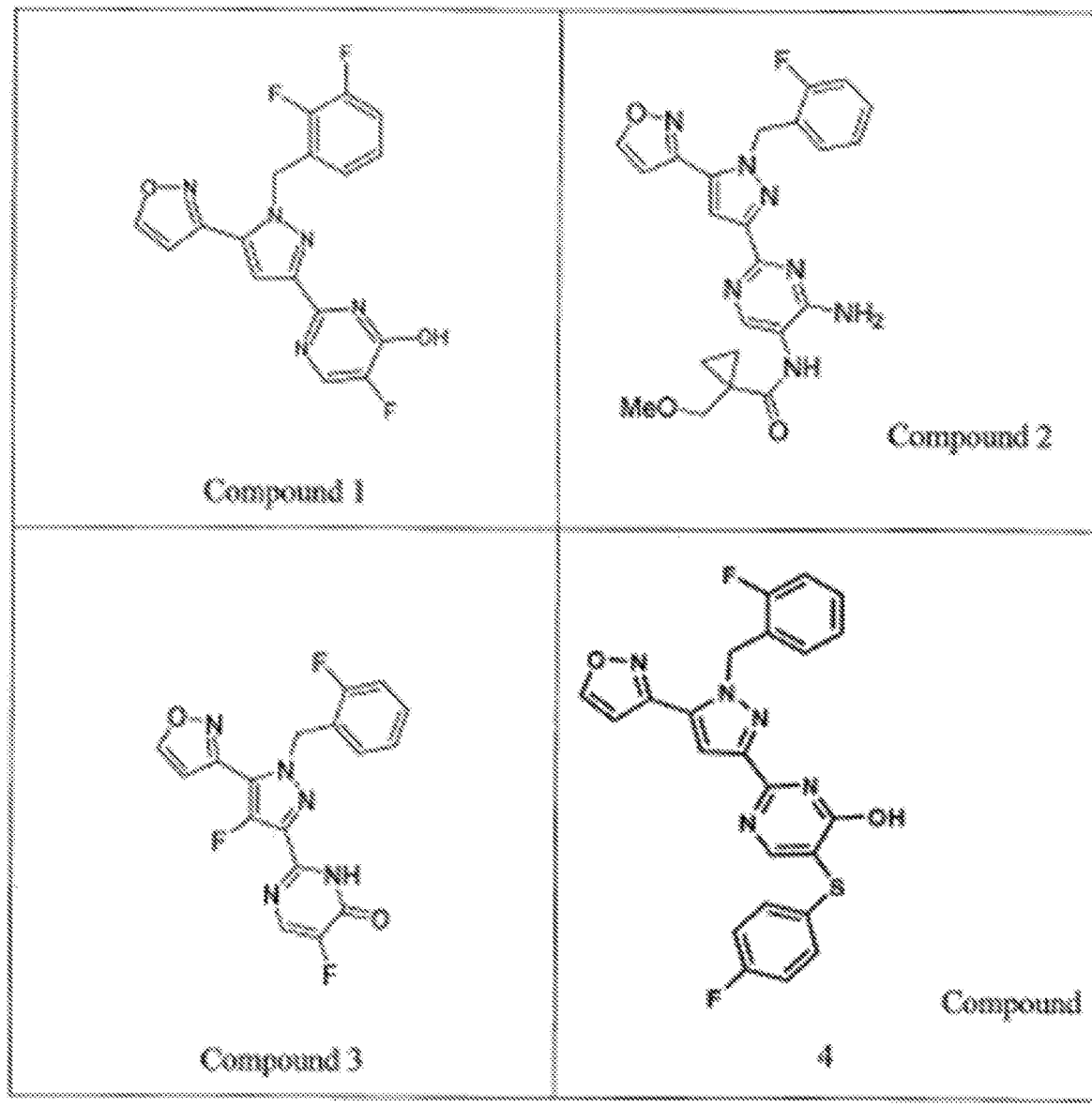
Figure 9B:
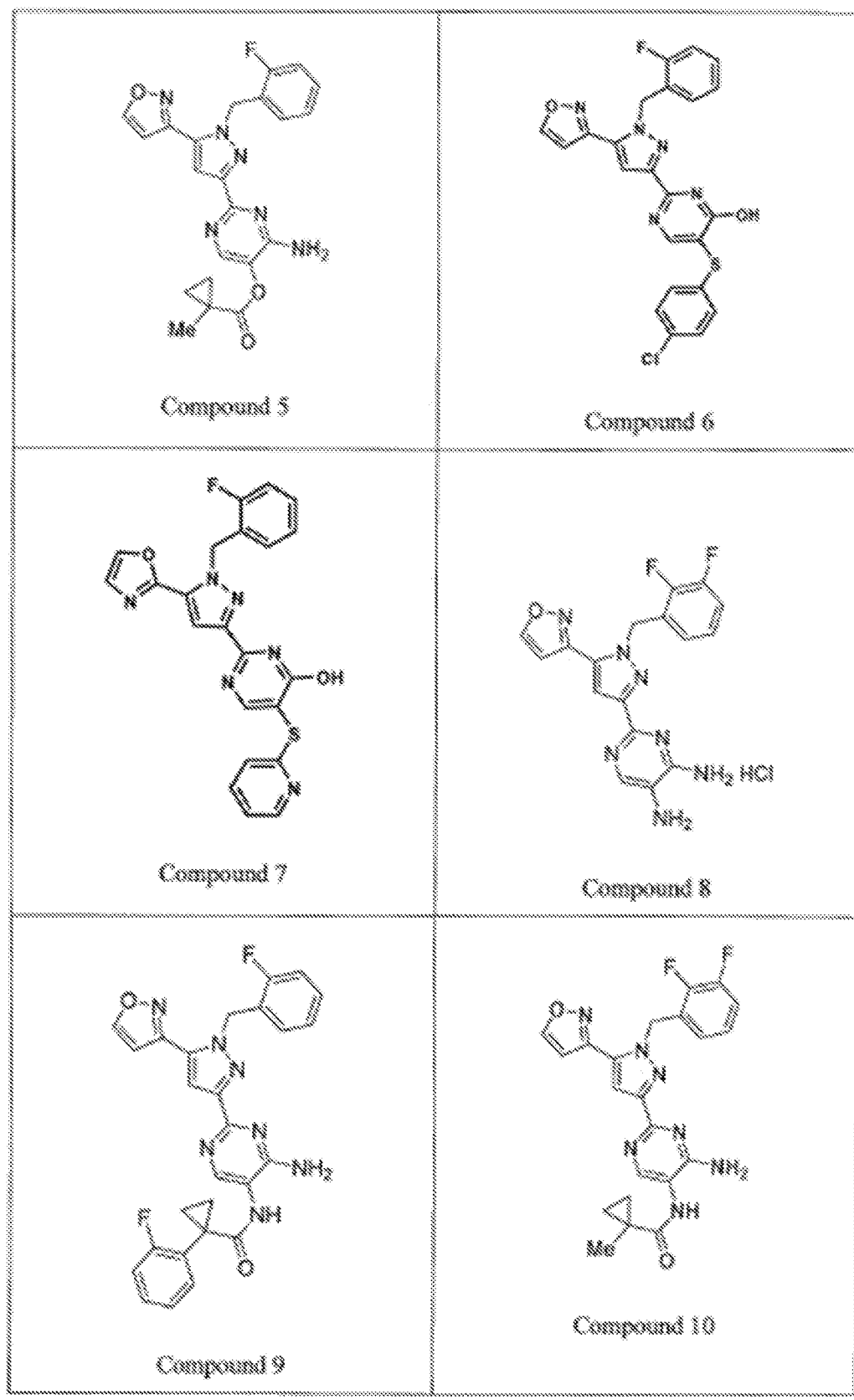
Figure 9C:
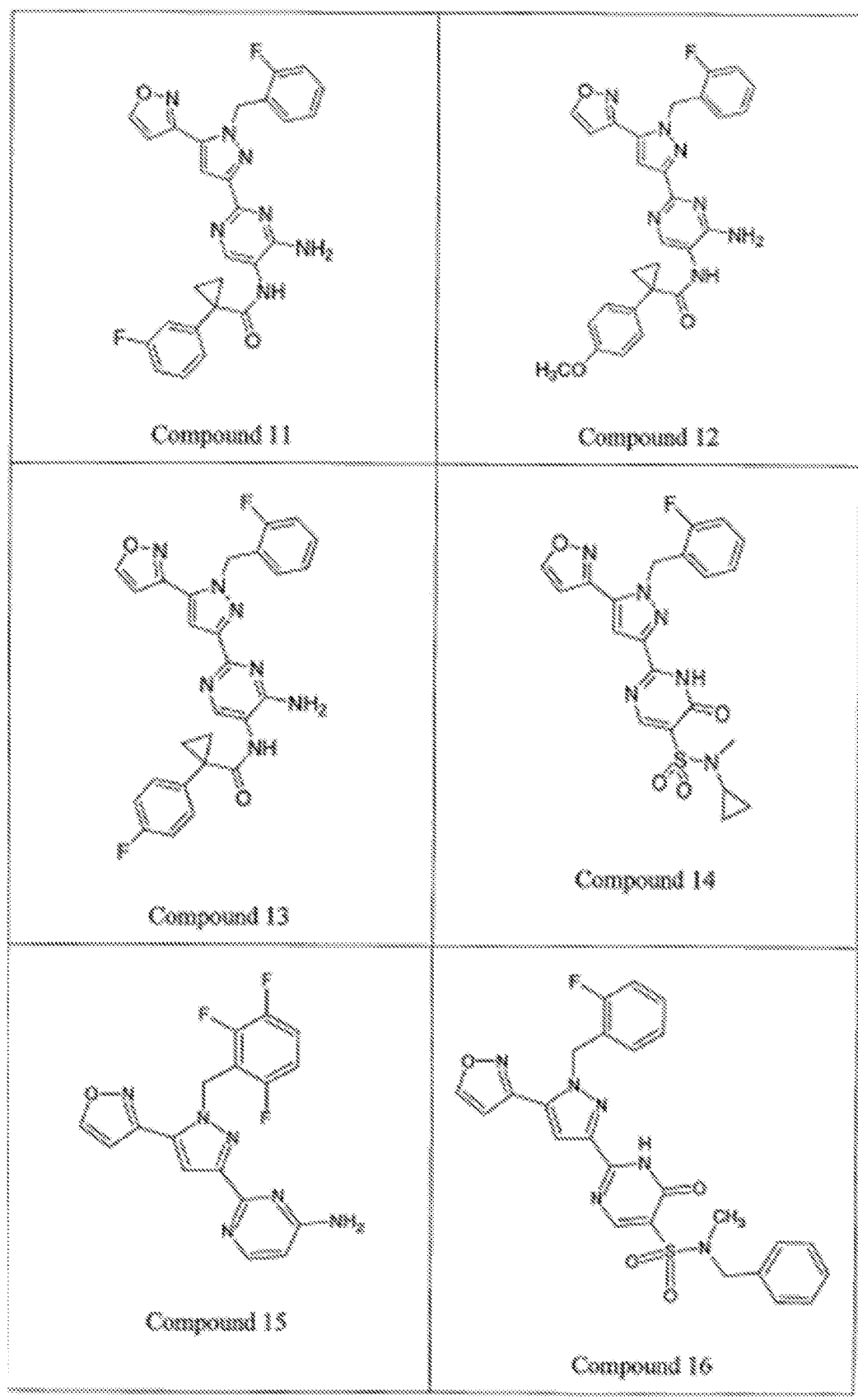
Figure 9C:
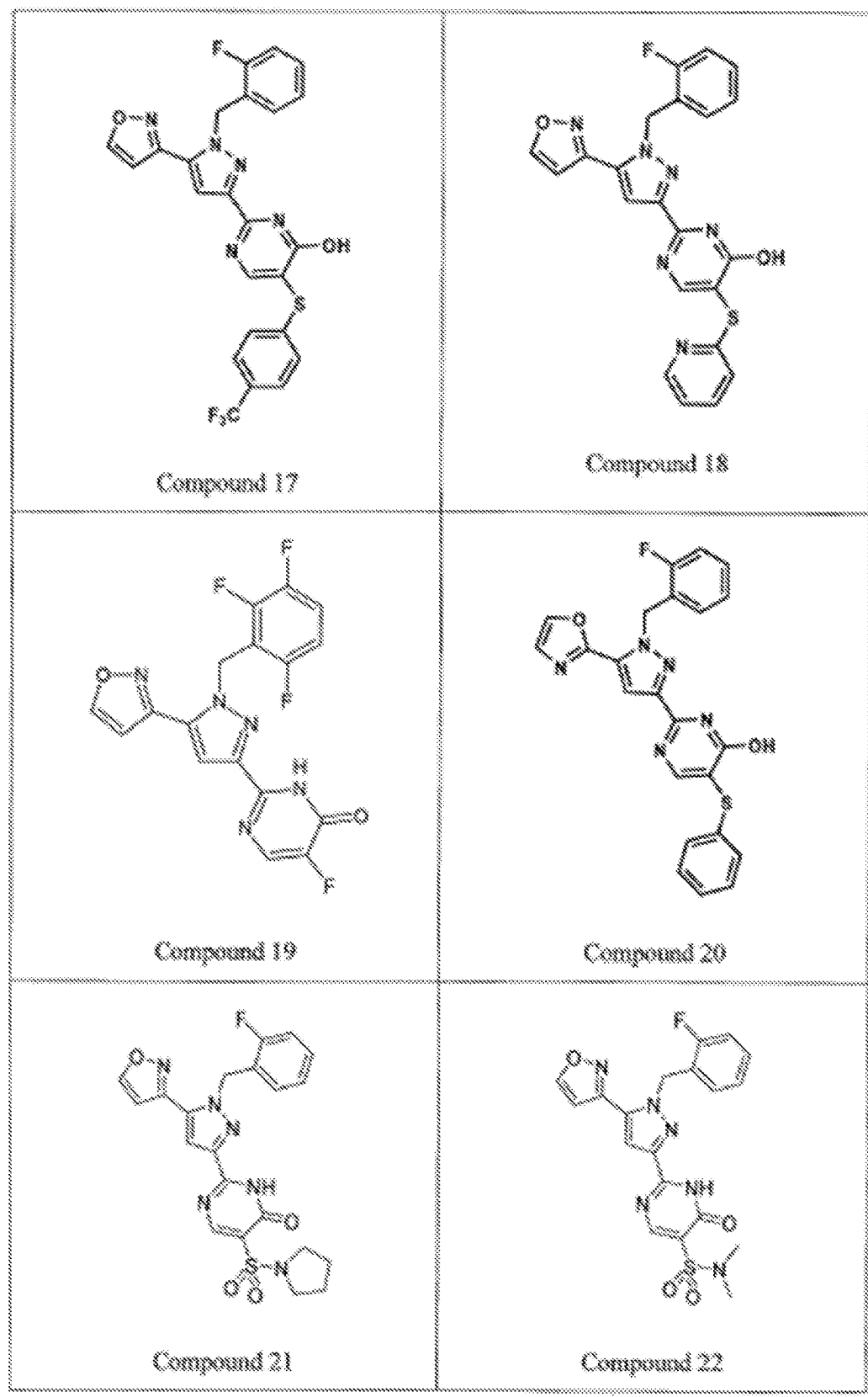
Figure 9D:
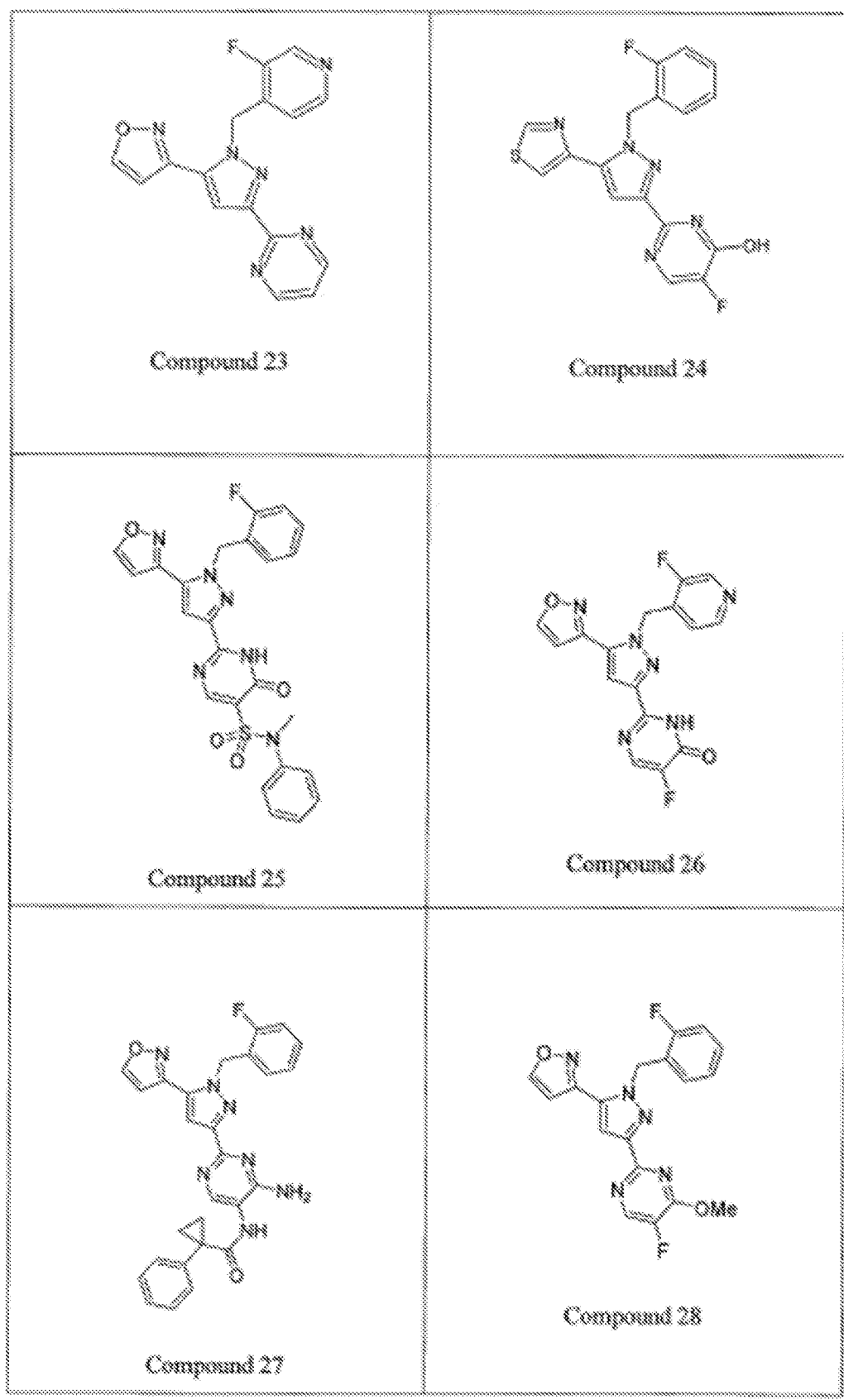
Figure 9D:
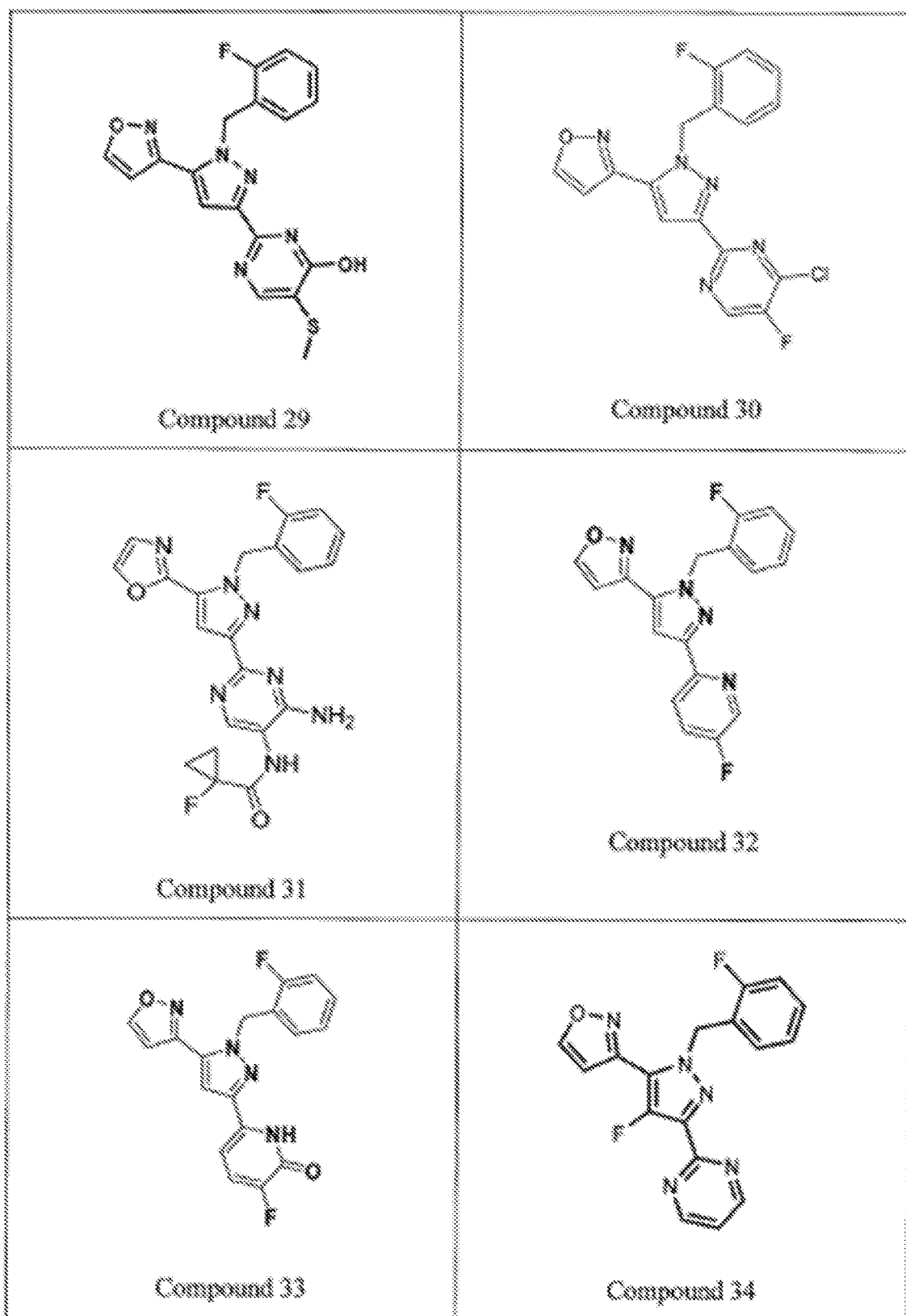
Figure 9E:
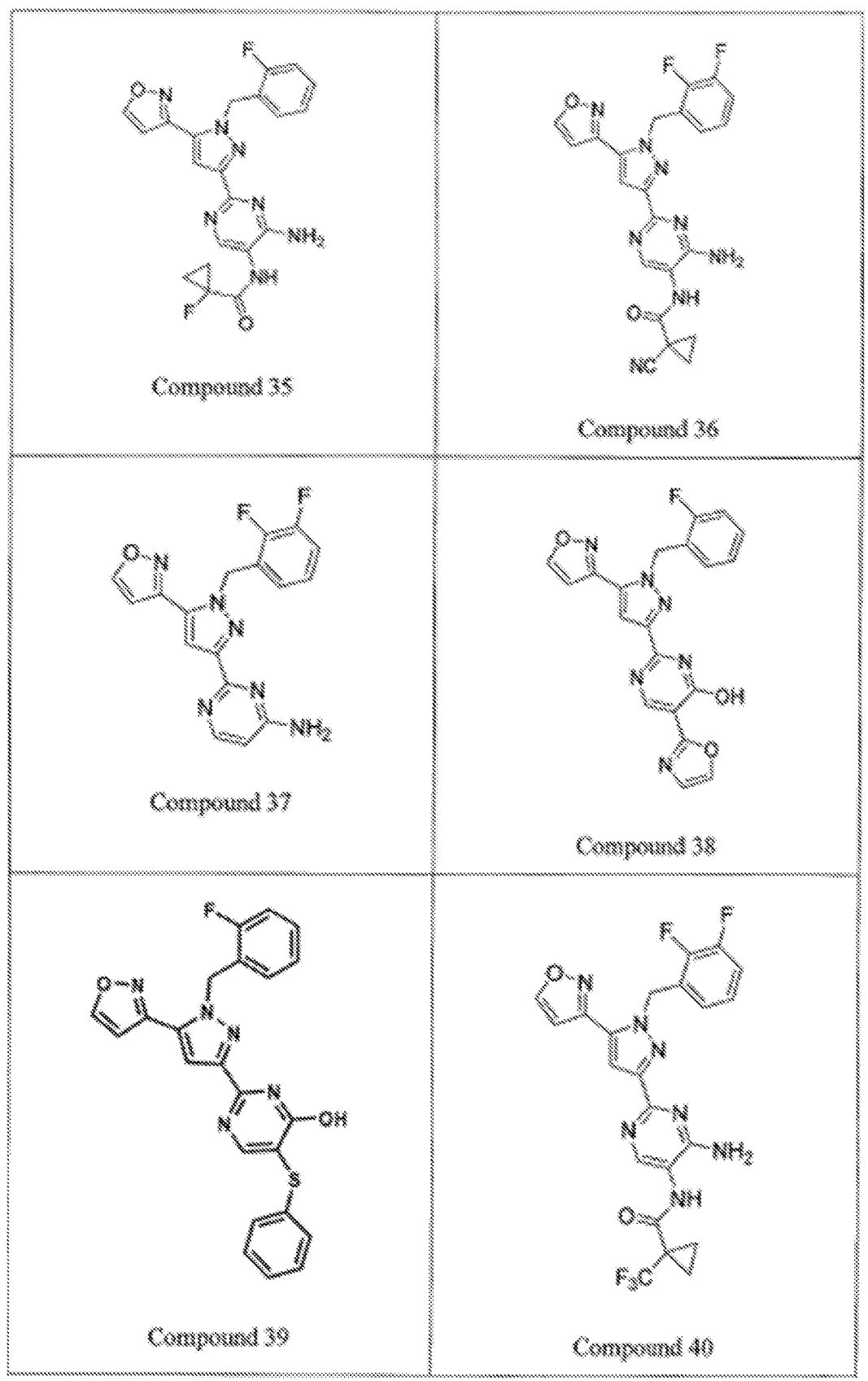
Figure 9E:
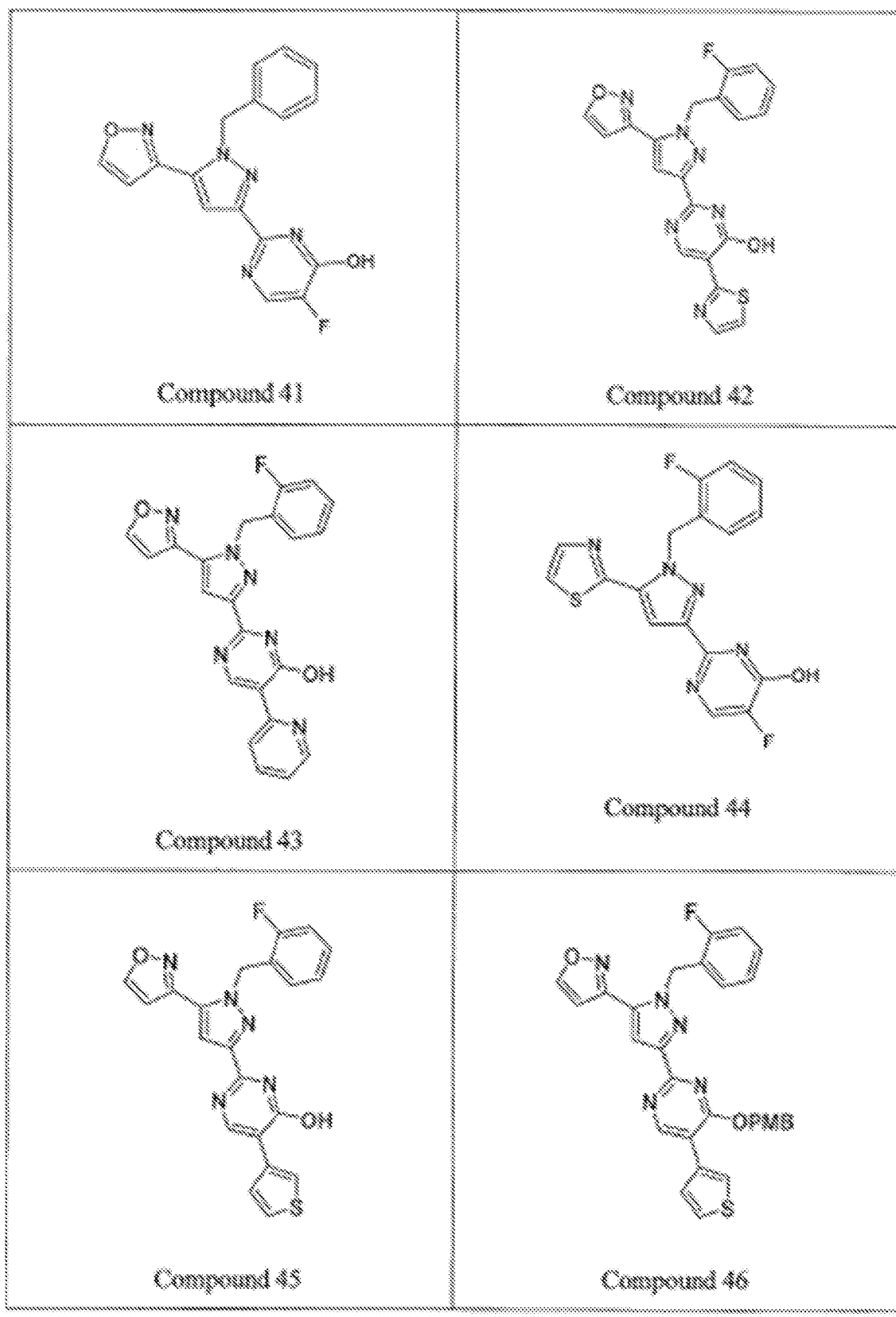
Figure 9F:
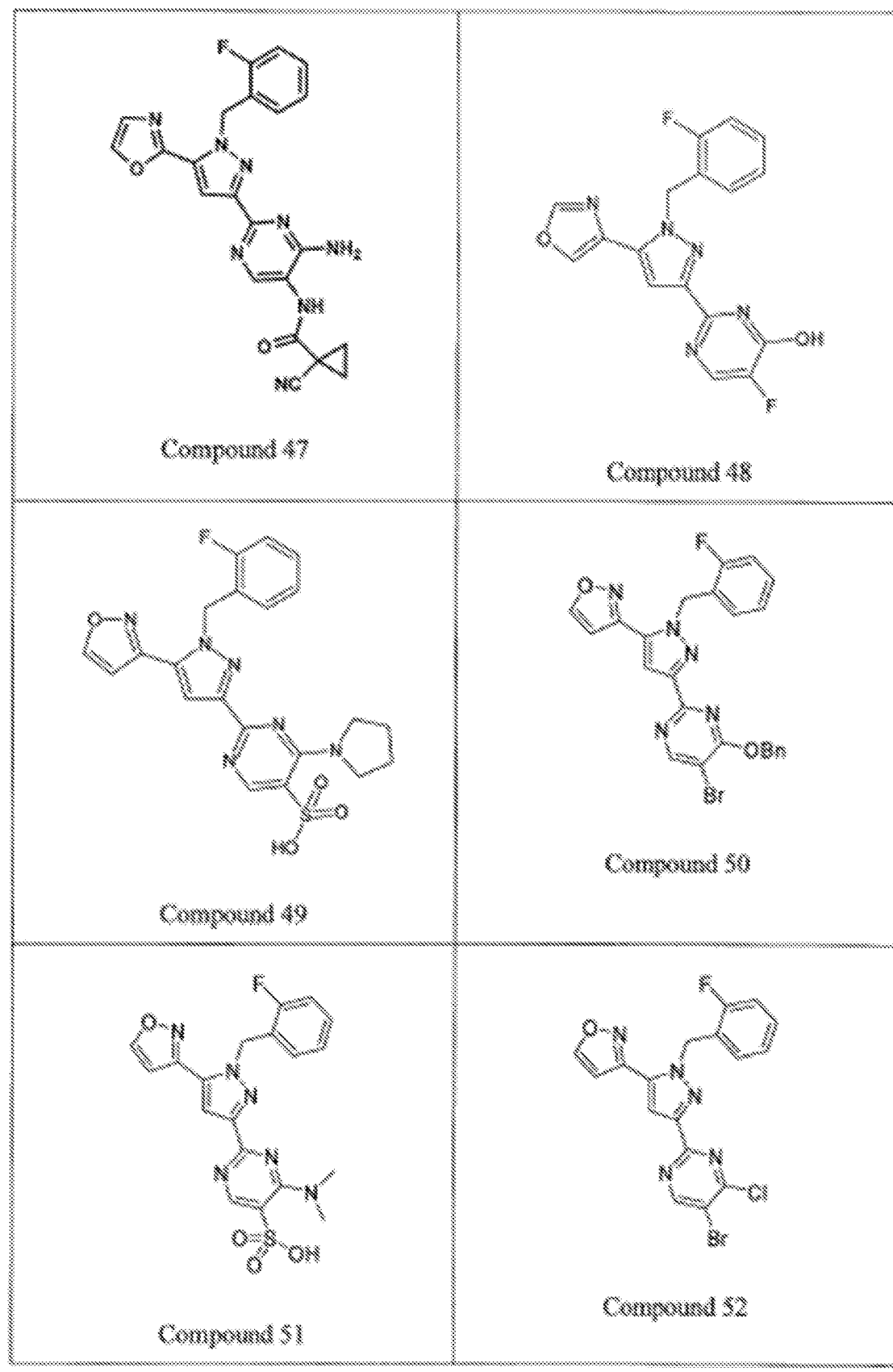
Figure 9F:
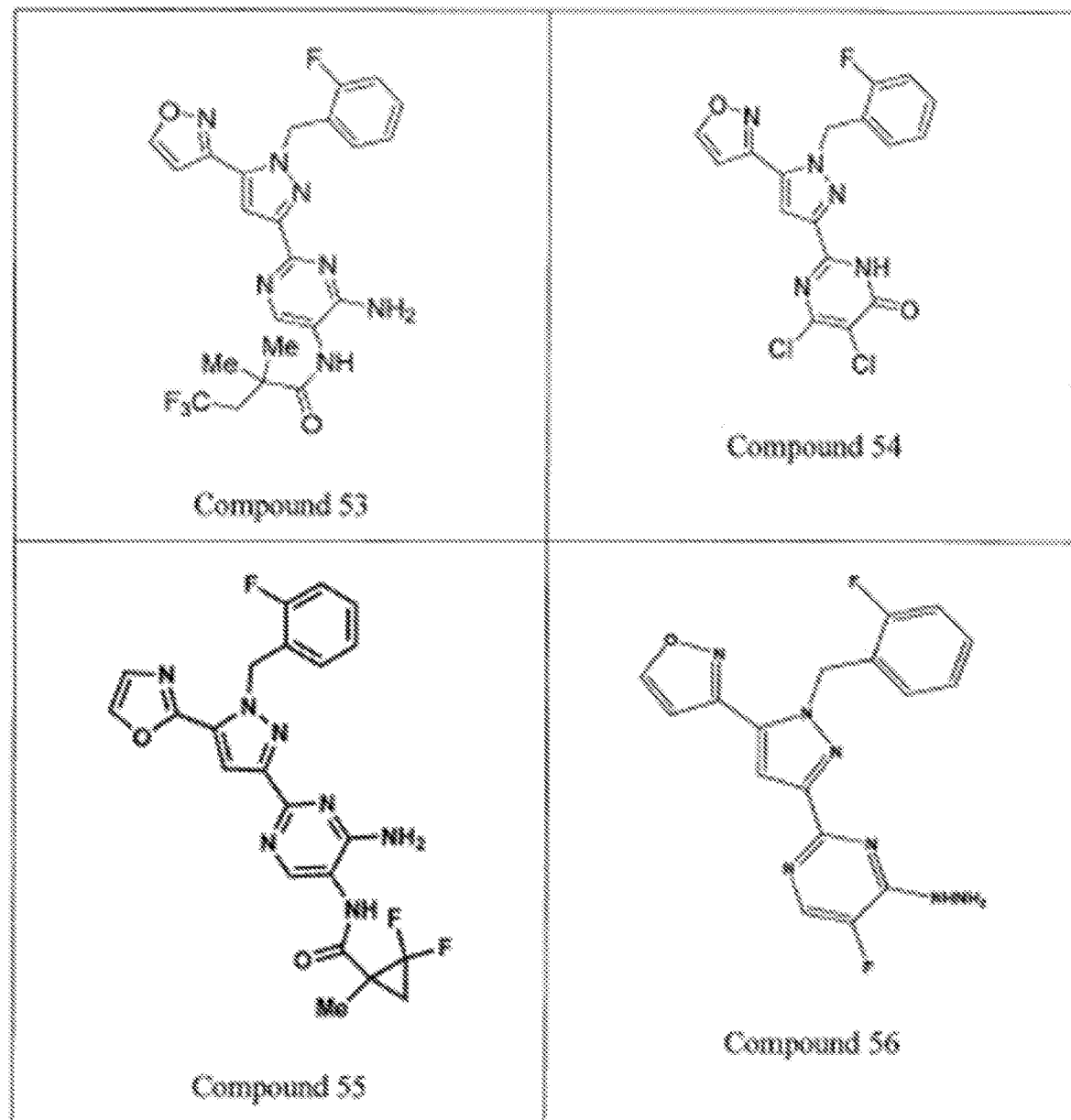
Figure 9G:
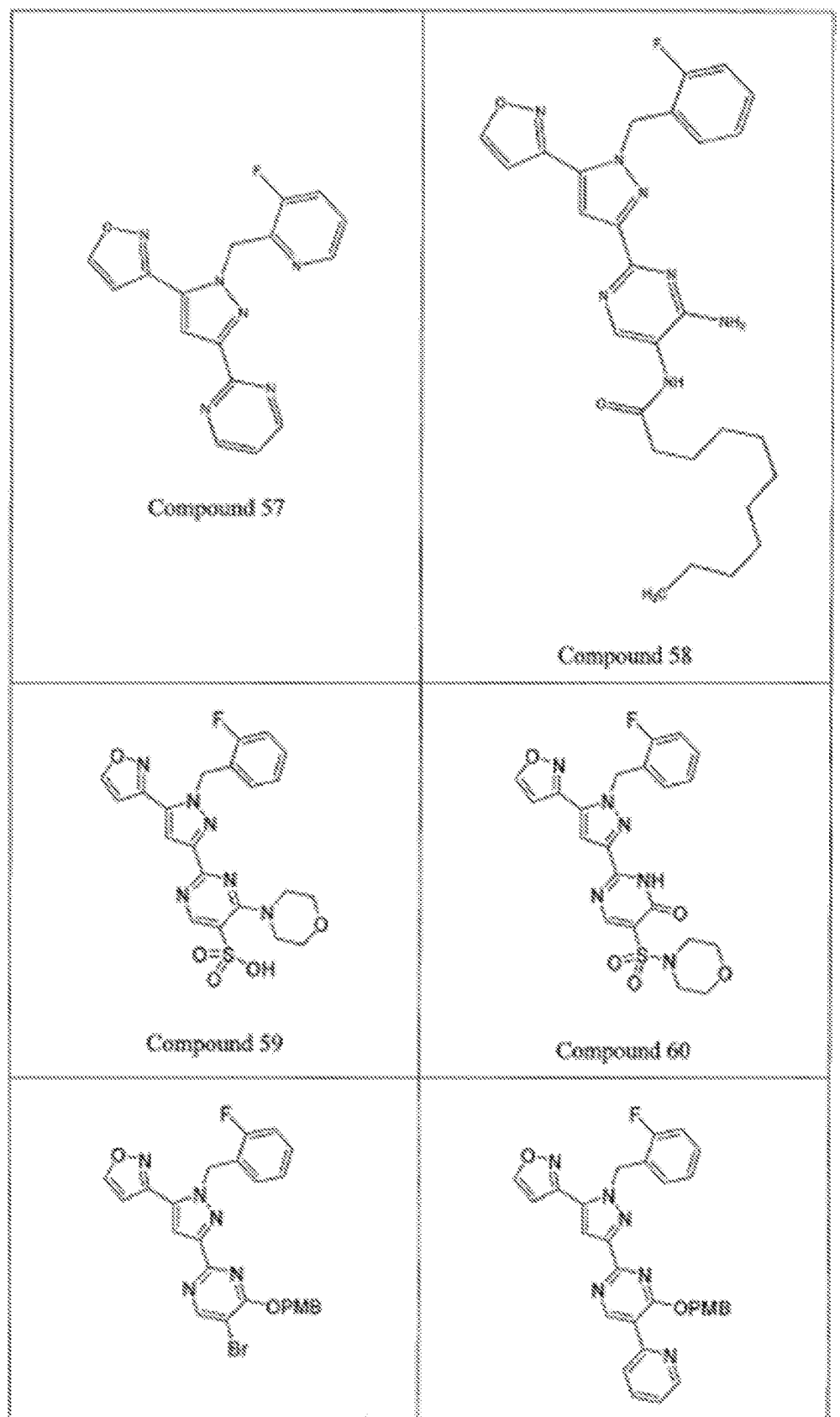
Figure 9G:
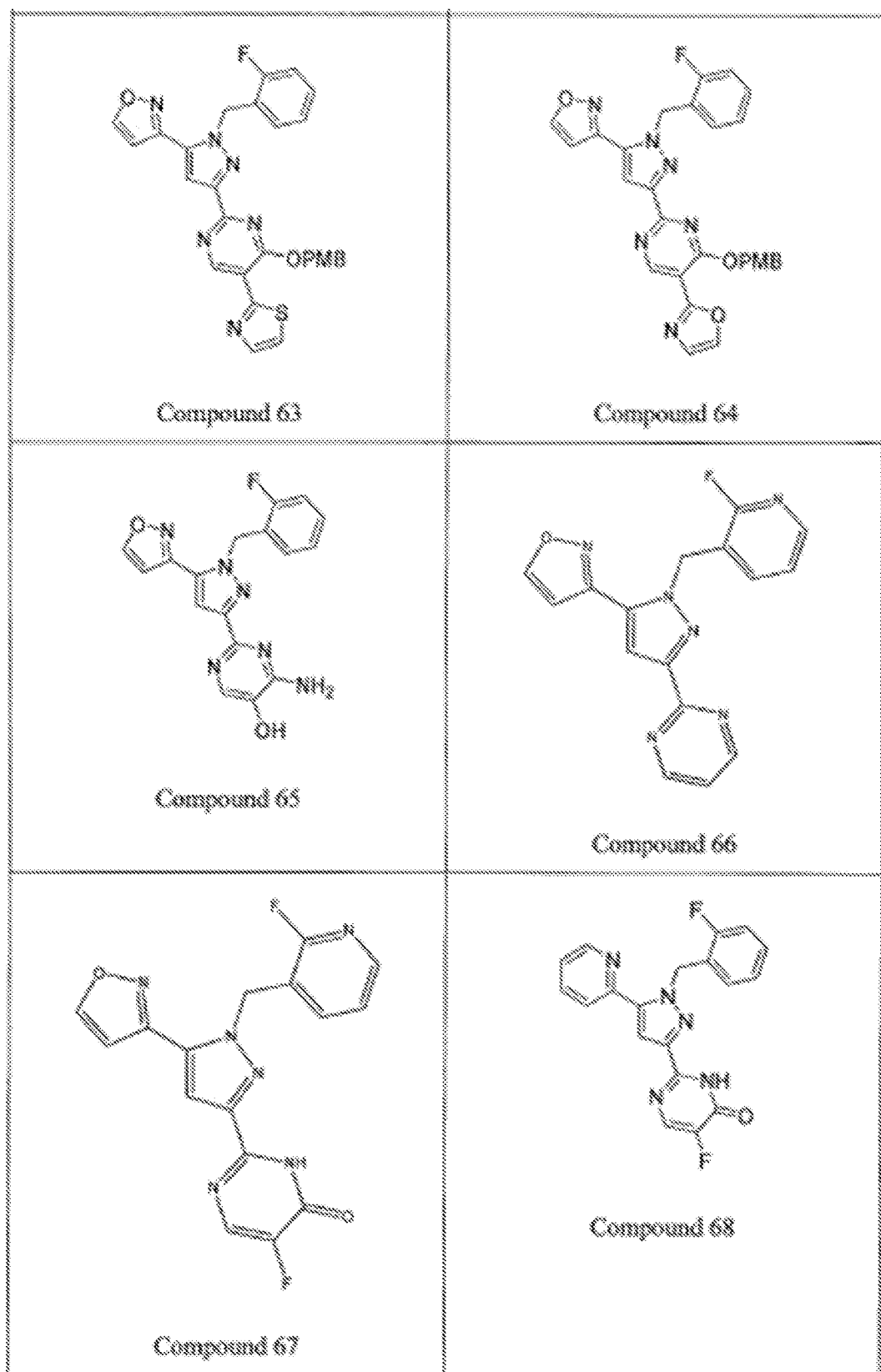
Figure 9H:
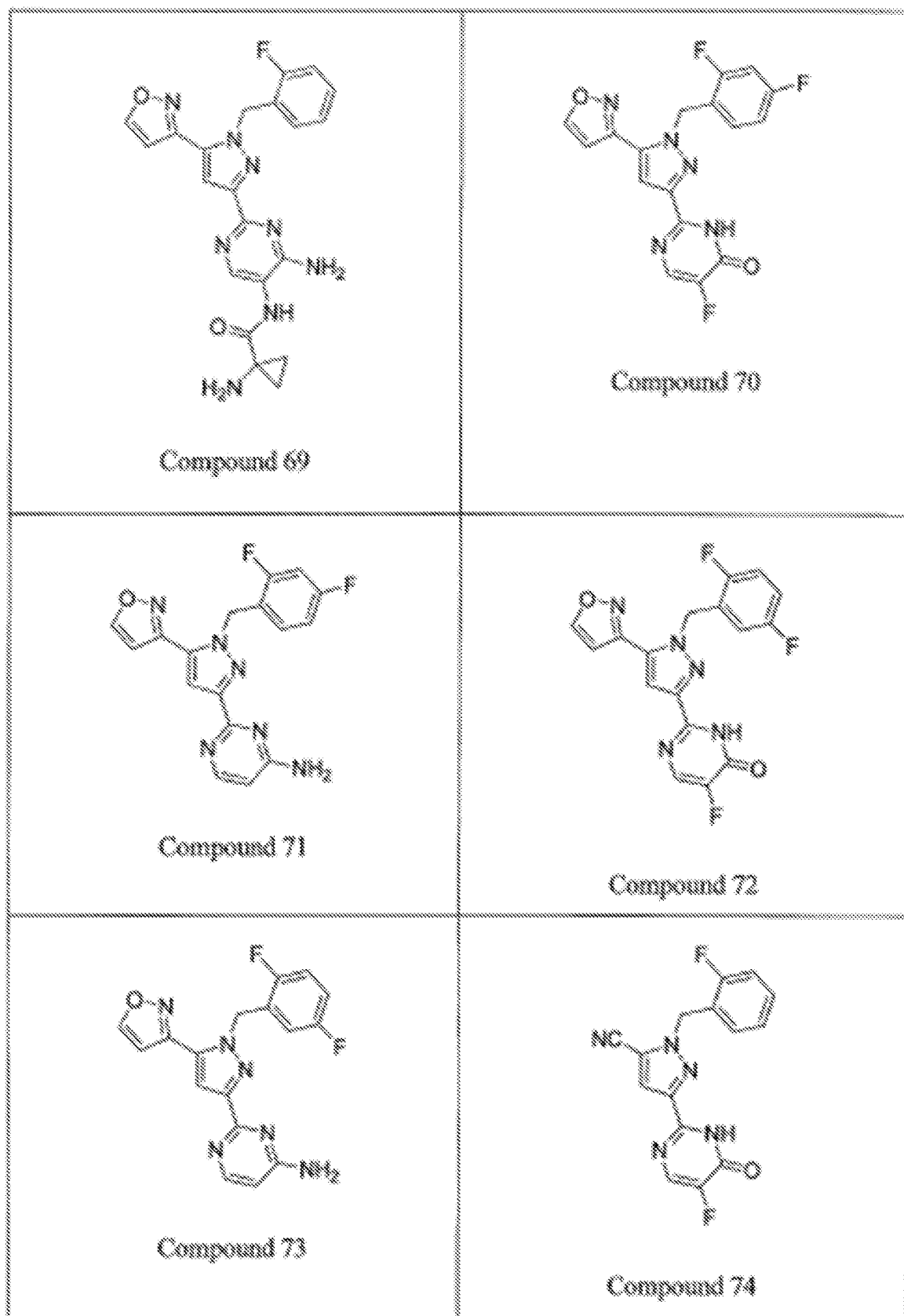
Figure 9I:
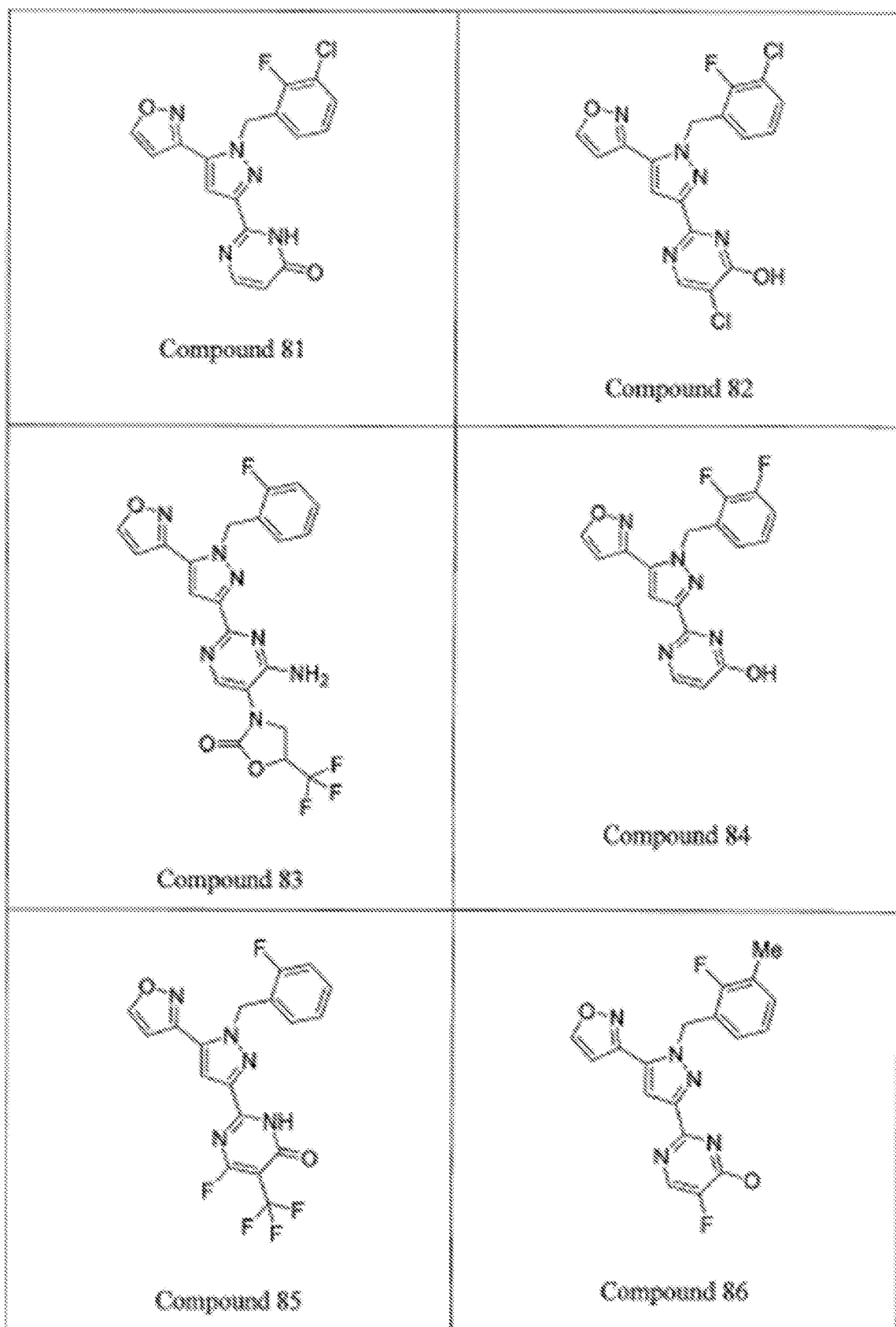
Figure 9I:
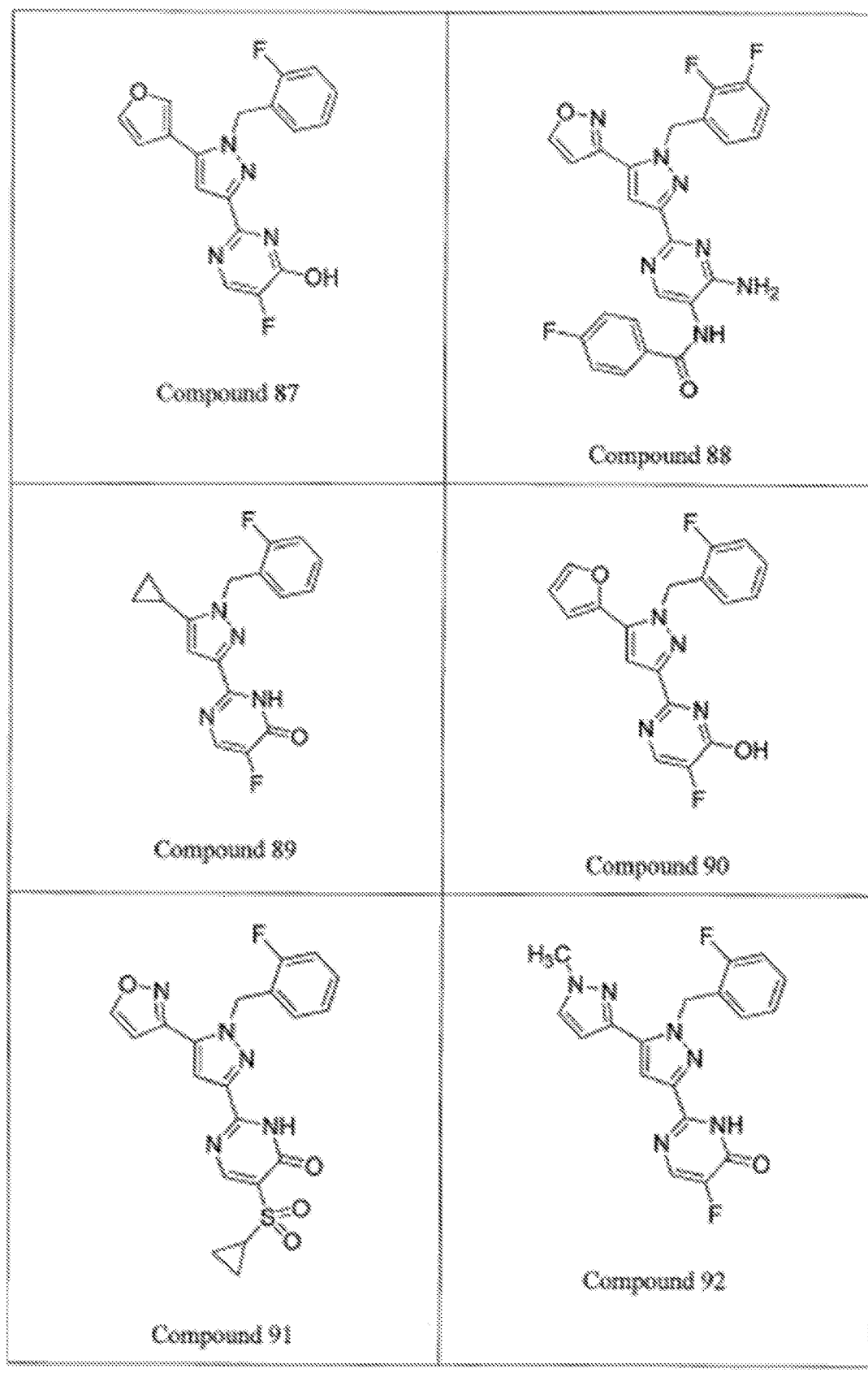
Figure 9J:
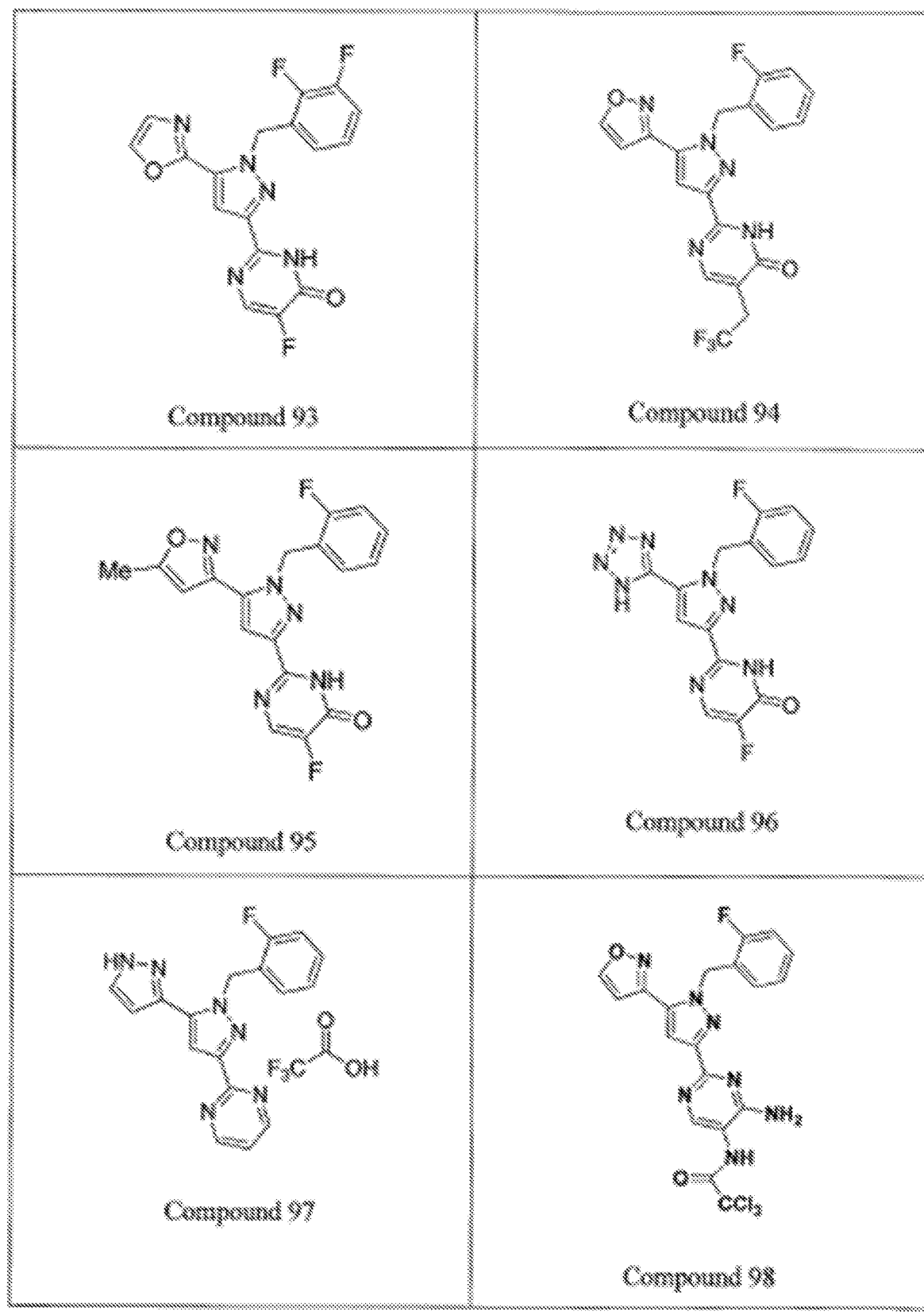
Figure 9J:
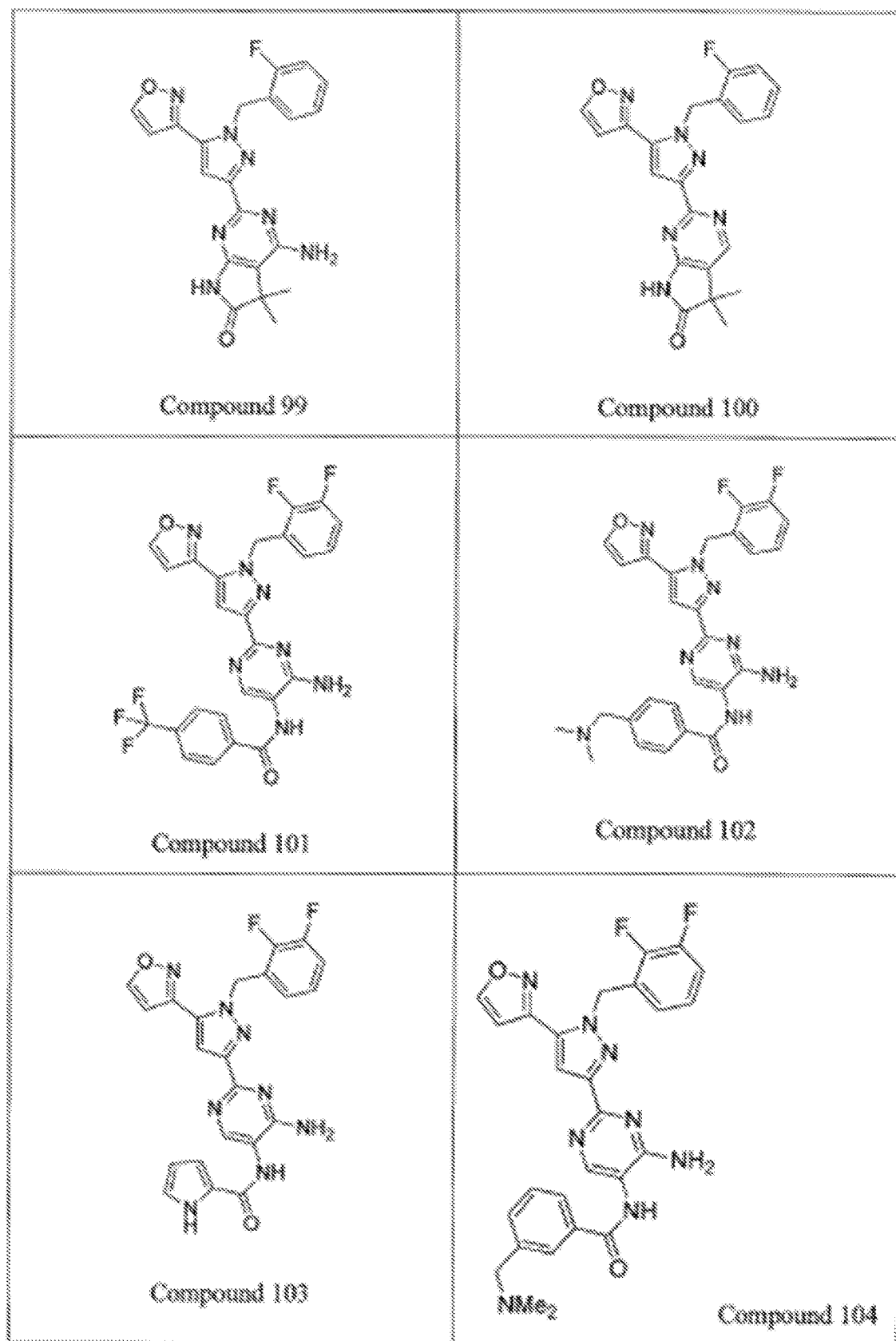
Figure 9K:
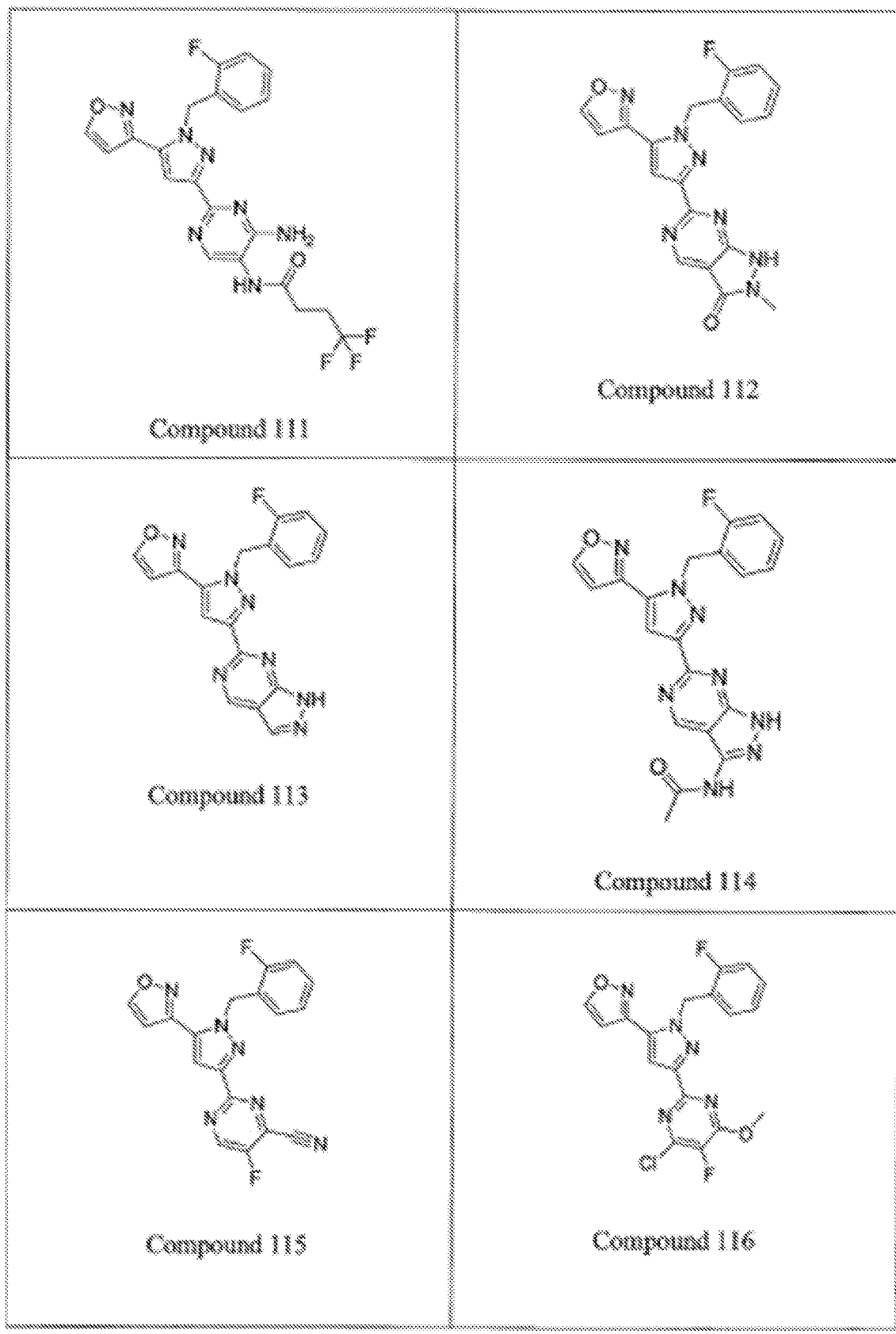

Examples of adenosine A2b receptor agonists are shown in FIGS. 6A-6C, and further disclosed, together with methods for their synthesis, in U.S. Application No. 2009/0221649 and PCT Publication Nos. WO 2006/027142, WO 2007/101531, and WO 2003/008384, each of which is incorporated by reference in its entirety.

C. Guanylate Cyclase C Receptor Agonists

In certain embodiments, the compound is a guanylyl cyclase C (GC-C) agonist, optionally a selective agonist. GC-C is an isoform of the guanylate cyclase family that is highly concentrated at the apical membrane of intestinal epithelial cells. It is also the target receptor for bacterially-secreted heat stable-enterotoxins, which are responsible for acute secretory diarrhea. GC-C is also known as guanylate cyclase 2C, intestinal guanylate cyclase, guanylate cyclase C receptor, and heat-stable enterotoxin receptor (hSTAR).

GC-C has an extracellular ligand-binding domain, a single transmembrane region, a region similar to protein kinases, and a C-terminal guanylate cyclase domain. Tyrosine kinase activity mediates the GC-C signaling pathway within the cell. Guanylin and uroguanylin are endogenous peptide ligands for GC-C. Activation of GC-C leads, for example, to intracellular cGMP elevation, PKGII-dependent phosphorylation of the cystic fibrosis transmembrane regulator (CFTR), and other downstream signals which trigger increased chloride and bicarbonate intraluminal secretion (via CFTR, and possibly DRA or PAT-1).

GC-C agonists such as linaclotide, guanylin, and *E. coli* heat stable enterotoxins (STa) have been shown to stimulate duodenal bicarbonate secretion. See, e.g., Rao et al., *Am J Physiol Gastrointest Liver Physiol* 286:G95-G101, 2004; Busby et al., *Eur J Pharmacol.* 649:328-35, 2010; Bryant et al., *Life Sci.* 86:760-5, 2010. Without being bound by any one mechanism, in certain aspects a GC-C agonist inhibits or reduces phosphate uptake in the gastrointestinal tract by stimulating bicarbonate secretion into the small intestine.

In some embodiments, and without being bound by any one mechanism, a GC-C agonist inhibits or reduces phosphate uptake in the gastrointestinal tract by decreasing water absorption in the small intestine.

General examples of GC-C agonists include peptide agonists and analogs thereof, including synthetic analogs of endogenous GC-C peptide agonists. Particular examples of GC-C agonists include, without limitation, heat stable enterotoxins (ST or STa peptides) including those from *E. coli*, guanylin, proguanylin, uroguanylin, prouroguanylin, lymphoguanylin, linaclotide (Linzess), SP-333, and plecanatide. See, e.g., *Drug Des Devel Ther.* 7:351-60, 2013. Linaclotide is a STa synthetic analog marketed for the treatment of irritable bowel syndrome—constipation dominant (IBS-C). See, e.g., Bryant et al., *Life Sci.* 86:760-5, 2010. Plecanatide is a synthetic analog of uroguanylin developed for the treatment of IBS-C. See, e.g., Pitari, supra; and Shailubhai et al., *Dig Dis Sci.* 2013 Apr. 27. [Epub ahead of print]. Additional examples of GC-C agonists are described in U.S. Application Nos. 2012/0064039, 2004/0258687, 2005/0287067, 2006/0281682, 2006/0258593, 2006/0094658, 2008/0025966, 2003/0073628, 2004/0121961 and 2004/0152868 and in U.S. Pat. Nos. 5,140,102, 7,041,786, and 7,304,036. These references are incorporated by reference in their entireties.

In some embodiments, the GC-C agonist is a bacterial ST (or STa) peptide, or a variant or analog or derivative thereof. In bacteria, ST or STa peptides are derived from a preproprotein that generally has at least 70 amino acids. The pre and pro regions are cleaved as part of the secretion process, and the resulting mature protein, which generally includes fewer than about 20 amino acids, is biologically active.

Exemplary bacterial ST peptides include: *E. coli* ST Ib (Moseley et al., *Infect. Immun.* 39:1167, 1983) having the mature amino acid sequence Asn Ser Ser Asn Tyr Cys Cys Glu Leu Cys Cys Asn Pro Ala Cys Thr Gly Cys Tyr (SEQ ID NO: 10); *E. coli* ST Ia (So and McCarthy, *PNAS USA.* 77:4011, 1980) having the mature amino acid sequence Asn Thr Phe Tyr Cys Cys Glu Leu Cys Cys Asn Pro Ala Cys Ala Gly Cys Tyr (SEQ ID NO: 11); *E. coli* ST I (Chan and Giannella, *J. Biol. Chem.* 256:7744, 1981) having the mature amino acid sequence Asn Thr Phe Tyr Cys Cys Glu Leu Cys Cys Tyr Pro Ala Cys Ala Gly Cys Asn (SEQ ID NO: 12); *C. freundii* ST peptide (Guarino et al., *Infect. Immun.* 57:649, 1989) having the mature amino acid sequence Asn Thr Phe Tyr Cys Cys Glu Leu Cys Cys Asn Pro Ala Cys Ala Gly Cys Tyr (SEQ ID NO: 13); *Y. enterocolitica* ST peptides, Y-ST(Y-STa), Y-STh, and Y-STc (reviewed in Huang et al., *Microb. Pathog.* 22:89, 1997) having the following pro-form amino acid sequences: Gln Ala Cys Asp Pro Pro Ser Pro Pro Ala Glu Val Ser Ser Asp Trp Asp Cys Cys Asp Val Cys Cys Asn Pro Ala Cys Ala Gly Cys (SEQ ID NO:14) (as well as a Ser-7 to Leu-7 variant of Y-STa (SEQ ID NO:15), (Takao et al., *Eur. J. Biochem.* 152:199, 1985); Lys Ala Cys Asp Thr Gln Thr Pro Ser Pro Ser Glu Glu Asn Asp Asp Trp Cys Cys Glu Val Cys Cys Asn Pro Ala Cys Ala Gly Cys (SEQ ID NO:16); Gln Glu Thr Ala Ser Gly Gln Val Gly Asp Val Ser Ser Ser Thr Ile Ala Thr Glu Val Ser Glu Ala Glu Cys Gly Thr Gln Ser Ala Thr Thr Gln Ser Ala Thr Thr Gln Gly Glu Asn Asp Trp Asp Tip Cys Cys Glu Leu Cys Cys Asn Pro Ala Cys Phe Gly Cys (SEQ ID NO: 17), respectively; *Y. kristensenii* ST peptide having the mature amino acid sequence Ser Asp Trp Cys Cys Glu Val Cys Cys Asn Pro Ala Cys Ala Gly Cys (SEQ ID NO: 18); *V. cholerae* non-01 ST peptide (Takao et al., *FEBS Lett.* 193:250, 1985) having the mature amino acid sequence Ile Asp Cys Cys Glu Ile Cys Cys Asn Pro Ala Cys Phe Gly Cys Leu Asn (SEQ ID NO: 19); and *V. mimicus* ST peptide (Arita et al., *FEMS Microbiol. Lett.* 79:105, 1991) having the mature amino acid sequence Ile Asp Cys Cys Gly Ile Cys Cys Asn Pro Ala Cys Phe Gly Cys Leu Asn (SEQ ID NO:20). Table A1 below shows the sequences of exemplary mature ST peptides.

TABLE A1

| Mature ST Peptides | SEQ ID NO: |
|---|---|
| NSSNYCCELCCNPACTGCY | 10 |
| NTFYCCELCCNPACAGCY | 11 |
| NTFYCCELCCNPACAPCY | 21 |
| NTFYCCELCCYPACAGCN | 12 |
| IDCCEICCNPACFGCLN | 19 |
| IDCCEICCNPACFGCLN | 19 |
| IDCCEICCNPACF | 22 |
| IDCCEICCNPACFG | 23 |
| IDCCEICCNPACFGCLN | 19 |
| IDRCEICCNPACFGCLN | 24 |
| DWDCCDVCCNPACAGC | 25 |
| DWDCCDVCCNPACAGC | 26 |
| NDDWCCEVCCNPACAGC | 27 |
| WDWCCELCCNPACFGC | 28 |
| SDWCCEVCCNPACAGC | 18 |
| QACDPPSPPAEVSSDWDCCDVCCDPAC AGC | 29 |
| QACDPPSPPAEVSSDWDCCDVCCNPAC AG C | 14 |
| KACDTQTPSPSEENDDTCCEVCCNPAC AG C | 16 |
| QETASGQVGDVSSSTIATEVSEAECGTQSAT | 30 |
| TQGENDWDWCCELCCNPACFGC | 31 |
| MKKLMLAIFISVLSFPSFSQSTESLDS | 32 |
| SKEKITLETKKCDVVKNNSEKKSEN | 33 |
| MNNTFYCCELCCNPACAGCY | 34 |
| MKKSILFIFLSVLSFSPFAQDAKPVES | 35 |
| SKEKITLESKKCNIAKKSNKSGPESM | 36 |
| NSSNYCCELCCNPACTGCY | 37 |
| MKKIVFVLVLMLSSFGAFGQETVSG | 38 |
| QFSDALSTPITAEVYKQACDPPLPPA | 39 |
| EVSSDWDCCDVCCNPACAGC | 40 |

The immature (including pre and pro regions) form of *E. coli* ST-IA (ST-P) protein has the sequence: mkklmlaifisvlsfpsfsqstesldsskekitletkkcdvvknnsekksenmnntfyccelccnpacagcy (SEQ ID NO:41); see GenBank® Accession No. P01559 (gi:123711). The pre sequence extends from residues 1-19. The pro sequence extends from residues 20-54. The mature protein extends from residues 55-72. The immature (including pre and pro regions) form of *E. coli* ST-1B (ST-H) protein has the sequence: mkksilfiflsvlsfspfaqdakpvesskekitleskkcniakksnksgpesmnssnyccelccnpactgcy (SEQ ID NO:42); see GenBank® Accession No. P07965 (gi:3915589)). The immature (including pre and pro regions) form of *Y. enterocolitica* ST protein has the sequence: mkkivfvlylmlssfgafgqetvsgqfsdalstpitaevykqacdpplppaevssdwdccdvccnpacagc (SEQ ID NO:43); see GenBank® Accession No. S25659 (gi:282047)).

Accordingly, a GC-C agonist peptide may comprise or consist of any one or more of the bacterial ST peptide sequences described herein, including variants thereof.

The bacterial ST peptides typically have six Cys residues. These six Cys residues form three disulfide bonds in the mature and active form of the peptide. If the six Cys residues are identified, from the amino to carboxy terminus of the peptide, as A, B, C, D, E, and F, then the disulfide bonds usually form as follows: A-D, B-E, and C-F. The formation of these bonds is believed to contribute GC-C receptor binding. Hence, in certain embodiments, a GC-C agonist peptide has at least one, two, or three disulfide bonds selected from any combination of A-D, B-E, and C-F, as shown above. In some embodiments, however, one or more cysteines of the GC-C peptide agonists described herein are deleted or replaced with a different amino acid. In some embodiments, 1, 2, 3, 4, 5, or 6 cysteines are deleted or replaced with a different amino acid. In particular aspects, the most N-terminal cysteine residues (e.g., A, B, or A and B) and/or the most C-terminal cysteine residue or residues (e.g., E, F, or E and F) are deleted or replaced with a different amino acid. In certain embodiments, the different amino acid is alanine or serine.

Certain of the GC-C agonist peptides include a potentially functional chymotrypsin cleavage site, e.g., a Trp, Tyr or Phe located between either Cys B/Cys D or between Cys E/Cys F. Cleavage at either chymotrypsin cleavage site may reduce the ability of the peptide to bind to the GC-C receptor. In the human body an inactive form of chymotrypsin, chymotrypsinogen is produced in the pancreas. When this inactive enzyme reaches the small intestine it is converted to active chymotrypsin by the excision of two di-peptides. Active chymotrypsin can cleave peptides at the peptide bond on the carboxy-terminal side of Trp, Tyr, or Phe. The presence of active chymotrypsin in the intestinal tract can lead to cleavage of certain of the GC-C peptide agonists having an appropriately positioned functional chymotrypsin cleavage site. In some instances, it is expected that chymotrypsin cleavage will moderate the action of a GC-C peptide agonist having an appropriately positioned chymotrypsin cleavage site as the peptide passes through the intestinal tract.

Certain of the GC-C agonist peptides include a potentially functional trypsin cleavage site, e.g., Lys or Arg. Trypsinogen, like chymotrypsin, is a serine protease that is produced in the pancreas and is present in the digestive tract. The active form, trypsin, will cleave peptides having a Lys or Arg. The presence of active trypsin in the intestinal tract can lead to cleavage of certain of the GC-C agonist peptides having an appropriately positioned functional trypsin cleavage site. In certain instances, it is expected that trypsin cleavage will moderate the action of a GC-C peptide agonist having an appropriately positioned trypsin cleavage site as the peptide passes through the intestinal tract.

In certain embodiments, the peptide comprises at least six cysteines that can form three disulfide bonds. In certain embodiments, the disulfide bonds are replaced by other covalent cross-links and in some cases the cysteines are substituted by other residues to provide for alternative covalent cross-links (described elsewhere herein). Certain peptides include a functional chymotrypsin or trypsin cleavage site located so as to allow inactivation of the peptide upon cleavage. Certain peptides having a functional cleavage site undergo cleavage and gradual inactivation in the digestive tract, and this is desirable in some circumstances. In certain peptides, a functional chymotrypsin site is altered, increasing the stability of the peptide in vivo.

In certain embodiments, the peptides include either one or two or more contiguous negatively charged amino acids (e.g., Asp or Glu) or one or two or more contiguous positively charged residues (e.g., Lys or Arg) or one or two or more contiguous positively or negatively charged amino acids at the carboxy terminus. In these and related embodiments, all of the flanking amino acids at the carboxy terminus are either positively or negatively charged. In some embodiments, the carboxy terminal charged amino acids are preceded by a Leu. For example, the following amino acid sequences can be added to the carboxy terminus of the peptide: Asp; Asp Lys; Lys Lys Lys Lys Lys Lys (SEQ ID NO:44); Asp Lys Lys Lys Lys Lys Lys (SEQ ID NO:45); Leu Lys Lys; and Leu Asp. In particular embodiments, a Leu is added to the carboxy terminus.

In some aspects, the (bacterial ST analog) GC-C agonist peptide comprises, consists, or consists essentially of the amino acid sequence shown below (I):

(SEQ ID NO: 46)
$Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$

In some embodiments, $Xaa_1$ $Xaa_2$ $Xaa_3$ $Xaa_4$ $Xaa_5$ is Asn Ser Ser Asn Tyr (SEQ ID NO:2) or is missing or $Xaa_1$ $Xaa_2$ $Xaa_3$ $Xaa_4$ is missing. In certain embodiments, $Xaa_8$, $Xaa_9$, $Xaa_{12}$, $Xaa_{14}$, $Xaa_{16}$, $Xaa_{17}$, and $Xaa_{15}$ are any amino acid. In certain embodiments, $Xaa_8$, $Xaa_9$, $Xaa_{12}$, $Xaa_{14}$, $Xaa_{16}$, $Xaa_{17}$, and $Xaa_{19}$ are any natural or non-natural amino acid or amino acid analog.

In certain embodiments, $Xaa_5$ is Asn, Trp, Tyr, Asp, or Phe. In other embodiments, $Xaa_5$ is Thr or Ile. In some embodiments, $Xaa_5$ is Tyr, Asp or Trp. In certain embodiments, $Xaa_5$ is Asn, Trp, Tyr, Asp, Ile, Thr or Phe. In specific embodiments $Xaa_5$ is Asn.

In certain embodiments, $Xaa_8$ is any natural or non-natural amino acid or amino acid analog. In some embodiments, $Xaa_8$ is Glu, Asp, Gln, Gly or Pro. In other embodiments, $Xaa_8$ is Glu. In some embodiments, $Xaa_8$ is Glu or Asp. In some embodiments, $Xaa_8$ is Asn, Glu, or Asp. In some embodiments, $Xaa_8$ is Glu, His, Lys, Gln, Asn, or Asp. In some embodiments, $Xaa_8$ is Glu, His, Gln, Asn, or Asp. In some embodiments, $Xaa_8$ is Glu, Asn, His, Gln, Lys, Asp or Ser. In specific embodiments, $Xaa_8$ is Pro.

In certain embodiments, $Xaa_9$ is any natural or non-natural amino acid or amino acid analog. In some embodiments, $Xaa_9$ is any natural or non-natural aromatic amino acid or amino acid analog. In some embodiments, $Xaa_9$ is Leu, Ile, Val, Ala, Lys, Arg, Trp, Tyr or Phe. In some embodiments, $Xaa_9$ is Leu, Ile, Val, Lys, Arg, Trp, Tyr or Phe. In some embodiments, $Xaa_9$ is Leu, Ile, Val, Trp, Tyr or Phe. In some embodiments, $Xaa_9$ is Leu, Ile or Val. In some embodiments, $Xaa_9$ is Trp, Tyr or Phe. In some embodiments, $Xaa_9$ is Leu, Ile, Lys, Arg, Trp, Tyr, or Phe. In some embodiments, $Xaa_9$ is Leu, Val, Ile, or Met. In some embodiments, $Xaa_9$ is Leu or Phe. In some embodiments, $Xaa_9$ is Leu, Phe, or Tyr. In some embodiments, $Xaa_9$ is Tyr, Phe or His. In some embodiments, $Xaa_9$ is Phe, His, Trp, or Tyr. In certain embodiments, $Xaa_9$ is not Leu. In specific embodiments, $Xaa_9$ is Tyr.

In certain embodiments, $Xaa_{12}$ is any natural or non-natural amino acid or amino acid analog. In certain embodiments, $Xaa_{12}$ is Asn, Tyr, Asp or Ala. In specific embodiments, $Xaa_{12}$ Asn. In certain embodiments, $Xaa_{12}$ is Asn, Met, Arg, Lys, His, or Gln. In certain embodiments, $Xaa_{12}$ is Asn, Lys, His, or Gln. In certain embodiments, $Xaa_{12}$ is Asn, Asp, Glu or Gln. In certain embodiments, $Xaa_{12}$ is Asn, Thr, Ser, Arg, Lys, Gln, or His. In some embodiments, $Xaa_{12}$ is Asn, Ser, or His.

In certain embodiments, $Xaa_{13}$ is Ala, Pro or Gly. In certain embodiments, $Xaa_{13}$ is Pro or Gly. In specific embodiments, $Xaa_{13}$ is Pro. In particular embodiments, $Xaa_{13}$ is Gly.

In certain embodiments, $Xaa_{14}$ is any natural or non-natural amino acid or amino acid analog. In certain embodiments, $Xaa_{14}$ is Ala, Leu, Ser, Gly, Val, Glu, Gln, Ile, Leu, Thr, Lys, Arg, or Asp. In certain embodiments, $Xaa_{14}$ is Ala or Gly. In some embodiments, $Xaa_{14}$ is Val or Ala. In certain embodiments, $Xaa_{14}$ is Ala or Thr. In specific embodiments, $Xaa_{14}$ is Ala. In certain embodiments, $Xaa_{14}$ is Val, Gln, Asn, Glu, Asp, Thr, or Ala. In certain embodiments, $Xaa_{14}$ is Gly, Cys or Ser.

In certain embodiments, $Xaa_{16}$ is any natural or non-natural amino acid or amino acid analog. In some embodiments, $Xaa_{16}$ is any natural or non-natural non-aromatic amino acid or amino acid analog. In certain embodiments, $Xaa_{16}$ Thr, Ala, Asn, Lys, Arg, Trp, Gly or Val. In certain embodiments, $Xaa_{16}$ is Thr, Ala, Asn, Lys, Arg or Trp. In certain embodiments, $Xaa_{16}$ is Thr, Ala, Lys, Arg or Trp. In some embodiments, $Xaa_{16}$ is Thr, Ala or Trp. In some embodiments, $Xaa_{16}$ is Thr. In some embodiments, $Xaa_{16}$ is Trp, Tyr or Phe. In some embodiments, $Xaa_{16}$ is Thr or Ala. In specific embodiments, $Xaa_{16}$ it is Val. In particular embodiments, $Xaa_{16}$ is Gly. In some embodiments, $Xaa_{16}$ is Thr, Ser, Met or Val. In some embodiments, $Xaa_{16}$ is Val, Ala, or Thr. In some embodiments, $Xaa_{16}$ is Ile, Val, Lys, Asn, Glu, Asp, or Thr.

In certain embodiments, $Xaa_{17}$ is any natural or non-natural amino acid or amino acid analog. In some embodiments, $Xaa_{17}$ is Gly, Pro or Ala. In specific embodiments, $Xaa_{17}$ is Gly. In particular embodiments, $Xaa_{17}$ is Ala. In some embodiments, $Xaa_{17}$ is Gly or Ala. In some embodiments, $Xaa_{17}$ is Gly, Asn, Ser or Ala. In some embodiments, $Xaa_{17}$ is Asn, Glu, Asp, Thr, Ala, Ser, or Gly. In some embodiments, $Xaa_{17}$ is Asp, Ala, Ser, or Gly.

In certain embodiments, $Xaa_{19}$ is any natural or non-natural amino acid or amino acid analog. In some embodiments, $Xaa_{19}$ is Trp, Tyr, Phe, Asn, Ile, Val, His, Leu, or Arg. In some embodiments, $Xaa_{19}$ is Trp, Tyr, Asn or Leu. In some embodiments, $Xaa_{19}$ is Trp, Tyr or Phe. In some embodiments, $Xaa_{19}$ is Tyr, Phe or His. In some embodiments, $Xaa_{19}$ is Tyr or Trp. In specific embodiments, $Xaa_{19}$ is Tyr. In some embodiments, $Xaa_{19}$ is Leu, Ile or Val. In particular embodiments, $Xaa_{19}$ is His. In some embodiments, $Xaa_{19}$ is Trp, Tyr, Phe, Asn, Ile, Val, His or Leu. In some embodiments, $Xaa_{19}$ is Trp, Tyr, Phe or Leu. In some embodiments, $Xaa_{19}$ is Tyr or Leu. In some embodiments, $Xaa_{19}$ is Lys or Arg. In some embodiments, $Xaa_{19}$ is any amino acid other than Pro, Arg, Lys, Asp or Glu. In some embodiments, $Xaa_{19}$ is any amino acid other than Pro. In some embodiments, $Xaa_{19}$ is missing.

In certain embodiments $Xaa_{20}$ is Asp or Asn. In certain embodiments $Xaa_{20}$ $Xaa_{21}$ is AspPhe or is missing. In some embodiments, $Xaa_{20}$ is Asn or Glu and $Xaa_{21}$ is missing. In some embodiments, $Xaa_{19}$ $Xaa_{20}$ $Xaa_{21}$ is missing.

In some aspects, the GC-C agonist peptide comprises, consists, or consists essentially of the amino acid sequence shown below (II):

(SEQ ID NO: 47)
$Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Asn_{12}$ $Pro_{13}$ $Ala_{14}$ $Cys_{15}$ $Xaa_{16}$ $Gly_{17}$ $Cys_{18}$ $Xaa_{19}$ $Xaa_{20}$ $Xaa_{21}$ where $Xaa_1$ $Xaa_2$ $Xaa_3$ $Xaa_4$ $Xaa_5$ is Asn Ser Ser Asn Tyr (SEQ ID NO:2) or is missing or $Xaa_1$ $Xaa_2$ $Xaa_3$ $Xaa_4$ is missing and $Xaa_5$ is Asn;

$Xaa_8$ is Glu or Asp;

$Xaa_9$ is Leu, Ile, Val, Trp, Tyr or Phe;

$Xaa_{16}$ is Thr, Ala, Trp;

$Xaa_{19}$ is Trp, Tyr, Phe or Leu or is missing; and $Xaa_{20}Xaa_{21}$ is AspPhe.

In some aspects, the GC-C agonist peptide comprises, consists, or consists essentially of the amino acid sequence (II): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Asn_{12}$ $Pro_{13}$ $Ala_{14}$ $Cys_{15}$ $Xaa_{16}$ $Gly_{17}$ $Cys_{18}$ $Xaa_{19}$ $Xaa_{20}$ $Xaa_{21}$ (SEQ ID NO:48) where, $Xaa_9$ is Leu, Ile or Val and $Xaa_{16}$ is Trp, Tyr or Phe; $Xaa_9$ is Trp, Tyr or Phe, and $Xaa_{16}$ is Thr or Ala; $Xaa_{19}$ is Trp, Tyr, Phe and $Xaa_{20}Xaa_{21}$ is AspPhe; and $Xaa_1$ $Xaa_2$ $Xaa_3$ $Xaa_4$ is missing and $Xaa_5$ is Asn; the peptide comprises fewer than 50, 40, 30 or 25 amino acids; or fewer than five amino acids precede $Cys_6$.

In some aspects, the GC-C agonist peptide comprises, consists, or consists essentially of the amino acid sequence $Xaa_1$ $Xaa_2$ $Xaa_3$ $Xaa_4$ $Xaa_5$ Cys Cys Glu $Xaa_9$ Cys Cys Asn Pro Ala Cys Thr Gly Cys Tyr $Xaa_{20}$ $Xaa_{21}$ (II) (SEQ ID NO:49) where $Xaa_9$ is any amino acid: where $Xaa_9$ is any amino acid other than Leu; where $Xaa_9$ is selected from Phe, Trp and Tyr; where $Xaa_9$ is selected from any other natural or non-natural aromatic amino acid; where $Xaa_9$ is Tyr; where $Xaa_9$ is Phe; where $Xaa_9$ is Trp; where $Xaa_1$ $Xaa_2$ $Xaa_3$ $Xaa_4$ $Xaa_5$ is Asn Ser Ser Asn Tyr; where $Xaa_1$, $Xaa_2$, $Xaa_3$, $Xaa_4$, and $Xaa_5$ are missing; where $Xaa_1$, $Xaa_2$, $Xaa_3$ and $Xaa_4$ are missing; where $Xaa_1$, $Xaa_2$ and $Xaa_3$ are missing; where $Xaa_1$ and $Xaa_2$ are missing; where $Xaa_1$ is missing; where $Xaa_{20}Xaa_{21}$ is AspPhe or is missing or $Xaa_{20}$ is Asn or Glu and $Xaa_{21}$ is missing or $Xaa_{19}Xaa_{20}Xaa_{21}$ is missing; where $Xaa_1$ $Xaa_2$ $Xaa_3$ $Xaa_4$ $Xaa_5$ and Tyr $Xaa_{20}$ $Xaa_{21}$ are missing. In some aspects, the GC-C agonist peptide comprises, consists, or consists essentially of the amino acid sequence $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{15}$ $Xaa_{19}$ $Xaa_{20}$ $Xaa_{21}$ (I) (SEQ ID NO:50) where: $Xaa_1$ $Xaa_2$ $Xaa_3$ $Xaa_4$ $Xaa_5$ is missing and/or the sequence $Xaa_{19}$ $Xaa_{20}$ $Xaa_{21}$ is missing, where the peptide optionally comprises additional carboxy-terminal and/or amino-terminal amino acids. In instances where the peptide is missing one or more terminal amino acids such as $Xaa_1$ or $Xaa_{2j}$, the peptide can optionally comprise additional carboxy-terminal and/or amino-terminal amino acids.

In certain embodiments, the peptide includes disulfide bonds between $Cys_6$ and $Cys_{11}$, between $Cys_7$ and $Cys_{15}$ and between $Cys_{10}$ and $Cys_{16}$. In some embodiments, the peptide is a reduced peptide having no disulfide bonds. In still other embodiments, the peptide has one or two disulfide bonds selected from: a disulfide bond between $Cys_6$ and $Cys_{11}$, a disulfide bond between $Cys_7$ and $Cys_{15}$ and a disulfide bond between $Cys_{10}$ and $Cys_{16}$.

In certain embodiments, one or more amino acids are replaced by a non-naturally occurring amino acid, or a naturally or non-naturally occurring amino acid analog. There are many amino acids beyond the standard 20 amino acids. Some are naturally-occurring others non-naturally-occurring (see, e.g., Hunt, The Non-Protein Amino Acids: In Chemistry and Biochemistry of the Amino Acids, Barrett, Chapman and Hall, 1985). For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, for example, a halogen, —$CH_3$, —OH, —$CH_2NH_3$, —C(O)H, —$CH_2CH_3$, —CN, —$CH_2CH_2CH_3$, —SH, or another group. Any amino acid can be substituted by the D-form of the amino acid.

With regard to non-naturally occurring amino acids or naturally and non-naturally occurring amino acid analogs, a number of substitutions in the peptide of formula I or the peptide of formula II are possible. For example, in some aspects $Xaa_8$ can be replaced by gamma-Hydroxy-Glu or gamma-Carboxy-Glu. In some aspects, $Xaa_9$ can be replaced by an alpha substituted amino acid such as L-alpha-methylphenylalanine or by analogues such as: 3-Amino-Tyr; Tyr($CH_3$); Tyr($PO_3(CH_3)_2$); Tyr(SO3H); beta-Cyclohexyl-Ala; beta-(1-Cyclopentenyl)-Ala; beta-Cyclopentyl-Ala; beta-Cyclopropyl-Ala; beta-Quinolyl-Ala; beta-2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-2-thienyl)-Ala; 5-Methyl-Trp; and 4-Methyl-Trp.

In some embodiments, $Xaa_{13}$ can be an N(alpha)-C(alpha) cyclized amino acid analogues with the structure:

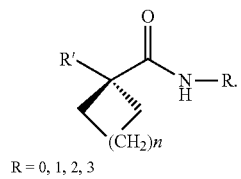

R = 0, 1, 2, 3

$Xaa_{13}$ can also be homopro (L-pipecolic acid); hydroxy-Pro; 3,4-Dehydro-Pro; 4-fluoro-Pro; or alpha-methyl-Pro.

In aspects where $Xaa_{13}$ is Gly, Ala, Leu or Val, $Xaa_{14}$ can be:

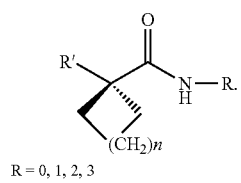

R = 0, 1, 2, 3

In certain aspects, $Xaa_{14}$ can be an alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala.

In some aspects, $Xaa_{17}$ can be alpha-amino isobutyric acid (aib) or L/D-alpha-ethylalanine (L/D-isovaline).

Additional examples of non-natural amino acids and amino acid analogs are known in the art and described elsewhere herein.

In some instances, for exeample, where $Xaa_9$ is Trp, Tyr, or Phe or where $Xaa_{16}$ is Trp, the peptide has a potentially functional chymotrypsin cleavage site that is located at a position where cleavage may alter GC-C receptor binding by the peptide. When $Xaa_9$ is Lys or Arg or when $Xaa_{16}$ is Lys or Arg, the peptide has a potentially functional trypsin cleavage site that is located at a position where cleavage may alter GC-C receptor binding by the peptide.

In certain instances, for example, where $Xaa_{19}$ is Trp, Tyr, or Phe, the peptide has a chymotrypsin cleavage site that is located at a position where cleavage will liberate the portion of the peptide carboxy-terminal to $Xaa_{19}$. When $Xaa_{19}$ is Leu, Ile or Val, the peptide can have a chymotrypsin cleavage site that is located at a position where cleavage will liberate the portion of the peptide amino-terminal to $Xaa_{19}$. At relatively high pH the same effect can be seen if $Xaa_{19}$ is His. Where $Xaa_{19}$ is Lys or Arg, the peptide has a trypsin cleavage site that is located at a position where cleavage will liberate portion of the peptide carboxy-terminal to $Xaa_{19}$.

In some instances, for example, where $Xaa_1$ or the amino-terminal amino acid of the peptide (e.g., $Xaa_2$ or $Xaa_3$) is Trp, Tyr, or Phe, the peptide has a chymotrypsin cleavage site that is located at a position where cleavage will liberate the portion of the peptide amino-terminal to $Xaa_1$ (or $Xaa_2$ or $Xaa_3$) along with $Xaa_1$, $Xaa_2$ or $Xaa_3$. If $Xaa_1$ or the amino-terminal amino acid of the peptide of the invention (e.g., $Xaa_2$ or $Xaa_3$) is Lys or Arg, the peptide has a trypsin cleavage site that is located at a position where cleavage will liberate portion of the peptide amino-terminal to $Xaa_1$ along with $Xaa_1$, $Xaa_2$ or $Xaa_3$). If $Xaa_1$ or the amino-terminal amino acid of the peptide of the invention is Leu, Ile or Val, the peptide can have a chymotrypsin cleavage site that is located at a position where cleavage will liberate the portion of the peptide amino-terminal to $Xaa_1$. At relatively high pH the same effect is seen when $Xaa_1$ is His.

If fully-folded, disulfide bonds may be present between: $Cys_6$ and $Cys_{11}$; $Cys_7$ and $Cys_{15}$; and $Cys_{10}$ and $Cys_{18}$. In some aspects, the GC-C agonist peptides are identical to or have sequence similarity to ST peptides. However, in some aspects the GC-C agonist peptides comprise amino acid changes and/or additions that improve functionality. These changes can, for example, increase or decrease activity (e.g., increase or decrease the ability of the peptide to reduce phosphate uptake), alter the ability of the peptide to fold correctly, alter the stability of the peptide, alter the ability of the peptide to bind the GC-C receptor, and/or decrease toxicity. In some instances, the peptides may function more desirably than a wild-type ST peptide. For example, in certain instances, undesirable side effects such as diarrhea and dehydration are reduced.

In the case of a peptide comprising or consisting of the sequence (I) $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:50) or $Xaa_1$ $Xaa_2$ $Xaa_3$ $Xaa_4$ $Xaa_5$ Cys Cys Glu $Xaa_9$ Cys Cys Asn Pro Ala Cys Thr Gly Cys Tyr $Xaa_{20}$ $Xaa_{21}$ (II) (SEQ ID NO:49) where: $Xaa_1$ $Xaa_2$ $Xaa_3$ $Xaa_4$ $Xaa_5$ is missing and/or the sequence $Xaa_{19}$ $Xaa_{20}$ $Xaa_{21}$ is missing, the peptide can optionally comprise additional carboxy-terminal and/or amino-terminal amino acids. For example, the peptide can include an amino terminal sequence that facilitates recombinant production of the peptide and is cleaved prior to administration of the peptide to a patient. The peptide can also include other amino-terminal or carboxy-terminal amino acids. In some instances, the additional amino acids protect the peptide, stabilize the peptide, and/or alter the activity of the peptide. In instances, some or all of the additional amino acids are removed prior to administration of the peptide to a patient. The peptide can include 1, 2, 3, 4, 5, 10, 15, 20, 25, 30, 40, 50, 60, 70 80, 90, 100 or more amino acids at its amino-terminus and/or carboxy-terminus. The number of flanking amino acids need not be the same. For example, there can be 10 additional amino acids at the amino-terminus of the peptide and none at the carboxy-terminus.

In some embodiments, the peptide comprises the amino acid sequence (I): $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ $Xaa_{17}$ $Cys_{18}$ $Xaa_{19}$ $Xaa_{20}$ $Xaa_{21}$ (SEQ ID NO:50) where: $Xaa_1$ $Xaa_2$ $Xaa_3$ $Xaa_4$ $Xaa_5$ is missing; $Xaa_8$ is Glu; $Xaa_9$ is Leu, Ile, Lys, Arg, Trp, Tyr or Phe; $Xaa_{12}$ is Asn; $Xaa_{13}$ is Pro; $Xaa_{14}$ is Ala; $Xaa_{16}$ is Thr, Ala, Lys, Arg, Trp; $Xaa_{17}$ is Gly; $Xaa_{19}$ is Tyr or Leu; and $Xaa_{20}$ $Xaa_{21}$ is Asp Phe or is missing. In instances where $Xaa_{20}$ $Xaa_{21}$ and/or $Xaa_1$ $Xaa_2$ $Xaa_3$ $Xaa_4$ $Xaa_5$ are missing, the peptide may optionally comprise additional flanking amino acids.

Examples of GC-C agonist peptides which comprise, consist, or consist essentially of the amino acid sequence $Xaa_1$ $Xaa_2$ $Xaa_3$ $Xaa_4$ $Xaa_5$ Cys Cys Glu $Xaa_9$ Cys Cys Asn Pro Ala Cys Thr Gly Cys Tyr $Xaa_{20}$ $Xaa_{21}$ (II) (SEQ ID NO:49) are shown in Table A2 below.

TABLE A2

Gln Ser Ser Asn Tyr Cys Cys Glu Tyr Cys
Cys Asn Pro Ala Cys Thr Gly Cys Tyr (SEQ
ID NO: 51)

Asn Leu Ser Asn Tyr Cys Cys Glu Tyr Cys
Cys Asn Pro Ala Cys Thr Gly Cys Tyr (SEQ
ID NO: 52)

Asn Ser Ser Gln Tyr Cys Cys Glu Tyr Cys
Cys Asn Pro Ala Cys Thr Gly Cys Tyr (SEQ
ID NO: 53)

Gln Ser Ser Gln Tyr Cys Cys Glu Tyr Cys
Cys Asn Pro Ala Cys Thr Gly Cys Tyr (SEQ
ID NO: 54)

Asn Ser Ser Asn Tyr Cys Cys Glu Ala Cys
Cys Asn Pro Ala Cys Thr Gly Cys Tyr (SEQ
ID NO: 55)

Asn Ser Ser Asn Tyr Cys Cys Glu Asn Cys
Cys Asn Pro Ala Cys Thr Gly Cys Tyr (SEQ
ID NO: 56)

Asn Ser Ser Asn Tyr Cys Cys Glu Cys Cys
Cys Asn Pro Ala Cys Thr Gly Cys Tyr (SEQ
ID NO: 57)

Asn Ser Ser Asn Tyr Cys Cys Glu Glu Cys
Cys Asn Pro Ala Cys Thr Gly Cys Tyr (SEQ
ID NO: 58)

Asn Ser Ser Asn Tyr Cys Cys Glu His Cys
Cys Asn Pro Ala Cys Thr Gly Cys Tyr (SEQ
ID NO: 59)

Asn Ser Ser Asn Tyr Cys Cys Glu Lys Cys
Cys Asn Pro Ala Cys Thr Gly Cys Tyr (SEQ
ID NO: 60)

Asn Ser Ser Asn Tyr Cys Cys Glu Phe Cys
Cys Asn Pro Ala Cys Thr Gly Cys Tyr (SEQ
ID NO: 61)

Asn Ser Ser Asn Tyr Cys Cys Glu Ser Cys
Cys Asn Pro Ala Cys Thr Gly Cys Tyr (SEQ
ID NO: 62)

Asn Ser Ser Asn Tyr Cys Cys Glu Trp Cys
Cys Asn Pro Ala Cys Thr Gly Cys Tyr (SEQ
ID NO: 63)

Cys Cys Glu Ala Cys Cys Asn Pro Ala Cys
Thr Gly Cys Tyr (SEQ ID NO: 64)

TABLE A2-continued

Cys Cys Glu Asn Cys Cys Asn Pro Ala Cys
Thr Gly Cys Tyr (SEQ ID NO: 65)

Cys Cys Glu Cys Cys Cys Asn Pro Ala Cys
Thr Gly Cys Tyr (SEQ ID NO: 66)

Cys Cys Glu Glu Cys Cys Asn Pro Ala Cys
Thr Gly Cys Tyr (SEQ ID NO: 67)

Cys Cys Glu His Cys Cys Asn Pro Ala Cys
Thr Gly Cys Tyr (SEQ ID NO: 68)

Cys Cys Glu Lys Cys Cys Asn Pro Ala Cys
Thr Gly Cys Tyr (SEQ ID NO: 69)

Cys Cys Glu Phe Cys Cys Asn Pro Ala Cys
Thr Gly Cys Tyr (SEQ ID NO: 70)

Cys Cys Glu Ser Cys Cys Asn Pro Ala Cys
Thr Gly Cys Tyr (SEQ ID NO: 71)

Cys Cys Glu Trp Cys Cys Asn Pro Ala Cys
Thr Gly Cys Tyr (SEQ ID NO: 72)

Cys Cys Glu Tyr Cys Cys Asn Pro Ala Cys
Thr Gly Cys (SEQ ID NO: 73)

Cys Cys Glu Arg Cys Cys Asn Pro Ala Cys
Thr Gly Cys (SEQ ID NO: 74)

Cys Cys Glu Asp Cys Cys Asn Pro Ala Cys
Thr Gly Cys (SEQ ID NO: 75)

Cys Cys Glu Gln Cys Cys Asn Pro Ala Cys
Thr Gly Cys (SEQ ID NO: 76)

Cys Cys Glu Gly Cys Cys Asn Pro Ala Cys
Thr Gly Cys (SEQ ID NO: 77)

Cys Cys Glu Ile Cys Cys Asn Pro Ala Cys
Thr Gly Cys (SEQ ID NO: 78)

Cys Cys Glu Met Cys Cys Asn Pro Ala Cys
Thr Gly Cys (SEQ ID NO: 79)

Cys Cys Glu Pro Cys Cys Asn Pro Ala Cys
Thr Gly Cys (SEQ ID NO: 80)

Cys Cys Glu Thr Cys Cys Asn Pro Ala Cys
Thr Gly Cys (SEQ ID NO: 81)

Cys Cys Glu Val Cys Cys Asn Pro Ala Cys
Thr Gly Cys (SEQ ID NO: 82)

Asn Thr Ser Asn Tyr Cys Cys Glu Tyr Cys
Cys Asn Pro Ala Cys Thr Gly Cys Tyr (SEQ
ID NO: 83)

Asn Ile Ser Asn Tyr Cys Cys Glu Tyr Cys
Cys Asn Pro Ala Cys Thr Gly Cys Tyr (SEQ
ID NO: 84)

Ser Ser Asn Tyr Cys Cys Glu Tyr Cys Cys
Asn Pro Ala Cys Thr Gly Cys Tyr (SEQ ID
NO: 85)

Ser Ser Gln Tyr Cys Cys Glu Tyr Cys Cys
Asn Pro Ala Cys Thr Gly Cys Tyr. (SEQ ID
NO: 86)

Asn Ser Ser Asn Tyr Cys Cys Glu Arg Cys
Cys Asn Pro Ala Cys Thr Gly Cys Tyr (SEQ
ID NO: 87)

TABLE A2-continued

Asn Ser Ser Asn Tyr Cys Cys Glu Asp Cys
Cys Asn Pro Ala Cys Thr Gly Cys Tyr (SEQ
ID NO: 88)

Asn Ser Ser Asn Tyr Cys Cys Glu Gln Cys
Cys Asn Pro Ala Cys Thr Gly Cys Tyr (SEQ
ID NO: 89)

Asn Ser Ser Asn Tyr Cys Cys Glu Gly Cys
Cys Asn Pro Ala Cys Thr Gly Cys Tyr (SEQ
ID NO: 90)

Asn Ser Ser Asn Tyr Cys Cys Glu Ile Cys
Cys Asn Pro Ala Cys Thr Gly Cys Tyr (SEQ
ID NO: 91)

Asn Ser Ser Asn Tyr Cys Cys Glu Met Cys
Cys Asn Pro Ala Cys Thr Gly Cys Tyr (SEQ
ID NO: 92)

Asn Ser Ser Asn Tyr Cys Cys Glu Pro Cys
Cys Asn Pro Ala Cys Thr Gly Cys Tyr (SEQ
ID NO: 93)

Asn Ser Ser Asn Tyr Cys Cys Glu Thr Cys
Cys Asn Pro Ala Cys Thr Gly Cys Tyr (SEQ
ID NO: 94)

Asn Ser Ser Asn Tyr Cys Cys Glu Val Cys
Cys Asn Pro Ala Cys Thr Gly Cys Tyr (SEQ
ID NO: 95)

Cys Cys Glu Arg Cys Cys Asn Pro Ala Cys
Thr Gly Cys Tyr (SEQ ID NO: 96)

Cys Cys Glu Asp Cys Cys Asn Pro Ala Cys
Thr Gly Cys Tyr (SEQ ID NO: 97)

Cys Cys Glu Gln Cys Cys Asn Pro Ala Cys
Thr Gly Cys Tyr (SEQ ID NO: 98)

Cys Cys Glu Gly Cys Cys Asn Pro Ala Cys
Thr Gly Cys Tyr (SEQ ID NO: 99)

Cys Cys Glu Ile Cys Cys Asn Pro Ala Cys
Thr Gly Cys Tyr (SEQ ID NO: 100)

Cys Cys Glu Met Cys Cys Asn Pro Ala Cys
Thr Gly Cys Tyr (SEQ ID NO: 101)

Cys Cys Glu Pro Cys Cys Asn Pro Ala Cys
Thr Gly Cys Tyr (SEQ ID NO: 102)

Cys Cys Glu Thr Cys Cys Asn Pro Ala Cys
Thr Gly Cys Tyr (SEQ ID NO: 103)

Cys Cys Glu Val Cys Cys Asn Pro Ala Cys
Thr Gly Cys Tyr (SEQ ID NO: 104)

Cys Cys Glu Ala Cys Cys Asn Pro Ala Cys
Thr Gly Cys (SEQ ID NO: 105)

Cys Cys Glu Asn Cys Cys Asn Pro Ala Cys
Thr Gly Cys (SEQ ID NO: 106)

Cys Cys Glu Cys Cys Cys Asn Pro Ala Cys
Thr Gly Cys (SEQ ID NO: 107)

Cys Cys Glu Glu Cys Cys Asn Pro Ala Cys
Thr Gly Cys (SEQ ID NO: 108)

Cys Cys Gln His Cys Cys Asn Pro Ala Cys
Thr Gly Cys (SEQ ID NO: 109)

Cys Cys Glu Lys Cys Cys Asn Pro Ala Cys
Thr Gly Cys (SEQ ID NO: 110)

Cys Cys Glu Phe Cys Cys Asn Pro Ala Cys
Thr Gly Cys (SEQ ID NO: 111)

TABLE A2-continued

Cys Cys Glu Ser Cys Cys Asn Pro Ala Cys
Thr Gly Cys (SEQ ID NO: 112)

Cys Cys Glu Trp Cys Cys Asn Pro Ala Cys
Thr Gly Cys (SEQ ID NO: 113)

Additional examples of GC-C agonist peptides are shown in Table A3 below.

TABLE A3

Cys Cys Glu Leu Cys Cys Ala Pro Ala Cys
Thr Gly Cys Tyr (SEQ ID NO: 114)

Cys Cys Glu Leu Cys Cys Leu Pro Ala Cys
Thr Gly Cys Tyr (SEQ ID NO: 115)

Cys Cys Glu Leu Cys Cys Pro Pro Ala Cys
Thr Gly Cys Tyr (SEQ ID NO: 116)

Cys Cys Glu Leu Cys Cys Phe Pro Ala Cys
Thr Gly Cys Tyr (SEQ ID NO: 117)

Cys Cys Glu Leu Cys Cys Gly Pro Ala Cys
Thr Gly Cys Tyr (SEQ ID NO: 118)

Cys Cys Glu Leu Cys Cys Thr Pro Ala Cys
Thr Gly Cys Tyr (SEQ ID NO: 119)

Cys Cys Glu Leu Cys Cys Gln Pro Ala Cys
Thr Gly Cys Tyr (SEQ ID NO: 120)

Cys Cys Glu Leu Cys Cys Asp Pro Ala Cys
Thr Gly Cys Tyr (SEQ ID NO: 121)

Cys Cys Glu Leu Cys Cys Lys Pro Ala Cys
Thr Gly Cys Tyr (SEQ ID NO: 122)

Cys Cys Glu Leu Cys Cys His Pro Ala Cys
Thr Gly Cys Tyr (SEQ ID NO: 123)

Cys Cys Glu Tyr Cys Cys Val Pro Ala Cys
Thr Gly Cys Tyr (SEQ ID NO: 124)

Cys Cys Glu Tyr Cys Cys Ile Pro Ala Cys
Thr Gly Cys Tyr (SEQ ID NO: 125)

Cys Cys Glu Tyr Cys Cys Met Pro Ala Cys
Thr Gly Cys Tyr (SEQ ID NO: 126)

Cys Cys Glu Tyr Cys Cys Trp Pro Ala Cys
Thr Gly Cys Tyr (SEQ ID NO: 127)

Cys Cys Glu Tyr Cys Cys Ser Pro Ala Cys
Thr Gly Cys Tyr (SEQ ID NO: 128)

Cys Cys Glu Tyr Cys Cys Cys Pro Ala Cys
Thr Gly Cys Tyr (SEQ ID NO: 129)

Cys Cys Glu Tyr Cys Cys Tyr Pro Ala Cys
Thr Gly Cys Tyr (SEQ ID NO: 130)

Cys Cys Glu Tyr Cys Cys Glu Pro Ala Cys
Thr Gly Cys Tyr (SEQ ID NO: 131)

Cys Cys Glu Tyr Cys Cys Arg Pro Ala Cys
Thr Gly Cys Tyr (SEQ ID NO: 132)

Cys Cys Glu Leu Cys Cys Ala Pro Ala Cys
Thr Gly Cys (SEQ ID NO: 133)

Cys Cys Glu Leu Cys Cys Leu Pro Ala Cys
Thr Gly Cys (SEQ ID NO: 134)

TABLE A3-continued

Cys Cys Glu Leu Cys Cys Pro Pro Ala Cys
Thr Gly Cys (SEQ ID NO: 135)

Cys Cys Glu Leu Cys Cys Phe Pro Ala Cys
Thr Gly Cys (SEQ ID NO: 136)

Cys Cys Glu Leu Cys Cys Gly Pro Ala Cys
Thr Gly Cys (SEQ ID NO: 137)

Cys Cys Glu Leu Cys Cys Thr Pro Ala Cys
Thr Gly Cys (SEQ ID NO: 138)

Cys Cys Glu Leu Cys Cys Gln Pro Ala Cys
Thr Gly Cys (SEQ ID NO: 139)

Cys Cys Glu Leu Cys Cys Asp Pro Ala Cys
Thr Gly Cys (SEQ ID NO: 140)

Cys Cys Glu Leu Cys Cys Lys Pro Ala Cys
Thr Gly Cys (SEQ ID NO: 141)

Cys Cys Glu Leu Cys Cys His Pro Ala Cys
Thr Gly Cys (SEQ ID NO: 142)

Cys Cys Glu Tyr Cys Cys Val Pro Ala Cys
Thr Gly Cys (SEQ ID NO: 143)

Cys Cys Glu Tyr Cys Cys Ile Pro Ala Cys
Thr Gly Cys (SEQ ID NO: 144)

Cys Cys Glu Tyr Cys Cys Met Pro Ala Cys
Thr Gly Cys (SEQ ID NO: 145)

Cys Cys Glu Tyr Cys Cys Trp Pro Ala Cys
Thr Gly Cys (SEQ ID NO: 146)

Cys Cys Glu Tyr Cys Cys Ser Pro Ala Cys
Thr Gly Cys (SEQ ID NO: 147)

Cys Cys Glu Tyr Cys Cys Cys Pro Ala Cys
Thr Gly Cys (SEQ ID NO: 148)

Cys Cys Glu Tyr Cys Cys Tyr Pro Ala Cys
Thr Gly Cys (SEQ ID NO: 149)

Cys Cys Glu Tyr Cys Cys Glu Pro Ala Cys
Thr Gly Cys (SEQ ID NO: 150)

Cys Cys Glu Tyr Cys Cys Arg Pro Ala Cys
Thr Gly Cys (SEQ ID NO: 151)

Cys Cys Glu Leu Cys Cys Asn Pro Thr Cys
Thr Gly Cys Tyr (SEQ ID NO: 152)

Cys Cys Glu Leu Cys Cys Asn Pro Thr Cys
Thr Gly Cys (SEQ ID NO: 153)

Cys Cys Glu Phe Cys Cys Asn Pro Thr Cys
Thr Gly Cys Tyr (SEQ ID NO: 154)

Cys Cys Glu Tip Cys Cys Asn Pro Thr Cys
Thr Gly Cys Tyr (SEQ ID NO: 155)

Cys Cys Glu Leu Cys Cys Asn Gly Ala Cys
Thr Gly Cys Tyr (SEQ ID NO: 156)

Cys Cys Glu Leu Cys Cys Asn Gly Ala Cys
Thr Gly Cys (SEQ ID NO: 157)

Cys Cys Glu Phe Cys Cys Asn Gly Ala Cys
Thr Gly Cys Tyr (SEQ ID NO: 158)

Cys Cys Glu Trp Cys Cys Asn Gly Ala Cys
Thr Gly Cys Tyr (SEQ ID NO: 159)

Cys Cys Glu Leu Cys Cys Asn Pro Ala Cys
Val Gly Cys Tyr (SEQ ID NO: 160)

Cys Cys Glu Leu Cys Cys Asn Pro Ala Cys
Val Gly Cys (SEQ ID NO: 161)

Cys Cys Glu Phe Cys Cys Asn Pro Ala Cys
Val Gly Cys Tyr (SEQ ID NO: 162)

Cys Cys Glu Trp Cys Cys Asn Pro Ala Cys
Val Gly Cys Tyr (SEQ ID NO: 163)

Cys Cys Glu Leu Cys Cys Asn Pro Ala Cys
Gly Gly Cys Tyr (SEQ ID NO: 164)

Cys Cys Glu Leu Cys Cys Asn Pro Ala Cys
Gly Gly Cys (SEQ ID NO: 165)

Cys Cys Glu Phe Cys Cys Asn Pro Ala Cys
Gly Gly Cys Tyr (SEQ ID NO: 166)

Cys Cys Glu Trp Cys Cys Asn Pro Ala Cys
Gly Gly Cys Tyr (SEQ ID NO: 167)

Cys Cys Glu Leu Cys Cys Asn Pro Ala Cys
Thr Ala Cys Tyr (SEQ ID NO: 168)

Cys Cys Glu Leu Cys Cys Asn Pro Ala Cys
Thr Ala Cys (SEQ ID NO: 169)

Cys Cys Glu Trp Cys Cys Asn Pro Ala Cys
Thr Ala Cys Tyr (SEQ ID NO: 170)

Cys Cys Glu Phe Cys Cys Asn Pro Ala Cys
Thr Ala Cys Tyr (SEQ ID NO: 171)

Cys Cys Glu Leu Cys Cys Asn Pro Ala Cys
Thr Gly Cys Ala (SEQ ID NO: 172)

Cys Cys Glu Leu Cys Cys Asn Pro Ala Cys
Thr Gly Cys Leu (SEQ ID NO: 173)

Cys Cys Glu Leu Cys Cys Asn Pro Ala Cys
Thr Gly Cys Pro (SEQ ID NO: 174)

Cys Cys Glu Leu Cys Cys Asn Pro Ala Cys
Thr Gly Cys Phe (SEQ ID NO: 175)

Cys Cys Glu Leu Cys Cys Asn Pro Ala Cys
Thr Gly Cys Gly (SEQ ID NO: 176)

Cys Cys Glu Leu Cys Cys Asn Pro Ala Cys
Thr Gly Cys Thr (SEQ ID NO: 177)

Cys Cys Glu Leu Cys Cys Asn Pro Ala Cys
Thr Gly Cys Asn (SEQ ID NO: 178)

Cys Cys Glu Leu Cys Cys Asn Pro Ala Cys
Thr Gly Cys Asp (SEQ ID NO: 179)

Cys Cys Glu Leu Cys Cys Asn Pro Ala Cys
Thr Gly Cys Lys (SEQ ID NO: 180)

Cys Cys Glu Leu Cys Cys Asn Pro Ala Cys
Thr Gly Cys His (SEQ ID NO: 181)

Cys Cys Glu Tyr Cys Cys Asn Pro Ala Cys
Thr Gly Cys Val (SEQ ID NO: 182)

Cys Cys Glu Tyr Cys Cys Asn Pro Ala Cys
Thr Gly Cys Ile (SEQ ID NO: 183)

Cys Cys Glu Tyr Cys Cys Asn Pro Ala Cys
Thr Gly Cys Met (SEQ ID NO: 184)

Cys Cys Glu Tyr Cys Cys Asn Pro Ala Cys
Thr Gly Cys Trp (SEQ ID NO: 185)

Cys Cys Glu Tyr Cys Cys Asn Pro Ala Cys
Thr Gly Cys Ser (SEQ ID NO: 186)

Cys Cys Glu Tyr Cys Cys Asn Pro Ala Cys
Thr Gly Cys Cys (SEQ ID NO: 187)

TABLE A3-continued

Cys Cys Glu Tyr Cys Cys Asn Pro Ala Cys
Thr Gly Cys Gln (SEQ ID NO: 188)

Cys Cys Glu Tyr Cys Cys Asn Pro Ala Cys
Thr Gly Cys Glu (SEQ ID NO: 189)

Cys Cys Glu Tyr Cys Cys Asn Pro Ala Cys
Thr Gly Cys Arg (SEQ ID NO: 190)

Cys Cys Ala Leu Cys Cys Asn Pro Ala Cys
Thr Gly Cys Tyr (SEQ ID NO: 191)

Cys Cys Leu Leu Cys Cys Asn Pro Ala Cys
Thr Gly Cys Tyr (SEQ ID NO: 192)

Cys Cys Met Leu Cys Cys Asn Pro Ala Cys
Thr Gly Cys Tyr (SEQ ID NO: 193)

Cys Cys Trp Leu Cys Cys Asn Pro Ala Cys
Thr Gly Cys Tyr (SEQ ID NO: 194)

Cys Cys Ser Leu Cys Cys Asn Pro Ala Cys
Thr Gly Cys Tyr (SEQ ID NO: 195)

Cys Cys Cys Leu Cys Cys Asn Pro Ala Cys
Thr Gly Cys Tyr (SEQ ID NO: 196)

Cys Cys Gln Leu Cys Cys Asn Pro Ala Cys
Thr Gly Cys Tyr (SEQ ID NO: 197)

Cys Cys Asp Leu Cys Cys Asn Pro Ala Cys
Thr Gly Cys Tyr (SEQ ID NO: 198)

Cys Cys Arg Leu Cys Cys Asn Pro Ala Cys
Thr Gly Cys Tyr (SEQ ID NO: 199)

Cys Cys Ala Leu Cys Cys Asn Pro Ala Cys
Thr Gly Cys (SEQ ID NO: 200)

Cys Cys Leu Leu Cys Cys Asn Pro Ala Cys
Thr Gly Cys (SEQ ID NO: 201)

Cys Cys Met Leu Cys Cys Asn Pro Ala Cys
Thr Gly Cys (SEQ ID NO: 202)

Cys Cys Trp Leu Cys Cys Asn Pro Ala Cys
Thr Gly Cys (SEQ ID NO: 203)

Cys Cys Ser Leu Cys Cys Asn Pro Ala Cys
Thr Gly Cys (SEQ ID NO: 204)

Cys Cys Cys Leu Cys Cys Asn Pro Ala Cys
Thr Gly Cys (SEQ ID NO: 205)

Cys Cys Gln Leu Cys Cys Asn Pro Ala Cys
Thr Gly Cys (SEQ ID NO: 206)

Cys Cys Asp Leu Cys Cys Asn Pro Ala Cys
Thr Gly Cys (SEQ ID NO: 207)

Cys Cys Arg Leu Cys Cys Asn Pro Ala Cys
Thr Gly Cys (SEQ ID NO: 208)

Cys Cys Ala Tyr Cys Cys Asn Pro Ala Cys
Thr Gly Cys Tyr (SEQ ID NO: 209)

Cys Cys Leu Tyr Cys Cys Asn Pro Ala Cys
Thr Gly Cys Tyr (SEQ ID NO: 210)

Cys Cys Met Tyr Cys Cys Asn Pro Ala Cys
Thr Gly Cys Tyr (SEQ ID NO: 211)

Cys Cys Trp Tyr Cys Cys Asn Pro Ala Cys
Thr Gly Cys Tyr (SEQ ID NO: 212)

Cys Cys Ser Tyr Cys Cys Asn Pro Ala Cys
Thr Gly Cys Tyr (SEQ ID NO: 213)

Cys Cys Cys Tyr Cys Cys Asn Pro Ala Cys
Thr Gly Cys Tyr (SEQ ID NO: 214)

Cys Cys Gln Tyr Cys Cys Asn Pro Ala Cys
Thr Gly Cys Tyr (SEQ ID NO: 215)

Cys Cys Asp Tyr Cys Cys Asn Pro Ala Cys
Thr Gly Cys Tyr (SEQ ID NO: 216)

Cys Cys Arg Tyr Cys Cys Asn Pro Ala Cys
Thr Gly Cys Tyr (SEQ ID NO: 217)

Cys Cys Ala Tyr Cys Cys Asn Pro Ala Cys
Thr Gly Cys (SEQ ID NO: 218)

Cys Cys Leu Tyr Cys Cys Asn Pro Ala Cys
Thr Gly Cys (SEQ ID NO: 219)

Cys Cys Met Tyr Cys Cys Asn Pro Ala Cys
Thr Gly Cys (SEQ ID NO: 220)

Cys Cys Trp Tyr Cys Cys Asn Pro Ala Cys
Thr Gly Cys (SEQ ID NO: 221)

Cys Cys Ser Tyr Cys Cys Asn Pro Ala Cys
Thr Gly Cys (SEQ ID NO: 222)

Cys Cys Cys Tyr Cys Cys Asn Pro Ala Cys
Thr Gly Cys (SEQ ID NO: 223)

Cys Cys Gln Tyr Cys Cys Asn Pro Ala Cys
Thr Gly Cys (SEQ ID NO: 224)

Cys Cys Asp Tyr Cys Cys Asn Pro Ala Cys
Thr Gly Cys (SEQ ID NO: 225)

Cys Cys Arg Tyr Cys Cys Asn Pro Ala Cys
Thr Gly Cys (SEQ ID NO: 226)

Cys Cys Glu Phe Cys Cys Ala Pro Ala Cys
Thr Gly Cys Tyr (SEQ ID NO: 227)

Cys Cys Glu Phe Cys Cys Leu Pro Ala Cys
Thr Gly Cys Tyr (SEQ ID NO: 228)

Cys Cys Glu Phe Cys Cys Pro Pro Ala Cys
Thr Gly Cys Tyr (SEQ ID NO: 229)

Cys Cys Glu Phe Cys Cys Phe Pro Ala Cys
Thr Gly Cys Tyr (SEQ ID NO: 230)

Cys Cys Glu Phe Cys Cys Gly Pro Ala Cys
Thr Gly Cys Tyr (SEQ ID NO: 231)

Cys Cys Glu Phe Cys Cys Thr Pro Ala Cys
Thr Gly Cys Tyr (SEQ ID NO: 232)

Cys Cys Glu Phe Cys Cys Gln Pro Ala Cys
Thr Gly Cys Tyr (SEQ ID NO: 233)

Cys Cys Glu Phe Cys Cys Asp Pro Ala Cys
Thr Gly Cys Tyr (SEQ ID NO: 234)

Cys Cys Glu Phe Cys Cys Lys Pro Ala Cys
Thr Gly Cys Tyr (SEQ ID NO: 235)

Cys Cys Glu Phe Cys Cys His Pro Ala Cys
Thr Gly Cys Tyr (SEQ ID NO: 236)

Cys Cys Glu Phe Cys Cys Val Pro Ala Cys
Thr Gly Cys (SEQ ID NO: 237)

Cys Cys Glu Phe Cys Cys Ile Pro Ala Cys
Thr Gly Cys (SEQ ID NO: 238)

Cys Cys Glu Phe Cys Cys Met Pro Ala Cys
Thr Gly Cys (SEQ ID NO: 239)

Cys Cys Glu Phe Cys Cys Trp Pro Ala Cys
Thr Gly Cys (SEQ ID NO: 240)

TABLE A3-continued

Cys Cys Glu Phe Cys Cys Ser Pro Ala Cys
Thr Gly Cys (SEQ ID NO: 241)

Cys Cys Glu Phe Cys Cys Cys Pro Ala Cys
Thr Gly Cys (SEQ ID NO: 242)

Cys Cys Glu Phe Cys Cys Tyr Pro Ala Cys
Thr Gly Cys (SEQ ID NO: 243)

Cys Cys Glu Phe Cys Cys Glu Pro Ala Cys
Thr Gly Cys (SEQ ID NO: 244)

Cys Cys Glu Phe Cys Cys Arg Pro Ala Cys
Thr Gly Cys (SEQ ID NO: 245)

Cys Cys Glu Trp Cys Cys Ala Pro Ala Cys
Thr Gly Cys Tyr (SEQ ID NO: 246)

Cys Cys Glu Trp Cys Cys Leu Pro Ala Cys
Thr Gly Cys Tyr (SEQ ID NO: 247)

Cys Cys Glu Trp Cys Cys Pro Pro Ala Cys
Thr Gly Cys Tyr (SEQ ID NO: 248)

Cys Cys Glu Trp Cys Cys Phe Pro Ala Cys
Thr Gly Cys Tyr (SEQ ID NO: 249)

Cys Cys Glu Trp Cys Cys Gly Pro Ala Cys
Thr Gly Cys Tyr (SEQ ID NO: 250)

Cys Cys Glu Trp Cys Cys Thr Pro Ala Cys
Thr Gly Cys Tyr (SEQ ID NO: 251)

Cys Cys Glu Trp Cys Cys Gln Pro Ala Cys
Thr Gly Cys Tyr (SEQ ID NO: 252)

Cys Cys Glu Trp Cys Cys Asp Pro Ala Cys
Thr Gly Cys Tyr (SEQ ID NO: 253)

Cys Cys Glu Trp Cys Cys Lys Pro Ala Cys
Thr Gly Cys Tyr (SEQ ID NO: 254)

Cys Cys Glu Trp Cys Cys His Pro Ala Cys
Thr Gly Cys Tyr (SEQ ID NO: 255)

Cys Cys Glu Trp Cys Cys Val Pro Ala Cys
Thr Gly Cys (SEQ ID NO: 256)

Cys Cys Glu Trp Cys Cys Ile Pro Ala Cys
Thr Gly Cys (SEQ ID NO: 257)

Cys Cys Glu Trp Cys Cys Met Pro Ala Cys
Thr Gly Cys (SEQ ID NO: 258)

Cys Cys Glu Trp Cys Cys Trp Pro Ala Cys
Thr Gly Cys (SEQ ID NO: 259)

Cys Cys Glu Trp Cys Cys Ser Pro Ala Cys
Thr Gly Cys (SEQ ID NO: 260)

Cys Cys Glu Trp Cys Cys Cys Pro Ala Cys
Thr Gly Cys (SEQ ID NO: 261)

Cys Cys Glu Trp Cys Cys Tyr Pro Ala Cys
Thr Gly Cys (SEQ ID NO: 262)

Cys Cys Glu Trp Cys Cys Glu Pro Ala Cys
Thr Gly Cys (SEQ ID NO: 263)

Cys Cys Glu Trp Cys Cys Arg Pro Ala Cys
Thr Gly Cys (SEQ ID NO: 264)

Cys Cys Glu Trp Cys Cys Asn Pro Ala Cys
Thr Gly Cys Ala (SEQ ID NO: 265)

Cys Cys Glu Trp Cys Cys Asn Pro Ala Cys
Thr Gly Cys Leu (SEQ ID NO: 266)

Cys Cys Glu Trp Cys Cys Asn Pro Ala Cys
Thr Gly Cys Pro (SEQ ID NO: 267)

TABLE A3-continued

Cys Cys Glu Trp Cys Cys Asn Pro Ala Cys
Thr Gly Cys Phe (SEQ ID NO: 268)

Cys Cys Glu Trp Cys Cys Asn Pro Ala Cys
Thr Gly Cys Gly (SEQ ID NO: 269)

Cys Cys Glu Trp Cys Cys Asn Pro Ala Cys
Thr Gly Cys Thr (SEQ ID NO: 270)

Cys Cys Glu Trp Cys Cys Asn Pro Ala Cys
Thr Gly Cys Asn (SEQ ID NO: 271)

Cys Cys Glu Trp Cys Cys Asn Pro Ala Cys
Thr Gly Cys Asp (SEQ ID NO: 272)

Cys Cys Glu Trp Cys Cys Asn Pro Ala Cys
Thr Gly Cys Lys (SEQ ID NO: 273)

Cys Cys Glu Trp Cys Cys Asn Pro Ala Cys
Thr Gly Cys His (SEQ ID NO: 274)

Cys Cys Glu Phe Cys Cys Asn Pro Ala Cys
Thr Gly Cys Val (SEQ ID NO: 275)

Cys Cys Glu Phe Cys Cys Asn Pro Ala Cys
Thr Gly Cys Ile (SEQ ID NO: 276)

Cys Cys Glu Phe Cys Cys Asn Pro Ala Cys
Thr Gly Cys Met (SEQ ID NO: 277)

Cys Cys Glu Phe Cys Cys Asn Pro Ala Cys
Thr Gly Cys Trp (SEQ ID NO: 278)

Cys Cys Glu Phe Cys Cys Asn Pro Ala Cys
Thr Gly Cys Ser (SEQ ID NO: 279)

Cys Cys Glu Phe Cys Cys Asn Pro Ala Cys
Thr Gly Cys Cys (SEQ ID NO: 280)

Cys Cys Glu Phe Cys Cys Asn Pro Ala Cys
Thr Gly Cys Gln (SEQ ID NO: 281)

Cys Cys Glu Phe Cys Cys Asn Pro Ala Cys
Thr Gly Cys Glu (SEQ ID NO: 282)

Cys Cys Glu Phe Cys Cys Asn Pro Ala Cys
Thr Gly Cys Arg (SEQ ID NO: 283)

Cys Cys Ala Phe Cys Cys Asn Pro Ala Cys
Thr Gly Cys Tyr (SEQ ID NO: 284)

Cys Cys Leu Phe Cys Cys Asn Pro Ala Cys
Thr Gly Cys Tyr (SEQ ID NO: 285)

Cys Cys Met Phe Cys Cys Asn Pro Ala Cys
Thr Gly Cys Tyr (SEQ ID NO: 286)

Cys Cys Trp Phe Cys Cys Asn Pro Ala Cys
Thr Gly Cys Tyr (SEQ ID NO: 287)

Cys Cys Ser Phe Cys Cys Asn Pro Ala Cys
Thr Gly Cys Tyr (SEQ ID NO: 288)

Cys Cys Cys Phe Cys Cys Asn Pro Ala Cys
Thr Gly Cys Tyr (SEQ ID NO: 289)

Cys Cys Gln Phe Cys Cys Asn Pro Ala Cys
Thr Gly Cys Tyr (SEQ ID NO: 290)

Cys Cys Asp Phe Cys Cys Asn Pro Ala Cys
Thr Gly Cys Tyr (SEQ ID NO: 291)

Cys Cys Arg Phe Cys Cys Asn Pro Ala Cys
Thr Gly Cys Tyr (SEQ ID NO: 292)

Cys Cys Ala Phe Cys Cys Asn Pro Ala Cys
Thr Gly Cys (SEQ ID NO: 293)

Cys Cys Leu Phe Cys Cys Asn Pro Ala Cys
Thr Gly Cys (SEQ ID NO: 294)

TABLE A3-continued

Cys Cys Met Phe Cys Cys Asn Pro Ala Cys
Thr Gly Cys (SEQ ID NO: 295)

Cys Cys Trp Phe Cys Cys Asn Pro Ala Cys
Thr Gly Cys (SEQ ID NO: 296)

Cys Cys Ser Phe Cys Cys Asn Pro Ala Cys
Thr Gly Cys (SEQ ID NO: 297)

Cys Cys Cys Phe Cys Cys Asn Pro Ala Cys
Thr Gly Cys (SEQ ID NO: 298)

Cys Cys Gln Phe Cys Cys Asn Pro Ala Cys
Thr Gly Cys (SEQ ID NO: 299)

Cys Cys Asp Phe Cys Cys Asn Pro Ala Cys
Thr Gly Cys (SEQ ID NO: 300)

Cys Cys Arg Phe Cys Cys Asn Pro Ala Cys
Thr Gly Cys (SEQ ID NO: 301)

Cys Cys Ala Trp Cys Cys Asn Pro Ala Cys
Thr Gly Cys Tyr (SEQ ID NO: 302)

Cys Cys Leu Trp Cys Cys Asn Pro Ala Cys
Thr Gly Cys Tyr (SEQ ID NO: 303)

Cys Cys Met Trp Cys Cys Asn Pro Ala Cys
Thr Gly Cys Tyr (SEQ ID NO: 304)

Cys Cys Trp Trp Cys Cys Asn Pro Ala Cys
Thr Gly Cys Tyr (SEQ ID NO: 305)

Cys Cys Ser Trp Cys Cys Asn Pro Ala Cys
Thr Gly Cys Tyr (SEQ ID NO: 306)

Cys Cys Cys Trp Cys Cys Asn Pro Ala Cys
Thr Gly Cys Tyr (SEQ ID NO: 307)

Cys Cys Gln Trp Cys Cys Asn Pro Ala Cys
Thr Gly Cys Tyr (SEQ ID NO: 308)

Cys Cys Asp Trp Cys Cys Asn Pro Ala Cys
Thr Gly Cys Tyr (SEQ ID NO: 309)

Cys Cys Arg Trp Cys Cys Asn Pro Ala Cys
Thr Gly Cys Tyr (SEQ ID NO: 310)

Cys Cys Ala Trp Cys Cys Asn Pro Ala Cys
Thr Gly Cys (SEQ ID NO: 311)

Cys Cys Leu Trp Cys Cys Asn Pro Ala Cys
Thr Gly Cys (SEQ ID NO: 312)

Cys Cys Met Trp Cys Cys Asn Pro Ala Cys
Thr Gly Cys (SEQ ID NO: 313)

Cys Cys Trp Trp Cys Cys Asn Pro Ala Cys
Thr Gly Cys (SEQ ID NO: 314)

Cys Cys Ser Trp Cys Cys Asn Pro Ala Cys
Thr Gly Cys (SEQ ID NO: 315)

Cys Cys Cys Trp Cys Cys Asn Pro Ala Cys
Thr Gly Cys (SEQ ID NO: 316)

Cys Cys Gln Trp Cys Cys Asn Pro Ala Cys
Thr Gly Cys (SEQ ID NO: 317)

Cys Cys Asp Trp Cys Cys Asn Pro Ala Cys
Thr Gly Cys (SEQ ID NO: 318)

Cys Cys Arg Trp Cys Cys Asn Pro Ala Cys
Thr Gly Cys (SEQ ID NO: 319)

Cys Cys Glu Leu Cys Cys Val Pro Ala Cys
Thr Gly Cys Tyr (SEQ ID NO: 320)

TABLE A3-continued

Cys Cys Glu Leu Cys Cys Ile Pro Ala Cys
Thr Gly Cys Tyr (SEQ ID NO: 321)

Cys Cys Glu Leu Cys Cys Met Pro Ala Cys
Thr Gly Cys Tyr (SEQ ID NO: 322)

Cys Cys Glu Leu Cys Cys Trp Pro Ala Cys
Thr Gly Cys Tyr (SEQ ID NO: 323)

Cys Cys Glu Leu Cys Cys Ser Pro Ala Cys
Thr Gly Cys Tyr (SEQ ID NO: 324)

Cys Cys Glu Leu Cys Cys Cys Pro Ala Cys
Thr Gly Cys Tyr (SEQ ID NO: 325)

Cys Cys Glu Leu Cys Cys Tyr Pro Ala Cys
Thr Gly Cys Tyr (SEQ ID NO: 326)

Cys Cys Glu Leu Cys Cys Glu Pro Ala Cys
Thr Gly Cys Tyr (SEQ ID NO: 327)

Cys Cys Glu Leu Cys Cys Arg Pro Ala Cys
Thr Gly Cys Tyr (SEQ ID NO: 328)

Cys Cys Glu Tyr Cys Cys Ala Pro Ala Cys
Thr Gly Cys Tyr (SEQ ID NO: 329)

Cys Cys Glu Tyr Cys Cys Leu Pro Ala Cys
Thr Gly Cys Tyr (SEQ ID NO: 330)

Cys Cys Glu Tyr Cys Cys Pro Pro Ala Cys
Thr Gly Cys Tyr (SEQ ID NO: 331)

Cys Cys Glu Tyr Cys Cys Phe Pro Ala Cys
Thr Gly Cys Tyr (SEQ ID NO: 332)

Cys Cys Glu Tyr Cys Cys Gly Pro Ala Cys
Thr Gly Cys Tyr (SEQ ID NO: 333)

Cys Cys Glu Tyr Cys Cys Thr Pro Ala Cys
Thr Gly Cys Tyr (SEQ ID NO: 334)

Cys Cys Glu Tyr Cys Cys Gln Pro Ala Cys
Thr Gly Cys Tyr (SEQ ID NO: 335)

Cys Cys Glu Tyr Cys Cys Asp Pro Ala Cys
Thr Gly Cys Tyr (SEQ ID NO: 336)

Cys Cys Glu Tyr Cys Cys Lys Pro Ala Cys
Thr Gly Cys Tyr (SEQ ID NO: 337)

Cys Cys Glu Tyr Cys Cys His Pro Ala Cys
Thr Gly Cys Tyr (SEQ ID NO: 338)

Cys Cys Glu Leu Cys Cys Val Pro Ala Cys
Thr Gly Cys (SEQ ID NO: 339)

Cys Cys Glu Leu Cys Cys Ile Pro Ala Cys
Thr Gly Cys (SEQ ID NO: 340)

Cys Cys Glu Leu Cys Cys Met Pro Ala Cys
Thr Gly Cys (SEQ ID NO: 341)

Cys Cys Glu Leu Cys Cys Trp Pro Ala Cys
Thr Gly Cys (SEQ ID NO: 342)

Cys Cys Glu Leu Cys Cys Ser Pro Ala Cys
Thr Gly Cys (SEQ ID NO: 343)

Cys Cys Glu Leu Cys Cys Cys Pro Ala Cys
Thr Gly Cys (SEQ ID NO: 344)

Cys Cys Glu Leu Cys Cys Tyr Pro Ala Cys
Thr Gly Cys (SEQ ID NO: 345)

Cys Cys Glu Leu Cys Cys Glu Pro Ala Cys
Thr Gly Cys (SEQ ID NO: 346)

Cys Cys Glu Leu Cys Cys Arg Pro Ala Cys
Thr Gly Cys (SEQ ID NO: 347)

TABLE A3-continued

Cys Cys Glu Tyr Cys Cys Ala Pro Ala Cys
Thr Gly Cys (SEQ ID NO: 348)

Cys Cys Glu Tyr Cys Cys Leu Pro Ala Cys
Thr Gly Cys (SEQ ID NO: 349)

Cys Cys Glu Tyr Cys Cys Pro Pro Ala Cys
Thr Gly Cys (SEQ ID NO: 350)

Cys Cys Glu Tyr Cys Cys Phe Pro Ala Cys
Thr Gly Cys (SEQ ID NO: 351)

Cys Cys Glu Tyr Cys Cys Gly Pro Ala Cys
Thr Gly Cys (SEQ ID NO: 352)

Cys Cys Glu Tyr Cys Cys Thr Pro Ala Cys
Thr Gly Cys (SEQ ID NO: 353)

Cys Cys Glu Tyr Cys Cys Gln Pro Ala Cys
Thr Gly Cys (SEQ ID NO: 354)

Cys Cys Glu Tyr Cys Cys Asp Pro Ala Cys
Thr Gly Cys (SEQ ID NO: 355)

Cys Cys Glu Tyr Cys Cys Lys Pro Ala Cys
Thr Gly Cys (SEQ ID NO: 356)

Cys Cys Glu Tyr Cys Cys His Pro Ala Cys
Thr Gly Cys (SEQ ID NO: 357)

Cys Cys Glu Tyr Cys Cys Asn Pro Thr Cys
Thr Gly Cys Tyr (SEQ ID NO: 358)

Cys Cys Glu Tyr Cys Cys Asn Pro Thr Cys
Thr Gly Cys (SEQ ID NO: 359)

Cys Cys Glu Phe Cys Cys Asn Pro Thr Cys
Thr Gly Cys (SEQ ID NO: 360)

Cys Cys Glu Trp Cys Cys Asn Pro Thr Cys
Thr Gly Cys (SEQ ID NO: 361)

Cys Cys Glu Tyr Cys Cys Asn Gly Ala Cys
Thr Gly Cys Tyr (SEQ ID NO: 362)

Cys Cys Glu Tyr Cys Cys Asn Gly Ala Cys
Thr Gly Cys (SEQ ID NO: 363)

Cys Cys Glu Phe Cys Cys Asn Gly Ala Cys
Thr Gly Cys (SEQ ID NO: 364)

Cys Cys Glu Trp Cys Cys Asn Gly Ala Cys
Thr Gly Cys (SEQ ID NO: 365)

Cys Cys Glu Tyr Cys Cys Asn Pro Ala Cys
Val Gly Cys Tyr (SEQ ID NO: 366)

Cys Cys Glu Tyr Cys Cys Asn Pro Ala Cys
Val Gly Cys (SEQ ID NO: 367)

Cys Cys Glu Phe Cys Cys Asn Pro Ala Cys
Val Gly Cys (SEQ ID NO: 368)

Cys Cys Glu Trp Cys Cys Asn Pro Ala Cys
Val Gly Cys (SEQ ID NO: 369)

Cys Cys Glu Tyr Cys Cys Asn Pro Ala Cys
Gly Gly Cys Tyr (SEQ ID NO: 370)

Cys Cys Glu Tyr Cys Cys Asn Pro Ala Cys
Gly Gly Cys (SEQ ID NO: 371)

Cys Cys Glu Phe Cys Cys Asn Pro Ala Cys
Gly Gly Cys (SEQ ID NO: 372)

Cys Cys Glu Trp Cys Cys Asn Pro Ala Cys
Gly Gly Cys (SEQ ID NO: 373)

Cys Cys Glu Tyr Cys Cys Asn Pro Ala Cys
Thr Ala Cys Tyr (SEQ ID NO: 374)

TABLE A3-continued

Cys Cys Glu Tyr Cys Cys Asn Pro Ala Cys
Thr Ala Cys (SEQ ID NO: 375)

Cys Cys Glu Trp Cys Cys Asn Pro Ala Cys
Thr Ala Cys (SEQ ID NO: 376)

Cys Cys Glu Phe Cys Cys Asn Pro Ala Cys
Thr Ala Cys (SEQ ID NO: 377)

Cys Cys Glu Leu Cys Cys Asn Pro Ala Cys
Thr Gly Cys Val (SEQ ID NO: 378)

Cys Cys Glu Leu Cys Cys Asn Pro Ala Cys
Thr Gly Cys Ile (SEQ ID NO: 379)

Cys Cys Glu Leu Cys Cys Asn Pro Ala Cys
Thr Gly Cys Met (SEQ ID NO: 380)

Cys Cys Glu Leu Cys Cys Asn Pro Ala Cys
Thr Gly Cys Tip (SEQ ID NO: 381)

Cys Cys Glu Leu Cys Cys Asn Pro Ala Cys
Thr Gly Cys Ser (SEQ ID NO: 382)

Cys Cys Glu Leu Cys Cys Asn Pro Ala Cys
Thr Gly Cys Cys (SEQ ID NO: 383)

Cys Cys Glu Leu Cys Cys Asn Pro Ala Cys
Thr Gly Cys Gln (SEQ ID NO: 384)

Cys Cys Glu Leu Cys Cys Asn Pro Ala Cys
Thr Gly Cys Glu (SEQ ID NO: 385)

Cys Cys Glu Leu Cys Cys Asn Pro Ala Cys
Thr Gly Cys Arg (SEQ ID NO: 386)

Cys Cys Glu Tyr Cys Cys Asn Pro Ala Cys
Thr Gly Cys Ala (SEQ ID NO: 387)

Cys Cys Glu Tyr Cys Cys Asn Pro Ala Cys
Thr Gly Cys Leu (SEQ ID NO: 388)

Cys Cys Glu Tyr Cys Cys Asn Pro Ala Cys
Thr Gly Cys Pro (SEQ ID NO: 389)

Cys Cys Glu Tyr Cys Cys Asn Pro Ala Cys
Thr Gly Cys Phe (SEQ ID NO: 390)

Cys Cys Glu Tyr Cys Cys Asn Pro Ala Cys
Thr Gly Cys Gly (SEQ ID NO: 391)

Cys Cys Glu Tyr Cys Cys Asn Pro Ala Cys
Thr Gly Cys Thr (SEQ ID NO: 392)

Cys Cys Glu Tyr Cys Cys Asn Pro Ala Cys
Thr Gly Cys Asn (SEQ ID NO: 393)

Cys Cys Glu Tyr Cys Cys Asn Pro Ala Cys
Thr Gly Cys Asp (SEQ ID NO: 394)

Cys Cys Glu Tyr Cys Cys Asn Pro Ala Cys
Thr Gly Cys Lys (SEQ ID NO: 395)

Cys Cys Glu Tyr Cys Cys Asn Pro Ala Cys
Thr Gly Cys His (SEQ ID NO: 396)

Cys Cys Val Leu Cys Cys Asn Pro Ala Cys
Thr Gly Cys Tyr (SEQ ID NO: 397)

Cys Cys Ile Leu Cys Cys Asn Pro Ala Cys
Thr Gly Cys Tyr (SEQ ID NO: 398)

Cys Cys Phe Leu Cys Cys Asn Pro Ala Cys
Thr Gly Cys Tyr (SEQ ID NO: 399)

Cys Cys Gly Leu Cys Cys Asn Pro Ala Cys
Thr Gly Cys Tyr (SEQ ID NO: 400)

TABLE A3-continued

Cys Cys Thr Leu Cys Cys Asn Pro Ala Cys
Thr Gly Cys Tyr (SEQ ID NO: 401)

Cys Cys Asn Leu Cys Cys Asn Pro Ala Cys
Thr Gly Cys Tyr (SEQ ID NO: 402)

Cys Cys Tyr Leu Cys Cys Asn Pro Ala Cys
Thr Gly Cys Tyr (SEQ ID NO: 403)

Cys Cys Lys Leu Cys Cys Asn Pro Ala Cys
Thr Gly Cys Tyr (SEQ ID NO: 404)

Cys Cys His Leu Cys Cys Asn Pro Ala Cys
Thr Gly Cys Tyr (SEQ ID NO: 405)

Cys Cys Val Leu Cys Cys Asn Pro Ala Cys
Thr Gly Cys (SEQ ID NO: 406)

Cys Cys Ile Leu Cys Cys Asn Pro Ala Cys
Thr Gly Cys (SEQ ID NO: 407)

Cys Cys Phe Leu Cys Cys Asn Pro Ala Cys
Thr Gly Cys (SEQ ID NO: 408)

Cys Cys Gly Leu Cys Cys Asn Pro Ala Cys
Thr Gly Cys (SEQ ID NO: 409)

Cys Cys Thr Leu Cys Cys Asn Pro Ala Cys
Thr Gly Cys (SEQ ID NO: 410)

Cys Cys Asn Leu Cys Cys Asn Pro Ala Cys
Thr Gly Cys (SEQ ID NO: 411)

Cys Cys Tyr Leu Cys Cys Asn Pro Ala Cys
Thr Gly Cys (SEQ ID NO: 412)

Cys Cys Lys Leu Cys Cys Asn Pro Ala Cys
Thr Gly Cys (SEQ ID NO: 413)

Cys Cys His Leu Cys Cys Asn Pro Ala Cys
Thr Gly Cys (SEQ ID NO: 414)

Cys Cys Val Tyr Cys Cys Asn Pro Ala Cys
Thr Gly Cys Tyr (SEQ ID NO: 415)

Cys Cys Ile Tyr Cys Cys Asn Pro Ala Cys
Thr Gly Cys Tyr (SEQ ID NO: 416)

Cys Cys Phe Tyr Cys Cys Asn Pro Ala Cys
Thr Gly Cys Tyr (SEQ ID NO: 417)

Cys Cys Gly Tyr Cys Cys Asn Pro Ala Cys
Thr Gly Cys Tyr (SEQ ID NO: 418)

Cys Cys Thr Tyr Cys Cys Asn Pro Ala Cys
Thr Gly Cys Tyr (SEQ ID NO: 419)

Cys Cys Asn Tyr Cys Cys Asn Pro Ala Cys
Thr Gly Cys Tyr (SEQ ID NO: 420)

Cys Cys Tyr Tyr Cys Cys Asn Pro Ala Cys
Thr Gly Cys Tyr (SEQ ID NO: 421)

Cys Cys Lys Tyr Cys Cys Asn Pro Ala Cys
Thr Gly Cys Tyr (SEQ ID NO: 422)

Cys Cys His Tyr Cys Cys Asn Pro Ala Cys
Thr Gly Cys Tyr (SEQ ID NO: 423)

Cys Cys Val Tyr Cys Cys Asn Pro Ala Cys
Thr Gly Cys (SEQ ID NO: 424)

Cys Cys Ile Tyr Cys Cys Asn Pro Ala Cys
Thr Gly Cys (SEQ ID NO: 425)

Cys Cys Phe Tyr Cys Cys Asn Pro Ala Cys
Thr Gly Cys (SEQ ID NO: 426)

Cys Cys Gly Tyr Cys Cys Asn Pro Ala Cys
Thr Gly Cys (SEQ ID NO: 427)

Cys Cys Thr Tyr Cys Cys Asn Pro Ala Cys
Thr Gly Cys (SEQ ID NO: 428)

Cys Cys Asn Tyr Cys Cys Asn Pro Ala Cys
Thr Gly Cys (SEQ ID NO: 429)

Cys Cys Tyr Tyr Cys Cys Asn Pro Ala Cys
Thr Gly Cys (SEQ ID NO: 430)

Cys Cys Lys Tyr Cys Cys Asn Pro Ala Cys
Thr Gly Cys (SEQ ID NO: 431)

Cys Cys His Tyr Cys Cys Asn Pro Ala Cys
Thr Gly Cys (SEQ ID NO: 432)

Cys Cys Glu Phe Cys Cys Val Pro Ala Cys
Thr Gly Cys Tyr (SEQ ID NO: 433)

Cys Cys Glu Phe Cys Cys Ile Pro Ala Cys
Thr Gly Cys Tyr (SEQ ID NO: 434)

Cys Cys Glu Phe Cys Cys Met Pro Ala Cys
Thr Gly Cys Tyr (SEQ ID NO: 435)

Cys Cys Glu Phe Cys Cys Trp Pro Ala Cys
Thr Gly Cys Tyr (SEQ ID NO: 436)

Cys Cys Glu Phe Cys Cys Ser Pro Ala Cys
Thr Gly Cys Tyr (SEQ ID NO: 437)

Cys Cys Glu Phe Cys Cys Cys Pro Ala Cys
Thr Gly Cys Tyr (SEQ ID NO: 438)

Cys Cys Glu Phe Cys Cys Tyr Pro Ala Cys
Thr Gly Cys Tyr (SEQ ID NO: 439)

Cys Cys Glu Phe Cys Cys Glu Pro Ala Cys
Thr Gly Cys Tyr (SEQ ID NO: 440)

Cys Cys Glu Phe Cys Cys Arg Pro Ala Cys
Thr Gly Cys Tyr (SEQ ID NO: 441)

Cys Cys Glu Phe Cys Cys Ala Pro Ala Cys
Thr Gly Cys (SEQ ID NO: 442)

Cys Cys Glu Phe Cys Cys Leu Pro Ala Cys
Thr Gly Cys (SEQ ID NO: 443)

Cys Cys Glu Phe Cys Cys Pro Pro Ala Cys
Thr Gly Cys (SEQ ID NO: 444)

Cys Cys Glu Phe Cys Cys Phe Pro Ala Cys
Thr Gly Cys (SEQ ID NO: 445)

Cys Cys Glu Phe Cys Cys Gly Pro Ala Cys
Thr Gly Cys (SEQ ID NO: 446)

Cys Cys Glu Phe Cys Cys Thr Pro Ala Cys
Thr Gly Cys (SEQ ID NO: 447)

Cys Cys Glu Phe Cys Cys Gln Pro Ala Cys
Thr Gly Cys (SEQ ID NO: 448)

Cys Cys Glu Phe Cys Cys Asp Pro Ala Cys
Thr Gly Cys (SEQ ID NO: 449)

Cys Cys Glu Phe Cys Cys Lys Pro Ala Cys
Thr Gly Cys (SEQ ID NO: 450)

Cys Cys Glu Phe Cys Cys His Pro Ala Cys
Thr Gly Cys (SEQ ID NO: 451)

Cys Cys Glu Trp Cys Cys Val Pro Ala Cys
Thr Gly Cys Tyr (SEQ ID NO: 452)

Cys Cys Glu Trp Cys Cys Ile Pro Ala Cys
Thr Gly Cys Tyr (SEQ ID NO: 453)

TABLE A3-continued

Cys Cys Glu Trp Cys Cys Met Pro Ala Cys
Thr Gly Cys Tyr (SEQ ID NO: 454)

Cys Cys Glu Trp Cys Cys Trp Pro Ala Cys
Thr Gly Cys Tyr (SEQ ID NO: 455)

Cys Cys Glu Trp Cys Cys Ser Pro Ala Cys
Thr Gly Cys Tyr (SEQ ID NO: 456)

Cys Cys Glu Trp Cys Cys Cys Pro Ala Cys
Thr Gly Cys Tyr (SEQ ID NO: 457)

Cys Cys Glu Trp Cys Cys Tyr Pro Ala Cys
Thr Gly Cys Tyr (SEQ ID NO: 458)

Cys Cys Glu Trp Cys Cys Glu Pro Ala Cys
Thr Gly Cys Tyr (SEQ ID NO: 459)

Cys Cys Glu Trp Cys Cys Arg Pro Ala Cys
Thr Gly Cys Tyr (SEQ ID NO: 460)

Cys Cys Glu Trp Cys Cys Ala Pro Ala Cys
Thr Gly Cys (SEQ ID NO: 461)

Cys Cys Glu Trp Cys Cys Leu Pro Ala Cys
Thr Gly Cys (SEQ ID NO: 462)

Cys Cys Glu Trp Cys Cys Pro Pro Ala Cys
Thr Gly Cys (SEQ ID NO: 463)

Cys Cys Glu Trp Cys Cys Phe Pro Ala Cys
Thr Gly Cys (SEQ ID NO: 464)

Cys Cys Glu Trp Cys Cys Gly Pro Ala Cys
Thr Gly Cys (SEQ ID NO: 465)

Cys Cys Glu Trp Cys Cys Thr Pro Ala Cys
Thr Gly Cys (SEQ ID NO: 466)

Cys Cys Glu Trp Cys Cys Gln Pro Ala Cys
Thr Gly Cys (SEQ ID NO: 467)

Cys Cys Glu Trp Cys Cys Asp Pro Ala Cys
Thr Gly Cys (SEQ ID NO: 468)

Cys Cys Glu Trp Cys Cys Lys Pro Ala Cys
Thr Gly Cys (SEQ ID NO: 469)

Cys Cys Glu Trp Cys Cys His Pro Ala Cys
Thr Gly Cys (SEQ ID NO: 470)

Cys Cys Glu Trp Cys Cys Asn Pro Ala Cys
Thr Gly Cys Val (SEQ ID NO: 471)

Cys Cys Glu Trp Cys Cys Asn Pro Ala Cys
Thr Gly Cys Ile (SEQ ID NO: 472)

Cys Cys Glu Trp Cys Cys Asn Pro Ala Cys
Thr Gly Cys Met (SEQ ID NO: 473)

Cys Cys Glu Trp Cys Cys Asn Pro Ala Cys
Thr Gly Cys Trp (SEQ ID NO: 474)

Cys Cys Glu Trp Cys Cys Asn Pro Ala Cys
Thr Gly Cys Ser (SEQ ID NO: 475)

Cys Cys Glu Trp Cys Cys Asn Pro Ala Cys
Thr Gly Cys Cys (SEQ ID NO: 476)

Cys Cys Glu Trp Cys Cys Asn Pro Ala Cys
Thr Gly Cys Gln (SEQ ID NO: 477)

Cys Cys Glu Trp Cys Cys Asn Pro Ala Cys
Thr Gly Cys Glu (SEQ ID NO: 478)

Cys Cys Glu Trp Cys Cys Asn Pro Ala Cys
Thr Gly Cys Arg (SEQ ID NO: 479)

Cys Cys Glu Phe Cys Cys Asn Pro Ala Cys
Thr Gly Cys Ala (SEQ ID NO: 480)

Cys Cys Glu Phe Cys Cys Asn Pro Ala Cys
Thr Gly Cys Leu (SEQ ID NO: 481)

Cys Cys Glu Phe Cys Cys Asn Pro Ala Cys
Thr Gly Cys Pro (SEQ ID NO: 482)

Cys Cys Glu Phe Cys Cys Asn Pro Ala Cys
Thr Gly Cys Phe (SEQ ID NO: 483)

Cys Cys Glu Phe Cys Cys Asn Pro Ala Cys
Thr Gly Cys Gly (SEQ ID NO: 484)

Cys Cys Glu Phe Cys Cys Asn Pro Ala Cys
Thr Gly Cys Thr (SEQ ID NO: 485)

Cys Cys Glu Phe Cys Cys Asn Pro Ala Cys
Thr Gly Cys Asn (SEQ ID NO: 486)

Cys Cys Glu Phe Cys Cys Asn Pro Ala Cys
Thr Gly Cys Asp (SEQ ID NO: 487)

Cys Cys Glu Phe Cys Cys Asn Pro Ala Cys
Thr Gly Cys Lys (SEQ ID NO: 488)

Cys Cys Glu Phe Cys Cys Asn Pro Ala Cys
Thr Gly Cys His (SEQ ID NO: 489)

Cys Cys Val Phe Cys Cys Asn Pro Ala Cys
Thr Gly Cys Tyr (SEQ ID NO: 490)

Cys Cys Ile Phe Cys Cys Asn Pro Ala Cys
Thr Gly Cys Tyr (SEQ ID NO: 491)

Cys Cys Phe Phe Cys Cys Asn Pro Ala Cys
Thr Gly Cys Tyr (SEQ ID NO: 492)

Cys Cys Gly Phe Cys Cys Asn Pro Ala Cys
Thr Gly Cys Tyr (SEQ ID NO: 493)

Cys Cys Thr Phe Cys Cys Asn Pro Ala Cys
Thr Gly Cys Tyr (SEQ ID NO: 494)

Cys Cys Asn Phe Cys Cys Asn Pro Ala Cys
Thr Gly Cys Tyr (SEQ ID NO: 495)

Cys Cys Tyr Phe Cys Cys Asn Pro Ala Cys
Thr Gly Cys Tyr (SEQ ID NO: 496)

Cys Cys Lys Phe Cys Cys Asn Pro Ala Cys
Thr Gly Cys Tyr (SEQ ID NO: 497)

Cys Cys His Phe Cys Cys Asn Pro Ala Cys
Thr Gly Cys Tyr (SEQ ID NO: 498)

Cys Cys Val Phe Cys Cys Asn Pro Ala Cys
Thr Gly Cys (SEQ ID NO: 499)

Cys Cys Ile Phe Cys Cys Asn Pro Ala Cys
Thr Gly Cys (SEQ ID NO: 500)

Cys Cys Phe Phe Cys Cys Asn Pro Ala Cys
Thr Gly Cys (SEQ ID NO: 501)

Cys Cys Gly Phe Cys Cys Asn Pro Ala Cys
Thr Gly Cys (SEQ ID NO: 502)

Cys Cys Thr Phe Cys Cys Asn Pro Ala Cys
Thr Gly Cys (SEQ ID NO: 503)

Cys Cys Asn Phe Cys Cys Asn Pro Ala Cys
Thr Gly Cys (SEQ ID NO: 504)

Cys Cys Tyr Phe Cys Cys Asn Pro Ala Cys
Thr Gly Cys (SEQ ID NO: 505)

Cys Cys Lys Phe Cys Cys Asn Pro Ala Cys
Thr Gly Cys (SEQ ID NO: 506)

TABLE A3-continued

```
Cys Cys His Phe Cys Cys Asn Pro Ala Cys
Thr Gly Cys (SEQ ID NO: 507)

Cys Cys Val Trp Cys Cys Asn Pro Ala Cys
Thr Gly Cys Tyr (SEQ ID NO: 508)

Cys Cys Ile Trp Cys Cys Asn Pro Ala Cys
Thr Gly Cys Tyr (SEQ ID NO: 509)

Cys Cys Phe Trp Cys Cys Asn Pro Ala Cys
Thr Gly Cys Tyr (SEQ ID NO: 510)

Cys Cys Gly Trp Cys Cys Asn Pro Ala Cys
Thr Gly Cys Tyr (SEQ ID NO: 511)

Cys Cys Thr Trp Cys Cys Asn Pro Ala Cys
Thr Gly Cys Tyr (SEQ ID NO: 512)

Cys Cys Asn Trp Cys Cys Asn Pro Ala Cys
Thr Gly Cys Tyr (SEQ ID NO: 513)

Cys Cys Tyr Trp Cys Cys Asn Pro Ala Cys
Thr Gly Cys Tyr (SEQ ID NO: 514)

Cys Cys Lys Trp Cys Cys Asn Pro Ala Cys
Thr Gly Cys Tyr (SEQ ID NO: 515)

Cys Cys His Trp Cys Cys Asn Pro Ala Cys
Thr Gly Cys Tyr (SEQ ID NO: 516)

Cys Cys Val Trp Cys Cys Asn Pro Ala Cys
Thr Gly Cys (SEQ ID NO: 517)

Cys Cys Ile Trp Cys Cys Asn Pro Ala Cys
Thr Gly Cys (SEQ ID NO: 518)

Cys Cys Phe Trp Cys Cys Asn Pro Ala Cys
Thr Gly Cys (SEQ ID NO: 519)

Cys Cys Gly Trp Cys Cys Asn Pro Ala Cys
Thr Gly Cys (SEQ ID NO: 520)

Cys Cys Thr Trp Cys Cys Asn Pro Ala Cys
Thr Gly Cys (SEQ ID NO: 521)

Cys Cys Asn Trp Cys Cys Asn Pro Ala Cys
Thr Gly Cys (SEQ ID NO: 522)

Cys Cys Tyr Trp Cys Cys Asn Pro Ala Cys
Thr Gly Cys (SEQ ID NO: 523)

Cys Cys Lys Trp Cys Cys Asn Pro Ala Cys
Thr Gly Cys (SEQ ID NO: 524)

Cys Cys His Trp Cys Cys Asn Pro Ala Cys
Thr Gly Cys (SEQ ID NO: 525)
```

In specific embodiments, the GC-C agonist peptide comprises, consists, or consists essentially of the amino acid sequence Cys Cys Glu Tyr Cys Cys Asn Pro Ala Cys Thr Gly Cys Tyr (SEQ ID NO:4).

Also included are deletion variants of any of the GC-C agonist peptides described herein. Examples include deletion variants where one, two, three or four amino acids (or non-natural amino acids or natural or non-natural amino acid analogs), other than a Cys (or an amino acid substituted for Cys, e.g., an amino acid capable of forming a covalent bond to another amino acid), are deleted. Specific examples include where two (or more) amino acids are deleted and the peptide comprises the sequence: $Cys_a$ $CyS_b$ Xaa Xaa $Cys_c$ $Cys_d$ Xaa Xaa Xaa $Cys_e$ Xaa Xaa $Cys_f$ (SEQ ID NO:526). In some of these and related embodiments, two or more deletions can be located between $Cys_b$ and $Cys_e$ and/or between $Cys_d$ and $Cys_e$ and/or between $Cys_e$ and $Cys_f$. However, in other embodiments there is at most one deletion between each of $Cys_b$ and $Cys_e$ or between $Cys_d$ and $Cys_e$ or between $Cys_e$ and $Cys_f$. Thus, included are any of the GC-C agonist peptides described herein comprising the sequence $Cys_a$ $CyS_b$ Xaa Xaa $Cys_e$ $Cys_d$ Xaa Xaa Xaa $Cys_e$ Xaa Xaa $Cys_f$ (SEQ ID NO:526) where: a) one amino acid between $Cys_b$ and $Cys_e$ is deleted; b) one amino acid between $Cys_d$ and $Cys_e$ is deleted; c) one amino acid between $Cys_e$ and $Cys_f$ is deleted; d) one amino acid between $Cys_b$ and $Cys_e$ is deleted and one amino acid between $Cys_d$ and $Cys_e$ is deleted; e) one amino acid between $Cys_d$ and $Cys_e$ is deleted and one amino acid between $Cys_e$ and $Cys_f$ is deleted; f) one amino acid between $Cys_b$ and $Cys_e$ is deleted and one amino acid between $Cys_e$ and $Cys_f$ is deleted or g) one amino acid between $Cys_b$ and $Cys_e$ is deleted, one amino acid between $Cys_d$ and $Cys_e$ is deleted and one amino acid between $Cys_e$ and $Cys_f$ is deleted. In certain embodiments, the deletion variants are peptides that bind to and/or agonize the GC-C receptor.

Also included are insertion variants of any of the GC-C agonist peptides described herein. Examples include insertion variants where one, two, three or four amino acids (e.g., Gly or Ala) are inserted before or after any amino acid in the peptide. In some embodiments, no more than one amino acid is inserted between two Cys residues. Particular examples include where two or more amino acids are inserted and the peptide comprises the sequence $Cys_a$ $CyS_b$ Xaa Xaa $Cys_e$ $CyS_d$ Xaa Xaa Xaa $Cys_e$ Xaa Xaa $Cys_f$ (SEQ ID NO:526). In some of these and related embodiments, two or more insertions can be located between $Cys_b$ and $Cys_e$ or between $Cys_d$ and $Cys_e$ or between $Cys_e$ and $Cys_f$. However, in other embodiments, no more than one insertion is located between $Cys_b$ and $Cys_e$ or between $Cys_d$ and $Cys_e$ or between $Cys_e$ and $Cys_f$. Thus, included are any of the GC-C agonist peptides described herein comprising the sequence $Cys_a$ $CyS_b$ Xaa Xaa $Cys_e$ $Cys_d$ Xaa Xaa Xaa $Cys_e$ Xaa Xaa $Cys_f$ (SEQ ID NO:526) where: a) one amino acid is inserted between $Cys_b$ and $Cys_e$; b) one amino acid is inserted between $Cys_d$ and $Cys_e$; c) one amino acid is inserted between $Cys_e$ and $Cys_f$; d) one amino acid is inserted between $Cys_b$ and $Cys_e$ and one amino acid is inserted between $Cys_d$ and $Cys_e$; e) one amino acid is inserted between $CyS_d$ and $Cys_e$ and one amino acid is inserted between $Cys_e$ and $Cys_f$; f) one amino acid is inserted between $Cys_b$ and $Cys_e$ and one amino acid is inserted between $Cys_e$ and $Cys_f$ or g) one amino acid is inserted between $Cys_b$ and $Cys_e$, one amino acid is inserted between $Cys_d$ and $Cys_e$ and one amino acid is inserted between $Cys_e$ and $Cys_f$. In addition, one or more amino acids can be inserted preceding $Cys_a$ and/or one or more amino acids can be inserted following $Cys_f$. In some embodiments, the insertion variants are peptides that bind to and/or agonize the GC-C receptor.

Examples of insertion variants of Cys Cys Glu Tyr Cys Cys Asn Pro Ala Cys Thr Gly Cys Tyr (SEQ ID NO:4) include those in which up to four amino acids (i.e., 0, 1, 2, 3 or 4) are inserted after each amino acid. Thus, included are peptides having the sequence: Cys $Xaa_{(0-4)}$ Cys $Xaa_{(0-4)}$ Glu $Xaa_{(0-4)}$ Tyr $Xaa_{(0-4)}$ Cys $Xaa_{(0-4)}$ Cys $Xaa_{(0-4)}$ Asn $Xaa_{(0-4)}$ Pro $Xaa_{(0-4)}$ Ala $Xaa_{(0-4)}$ Cys $Xaa_{(0-4)}$ Thr $Xaa_{(0-4)}$ Gly $Xaa_{(0-4)}$ Cys $Xaa_{(0-4)}$ Tyr $Xaa_{(0-4)}$ (SEQ ID NO:527). The inserted amino acids can be any amino acid or amino acid analog (natural or non-natural) and can be the same or different. In certain embodiments, the inserted amino acids are all Gly or all Ala or a combination of Gly and Ala.

Also included are GC-C agonist peptides comprising or consisting of the sequence $Xaa_1$ $Xaa_2$ $Xaa_3$ $Xaa_4$ $Xaa_5$ $Cys_6$ $Cys_7$ $Xaa_8$ $Xaa_9$ $Cys_{10}$ $Cys_{11}$ $Xaa_{12}$ $Xaa_{13}$ $Xaa_{14}$ $Cys_{15}$ $Xaa_{16}$ Xaa₁₇ Cys₁₈ Xaa₁₉ Xaa₂₀ Xaa₂₁ (SEQ ID NO:46), and including, for example, variants of Cys Cys Glu Tyr Cys Cys Asn Pro Ala Cys Thr Gly Cys Tyr (SEQ ID NO:4), in which up to four amino acids are deleted and/or up to four amino acids are inserted. In some instances, the insertions and/or deletions can be between Cys₆ and Cys₁₅ or they can be amino terminal to Cys₆ and/or carboxy terminal to Cys₁₈s.

In certain embodiments, a GC-C agonist peptide is based on the core sequence: Cys Cys Glu Leu Cys Cys Asn Pro Ala Cys Thr Gly Cys Tyr (SEQ ID NO:528). To create a variant having a potentially functional chymotrypsin cleavage site capable of inactivating the peptide, either the Leu (underlined) or the Thr (underlined) can be replaced by Trp, Phe or Tyr; or both the Leu and the Thr can be replaced by (independently) Trp, Phe, or Tyr. The core sequence can be optionally be preceded by Asn Ser Ser Asn Tyr or Asn. Specific examples of GC-C agonist peptides based on the core sequence include those in Table A4 below.

TABLE A4

| Sequence | SEQ ID NO: |
|---|---|
| Asn Ser Ser Asn Tyr Cys Cys Glu Leu Cys Cys Asn Pro Ala Cys Thr Gly Cys Tyr | 529 |
| Asn Ser Ser Asn Tyr Cys Cys Glu Leu Cys Cys Asn Pro Ala Cys Trp Gly Cys Tyr | 530 |
| Asn Ser Ser Asn Tyr Cys Cys Glu Tyr Cys Cys Asn Pro Ala Cys Thr Gly Cys Tyr | 531 |
| Cys Cys Glu Leu Cys Cys Asn Pro Ala Cys Thr Gly Cys Tyr | 528 |
| Cys Cys Glu Leu Cys Cys Asn Pro Ala Cys Trp Gly Cys Tyr | 532 |
| Cys Cys Glu Tyr Cys Cys Asn Pro Ala Cys Thr Gly Cys Tyr | 532 |
| Asn Cys Cys Glu Leu Cys Cys Asn Pro Ala Cys Thr Gly Cys Tyr | 533 |
| Asn Cys Cys Glu Leu Cys Cys Asn Pro Ala Cys Trp Gly Cys Tyr | 534 |
| Asn Cys Cys Glu Phe Cys Cys Asn Pro Ala Cys Thr Gly Cys Tyr | 535 |
| Asn Cys Cys Glu Tyr Cys Cys Asn Pro Ala Cys Thr Gly Cys Tyr | 536 |
| Asn Cys Cys Glu Trp Cys Cys Asn Pro Ala Cys Thr Gly Cys Tyr | 537 |
| Asn Cys Cys Glu Arg Cys Cys Asn Pro Ala Cys Thr Gly Cys Tyr | 538 |
| Asn Cys Cys Glu Lys Cys Cys Asn Pro Ala Cys Thr Gly Cys Tyr | 539 |
| Asn Ser Ser Asn Tyr Cys Cys Glu Leu Cys Cys Asn Pro Ala Cys Thr Gly Cys Tyr Asp Phe | 540 |
| Asn Ser Ser Asn Tyr Cys Cys Glu Leu Cys Cys Asn Pro Ala Cys Trp Gly Cys Tyr Asp Phe | 541 |
| Asn Ser Ser Asn Tyr Cys Cys Glu Phe Cys Cys Asn Pro Ala Cys Thr Gly Cys Tyr Asp Phe | 542 |
| Asn Ser Ser Asn Tyr Cys Cys Glu Tyr Cys Cys Asn Pro Ala Cys Thr Gly Cys Tyr Asp Phe | 543 |
| Asn Ser Ser Asn Tyr Cys Cys Glu Trp Cys Cys Asn Pro Ala Cys Thr Gly Cys Tyr Asp Phe | 544 |
| Asn Ser Ser Asn Tyr Cys Cys Glu Arg Cys Cys Asn Pro Ala Cys Thr Gly Cys Tyr Asp Phe | 545 |
| Asn Ser Ser Asn Tyr Cys Cys Glu Lys Cys Cys Asn Pro Ala Cys Thr Gly Cys Tyr Asp Phe | 546 |
| Cys Cys Glu Leu Cys Cys Asn Pro Ala Cys Thr Gly Cys Tyr Asp Phe | 547 |
| Cys Cys Glu Leu Cys Cys Asn Pro Ala Cys Trp Gly Cys Tyr Asp Phe | 548 |
| Cys Cys Glu Phe Cys Cys Asn Pro Ala Cys Thr Gly Cys Tyr Asp Phe | 549 |
| Cys Cys Glu Tyr Cys Cys Asn Pro Ala Cys Thr Gly Cys Tyr Asp Phe | 550 |
| Cys Cys Glu Trp Cys Cys Asn Pro Ala Cys Thr Gly Cys Tyr Asp Phe | 551 |
| Cys Cys Glu Arg Cys Cys Asn Pro Ala Cys Thr Gly Cys Tyr Asp Phe | 552 |
| Cys Cys Glu Lys Cys Cys Asn Pro Ala Cys Thr Gly Cys Tyr Asp Phe | 553 |
| Asn Cys Cys Glu Leu Cys Cys Asn Pro Ala Cys Thr Gly Cys Tyr Asp Phe | 554 |

TABLE A4-continued

| | SEQ ID NO: |
|---|---|
| Asn Cys Cys Glu Leu Cys Cys Asn Pro Ala Cys Trp Gly Cys Tyr Asp Phe | 555 |
| Asn Cys Cys Glu Phe Cys Cys Asn Pro Ala Cys Thr Gly Cys Tyr Asp Phe | 556 |
| Asn Cys Cys Glu Tyr Cys Cys Asn Pro Ala Cys Thr Gly Cys Tyr Asp Phe | 557 |
| Asn Cys Cys Glu Trp Cys Cys Asn Pro Ala Cys Thr Gly Cys Tyr Asp Phe | 558 |
| Asn Cys Cys Glu Arg Cys Cys Asn Pro Ala Cys Thr Gly Cys Tyr Asp Phe | 559 |
| Asn Cys Cys Glu Lys Cys Cys Asn Pro Ala Cys Thr Gly Cys Tyr Asp Phe | 560 |

In certain embodiments, the GC-agonist peptide is a guanylin, lymphoguanylin, uroguanylin, or a renoguanylin peptide, optionally a human peptide, or a variant or derivative or analog thereof. The amino acid sequence of human guanylin is Pro Gly Thr Cys Glu Ile Cys Ala Tyr Ala Ala Cys Thr Gly Cys (SEQ ID NO:562). Exemplary analogs of the human guanylin sequence are shown in Table A5 below.

TABLE A5

| Human Guanylin Analogs | SEQ ID NO: |
|---|---|
| Pro-Gly-Thr-Cys-Glu-Gly-Ile-Cys-Ala-Tyr-Ala-Ala-Cys-Thr-Gly-Cys | 563 |
| Pro-Gly-Thr-Cys-Glu-Ile-Gly-Cys-Ala-Tyr-Ala-Ala-Cys-Thr-Gly-Cys | 564 |
| Pro-Gly-Thr-Cys-Glu-Ile-Gly-Cys-Gly-Ala-Tyr-Ala-Ala-Cys-Thr-Gly-Cys | 565 |
| Pro-Gly-Thr-Cys-Glu-Ile-Gly-Cys-Ala-Gly-Tyr-Ala-Ala-Cys-Thr-Gly-Cys | 566 |
| Pro-Gly-Thr-Cys-Glu-Ile-Gly-Cys-Ala-Tyr-Gly-Ala-Ala-Cys-Thr-Gly-Cys | 567 |
| Pro-Gly-Thr-Cys-Glu-Ile-Gly-Cys-Ala-Tyr-Ala-Gly-Ala-Cys-Thr-Gly-Cys | 568 |
| Pro-Gly-Thr-Cys-Glu-Ile-Gly-Cys-Ala-Tyr-Ala-Ala-Gly-Cys-Thr-Gly-Cys | 569 |
| Pro-Gly-Thr-Cys-Glu-Ile-Gly-Cys-Ala-Tyr-Ala-Ala-Cys-Gly-Thr-Gly-Cys | 570 |
| Pro-Gly-Thr-Cys-Glu-Ile-Gly-Cys-Ala-Tyr-Ala-Ala-Cys-Thr-Gly-Gly-Cys | 571 |
| Pro-Gly-Thr-Cys-Ala-Glu-Ile-Cys-Ala-Tyr-Ala-Ala-Cys-Thr-Gly-Cys | 572 |
| Pro-Gly-Thr-Cys-Glu-Ala-Ile-Cys-Ala-Tyr-Ala-Ala-Cys-Thr-Gly-Cys | 573 |
| Pro-Gly-Thr-Cys-Glu-Ile-Ala-Cys-Ala-Tyr-Ala-Ala-Cys-Thr-Gly-Cys | 574 |
| Pro-Gly-Thr-Cys-Glu-Ile-Gly-Cys-Ala-Ala-Tyr-Ala-Ala-Cys-Thr-Gly-Cys | 575 |
| Pro-Gly-Thr-Cys-Glu-Ile-Gly-Cys-Ala-Tyr-Ala-Ala-Cys-Thr-Gly-Cys | 576 |
| Pro-Gly-Thr-Cys-Glu-Ile-Gly-Cys-Ala-Tyr-Ala-Ala-Cys-Ala-Thr-Gly-Cys | 577 |
| Pro-Gly-Thr-Cys-Glu-Ile-Gly-Cys-Ala-Tyr-Ala-Ala-Cys-Thr-Ala-Gly-Cys | 578 |
| Pro-Gly-Thr-Cys-Glu-Ile-Gly-Cys-Ala-Tyr-Ala-Ala-Cys-Thr-Gly-Ala-Cys | 579 |
| Pro-Gly-Thr-Cys-Ala-Glu-Ile-Cys-Ala-Ala-Tyr-Ala-Ala-Cys-Thr-Gly-Cys | 580 |
| Pro-Gly-Thr-Cys-Glu-Ala-Ile-Cys-Ala-Ala-Tyr-Ala-Ala-Cys-Thr-Gly-Cys | 581 |
| Pro-Gly-Thr-Cys-Glu-Ile-Ala-Cys-Ala-Ala-Tyr-Ala-Ala-Cys-Thr-Gly-Cys | 582 |
| $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 583 |

TABLE A5-continued

| Human Guanylin Analogs | SEQ ID NO: |
|---|---|
| Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 584 |
| Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 585 |
| Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 586 |
| Ser$^1$-His$^2$-Thr$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 587 |
| Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 588 |
| Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 589 |
| Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 590 |
| Ser$^1$-His$^2$-Thr$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 591 |
| Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 592 |
| Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 593 |
| Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 594 |
| Ser$^1$-His$^2$-Thr$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 595 |
| Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 596 |
| Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 597 |
| Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 598 |
| Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 599 |
| Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 600 |
| Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 601 |
| Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 602 |
| Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 603 |
| Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 604 |
| Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 605 |
| Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 606 |
| Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 607 |
| Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 608 |
| Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 609 |

TABLE A5-continued

| Human Guanylin Analogs | SEQ ID NO: |
|---|---|
| Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 610 |
| Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 611 |
| Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 612 |
| Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 613 |
| Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 614 |

Hence, in some embodiments, the GC-C agonist peptide comprises, consists, or consists essentially of the human guanylin sequence or a variant or derivative or analog thereof.

The amino acid sequence of lymphoguanylin is: Gln-Glu-Glu-Cys-Glu-Leu-Cys-Ile-Asn-Met-Ala-Cys-Thr-Gly-Tyr. (SEQ ID NO:615). Exemplary analogs of the human lymphoguanylin sequence are shown in Table A6 below.

TABLE A6

| Human Lymphoguanylin Analogs | SEQ ID NO: |
|---|---|
| Gln$^1$-Glu$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 616 |
| Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 617 |
| Gln$^1$-Asp$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 618 |
| Gln$^1$-Glu$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 619 |
| Gln$^1$-Glu$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 620 |
| Gln$^1$-Asp$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 621 |
| Gln$^1$-Asp$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 622 |
| Gln$^1$-Glu$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 623 |
| Gln$^1$-Glu$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 624 |
| Gln$^1$-Asp$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 625 |
| Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 626 |
| Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 627 |
| Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 628 |
| Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 629 |
| Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 630 |
| Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 631 |

TABLE A6-continued

| Human Lymphoguanylin Analogs | SEQ ID NO: |
|---|---|
| Gln$^1$-Glu$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 632 |
| Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 633 |
| Gln$^1$-Asp$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 634 |
| Gln$^1$-Glu$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 635 |
| Gln$^1$-Glu$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 636 |
| Gln$^1$-Asp$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 637 |
| Gln$^1$-Asp$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 638 |
| Gln$^1$-Glu$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 639 |
| Gln$^1$-Glu$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 640 |
| Gln$^1$-Asp$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 641 |
| Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 642 |
| Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 643 |
| Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 644 |
| Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 645 |
| Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 646 |
| Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 647 |

Hence, in some embodiments, the GC-C agonist peptide comprises, consists, or consists essentially of the human lymphoguanylin sequence or a variant or derivative or analog thereof.

The amino acid sequence of human uroguanylin is Asn Asp Asp Cys Glu Leu Cys Val Asn Val Ala Cys Thr Gly Cys Leu (SEQ ID NO:648). In some embodiments, the GC-C agonist peptide comprises, consists, or consists essentially of the human uroguanylin sequence or an analog thereof. In specific embodiments, the human uroguanylin analog has the amino acid sequence Asn Asp Glu Cys Glu Leu Cys Val Asn Val Ala Cys Thr Gly Cys Leu (SEQ ID NO:6; Plecanatide), or Gln Asp Asp Cys Glu Thr Cys Ile Asn Met Ala Cys Thr Gly Tyr (SEQ ID NO:649). In particular embodiments, the N-terminal Asn of the peptide (e.g., plecanatide) is a pyroglutamic acid. In some embodiments, the C-terminal Leu of the peptide (e.g., plecanatide) is a D-amino acid (d-Leu).

In certain embodiments, the human uroguanylin peptide or analog comprise, consists, or consists essentially of the amino acid sequence shown below (III):

(SEQ ID NO: 650)
Xaa$_1$ Xaa$_2$ Xaa$_3$ Cys$_4$ Xaa$_5$ Xaa$_6$ Xaa$_7$ Xaa$_8$ Xaa$_9$ Xaa$_{10}$

Xaa$_{11}$ Cys$_{12}$ Xaa$_{13}$ Xaa$_{14}$ Xaa$_{15}$ Xaa$_{16}$

In some embodiments, the GC-C agonist peptide of formula III is defined as follows:

Xaa$_1$ is any any natural or non-natural amino acid or amino acid analog or is missing;

Xaa$_2$ is any natural or non-natural amino acid or amino acid analog or is missing;

Xaa$_3$ is any natural or non-natural amino acid or amino acid analog or is missing;

Xaa$_5$ is Glu;

Xaa$_6$ is Tyr, Trp, Phe or Leu;

Xaa$_7$ is Cys;

Xaa$_8$ is any natural or non-natural amino acid or amino acid analog (optionally any of the 20 naturally-occurring amino acids) other than Cys or is missing;

Xaa$_9$ is any natural or non-natural amino acid or amino acid analog (optionally any of the 20 naturally-occurring amino acids) other than Cys;

Xaa$_{10}$ is Pro or Gly;

$Xaa_{11}$ is any natural or non-natural amino acid or amino acid analog (optionally any of the 20 naturally-occurring amino acids);

$Xaa_{13}$ is Thr, Val or Gly;

$Xaa_{14}$ is Gly or Ala;

$Xaa_{15}$ is Cys; and $Xaa_{16}$ is any natural or non-natural amino acid or amino acid analog (optionally any of the 20 naturally-occurring amino acids) or is missing.

In certain embodiments: $Xaa_9$ is Asn; $Xaa_{11}$ is Ala or Thr; $Xaa_8$ is missing; and $Xaa_{16}$ is Tyr.

In some embodiments $Xaa_4$ is immediately preceded by an amino acid sequence selected from: Ser His Thr; Pro Ser Thr; Thr; Pro Asp Pro; Ile Ala Glu Asp Ser His Thr (SEQ ID NO:651); Ile Ala Gln Asp Pro Ser Thr (SEQ ID NO:652); Ala Asn Thr; Asn Thr; Asp Pro Asn Thr (SEQ ID NO:653); Lys Asn Thr; Pro Asn Thr; Ile Ala Gln Asp Pro Asn Thr (SEQ ID NO:654); Lys Pro Asn Thr (SEQ ID NO:655); Asp Pro Gly Thr (SEQ ID NO:656); Glu Asp Pro Gly Thr (SEQ ID NO:657); Pro Gly Thr; Pro Ala Thr; Val Ala Ala Arg Ala Asp Leu (SEQ ID NO:658); Gly Asp Asp; Asn Asp Glu; Gln Glu Asp; Asn Asp Asp; Arg Thr Ile Ala Asn Asp Asp (SEQ ID NO:659); Thr Ile Ala Asn Asp Asp (SEQ ID NO:660); Asp Asp; Arg Thr Met Asp Asn Asp Glu (SEQ ID NO:661); Arg Thr Ile Ala Gly Asp Asp (SEQ ID NO:662); Arg Thr Ile Ala Asn Asp (SEQ ID NO:663); Asp; Glu Asp; Arg Ser Ile Ser Gln Glu Asp (SEQ ID NO:664); Thr Asp Glu; Arg Thr Ile Ala Thr Asp Glu (SEQ ID NO:665); Glu; Ile Ile Thr Pro Pro Asp Pro (SEQ ID NO:666); Gln Glu Leu; Lys Asp Asp; Gln Glu Glu; Arg Tyr Ile Asn Gln Glu Glu (SEQ ID NO:667); Ala Ser Ser Tyr Ala Ser (SEQ ID NO:668); and Thr Ser Ser Tyr Ala Ser (SEQ ID NO:669).

In particular embodiments, the GC-C agonist peptide of formula III is defined as follows:

$Xaa_1$ is: a) Ser, Asn, Tyr, Ala, Gln, Pro, Lys, Gly, or Thr, or is missing; b) preceded by Lys or Tyr; c) any amino acid; d) missing; e) any amino acid other than Cys; or f) Lys or Arg;

$Xaa_2$ is: a) His, Asp, Glu, Ala, Ser, Asn, Gly, or is missing; b) His, Asp, Glu, Ala, Ser, Asn, Gly, Pro or is missing; c) Asp, Glu, any amino acid or is missing; d) Asp or Glu; e) any amino acid other than Cys; e) Glu; f) missing; g) Trp, Tyr or Phe; or h) Lys or Arg;

$Xaa_3$ is: a) Thr, Asp, Ser, Glu, Pro, Val or Leu; Asp or Glu; b) any amino acid other than Cys; c) Glu; d) Thr; e) Thr, Asp, Ser, Glu, Pro, Val or Leu or is missing; f) Trp, Tyr or Phe; or g) Lys or Arg;

$Cys_4$ is optionally $Xaa_4$ and is Cys, Mpt (mercaptoproline), Pen (penicillamine), Dpr (diaminopropionic acid), Asp, or Glu;

$Xaa_5$ is: a) any amino acid; b) Glu, Asp, Gln, Gly or Pro; c) Glu; d) Glu or Asp; e) Asp, Ile or Glu; f) any amino acid; or g) any amino acid other than Cys; $Xaa_6$ is: a) Leu, Ile, Val, Ala, Lys, Arg, Trp, Tyr or Phe; b) Leu, Ile, Val, Lys, Arg, Trp, Tyr or Phe; Leu, Ile, Lys, Arg, Trp, Tyr or Phe; c) Leu, Ile, Val, Trp, Tyr or Phe; d) Trp, Tyr, Phe or Leu; e) Leu, Ile or Val; f) Ile, Trp or Leu; g) Trp, Tyr or Phe; h) Ile or Leu; i) Tyr; j) any amino acid; k) any amino acid except Leu; l) any natural or non-natural aromatic amino acid; or m) any amino acid other than Cys;

$Xaa_7$ is: a) Cys, Ser, or Tyr; Cys; b) Cys, Mpt (mercaptoproline), Pen (penicillamine), Dpr (diaminopropionic acid), Asp or Glu; c) Ser; or d) an amino acid other than Cys;

$Xaa_8$ is: a) Ala, Val, or Ile; b) Ala, Val, Thr, Ile, Met or is missing; c) any amino acid; d) Val; e) any amino acid other than Cys; or f) missing;

$Xaa_9$ is: a) any amino acid; b) any amino acid other than Phe and Tyr; c) any amino acid other than Phe, Tyr, and Trp; d) any amino acid other than Phe, Tyr, Trp, Ile, Leu and Val; e) any amino acid other than Phe, Tyr, Trp, Ile, Leu, Val, and His; i) any amino acid other than Gln; g) any amino acid other than Lys, Arg, Phe, Tyr, and Trp; h) any amino acid other than Lys, Arg, Phe, Tyr, Trp, Ile, Leu and Val; i) any amino acid other than Lys, Arg, Phe, Tyr, Trp, Ile, Leu, Val, and His; j) any non-aromatic amino acid; k) missing; l) Phe, Tyr, Asn, or Trp; m) Asn, Tyr, Asp or Ala; n) Asn, Gln, or Tyr; o) Phe or Tyr; p) Asn; or q) any amino acid other than Cys;

$Xaa_{10}$ is: a) Ala, Pro or Gly; b) Pro or Gly; c) Pro; d) Ala, Val, Met, Thr or Ile; e) any amino acid; f) Val; g) Val or Pro; h) Ala or Val; i) any amino acid other than Cys; j) Pro; or k) Gly;

$Xaa_{11}$ is: a) any amino acid; b) Ala, Leu, Ser, Gly, Val, Glu, Gln, Ile, Leu, Lys, Arg, or Asp; c) Ala or Gly; d) Ala; e) Ala or Val; f) any amino acid; g) Ala or Aib (alpha-aminoisobutyric acid); h) any amino acid other than Cys; i) Ala or Thr; or j) Thr;

$Cys_{12}$ is optionally $Xaa_{12}$ and is a) Cys, Mpt (mercaptoproline), Pen (penicillamine), Dpr (diaminopropionic acid), Asp, or Glu; or b) any amino acid other than Cys;

$Xaa_{13}$ is: a) Thr, Ala, Asn, Lys, Arg, or Trp; b) Thr, Ala, Lys, Arg, or Trp; c) any amino acid; d) any non-aromatic amino acid; e) Thr, Ala, or Trp; f) Trp, Tyr or Phe; g) Thr or Ala; h) any amino acid; i) Thr; j) any amino acid other than Cys; k) Thr, Val, or Gly; l) Thr or Val, m) Thr or Gly, n) Val or Thr; o) Val; p) Thr; or q) Gly;

$Xaa_{14}$ is: a) Gly, Pro or Ala; b) Gly; c) any amino acid; d) Gly, Ala or Ser; e) Gly or Ala; f) any amino acid other than Cys; or g) Ala;

$Xaa_{15}$ is: a) Cys, Tyr or is missing; b) Cys; c) Cys, Mpt (mercaptoproline), Pen (penicillamine), Dpr (diaminopropionic acid), Asp, Glu; or d) any amino acid other than Cys or is missing; and $Xaa_{16}$ is: a) Trp, Tyr, Phe, Asn, Ile, Val, His or Leu; b) Trp, Tyr, Phe, Asn or Leu; c) Tip, Tyr, Phe or Leu; d) Trp, Tyr, or Phe; e) Leu, Ile or Val; f) His, Leu or Ser; g) Tyr or Leu; Lys or Arg; h) His; i) any amino acid, j) Leu, or missing; k) Trp, Tyr, Phe, Lys, Arg or is missing; l) missing; m) any amino acid other than Cys; or n) Tyr.

In some embodiments, the GC-C agonist peptide of formula III is defined as follows:

$Xaa_1$ is any natural or non-natural amino acid or amino acid analog or is missing;

$Xaa_2$ is any natural or non-natural amino acid or amino acid analog or is missing;

$Xaa_3$ is any natural or non-natural amino acid or amino acid analog or is missing;

$Xaa_4$ is Cys, Mpt (mercaptoproline), Pen (penicillamine), Dpr (diaminopropionic acid), Asp or Glu;

$Xaa_5$ is Glu;

$Xaa_6$ is Tyr, Trp, Phe or Leu;

$Xaa_7$ is Cys, Mpt (mercaptoproline), Pen (penicillamine), Dpr (diaminopropionic acid), Asp or Glu;

$Xaa_8$ is any natural or non-natural amino acid or amino acid analog other than Cys or is missing;

$Xaa_9$ is any amino acid;

$Xaa_{10}$ is Pro or Gly;

$Xaa_{11}$ is any amino acid;

$Xaa_{12}$ is Cys, Mpt (mercaptoproline), Pen (penicillamine), Dpr (diaminopropionic acid), Asp or Glu;

$Xaa_{13}$ is Thr, Val or Gly;

$Xaa_{14}$ is Gly or Ala;

$Xaa_{15}$ is Cys, Mpt (mercaptoproline), Pen (penicillamine), Dpr (diaminopropionic acid), Asp or Glu; and $Xaa_{16}$ is any amino acid or is missing.

In particular embodiments, the GC-C agonist peptide of formula III is defined as follows:

$Xaa_1$ is Asn, any amino acid or is missing;
$Xaa_2$ is Asp, Glu, any amino acid or is missing;
$Xaa_3$ is Asp or Glu;
$Xaa_5$ is any amino acid or Glu;
$Xaa_6$ is any amino acid or Leu;
$Xaa_7$ is Cys;
$Xaa_8$ is any amino acid or Val;
$Xaa_9$ is Asn, Gln, or Tyr;
$Xaa_{10}$ is any amino acid or Val;
$Xaa_{11}$ is any amino acid or Ala;
$Xaa_{13}$ is any amino acid or Thr;
$Xaa_{14}$ is any amino acid or Gly;
$Xaa_{15}$ is Cys;
$Xaa_{16}$ is any amino acid, Leu or missing In some embodiments, the GC-C agonist peptide of formula III is not cleaved after $Xaa_9$ by chymotrypsin, and is defined as follows:

$Xaa_1$ is Ser, Asn, Tyr, Ala, Gln, Pro, Lys, Gly or Thr, or is missing;
$Xaa_2$ is His, Asp, Glu, Ala, Ser, Asn, or Gly or is missing;
$Xaa_3$ is Thr, Asp, Ser, Glu, Pro, Val or Leu or is missing;
$Xaa_5$ is Asp, Ile or Glu;
$Xaa_6$ is Ile, Trp or Leu;
$Xaa_7$ is Cys, Ser, or Tyr;
$Xaa_8$ is Ala, Val, Thr, Ile, or Met or is missing;
$Xaa_9$ is either: a) any amino acid other than Phe and Tyr, b) any amino acid other than Phe, Tyr, and Trp, c) any amino acid other than Phe, Tyr, Trp, Ile, Leu and Val; d) any amino acid other than Phe, Tyr, Trp, Ile, Leu, Val, and His; d) any non-aromatic amino acid or e) is missing;
$Xaa_{10}$ is Ala, Val, Met, Thr or Ile;
$Xaa_{11}$ is Ala or Val;
$Xaa_{13}$ is Ala or Thr;
$Xaa_{14}$ is Gly, Ala or Ser;
$Xaa_{15}$ is Cys, Tyr or is missing; and $Xaa_{16}$ is: a) Trp, Tyr or Phe to create a chymotrypsin cleavage site; b) Lys or Arg to create a trypsin cleavage site; c) is missing or d) His or Leu or Ser.

In specific embodiments, the human uroguanylin peptide or analog comprises, consists, or consists essentially of the amino acid sequence shown below (IV):

(SEQ ID NO: 670)
$Asn_1$ $Xaa_2$ $Xaa_3$ $Xaa_4$ $Glu_5$ $Leu_6$ $Xaa_7$ $Val_8$ $Asn_9$ $Xaa_{10}$
$Xaa_{11}$ $Xaa_{12}$ $Thr_{13}$ $Xaa_{14}$ $Xaa_{15}$ $Leu_{16}$

Where, $Xaa_2$ is Asp or Glu;
$Xaa_3$ is Asp or Glu;
$Xaa_4$ is Cys or Mpt (mercaptoproline) or Pen (penicillamine) or Dpr (diaminopropionic acid) or Asp or Glu;
$Xaa_7$ is Cys or Mpt (mercaptoproline) or Pen (penicillamine) or Dpr (diaminopropionic acid) or Asp or Glu;
$Xaa_{10}$ is Val or Pro;
$Xaa_{11}$ is Ala or Aib (alpha-aminoisobutyric acid);
$Xaa_{12}$ is Cys or Mpt (mercaptoproline) or Pen (penicillamine) or Dpr (diaminopropionic acid) or Asp or Glu;
$Xaa_{14}$ is Gly or Ala; and
$Xaa_{15}$ is Cys or Mpt (mercaptoproline) or Pen (penicillamine) or Dpr (diaminopropionic acid) or Asp or Glu.

In certain embodiments of Formula IV, $Xaa_{15}$ is other than Cys or is missing, $Xaa_7$ is Ser or an amino acid other than Cys.

In certain embodiments 1, 2, 3, 4, 5, 6, 7, 8, 9, 10, 11 or 12 of $Xaa_1$, $Xaa_2$, $Xaa_3$, $Xaa_5$, $Xaa_6$, $Xaa_7$, $Xaa_8$, $Xaa_9$, $Xaa_{10}$, $Xaa_1$, $Xaa_{13}$, $Xaa_{14}$, and $Xaa_{16}$ are any amino acid other than Cys. In some embodiments, $Xaa_9$ is any amino acid other than Gln. In embodiments where $Xaa_2$ and $Xaa_3$ are Glu, $Xaa_9$ is any amino acid other than Gln. In certain embodiments, $Xaa_1$ and $Xaa_2$ are missing; $Xaa_3$ is Thr; $Xaa_5$ is Glu; $Xaa_6$ is Ile or Leu; $Xaa_8$ is Ala, Val, or Ile; $Xaa_9$ is Phe or Tyr; $Xaa_{10}$ is Ala or Val; $Xaa_{11}$ is Ala; $Xaa_{13}$ is Ala or Thr; $Xaa_{14}$ is Gly; and $Xaa_{16}$ is Trp, Tyr, Phe, Lys, or Arg or is missing.

Specific examples of human uroguanylin analogs are provided in Table A7 below.

TABLE A7

| Exemplary Human Uroguanylin Analogs | SEQ ID NO: |
|---|---|
| $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 671 |
| $Glu^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 672 |
| $Glu^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 673 |
| $Glu^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 674 |
| $Glu^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 675 |
| $Asp^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 676 |
| $Asp^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 677 |
| $Asp^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 678 |
| $Asp^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 679 |

TABLE A7-continued

| Exemplary Human Uroguanylin Analogs | SEQ ID NO: |
|---|---|
| Gln$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 680 |
| Gln$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 681 |
| Gln$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 682 |
| Gln$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 683 |
| Lys$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 684 |
| Lys$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 685 |
| Lys$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 686 |
| Lys$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 687 |
| Glu$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 688 |
| Glu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 689 |
| Glu$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 690 |
| Glu$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 691 |
| Asp$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 692 |
| Asp$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 693 |
| Asp$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 694 |
| Asp$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 695 |
| Gln$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 696 |
| Gln$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 697 |
| Gln$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 698 |
| Gln$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 699 |
| Lys$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 700 |
| Lys$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 701 |
| Lys$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 702 |
| Lys$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 703 |
| Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 704 |

TABLE A7-continued

| Exemplary Human Uroguanylin Analogs | SEQ ID NO: |
|---|---|
| Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 705 |
| Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 706 |
| Glu$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 707 |
| Asp$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 708 |
| Asp$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 709 |
| Asp$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 710 |
| Asp$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 711 |
| Gln$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 712 |
| Gln$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 713 |
| Gln$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 714 |
| Gln$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 715 |
| Lys$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 716 |
| Lys$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 717 |
| Lys$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 718 |
| Lys$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 719 |
| Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 720 |
| Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 721 |
| Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 722 |
| Glu$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 723 |
| Asp$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 724 |
| Asp$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 725 |
| Asp$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 726 |
| Asp$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 727 |
| Gln$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 728 |
| Gln$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 729 |
| Gln$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 730 |

TABLE A7-continued

| Exemplary Human Uroguanylin Analogs | SEQ ID NO: |
|---|---|
| Gln$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 731 |
| Lys$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 732 |
| Lys$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 733 |
| Lys$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 734 |
| Lys$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 735 |
| Asn$^1$-Glu$^2$-Cys$^3$-Glu$^4$-Leu$^5$-Cys$^6$-Val$^7$-Asn$^8$-Val$^9$-Ala$^{10}$-Cys$^{11}$-Thr$^{12}$-Gly$^{13}$-Cys$^{14}$-Leu$^{15}$ | 736 |
| Asp$^1$-Glu$^2$-Cys$^3$-Glu$^4$-Leu$^5$-Cys$^6$-Val$^7$-Asn$^8$-Val$^9$-Ala$^{10}$-Cys$^{11}$-Thr$^{12}$-Gly$^{13}$-Cys$^{14}$ | 737 |
| Glu$^1$-Cys$^2$-Glu$^3$-Leu$^4$-Cys$^5$-Val$^6$-Asn$^7$-Val$^8$-Ala$^9$-Cys$^{10}$-Thr$^{11}$-Gly$^{12}$-Cys$^{13}$-Leu$^{14}$ | 738 |
| Glu$^1$-Cys$^2$-Glu$^3$-Leu$^4$-Cys$^5$-Val$^6$-Asn$^7$-Val$^8$-Ala$^9$-Cys$^{10}$-Thr$^{11}$-Gly$^{12}$-Cys$^{13}$ | 739 |
| Cys$^1$-Glu$^2$-Leu$^3$-Cys$^4$-Val$^5$-Asn$^6$-Val$^7$-Ala$^8$-Cys$^9$-Thr$^{10}$-Gly$^{11}$-Cys$^{12}$-Leu$^{13}$ | 740 |
| Cys$^1$-Glu$^2$-Leu$^3$-Cys$^4$-Val$^5$-Asn$^6$-Val$^7$-Ala$^8$-Cys$^9$-Thr$^{10}$-Gly$^{11}$-Cys12 | 741 |
| Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| dAsn$^1$-Asp$^2$-Glu$^3$-Cys$^4$-Glu$^5$-dLeu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 671 |
| Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$ | 742 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dNal$^{16}$ | 743 |
| dAsn$^1$-Asp$^2$-Glu$^3$-Cys$^4$-Glu$^5$-Leu$^6$-Cys$^7$-AIB$^8$-Asn$^9$-AIB$^{10}$-Ala$^{11}$-Cys$^{12}$-Thr$^{13}$-Gly$^{14}$-Cys$^{15}$-dLeu$^{16}$ | 744 |
| dAsn$^1$-Asp$^2$-Glu$^3$-Cys$^4$-Glu$^5$-Leu$^6$-Asp[Lactam]$^7$-Val$^8$-Asn$^9$-Val$^{10}$-Ala$^{11}$-Cys$^{12}$-Thr$^{13}$-Gly$^{14}$-Orn$^{15}$-dLeu$^{16}$ | 745 |
| dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 746 |
| dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 747 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-AMIDE$^{16}$ | 671 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 748 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer-AMIDE$^{16}$ | 748 |
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr$^{16}$ | 749 |

TABLE A7-continued

| Exemplary Human Uroguanylin Analogs | SEQ ID NO: |
|---|---|
| dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr-AMIDE$^{16}$ | 749 |
| Pyglu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-8AMIDE$^{16}$ | 750 |
| Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 751 |
| Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 752 |
| Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$ | 753 |
| Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$ | 754 |
| Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$-Tyr$^{14}$ | 755 |
| Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$ | 756 |

Also included are variants of the GC-C agonist peptides described herein. Examples include variant peptides which comprise about, at least about, or no more than about 1, 2, 3, 4, 5, 6, 7, 8, 9, 10, 11, or 12 amino acid substitutions, insertions, and/or deletions relative to any of Formulas I, II, III, or IV, or SEQ ID Nos. 1,5,46-50,650 and 670, or the sequences in any of Tables A1-A7. The substitution(s) can be conservative or non-conservative. One example of a conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A conservative substitution can substitute a naturally-occurring amino acid for a non-naturally-occurring amino acid or an amino acid analog. The insertions and/or deletions can be at the N-terminus, C-terminus, and/or the internal regions of the peptide (e.g., an insertion or deletion of about 1, 2, 3, 4, 5, 6, 7, 8, 9, 10 amino acids at the C-terminus, N-terminus, and/or within about 2, 3, 4, 5, 6, 7, 8, 9, or 10 amino acids of the N-terminus and/or C-terminus). In some instances it can be desirable to use a variant peptide that binds to and agonizes the intestinal GC-C receptor, but is less active than the non-variant form the peptide. This reduced activity can arise from reduced affinity for the receptor or a reduced ability to activate the receptor once bound or reduced stability of the peptide.

The GC-C agonist peptides can be cyclic peptides or linear peptides. In addition, multiple copies of the same peptide can be incorporated into a single cyclic or linear peptide. Cyclic peptides can be prepared by methods known in the art. For example, macrocyclization is often accomplished by forming an amide bond between the peptide N- and C-termini, between a side chain and the N- or C-terminus [e.g., with $K_3Fe(CN)_6$ at pH~8.5] (Samson et al., Endocrinology, 137:5182-5185, 1996), or between two amino acid side chains, such as cysteine (DeGrado, *Adv Protein Chem*, 39:51-124, 1988).

The peptides can include the amino acid sequence of a peptide that occurs naturally in a vertebrate (e.g., mammalian) species or in a bacterial species. In addition, the peptides can be partially or completely non-naturally occurring peptides.

Also included are peptide analogs corresponding to the GC-C agonist peptides described herein. Peptide analogs are commonly used in the pharmaceutical industry as non-peptide drugs with properties analogous to those of the template peptide. These types of non-peptide compound are termed "peptide mimetics" or "peptidomimetics" (Luthman, et al., *A Textbook of Drug Design and Development*, 14:386-406, 2nd Ed., Harwood Academic Publishers, 1996; Joachim Grante, *Angew. Chem. Int. Ed. Engl.*, 33:1699-1720, 1994; Fauchere, J., *Adv. Drug Res.*, 15:29 (1986); Veber and Freidinger TINS, p. 392 (1985); and Evans et al., *J. Med. Chem.* 30:229, 1987). A peptidomimetic is a molecule that mimics the biological activity of a peptide but is no longer peptidic in chemical nature. Peptidomimetic compounds are known in the art and are described, for example, in U.S. Pat. No. 6,245,886.

The present invention also includes peptoids. Peptoid derivatives of peptides represent another form of modified peptides that retain the important structural determinants for biological activity, yet eliminate the peptide bonds, thereby conferring resistance to proteolysis (see, e.g., Simon et al., *PNAS USA*. 89:9367-9371, 1992). Peptoids are oligomers of N-substituted glycines. A number of N-alkyl groups have been described, each corresponding to the side chain of a natural amino acid. The peptoids of the present invention include compounds in which at least one amino acid, a few amino acids, or all amino acid residues are replaced by the corresponding N-substituted glycines. Peptoid libraries are described, for example, in U.S. Pat. No. 5,811,387.

In some aspects, the GC-C agonist peptide comprises or consists of about, at least about, or less than about 150, 140, 130, 120, 110, 100, 90, 80, 70, 60, 50, 40, 30, 29, 28, 27, 26, 25, 24, 23, 22, 21, 20, 19, 18, 17, 16, 15, 14, 13, 12, 11, 10, 8, 7, 6, or 5 amino acids. In some aspects, the peptide comprises no more than 5 amino acids that are N-terminal of $Cys_6$ (of Formula I or II) In some aspects, the peptide comprises no more than 20, 15, 10, or 5 amino acids that are C-terminal of $Cys_{18}$ (of Formula I or II).

In some aspects, the peptides are purified. A purified peptides is separated from other proteins, lipids, and nucleic acids or from the compounds from which is it synthesized or otherwise prepared. A purified peptide can constitute at least about 50, 60, 70, 80, 85, 90, 95, 96, 97, or 98% by dry weight of the purified preparation.

As noted above, certain peptides described herein can include one or more or all non-natural amino acids or amino acid analogs. Further to those described elsewhere herein (e.g., supra), examples include: a non-natural analogue of tyrosine; a non-natural analogue of glutamine; a non-natural analogue of phenylalanine; a non-natural analogue of serine; a non-natural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}C$, $^{15}N$, or $^{18}O$); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α.-hydroxy containing acid; an amino thio acid containing amino acid; an a, a disubstituted amino acid; a β-amino acid; a cyclic amino acid other than proline; an O-methyl-L-tyrosine; an L-3-(2-naphthyl)alanine; a 3-methyl-phenylalanine; a p-acetyl-L-phenylalanine; an 0-4-allyl-L-tyrosine; a 4-propyl-L-tyrosine; a tri-O-acetyl-GlcNAcPβ-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; a isopropyl-L-phenylalanine; L-3-(2-naphthyl)alanine; an amino-, isopropyl-, or O-allyl-containing phenylalanine analogue; a dopa, O-methyl-L-tyrosine; a glycosylated amino acid; a p-(propargyloxy)phenylalanine; dimethyl-Lysine; hydroxy-proline; mercaptopropionic acid; methyl-lysine; 3-nitro-tyrosine; norleucine; pyro-glutamic acid; Z (Carbobenzoxyl); ε-Acetyl-Lysine; β-alanine; aminobenzoyl derivative; aminobutyric acid (Abu); citrulline; aminohexanoic acid; aminoisobutyric acid; cyclohexylalanine; d-cyclohexylalanine; hydroxyproline; nitro-arginine; nitro-phenylalanine; nitro-tyrosine; norvaline; octahydroindole carboxylate; ornithine; penicillamine; tetrahydroisoquinoline; acetamidomethyl protected amino acids and pegylated amino acids. Further examples of non-natural amino acids and amino acid analogs can be found in U.S. Application Nos. 2003/0108885 and 2003/0082575, and the references cited therein.

In some embodiments, an amino acid can be replaced by a naturally-occurring, non-essential amino acid, e.g., taurine.

In some embodiments, 1, 2, 3, 4, 5, or 6 cysteines are deleted or replaced with a different amino acid. In particular aspects, the most N-terminal and/or C-terminal cysteine residue or residues are deleted or replaced with a different amino acid. In certain embodiments, the different amino acid is alanine or serine.

Peptides can be polymers of L-amino acids, D-amino acids, or a combination thereof. For example, in certain embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature. 368:744-746, 1994; Brady et al., Nature. 368:692-693, 1994. The net result of combining D-enantiomers and reverse synthesis is that the positions of carbonyl and amino groups in each amide bond are exchanged, while the position of the side-chain groups at each alpha carbon is preserved. Unless specifically stated otherwise, any given L-amino acid sequence of the invention can be made into a D retro-inverso peptide by synthesizing a reverse of the sequence for the corresponding native L-amino acid sequence Methods of manufacturing peptides containing non-natural amino acids can be found, for example, in U.S. Application Nos. 2003/0108885 and 2003/0082575, Deiters et al., *J Am Chem. Soc.* 125:11782-3, 2003; Chin et al., *Science*. 301:964-7, 2003, and the references cited therein.

In some aspects, the GC-C agonist peptides can have one or more conventional peptide bonds replaced by an alternative bond. Such replacements can increase the stability of the peptide. For example, replacement of the peptide bond between Cys$_{15}$ and Xaa$_{19}$ (of Formula I or II) with an alternative bond can reduce cleavage by carboxy peptidases and may increase half-life in the digestive tract. Bonds that can replace peptide bonds include without limitation: a retro-inverso bonds (C(O)—NH instead of NH—C(O); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefine bond (CH=CH); an fluoro substituted trans-olefine bond (CF=CH); a ketomethylene bond (C(O)—CHR or CHR—C(O) where R is H or CH$_3$; and a fluoro-ketomethylene bond (C(O)—CFR or CFR—C(O) where R is H or F or CH$_3$.

In some GC-C agonist peptides, one or both members of one or more pairs of Cys residues which normally form a disulfide bond are replaced by homocysteine, penicillamine, 3-mercaptoproline (see, e.g., Kolodziej et al., *Int J Pept Protein Res*. 48:274, 1996); β, β dimethylcysteine (see, e.g., Hunt et al., *Int J Pept Protein Res*. 42:249, 1993) or diaminopropionic acid (see, e.g., Smith et al., *J Med Chem*. 21:117, 1978), to form alternative internal cross-links at the positions of the normal disulfide bonds.

In some embodiments, one or more disulfide bonds can be replaced by alternative covalent cross-linkages, e.g., an amide linkage (—CH$_2$CH(O)NHCH$_2$— or —CH$_2$NHCH(O)CH$_2$—), an ester linkage, a thioester linkage, a lactam bridge, a carbamoyl linkage, a urea linkage, a thiourea linkage, a phosphonate ester linkage, an alkyl linkage (—CH$_2$CH$_2$CH$_2$CH$_2$—), an alkenyl linkage (—CH$_2$CH=CHCH$_2$—), an ether linkage (—CH$_2$CH$_2$OCH$_2$— or —CH$_2$OCH$_2$CH$_2$—), a thioether linkage (—CH$_2$CH$_2$SCH$_2$— or —CH$_2$SCH$_2$CH$_2$—), an amine linkage (—CH$_2$CH$_2$NHCH$_2$— or —CH$_2$NHCH$_2$CH$_2$—) or a thioamide linkage (—CH$_2$CH(S)HNHCH$_2$— or —CH$_2$NHCH(S)CH$_2$—). For example, Ledu et al. (*PNAS*. 100:11263-78, 2003) describe methods for preparing lactam and amide cross-links. Schafmeister et al. (*J. Am. Chem. Soc.* 122:5891, 2000) describe stable, hydrocarbon cross-links. Hydrocarbon cross links can be produced via metathesis (or methathesis followed by hydrogenation in the case of saturated hydrocarbons cross-links) using one or another of the Grubbs catalysts (available from Materia, Inc. and Sigma-Aldrich and described, for example, in U.S. Pat. Nos. 5,831,108 and 6,111,121). In some instances, the generation of such alternative cross-links requires replacing the Cys residues with other residues such as Lys or Glu or non-naturally occurring amino acids. In addition, the lactam, amide and hydrocarbon cross-linkages can be used to stabilize the peptide even if they link amino acids at positions other than those occupied by Cys. Such cross-linkages can occur, for example, between two amino acids that are separated by two amino acids or between two amino acids that are separated by six amino acids (see, e.g., Schafmeister et al., J. Am. Chem. Soc. 122:5891, 2000).

The GC-C agonist peptides can be modified using standard modifications. Modifications may occur at the amino (N—), carboxy (C—) terminus, internally or a combination of any of the foregoing. In some aspects, there may be more than one type of modification of the peptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cy3 or Cy5. The peptides of the invention may also be modified by 2,4-dinitrophenyl (DNP), DNP-lysin, modification by 7-Amino-4-methyl-coumarin (AMC), fluorescein, NBD (7-Nitrobenz-2-Oxa-1,3-Diazole), p-nitro-anilide, rhodamine B, EDANS (5-((2-aminoethyl)amino) naphthalene-1-sulfonic acid), dabcyl, dabsyl, dansyl, Texas red, FMOC, and Tamra (Tetramethylrhodamine). The peptides of the invention may also be conjugated to, for example, polyethylene glycol (PEG); alkyl groups (e.g., C1-C20 straight or branched alkyl groups); fatty acid radicals; combinations of PEG, alkyl groups and fatty acid radicals (see U.S. Pat. No. 6,309,633; Soltero et al., Innovations in Pharmaceutical Technology. 106-110, 2001); BSA and KLH (Keyhole Limpet Hemocyanin). For instance, in certain embodiments, the N-terminal amino acid, C-terminal amino acid, or both, is conjugated to a PEG molecule.

In certain embodiments, the GC-C agonist peptides described herein can be present with a counterion. Exemplary counterions include salts of: acetate, benzenesulfonate, benzoate, calcium edetate, camsylate, carbonate, citrate, edetate (EDTA), edisylate, embonate, esylate, fumarate, glucepate, gluconate, glutamate, glycollylarsanilate, hexylresorcinate, iodide, bromide, chloride, hydroxynaphthoate, isethionate, lactate, lactobionate, estolate, maleate, malate, mandelate, mesylate, mucate, napsylate, nitrate, pantothenate, phosphate, salicylate, stearate, succinate, sulfate, tartarate, theoclate, acetamidobenzoate, adipate, alginate, aminosalicylate, anhydromethylenecitrate, ascorbate, aspartate, camphorate, caprate, caproate, caprylate, cinnamate, cyclamate, dichloroacetate, formate, gentisate, glucuronate, glycerophosphate, glycolate, hippurate, fluoride, malonate, napadisylate, nicotinate, oleate, orotate, oxalate, oxoglutarate, palmitate, pectinate, pectinate polymer, phenylethylbarbiturate, picrate, propionate, pidolate, sebacate, rhodanide, tosylate, and tannate.

GC-C agonist peptides can be produced according to a variety of techniques. For instance, peptides can be produced in bacteria including, without limitation, E. coli, or in other systems for peptide or protein production (e.g., Bacillus subtilis, baculovirus expression systems using Drosophila Sf9 cells, yeast or filamentous fungal expression systems, mammalian cell expression systems), or they can be chemically synthesized. If the peptide or variant peptide is to be produced in bacteria, e.g., E. coli, the nucleic acid molecule encoding the peptide may optionally encode a leader sequence that permits the secretion of the mature peptide from the cell. Thus, the sequence encoding the peptide can include the pre sequence and the pro sequence of, for example, a naturally-occurring bacterial ST peptide. The secreted, mature peptide can be purified from the culture medium.

In some instances, the sequence encoding a peptide of the invention is inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, E. coli B. subtilis, Pseudomonas, Salmonella. The genetic construct may also include, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production. In some embodiments, the vectors, expression systems and methods described in U.S. Pat. No. 5,395,490 can be used to produce the GC-C agonist peptides described herein.

The protein coding sequence that includes a peptide of the invention can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single polypeptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants of the invention in protein expression systems other than bacteria, and well known to those skilled in the art, can also be used to produce peptides in a biological system.

Peptides and variants thereof can be synthesized by the solid-phase chemical synthesis. For example, the peptide can be synthesized on Cyc(4-$CH_2$Bxl)-$OCH_2$-4-(oxymethyl)-phenylacetamidomethyl resin using a double coupling program. Protecting groups must be used appropriately to create the correct disulfide bond pattern. For example, the following protecting groups can be used: t-butyloxycarbonyl (alpha-amino groups); acetamidomethyl (thiol groups of Cys residues B and E); 4-methylbenzyl (thiol groups of Cys residues C and F); benzyl (y-carboxyl of glutamic acid and the hydroxyl group of threonine, if present); and bromobenzyl (phenolic group of tyrosine, if present). Coupling is effected with symmetrical anhydride of t-butoxylcarbonylamino acids or hydroxybenzotriazole ester (for asparagine or glutamine residues), and the peptide is deprotected and cleaved from the solid support in hydrogen fluoride, dimethyl sulfide, anisole, and p-thiocresol using 8/1/1/0.5 ratio (v/v/v/w) at 0° C. for 60 min. After removal of hydrogen fluoride and dimethyl sulfide by reduced pressure and anisole and p-thiocresol by extraction with ethyl ether and ethyl acetate sequentially, crude peptides are extracted with a mixture of 0.5M sodium phosphate buffer, pH 8.0 and N,N-dimethylformamide using 1/1 ratio, v/v. The disulfide bond for Cys residues B and E is the formed using dimethyl sulfoxide (Tam et al., *J. Am. Chem. Soc.* 113:6657-62, 1991). The resulting peptide can be purified by reverse-phase chromatography. The disulfide bond between Cys residues C and F is formed by first dissolving the peptide in 50% acetic acid in water. Saturated iodine solution in glacial acetic acid is added (1 ml iodine solution per 100 ml solution). After incubation at room temperature for 2 days in an enclosed glass container, the solution is diluted five-fold with deionized water and extracted with ethyl ether four times for removal of unreacted iodine. After removal of the residual amount of ethyl ether by rotary evaporation the solution of crude product is lyophilized and purified by successive reverse-phase chromatography.

Peptides can also be synthesized by many other methods including solid phase synthesis using traditional FMOC protection (i.e., coupling with DCC-HOBt and deprotection with piperidine in DMF). Cys thiol groups can be trityl protected. Treatment with TFA can be used for final deprotection of the peptide and release of the peptide from the solid-state resin. In many cases air oxidation is sufficient to achieve proper disulfide bond formation.

The ability of peptides and other agents to bind and/or agonize to the intestinal GC-C receptor can be tested, for example, in assays such as intestinal GC-C receptor binding assays. In one example, cells of the T84 human colon carcinoma cell line (American Type Culture Collection (Bethesda, Md.)) are grown to confluence in 24-well culture plates with a 1:1 mixture of Ham's F12 medium and Dulbecco's modified Eagle's medium (DMEM), supplemented with 5% fetal calf serum. Cells used in the assay are optionally between passages 54-60. Briefly, T84 cell monolayers in 24-well plates are washed twice with 1 ml of binding buffer (DMEM containing 0.05% bovine serum albumin and 25 mM HEPES, pH 7.2), then incubated for 30 min at 37° C. in the presence of mature radioactively labeled *E. coli* ST peptide and the test material at various concentrations. The cells are then washed four times with 1 ml of DMEM and solubilized with 0.5 ml/well 1N NaOH. The level of radioactivity in the solubilized material is determined using standard methods.

Additional examples of GC-C agonist peptides are described, for instance, in U.S. Pat. Nos. 7,041,786; 7,304,036; 7,371,727; 7,494,979; 7,704,947; 7,799,897; 7,745,409; 7,772,188; 7,879,802; 7,910,546; 8,034,782; 8,080,526; 8,101,579; 8,114,831; 8,110,553; 8,357,775; and 8,367,800; U.S. Application Nos. 2013/0096071; 2013/0190238; 2012/0040892; 2012/0040025; 2012/0213846; 2012/0289460; 2011/0118184; 2010/0152118; 2010/0048489; 2010/0120694; 2010/0261877; 2009/0253634; 2009/0192083; 2009/0305993; and PCT Publication Nos. WO 2006/086653 and WO 2002/098912, each of which is incorporated by reference in its entirety.

D. Soluble Guanylate Cyclase Agonists

In certain embodiments, the compound is a soluble guanylate cyclase (sGC) agonist. Guanine nucleotidyl (guanylyl; guanylate) cyclases (GCs) are widely distributed signal transduction enzymes that, in response to various cellular stimuli, convert GTP into the second messenger cyclic GMP (cGMP). There are both membrane-associated and soluble guanylate cyclases, both of which can increase the intracellular concentrations of cGMP.

In the enterocytes of the intestine, increased cGMP production inhibits intestinal Na+/H+ exchange activity, resulting in alkalinization of the intestinal mucosa. See, e.g., Fawcus et al., *Comp Biochem. Physiol A Physiol.* 118:291-295, 1997. Without being bound by any one mechanism, in certain aspects a soluble guanylate cyclase activator inhibits or reduces phosphate uptake in the gastrointestinal tract increasing cGMP production and thereby increasing the alkalinization of the intestinal mucosa.

General examples of sGC agonists include heme-dependent and heme-independent activators. See, e.g., Evgenov et al., *Nat. Rev. Drug Discov.* 5:755-768, 2006. According to one non-limiting theory, these and other sGC activators can be used to selectively activate sGC in the intestine, increase concentrations of cGMP, and thereby inhibit phosphate uptake as described herein.

In some embodiments, and without being bound by any one mechanism, a sGC agonist inhibits or reduces phosphate uptake in the gastrointestinal tract by decreasing water absorption in the small intestine.

Non-limiting examples of sGC agonists include Bay 41-2271, Bay 58-2667, and the compounds shown in FIGS. 9A-9L. Additional structures of exemplary sGC agonists are disclosed, together with methods for their synthesis, in U.S. Pat. No. 7,087,644 and PCT Publication No. WO 2013/101830, each of which is incorporated by reference in its entirety.

E. Adenylate Cyclase Agonists

In certain embodiments, the compound is an adenylate cyclase agonist, optionally a selective agonist. Adenylate cyclase (or adenylyl cyclase) refers to a class of enzymes that catalyze the conversion of ATP to 3',5'-cyclic AMP (cAMP) and pyrophosphate. Divalent cations (e.g., Mg) are often involved in this enzymatic activity. The cAMP produced by adenylate cyclase serves as a regulatory signal via specific cAMP-binding proteins, including transcription factors or other enzymes (e.g., cAMP-dependent kinases).

Adenylyl cyclase is the effector molecule of one of the most widely utilized signal transduction pathways. Its product, cAMP, modulates cell growth and differentiation in organisms from bacteria to higher eukaryotes. In animals, there are transmembrane adenylyl-cyclases (tmACs) and soluble adenylate cyclase (sAC). See, e.g., Tresguerres et al., *Kidney Int.* 79:1277-1288, 2011. Unlike tmACs, sACs are not transmembrane proteins and are found distributed throughout the cytoplasm and in specific organelles where they are thought to be the source of second messenger mediating the intracellular functions of cAMP. See, e.g., Buck and Levin, *Sensors. (Basel)* 11:2112-2128, 2011. Thus, tmACs are directly modulated by G proteins which transduce extracellular signals into intracellular cAMP changes. In contrast, sAC isoforms are regulated by intracellular signals, including bicarbonate, calcium, and ATP.

Cystic fibrosis transmembrane regulator (CFTR) is a chloride and bicarbonate ion channel that functions at the epithelium of multiple tissues. This channel has been shown to be in charge of $HCO^{3-}$ secretion in the small intestine, where said bicarbonate determines the pH on the surface of the mucosa. See, e.g., Kunzelmann and Mall, *Physiol Rev.*

82:245-289, 2002. CFTR is regulated by cAMP: phosphorylation of the CFTR regulatory domain by cAMP-dependent protein kinase A (PKA) increases its activity. Selective activation of this ion channel can thus result in alkalinization of the luminal membrane and thereby reduce or decrease the CEPG. According to one non-limiting theory, selective stimulation of tmACs in the intestinal tract should therefore increase intracellular cAMP, stimulate PKA, increase CFTR activity and thereby inhibit the uptake of Pi via CEPG effects. In specific aspects, the compound selectively activates tmACs, for instance, relative to sACs.

Adenylate cyclase agonists such as forskolin have been shown to increase cAMP-mediated duodenal bicarbonate secretion (without increasing gastric bicarbonate secretion), optionally via signaling of CFTR. See, e.g., Takeuchi et al., *Am. J. Physiol.* 272(3 Pt 1):G646-53, 1997. Without being bound by any one mechanism, in certain aspects an adenylate cyclase agonist inhibits or reduces phosphate uptake in the gastrointestinal tract by stimulating bicarbonate secretion into the small intestine.

In some embodiments, and without being bound by any one mechanism, an adenylate cyclase agonist inhibits or reduces phosphate uptake in the gastrointestinal tract by decreasing water absorption in the small intestine.

In particular embodiments, the compound is an agonist of adenylate cyclase III (AC-III), optionally an agonist of one or more of the AC-III isoforms ADCY1, ADCY2, ADCY3, ADCY4, ADCY5, ADCY6, ADCY7, ADCY8, ADCY9, and/or ADCY10.

Figure 10:
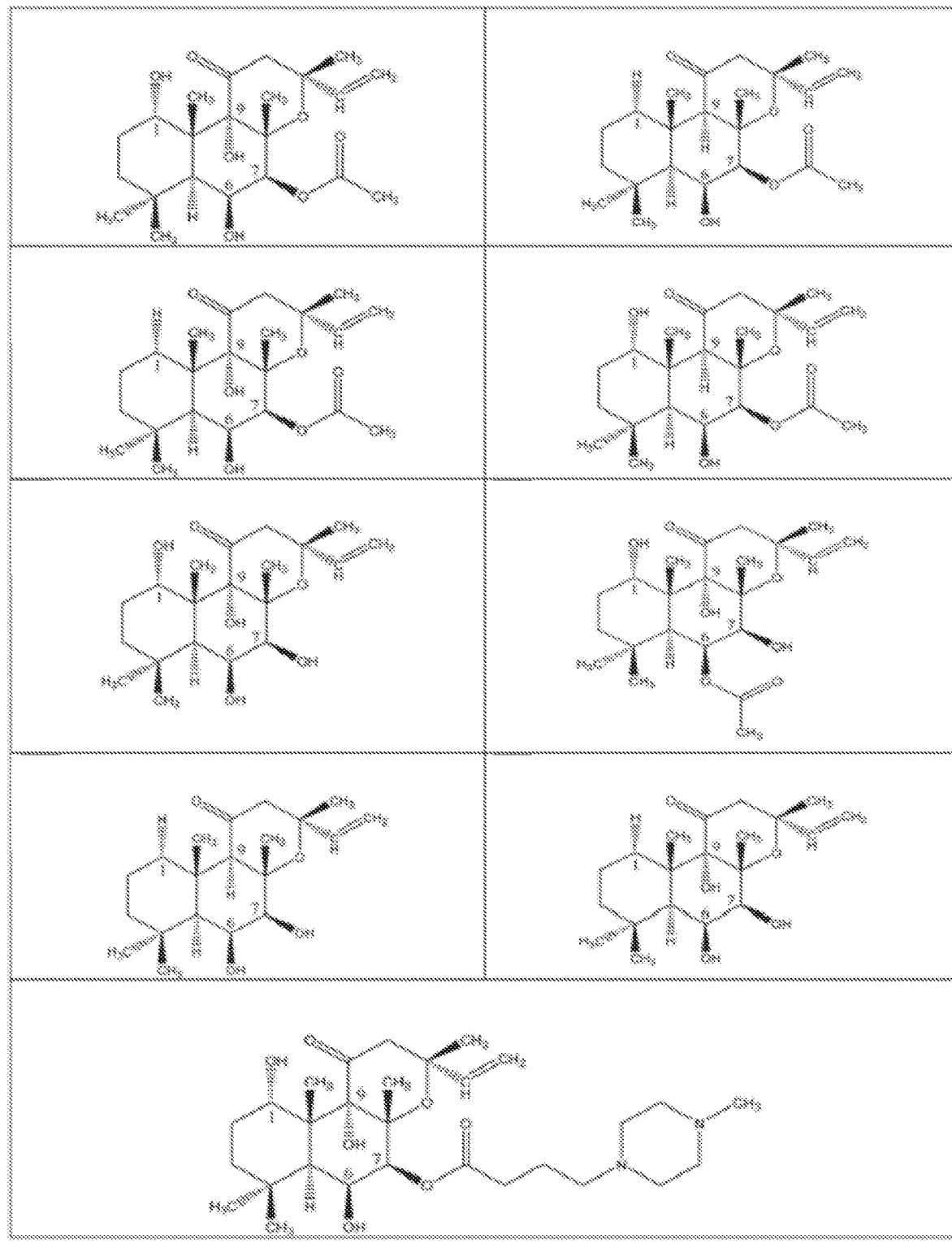
FIG. 10 shows exemplary adenylate cyclase receptor agonists.
Figure 10:
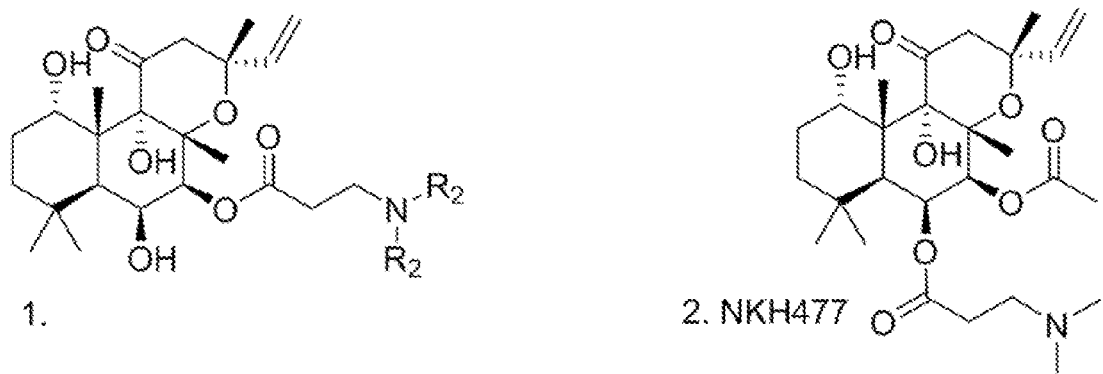

Particular examples of adenylate cyclase agonists include labdane diterpenes such as forskolin and analogs/derivatives thereof, including water-soluble forskolin analogs such as colforsin (NKH477). Forskolin is a diterpene compound isolated from plants that activates all mammalian tmACs with the exception of tmAC IX (mammalian sAC is insensitive to forskolin). See, e.g., Kamenetsky et al., *J. Mol. Biol.* 362:623-639, 2006. Forskolin stimulation can produce potent and prolonged cAMP changes. See, e.g., Tresguerres et al., *Kidney Int.* 79:1277-1288, 2011. The structure of forskolin and several forskolin analogs is illustrated in FIG. 10. Water soluble derivatives of forskolin include those acylated at C-6 or C-7 with a polar aliphatic amine. These derivatives are typically more selective for ACs, with fewer off-target activities. See, e.g., Hartzell and Budnitz, *Molecular Pharmacology* 41:880-888, 1992. Thus, certain aspects include the use of soluble forskolin analogs that selectively activate adenylate cyclases in the cells lining the gastrointestinal tract.

Particular examples of forskolin analogs/derivatives include aminoalkylcarbamyl derivatives of forskolin, including 1-aminoalkylcarbamates, 9-aminoalkylcarbamates, 7-aminoalkylcarbamates, 6-aminoalkycarbamates, 6,7-diaminoalkylcarbamates, 1,6-diaminoalkylcarbamates, 1,7-diaminoalkylcarbamates, and 1,6,7-triaminoalkylcarbamates of forskolin, which can be used as intermediates in the synthesis of forskolin derivatives. See U.S. Pat. No. 5,350,864. Additional examples of forskolin analogs/derivatives include 12-halogenated forskolin derivatives, including 12-chlorodesacetylforskolin, 12-chloroforskolin, 12-bromodesacetylforskolin, 12-bromodesacetylforskolin, 12-fluorodesacetylforskolin, and 12-fluoroforskolin. See U.S. Pat. No. 4,871,764.

In some embodiments, the forskolin analog/derivative is 6-acetyl-7-deacetyl-forskolin, 7-deacetyl-forskolin, 7-deacetyl-6-(N-acetylglycyl)-forskolin, 7-deacetyl-7-β-hemisuccunyl-forskolin, 7-deacetyl-7-(O—N-methylpiperazino)-γ-butryl-dihydrochlonde-forskolin, 7-HPP-forskolin, 6-HPP-forskolin, or colforsin daropate hydrochloride (NKH477). See, e.g., U.S. Application Nos. 2011/0171195, 2006/0004090, and 2011/0077292; Laurenza et al., *Mol Pharmacol.* 32:133-9, 1987; Lal et al., *Bioorg Med Chem.* 6:2075-83, 1998; Mori et al., *J. Cardiovasc. Pharmacol.* 24:310-6, 2004. See also Levin, *Tetrahedon Letters.* 37:3079-3082, 1996 for exemplary methods of synthesizing forskolin analogs, and Lal et al., *Indian J. Chemistry.* 45B:232-246, 2006, for additional examples of water soluble forskolin analogs and methods of synthesizing the same. Additional structures of exemplary adenylate cyclase agonists are disclosed, together with methods for their synthesis, in U.S. Pat. No. 4,954,642 and Khandelwal et al., *J Med Chem.* 31:1872-9, 1988. See also Cunliffe et al., *Electrophoresis.* 28:1913-20, 2007 for exemplary methods/assays of detecting agonist-stimulated adenylate cyclase activity. These references are incorporated by reference in their entireties.

F. Imidazoline-1 Receptor Agonists

In certain embodiments, the compound is an imidazoline-1 receptor agonist, optionally a selective agonist. Imidazoline receptors include a family of nonadrenergic high-affinity binding sites for clonidine, idazoxan, and other imidazoles. There are three classes of imidazoline receptors: the I1 receptor, which mediates the sympatho-inhibitory actions of imidazolines to lower blood pressure; the I2 receptor, an allosteric binding site of monoamine oxidase and is involved in pain modulation and neuroprotection; and the I3 receptor, which regulates insulin secretion from pancreatic beta cells. In some aspects, the compound is a selective imidazoline-1 receptor agonist, for instance, relative to imidazoline-2 and/or imidazoline-3 receptors.

The subclass of imidazoline-1 receptors mediate in part the central hypotensive effects of clonidine-like drugs. According to one non-limiting theory, activated imidazoline-1 receptors trigger the hydrolysis of phosphatidylcholine into DAG, which then triggers the synthesis of second messengers such as arachidonic acid and downstream eicosanoids such as $PGE_2$. See, e.g., Ernsberger, *Ann. NY Acad. Sci.* 881:35-53 1999. $PGE_2$ is an endogenous inducer of DBS. See, e.g., Takeuchi et al., *Gastroenterology.* 113:1553-1559, 1997). Without being bound by any one mechanism, in some aspects an imidazoline-1 receptor agonist inhibits or reduces phosphate uptake in the gastrointestinal tract by increasing DBS.

According to another non-limiting theory, imidazoline-1 receptor agonists such as moxonidine have also been shown to decrease acid secretion in the gastrointestinal tract. See, e.g., Glavin and Smyth, Br J Pharmacol. 114:751-4, 1995. Hence, and without being bound by any one mechanism, in certain aspects an imidazoline-1 receptor agonist inhibits or reduces phosphate uptake in the gastrointestinal tract by inhibiting or reducing acid secretion in the gastrointestinal tract, e.g., the small intestine. In specific aspects, and without being bound by any one mechanism, an imidazoline-1 receptor agonist inhibits or reduces phosphate uptake in the gastrointestinal tract by increasing DBS and reducing acid secretion in the small intestine.

In some embodiments, and without being bound by any one mechanism, an imidazoline-2 receptor agonist inhibits or reduces phosphate uptake in the gastrointestinal tract by decreasing water absorption in the small intestine.

Non-limiting examples of imidazoline-1 receptor agonists include agmatine, apraclonidine, clonidine, efaroxan, moxonidine, rilmenidine, S-23515, S-23757, LNP-509, LNP-911, LNP-509, S-23515, PMS-812, PMS-847, BU-98008 and TVP1022 (S-enantiomer of rasagiline). See also Head and Mayorov, *Cardiovasc HematolAgents Med Chem.* 4:17-32, 2006, incorporated by reference in its entirety.

Figure 11:
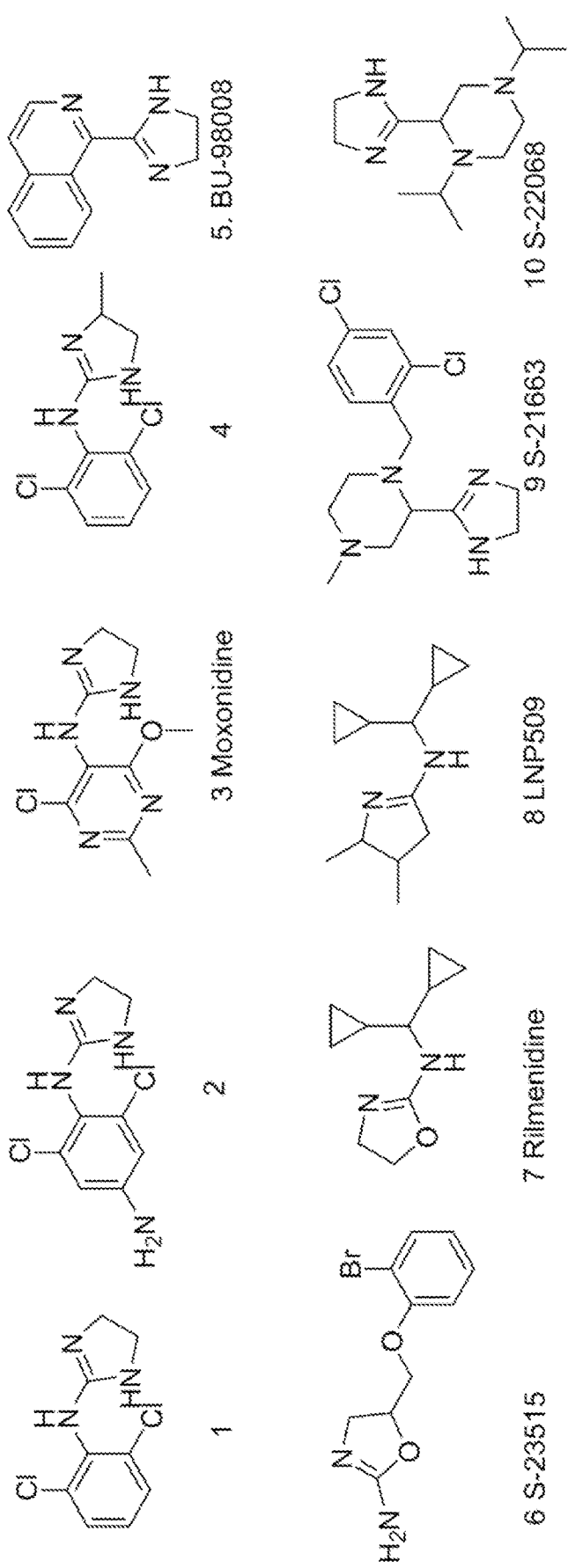
FIG. 11 shows exemplary imidazoline receptor agonists.

Structures of exemplary imidazoline receptor agonists are shown in FIG. 11, and are further disclosed, together with methods for their synthesis, in U.S. Pat. Nos. 4,323,570; 5,686,477; 3,988,464; 6,300,366; 5,492,912; 5,492,912; and PCT Publication No. WO200141764, each of which is incorporated by reference in its entirety.

Additional examples of imidazoline receptor agonists include those described in U.S. Pat. Nos. 7,309,706; 5,686,477 (EP 710,658); U.S. Pat. No. 5,925,665 (EP 846,688); WO 2001/41764; and WO 2000/02878. The 5-(aryloxymethyl)-oxazoline derivatives described in U.S. Pat. No. 5,686,477 are characterized by a selective affinity for the imidazoline-1 receptor. The imidazoline derivatives described in U.S. Pat. No. 5,925,665 bind to imidazoline receptors without significantly binding to adrenergic receptors. WO 2001/41764 describes isoquinoline and quinoline derivatives which possess an affinity for imidazoline receptors. WO 2000/02878 describes exemplary β-carboline derivatives as potential ligands for imidazoline receptors. These references are incorporated by reference in their entireties.

G. Cholinergic Agonists

In certain embodiments, the compound is a cholinergic agonist, optionally a selective cholinergic agonist. Examples of cholinergic agonists include indirect cholinergic agonists, which stimulate the production or release of acetylcholine (e.g., actetylcholinesterase inhibitors), and direct cholinergic agonists, which bind to and stimulate one or more acetylcholine receptors. The neurotransmitter acetylcholine (2-acetoxy-N,N,N-trimethylethanaminium) is an ester of acetic acid and choline. General examples of acetylcholine receptors include nicotinic acetylcholine receptors and muscarinic acetylcholine receptors. Nicotinic acetylcholine receptors are ligand-gated ion channels composed of five protein subunits.

Muscarinic acetylcholine receptors (i.e., M1, M2, M3, M4, and M5) are G-protein-coupled receptors that activate other ionic channels via a second messenger cascade. These receptors are expressed in the digestive tract including the salivary glands and the smooth muscle and mucosal cells in the stomach and the intestine In certain embodiments, the compound is a pan-agonist of muscarinic receptor subtypes. The endogenous agonist of all five muscarinic receptor subtypes is acetylcholine, which exerts physiological control by both hormonal and neuronal mechanisms. See, e.g., Eglen, *Ann. N. Y. Acad. Sci.* 881:35-53, 2012. Several naturally-occurring compounds also modulate the muscarinic receptors (see FIG. 12), including agonists such as muscarine (a toxin from the mushroom Aminita *muscaria* and from which the receptor family derives its name) and pilocarpine, and antagonists such as atropine or (−)-hyoscine (from the solanaceae plant family). When administered in vivo, muscarinic agonists elicit salivation whereas muscarinic antagonists cause dry mouth.

In some embodiments, the compound is a relatively selective agonist of the M3 muscarinic receptor. The secretory response of M3 is stimulated physiologically by acetylcholine (ACh). Specifically, ACh binds to the G protein-linked M3 muscarinic ACh receptor, which causes phospholipase C to generate inositol 1,4,5-trisphosphate (InP3). InP3 binds to and opens the InP3 receptor on the endoplasmic reticulum, which, according to one non-limiting theoery, releases $Ca^{2+}$. Increased $[Ca^{2+}]_i$ activates the apical membrane Cl— channel and the basolateral K+ channel. Efflux of $Cl^-$ into the acinar lumen draws Na+ across the cells, and the osmotic gradient generates fluid secretion. See, e.g., Tobin et al., *J. Physiol Pharmacol.* 60:3-21, 2009. This fluid is bicarbonate rich.

Muscarinic receptor control of bicarbonate secretion has been demonstrated repeatedly: intravascularly or subcutaneously administered muscarinic agonists increase bicarbonate release into the intestinal lumen, a response blocked by muscarinic antagonists. For instance, according to one non-limiting theory, cholinergic agonists such as bethanechol (muscarinic receptor selective agonist), carbachol (muscarinic and nicotinic acetylcholine receptor agonist), and McN-A-343 (M1 receptor-selective agonist) have been shown to increase duodenal bicarbonate secretion. See, e.g., Safsten et al., *Am J Physiol.* 267(1 Pt 1):G10-7, 1994. Without being bound by any one mechanism, in certain aspects a cholinergic agonist inhibits or reduces phosphate uptake in the gastrointestinal tract by stimulating bicarbonate secretion into the small intestine.

In some embodiments, and without being bound by any one mechanism, a cholinergic agonist inhibits or reduces phosphate uptake in the gastrointestinal tract by decreasing water absorption in the small intestine.

Figure 12:
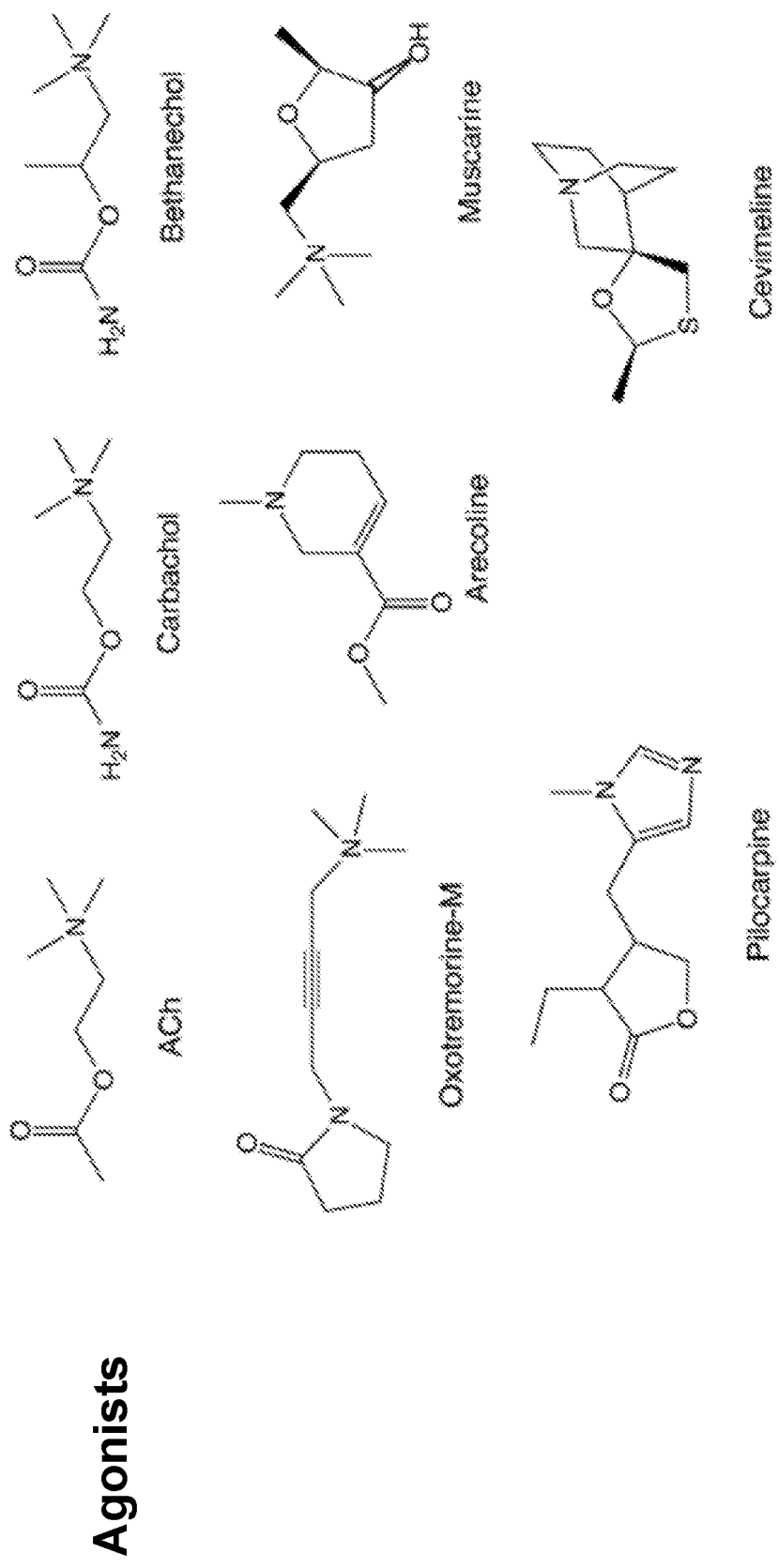
FIG. 12 shows exemplary cholinergic agonists and the antagonists atropine and (−)-hyosine.
Figure 12:
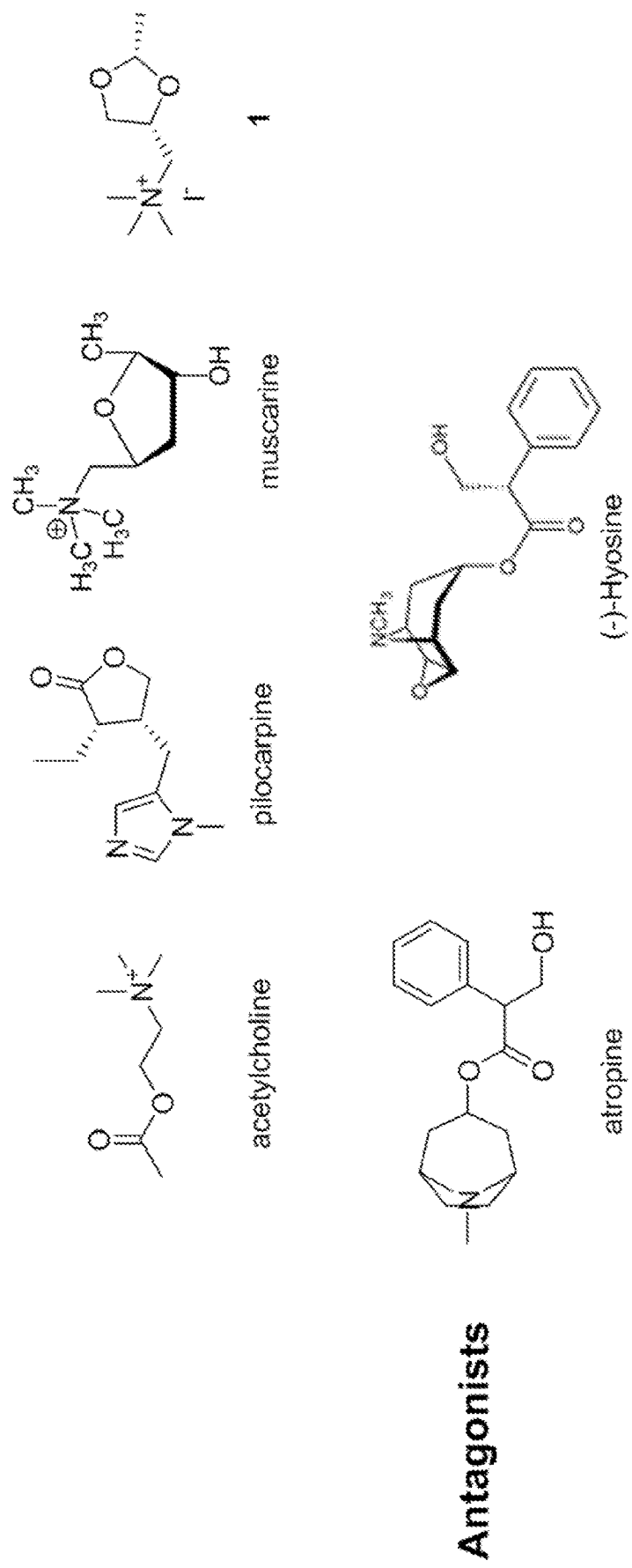

In some aspects, a muscarinic receptor agonist possesses a conformationally-constrained structure with respect to the endogenous ligand acetylcholine, such as the cis-trimethyl-(2-methyl-[1,3]dioxolan-4-ylmethyl)ammonium iodide structure in FIG. 12. See, e.g., Piergentili et al., *Bioorganic & Medicinal Chemistry* 15:886-896, 2007. This structure contains a ketal in place of the labile ester of acetylcholine, which is a bioisostere that retains both hydrogen bond acceptors of ACh but is much more stable. Similarly, carbechol and bethanechol (also shown in FIG. 12) are examples of agonists because these structures replace the labile ester group of ACh with non-hydrolyzable carbamate functionality.

Non-limiting examples of indirect-acting cholinergic agonists include acetylcholinesterase inhibitors such as carbamates (e.g., physostigmine, neostigmine, pyridostigmine), piperidines (e.g., donepizil), edrophonium, huperzine A, ladostigil, ungeremine, lactucopicrin, tacrine, galantamine, trans-delta-9-tetrahydrocannabinol, and phosphates (e.g., isoflurophate, echothiophate, parathion, malathion). Preferably, the methods provided herein will employ reversible acetylcholinesterase inhibitors.

Non-limiting examples of direct-acting cholinergic agonists include acetylcholine, nicotine, succinylcholine, methacholine (acetyl-β-methylcholine), McN-A-343, carbachol (carbamoylcholine), bethanecol (carbamoyl-β-methlycholine), muscarine, pilocarpine, oxotremorine, lobeline, and dimethylphenylpiparazinium.

H. Prostaglandin EP4 Receptor Agonists

In certain embodiments, the compound is E-type prostanoid receptor 4 (EP4) agonist (or prostaglandin EP4 receptor agonist), optionally a selective agonist. The EP4 receptor was initially described as a $G_{\alpha s}$ protein-coupled receptor leading to stimulation of adenylate cyclase and elevation of intracellular cAMP levels. When first cloned as a prostaglandin E2 ($PGE_2$) receptor that stimulated cAMP formation, the EP4 receptor was designated as "EP2." However, after another cAMP-stimulating $PGE_2$ receptor had been discovered which was sensitive to butaprost, the butaprost-insensitive receptor which mediated vasorelaxation was renamed "EP4." It is one of four receptors identified for $PGE_2$.

According to one non-limiting theory, prostaglandin EP4 receptor agonists have been shown to stimulate duodenal bicarbonate secretion, for instance, by a mechanism that is mediated by cAMP. See, e.g., Aoi et al., *Am J Physiol Gastrointest Liver Physiol.* 287:G96-103, 2004; Lundgren, *Acta Physiol Scand.* 185:87, 2005; Takeuchi et al., *Gastroenterology.* 113:1553-1559, 1997. Hence, and without being bound by any one mechanism, in certain aspects a prostaglandin EP4 receptor agonist inhibits or reduces phosphate uptake in the gastrointestinal tract by stimulating bicarbonate secretion into the small intestine.

In some embodiments, and without being bound by any one mechanism, an EP4 agonist inhibits or reduces phosphate uptake in the gastrointestinal tract by decreasing water absorption in the small intestine.

Non-limiting examples of prostaglandin EP4 receptor agonists include $PGE_2$, $PGE_2$ analogs, AE1-329, AGN205203, APS-999 Na, Cay10598 (19a), CP-044519-02, CJ-023,423, EP4RAG, ER-819762, L-902688, lubiprostone, ONO-4819CD, ONO AE1-329, ONO AE1-734, $PGE_1$-OH, TCS2510, γ-Lactam PGE analog 3, 11-Deoxy-$PGE_1$, γ-Lactam PGE analog 2a, γ-Lactam PGE analog 4. See, e.g., Konya et al., *Pharmacol Ther.* 138:485-502, 2013.

Non-limiting examples of $PGE_2$ analogs include 16,16-dimethyl $PGE_2$, 16-16 dimethyl$PGE_2$ p-(p-acetamidobenzamido)phenyl ester, 11-deoxy-16,16-dimethyl $PGE_2$, 9-deoxy-9-methylene-16, 16-dimethyl $PGE_2$, 9-deoxy-9-methylene $PGE_2$, 9-keto fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso $PGE_2$ isopropyl ester, 20-hydroxy $PGE_2$, 11-deoxy $PGE_1$, nocloprost, sulprostone, butaprost, 15-keto PGE2, and 19(R) hydroxyyPGE2. See, e.g., U.S. Application No. 2012/0202288.

Additional examples of prostaglandin EP4 receptor agonists include those described in U.S. Application Nos. 2001/0056060, 2002/0040149, 2005/0164949, and 2011/0098481. Also included are prostaglandin EP4 receptor agonists described (along with related methods of synthesis) in U.S. Pat. Nos. 4,219,479; 4,049,582; 4,423,067; 4,474,802; 4,692,464; 4,708,963; 5,010,065; 5,013,758; 6,747,037; and 7,776,896; European Patent No. EP0084856; Canadian Patent No. 1248525; U.S. Application Nos. 2004/0102499, 2005/049227, 2005/228185, 2006/106088, 2006/111430, 2007/0010495, 2007/0123568, 2007/0123569, 2005/0020686, 2008/0234337, 2010/0010222, 2010/0216689, 2004/0198701, 2004/0204590, 2005/0227969, 2005/0239872, 2006/0154899, 2006/0167081, 2006/0258726, 2006/0270721, 2009/0105234, 2009/0105321, 2009/0247596, 2009/0258918, 2009/0270395, 2004/0087624, 2004/0102508, 2006/0252799, 2009/0030061, 2009/0170931, 2010/0022650, 2009/0312388, 2009/0318523, 2010/0069457, 2010/0076048, 2007/0066618, 2004/0259921, 2005/0065133, and 2007/0191319; and PCT Publication Nos. WO 2004/071428, WO 2006/052630, WO 2006/047476, WO 2006/058080, WO 2004/065365, WO 2003/047513, WO 2004/085421, WO 2004/085430, WO 2005/116010, WO 2005/116010, WO 2007/014454, WO 2006/080323, and WO 2006/137472, each of which is incorporated by reference in its entirety.

Figure 13:
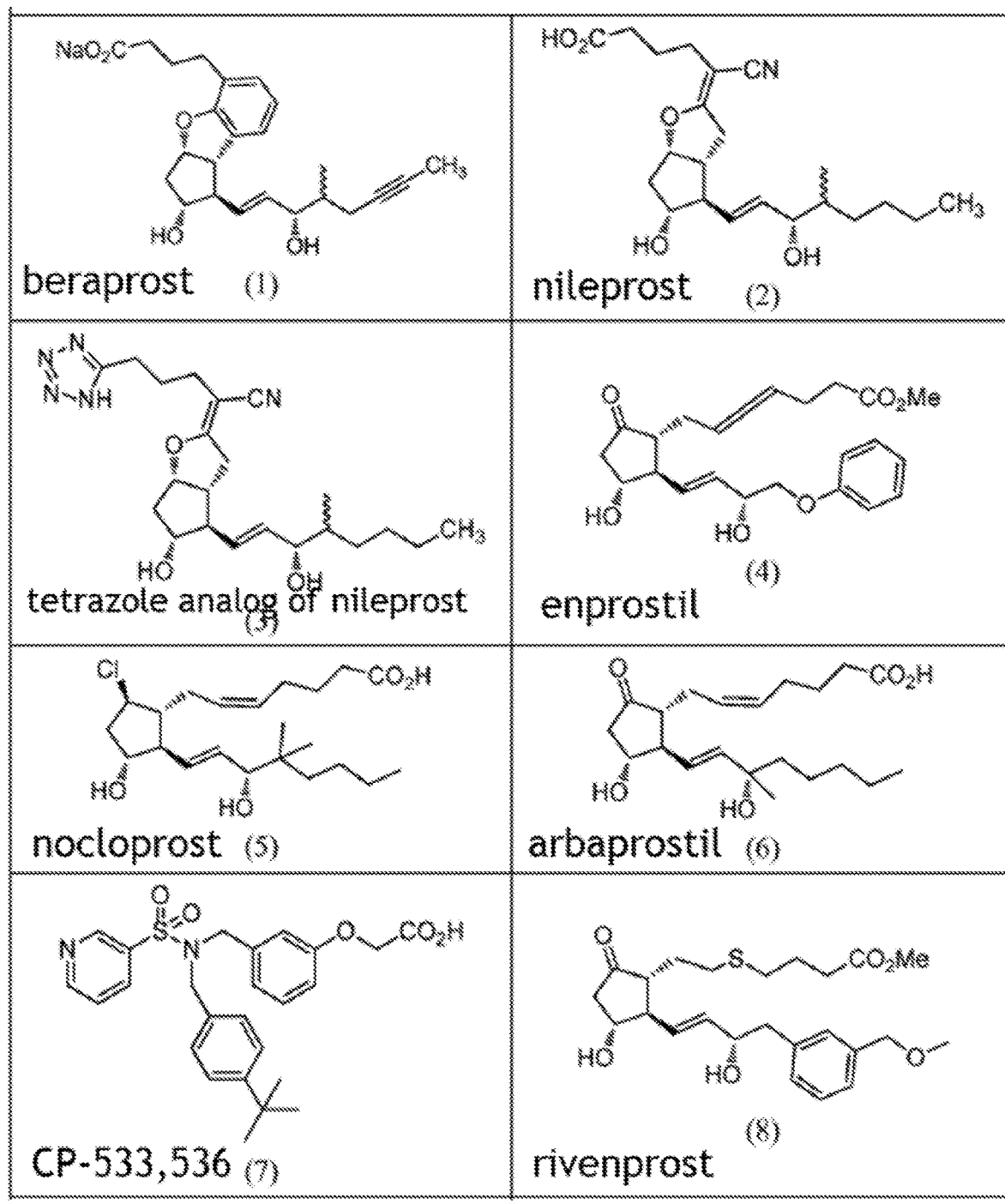
FIG. 13 shows exemplary EP4 receptor agonists.
Figure 13:
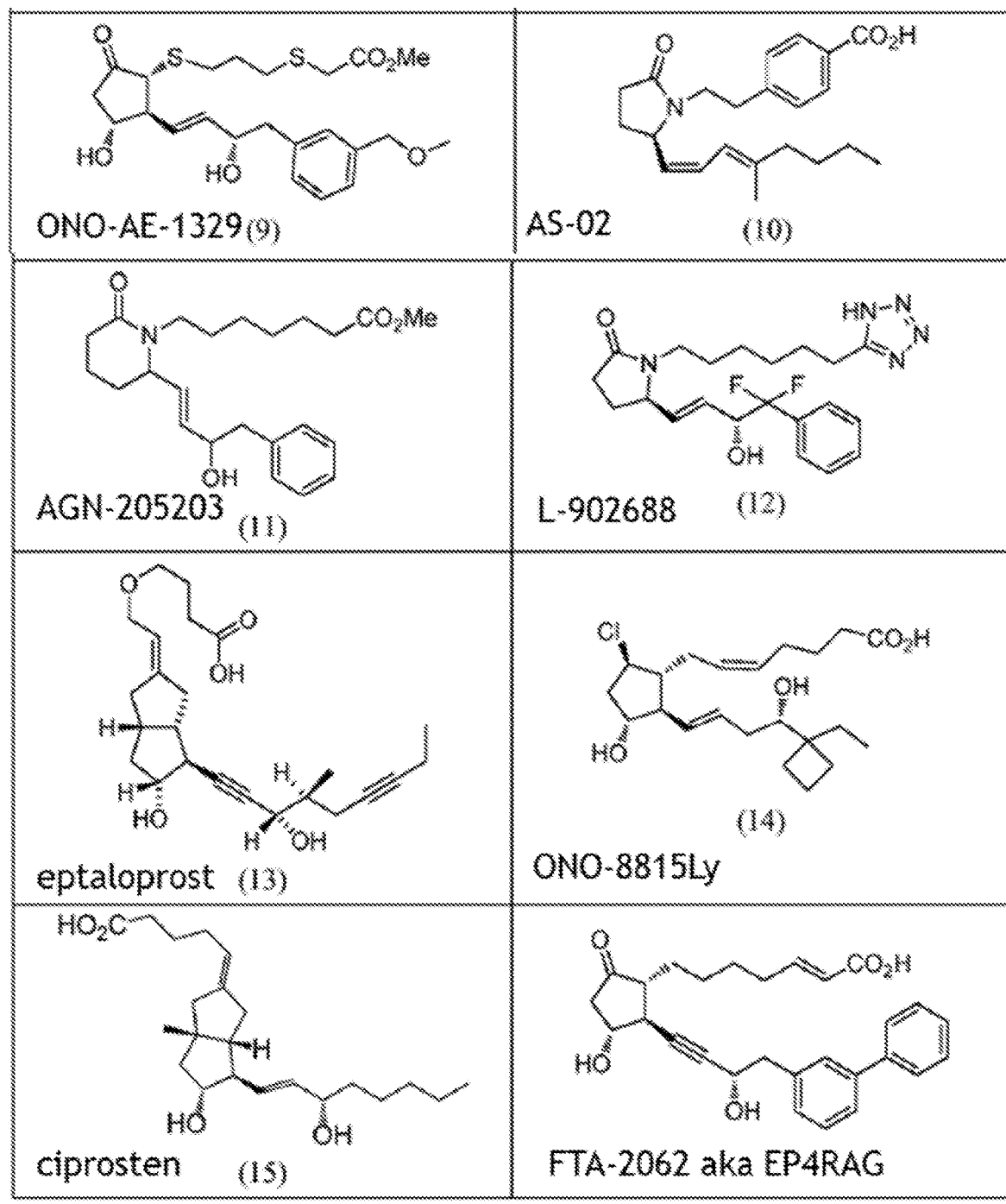

Particular examples of EP4 receptor agonists are shown in FIG. 13.

In specific embodiments, the EP4 receptor agonist is lubiprostone (also a calcium-activated chloride channel agonist). Lubiprostone is a bicyclic fatty acid derived from prostaglandin E1 that acts by specifically activating ClC-2 chloride channels on the apical aspect of gastrointestinal epithelial cells, producing a chloride-rich fluid secretion. These secretions soften the stool, increase motility, and promote spontaneous bowel movements (SBM). Lubiprostone stimulates CFTR-dependent duodenal bicarbonate secretion without changing net Cl— secretion. See, e.g., Muzimori et al., *J Physiol.* 573:827-842, 2006. Here, lubiprostone-induced duodenal bicarbonate secretion was abolished by the co-perfusion of the potent EP4 receptor antagonist AH23848, whereas an EP1/EP2 receptor antagonist AH6809 had no effect. These results suggest that lubiprostone can increase duodenal bicarbonate secretion by agonizing the prostaglandin EP4 receptor. Hence, in certain aspects lubiprostone inhibits or reduces phosphate uptake in the gastrointestinal tract by stimulating bicarbonate secretion into the small intestine.

As noted above, certain aspects include a prostaglandin EP4 receptor selective agonist. EP4 selective agonists include compounds having an $IC_{50}$ at the EP1, EP2, and/or EP3 receptor subtypes which is at least 5, at least 10, at least 20, at least 30, at least 40, or at least 50-fold greater than the $IC_{50}$ at the EP4 receptor subtype.

I. Dopamine D1 Receptor Agonists

In certain embodiments, the compound is a dopamine D-1 receptor agonist, optionally a selective agonist. The dopamine D1 G protein-coupled receptor is the most highly expressed dopamine receptor subtype among the dopamine receptor family. It stimulates adenylate cyclase and activates cyclic AMP-dependent protein kinases.

Based on one non-limiting theory, dopamine D1 receptor agonists and the peripherally acting catechol-O-methyl-transferase (COMT) inhibitor nitecapone (COMT inhibitors decrease tissue degradation of catecholamines, including dopamine) have been shown to stimulate bicarbonate secretion in the gut and increase the production of cyclic AMP in isolated duodenal enterocytes. See, e.g., Flemstrom and Safsten, *Dig Dis Sci.* 39:1839-42, 1994; and Knutson et al., *Gastroenterology.* 104:1409-13 1993; Iwatsuki et al., *Eur J Pharmacol.* 218:237-41, 1992; and Fraga et al., *Cell Physiol Biochem.* 18:347-60, 2006. Without being bound by any one mechanism, in certain aspects a dopamine D1 receptor agonist inhibits or reduces phosphate uptake in the gastrointestinal tract by stimulating bicarbonate secretion into the small intestine.

In some embodiments, and without being bound by any one mechanism, a dopamine D1 agonist inhibits or reduces phosphate uptake in the gastrointestinal tract by decreasing water absorption in the small intestine.

Non-limiting examples of dopamine D1 receptor agonists include dopamine (e.g., dopamine hydrochloride, NPEC-caged dopamine), dihydrexidine (e.g., dihydrexidine hydrochloride), benzazepaine, and analogs/derivatives thereof. Specific examples of dihydrexidine derivatives include A86929, dinapsoline, dinoxyline and doxanthrine, and specific examples of benzazepine derivatives include SKF81297, SKF82958, SKF38393, fenoldopam, and 6-Br-APB. Also included are the dopamine D1 receptor agonists shown in FIG. 14.

Additional non-limiting examples of dopamine D1 receptor agonists include A68930, A77636, (R)-(-)-apomorphine hydrochloride, CY208-243, SKF89145, SKF89626, 7,8-Dihydroxy-5-phenyl-octahydrobenzo[h]isoquinoline, YM435, ABT-431, NNC01-0012, SCH23390, SKF7734, SKF81297, SKF38322, SKF83959, cabergoline, fenoldopam (e.g., fenoldapam hydrochloride), bromocriptine, ropinirole, pramipexole, entacapone, tolcapone, dihexadine, IPX-750, and pergolide. See also Zhang et al., *Med Res Rev.* 29:272-94, 2009; Yvonne Connolly Martin, *International Journal of Medicinal Chemistry*, vol. 2011, Article ID 424535, 8 pages, 2011. doi:10.1155/2011/424535; Salmi et al., *CNS Drug*

Rev. 10:230-42, 2004; Bourne, *CNS Drug Rev.* 7:399-414, 2001. Moreover, D1 receptor agonists can be identified using standard screening methods known in the art. As a non-limiting example, a cell based functional assay for high-throughput drug screening for dopamine D1 receptor agonists is described in Jiang et al., *Acta Pharmacol Sin.* 26:1181-6, 2005. These references are incorporated by reference in their entireties.

As noted above, certain aspects include a dopamine D1 receptor selective agonist. Dopamine D1 selective agonists include compounds having an $IC_{50}$ at the D2, D3, D4, and/or D5 receptor subtypes which is at least 5, at least 10, at least 20, at least 30, at least 40, or at least 50-fold greater than the $IC_{50}$ at the D1 receptor subtype.

J. Melatonin Receptor Agonists

In certain embodiments, the compound is a melatonin receptor agonist, optionally a selective agonist. Melatonin receptors refer to a family of high-affinity G protein-coupled receptors which bind to the pineal hormone melatonin. See Reppert, *Biol Rhythms.*12:528-31, 1997.

Examples of melatonin receptors include the MT1 and MT2 receptors. In some aspects, the melatonin receptor agonists binds to both of the MT1 and MT2 receptors. In some embodiments, the melatonin receptor agonist binds selectively to the MT1 or MT2 receptor, e.g., binds to MT2 but not significantly to MT1, or binds to MT1 but not significantly to MT2.

According to non non-limiting theory, melatonin receptor agonists such as melatonin have been shown to stimulate duodenal bicarbonate secretion, for example, via action at enterocyte MT2-receptors. See, e.g., Sjoblom et al., *J Clin Invest.* 108:625-33, 2001; Sjoblom and Flemstrom, *J. Pineal Res.* 34:288-293, 2003. Without being bound by any one mechanism, in certain aspects a melatonin receptor agonist inhibits or reduces phosphate uptake in the gastrointestinal tract by stimulating bicarbonate secretion into the small intestine.

In some embodiments, and without being bound by any one mechanism, a melatonin receptor agonist inhibits or reduces phosphate uptake in the gastrointestinal tract by decreasing water absorption in the small intestine.

Examples of melatonin receptor agonists include melatonin (N-acetyl-5-methoxytryptamine) and melatonin analogs which bind to and activate the melatonin receptor. The general structure of melatonin comprises an indole ring with methoxy group at position 5 (5-methoxy group) and an acylaminoethyl side-chain at position 3; the two side-chains contribute to binding to and activating the melatonin receptor(s). The indole ring has been evaluated at all positions by the effect of substitutions. See, e.g., Rivara et al., *Curr Top Med Chem.* 8:954-68, 2008; and Sugen et al., *Pigment Cell Research.* 17:454-460, 2004.

Figure 15:
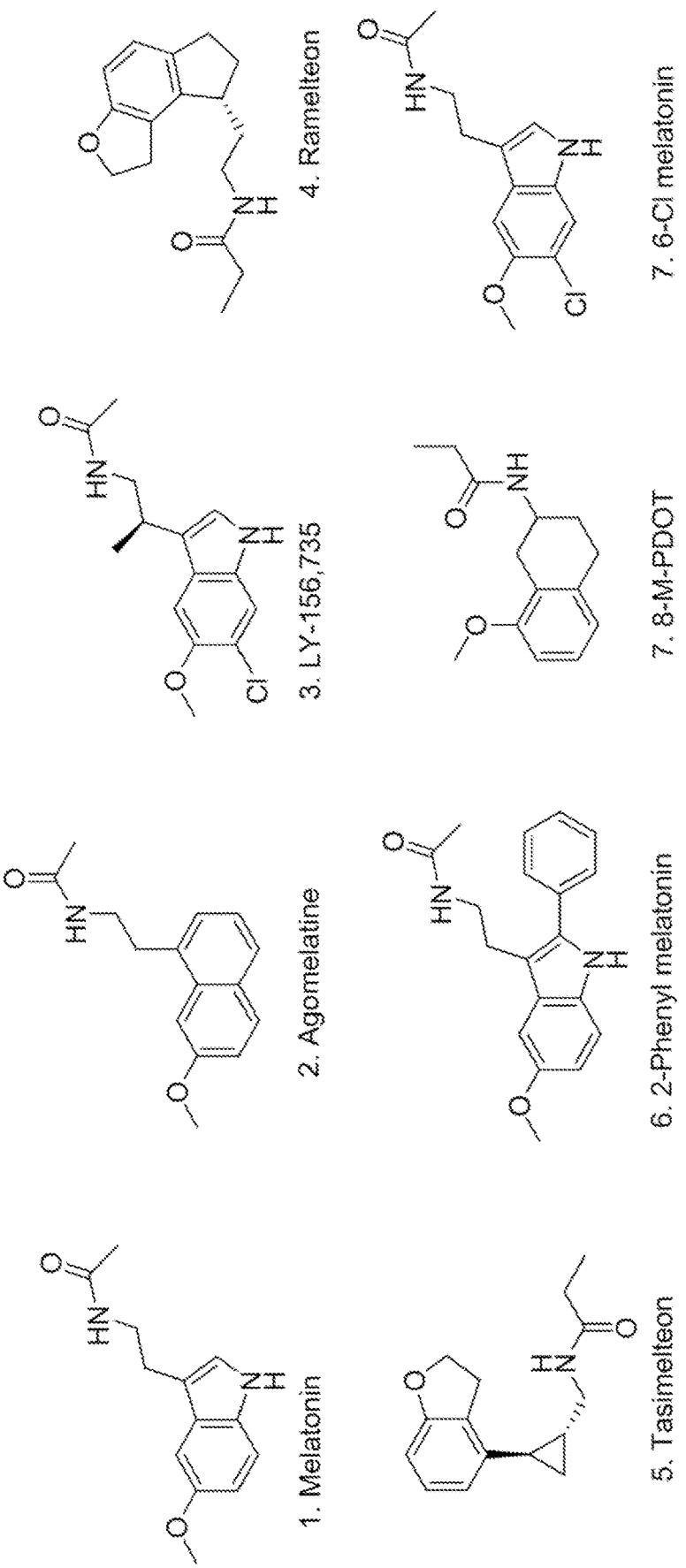
FIG. 15 shows exemplary melatonin (MT2) receptor agonists.

Particular examples of melatonin receptor agonists include 2-iodomelatonin, 6-chloromelatonin, 6,7-dichloro-2-methylmelatonin and 8-hydroxymelatonin, all of which contain the 5-methoxy indole ring as a moiety, in addition to circadin, agomelatine, ramelteon, tasimelteon, beta-methyl-6-chloromelatonin (TIK-301 or LY156735), TAK-375, VEC-162, GR196429, S20242, S23478, S24268, S25150, GW290569, BMS-214778, 8-methoxy-2-chloroacetamido-tetralin, 8-methoxy-2-propionamido-tetralin, N-acetyltryptamine, 6-chloromelatonin, 2-iodomelatonin, 8-M-PDOT, and 2-phenylmelatonin. See, e.g., U.S. Application No. 2005/0164987, which is incorporated by reference in its entirety. Also included are the exemplary melatonin receptor (MT2) agonists shown in FIG. 15.

Methods of screening for melatonin receptor agonists are described, for example, in U.S. Application No. 2003/0044909, which is incorporated by reference in its entirety.

K. 5HT4 Receptor Agonists

In certain embodiments, the compound is a 5HT4 receptor agonist, optionally a selective agonist. The 5-hydroxytryptamine receptor 4 (5HT4) is a G protein-coupled serotonin receptor, which stimulates cAMP production in response to serotonin (5-hydroxytryptamine or 5-HT) or other agonist.

Based on one non-limiting theory, serotonin has been shown to increases protective duodenal bicarbonate secretion, for example, via enteric ganglia, cAMP- and Ca2+-dependent signaling pathways, and a 5HT4-dependent pathway. See, e.g., Safsten et al., *Scand J Gastroenterol.* 41:1279-89, 2006; Tuo et al., *Am J Physiol Gastrointest Liver Physiol* 286:G444-G451, 2004. Without being bound by any one mechanism, in certain aspects a 5HT4 receptor agonist inhibits or reduces phosphate uptake in the gastrointestinal tract by stimulating bicarbonate secretion into the small intestine.

In some embodiments, and without being bound by any one mechanism, a 5HT4 agonist inhibits or reduces phosphate uptake in the gastrointestinal tract by decreasing water absorption in the small intestine.

Non-limiting examples of 5HT4 agonists include serotonin and its analogs, BIMU-8, cisapride, cleobopride, CL033466, ML10302, mosapride, prucalopride, renzapride, RS67506, RS67333, SL650155, tegaserod, zacopride, naronopride (ATI-7505), velusetrag (TD-5108).

In some embodiments, the 5HT4 receptor agonist or partial agonist is a substituted benzamide, such as cisapride, including individual or combinations of cisapride enantiomers ((+) cisapride and (−) cisapride), mosapride, or renzapride. In some embodiments, the 5HT4 receptor agonist is a benzofuran derivative, such as prucalopride, an indole such as tegaserod, or a benzimidazolone. Other non-limiting examples of 5HT4 receptor agonists or partial agonists include zacopride (CAS RN 90182-92-6), SC-53116 (CAS RN 141196-99-8) and its racemate SC-49518 (CAS RN 146388-57-0), BIMU1 (CAS RN 127595-43-1), TS-951 (CAS RN 174486-39-6), ML10302 (CAS RN 148868-55-7), metoclopramide, 5-methoxytryptamine, RS67506, 2-[1-(4-piperonyl)piperazinyl]benzothiazole, RS66331, BIMU8, SB 205149 (the n-butyl quaternary analog of renzapride), and an indole carbazimidamide described in Buchheit et al., *J Med. Chem.* 38:2331-8, 1995. Also included are norcisapride (CAS RN 102671-04-5), which is the metabolite of cisapride; mosapride citrate; the maleate form of tegaserod (CAS RN 189188-57-6); zacopride hydrochloride (CAS RN 99617-34-2); mezacopride (CAS RN 89613-77-4); SK-951 ((+−)-4-amino-N-(2-(1-azabicyclo(3.3.0)octan-5-yl)ethyl)-5-chloro-2,3-dihydro-2-methylbenzo[b]furan-7-carboxamide hemifumarate); ATI-7505, a cisapride analog; SDZ-216-454, a selective 5HT4 receptor agonist that stimulates cAMP formation in a concentration dependent manner (see, e.g., Markstein et al., Naunyn-Schmiedebergs Arch Pharmacol. 359:454-9, 1999); SC-54750, or aminomethylazaadamantane; Y-36912, or 4-amino-N-[1-[3-(benzylsulfonyl)propyl]piperidin-4-ylmethyl]-5-chloro-2-methoxybenzamide (see Sonda et al., *Bioorg Med. Chem.* 12:2737-47, 2004); TKS159, or 4-amino-5-chloro-2-methoxy-N-[(2S,4S)-1-ethyl-2-hydroxymethyl-4-pyrrolidinyl]benzamide; RS67333, or 1-(4-amino-5-chloro-2-methoxyphenyl)-3-(1-n-butyl-4-piperidinyl)-1-propanone; KDR-5169, or 4-amino-5-chloro-N-[1-(3-fluoro-4-methoxybenzyl)piperidin-4-yl]-2-(2-hydr-oxyethoxy)benzamide hydrochloride dihydrate (see Tazawa, et al., Eur J Pharmacol. 434: 169-76, 2002); SL65.0155, or 5-(8-amino-7-chloro-2,3-dihydro-1,4-benzodioxin-5-yl)-3-[1-(2-phenylethyl)-4-piperidinyl]-1,3,4-oxadiazol-2(3H)-one monohydrochloride; and Y-34959, or 4-amino-5-chloro-2-methoxy-N-[1-[5-(1-methylindol-3-ylcarbonylamino)pentyl]piperidin-4-ylmethyl]benzamide.

Additional examples of 5HT4 receptor agonists and partial agonists metoclopramide (CAS RN 364-62-5), 5-methoxytryptamine (CAS RN 608-07-1), RS67506 (CAS RN 168986-61-6), 2-[1-(4-piperonyl)piperazinyl]benzothiazole (CAS RN 155106-73-3), RS66331 (see Buccafusco et al., Pharmacology. 295:438-446, 2000); BIMU8 (endo-N-8-methyl-8-azabicyclo[3.2.1]oct-3-yl)-2,3-dehydro-2-oxo-3-(prop-2-yl)-1H-benzimid-azole-1-carboxamide), or SB 205149 (the n-butyl quaternary analog of renzapride). Also included are compounds related to metoclopramide, such as metoclopramide dihydrochloride (CAS RN 2576-84-3), metoclopramide dihydrochloride (CAS RN 5581-45-3), and metoclopramide hydrochloride (CAS RN 7232-21-5 or 54143-57-6). See, e.g., U.S. Application No. 2009/0325949; De Maeyer et al., *Neurogastroenterology and Motility.* 20:99-112, 2008; Manabe et al., *Expert Opin Investig Drugs.* 19:765-75, 2010; Tack et al., *Alimentary Pharmacology & Ther.* 35:745-767, 2012. These references are incorporated by reference in their entireties.

L. Atrial Natriuretic Peptide Receptor Agonists

In some embodiments, the compound is an atrial natriuretic peptide (NP) receptor agonist. NP receptors are single transmembrane catalytic receptors with intracellular guanylyl cyclase (GC) activity. There are three isoforms of NP receptors; NPR1, NPR2 and NPR3. These receptors have conserved catalytic and regulatory domains and divergent ligand binding domains.

Natriuretic peptide receptors are found in the brain, vasculature kidney, and gastrointestinal tract and bind α-atrial natriuretic peptide, brain natriuretic peptide, and type C-natriuretic peptide with varying affinities. The main physiological role of NP receptors is the homeostasis of body fluid volume. According to one non-limiting theory, exogenous natriuretic peptide stimulates GC activity in the gastrointestinal tract. See, e.g., Rambotti et al., *Histochem. J.* 29:117-126, 1997.

Without being bound by any one mechanism, in certain aspects an NP receptor agonist inhibits or reduces phosphate uptake in the gastrointestinal tract by stimulating bicarbonate secretion and/or inhibiting acid secretion in the small intestine.

In some embodiments, and without being bound by any one mechanism, an NP receptor agonist inhibits or reduces phosphate uptake in the gastrointestinal tract by decreasing water absorption in the small intestine.

Figure 16:
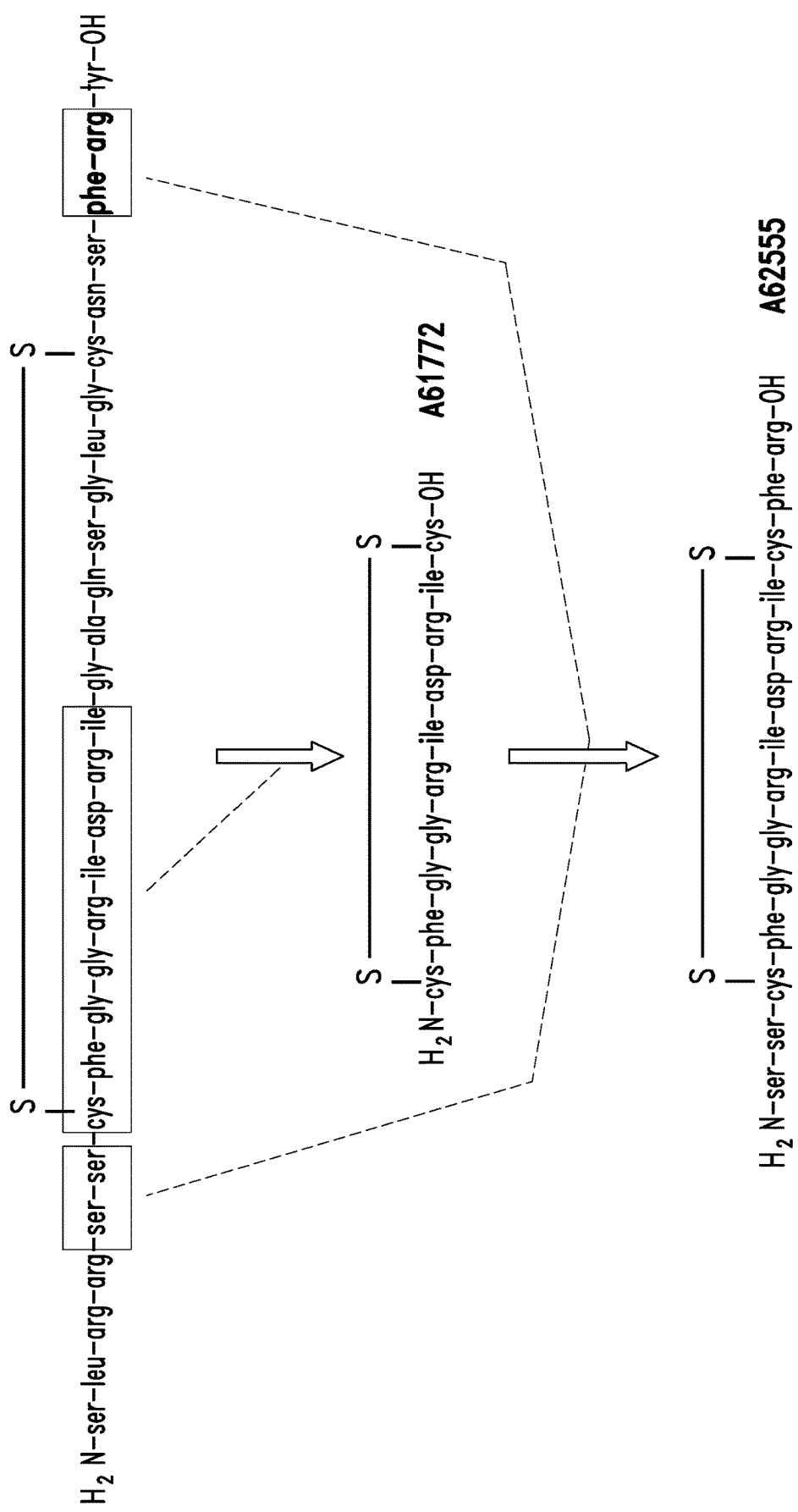
FIG. 16 shows the structures of exemplary peptide agonists (SEQ ID Nos. 7, 8 and 9) of the NP receptor(s).

The structures of exemplary peptide agonists of the NP receptor(s) are shown in FIG. 16, and described, for example, in von Geldern et al., *J. Med. Chem.* 35:808-816, 1992, which is incorporated by reference in its entirety.

In certain embodiments, the NP receptor agonist comprises, consists, or consists essentially of the atrial natriuretic peptide amino acid sequence: Ser Leu Arg Arg Ser Ser Cys Phe Gly Gly Arg Ile Asp Arg Ile Gly Ala Gln Ser Gly Leu Gly Cys Asn Ser Phe Arg Tyr (SEQ ID NO:7), including active variants thereof having 1, 2, 3, 4, 5, 6, 7, 8, 9, 10, 11, or 12 deletions, insertions, and/or substitutions. Specific examples of deletion mutants include those having the sequence; Cys Phe Gly Gly Arg Ile Asp Arg Ile Gly Ala Gln Ser Gly Leu Gly Cys (SEQ ID NO:8); and Ser Ser Cys Phe Gly Gly Arg Ile Asp Arg Ile Gly Ala Gln Ser Gly Leu Gly Cys Asn Ser Phe Arg (SEQ ID NO:9). As described elsewhere herein, such peptides can be composed of any combination of naturally-occurring and non-naturally-occurring amino acids.

M. Carbonic Anhydrase Inhibitors

In some embodiments, the compound is a carbonic anhydrase inhibitor. Bicarbonate uptake into epithelial cells occurs by $CO_2$ diffusion with subsequent conversion to $HCO_3^-$ and $H^+$ by cellular carbonic anhydrase (CA). Bicarbonate is then secreted across the apical membrane by anion exchange. CA is the enzyme that hydrates $CO_2$ to produce $HCO_3^-$ and $H^+$ and is present in most tissues, including duodenal epithelial cells. See, e.g., Kaunitz and Akiba, 2006. This endogenously produced $HCO_3^-$ is a significant source of transported bicarbonate.

There are at least 15 isoforms of carbonic anhydrase. Carbonic anhydrase IV (CAIV) is a membrane-bound isoform, while CAII is cytosolic, ubiquitous and highly active (turnover rate $\sim 10^6$ $s^{-1}$). See, e.g., Shandro and Casey, 2007. Carbonic anhydrase II appears to be functionally coupled—directly and indirectly—with bicarbonate transporting proteins such as CFTR, SLC26A6 and DRA. See, e.g., Seidler and Sjoblom, 2012. In general, the COOH-terminal tail of all bicarbonate transport proteins, with the exception of DRA, possesses a consensus carbonic anhydrase II-binding motif. See, e.g., Dudeja and Ramaswamy, 2006.

Carbonic anhydrases are involved in several physiological processes, including pH homeostasis. The classical carbonic anhydrase inhibitors, such as acetazolamide and benzolamide, have been shown to inhibit multiple CA isoforms, including CAII and CAIV. See, e.g., Scozzafava et al., *J. Med. Chem.* 45:1466-1476, 2002. According to one non-limiting theory, inhibition of carbonic anhydrase would be expected to decrease subapical intracellular pHi. Without being bound by any one mechanism, selective inhibition of CA in the enterocytes of the duodenum could thereby decrease the CEPG, resulting in a decrease in phosphate transport.

In some embodiments, and without being bound by any one mechanism, a carbonic anhydrase inhibitor inhibits or reduces phosphate uptake in the gastrointestinal tract by decreasing water absorption in the small intestine.

Figure 17:
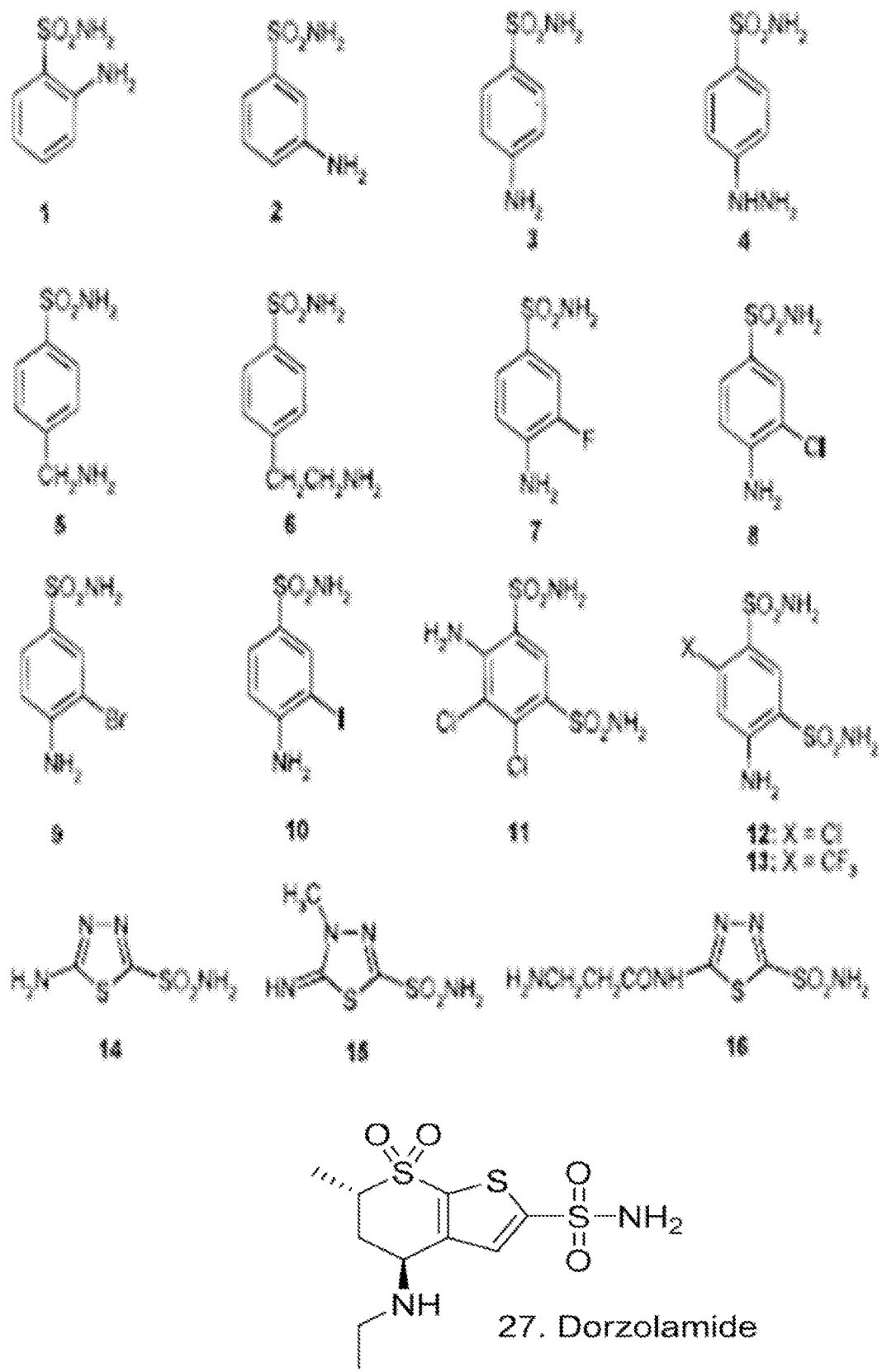
FIG. 17 shows exemplary carbonic anhydrase inhibitors.
Figure 17:
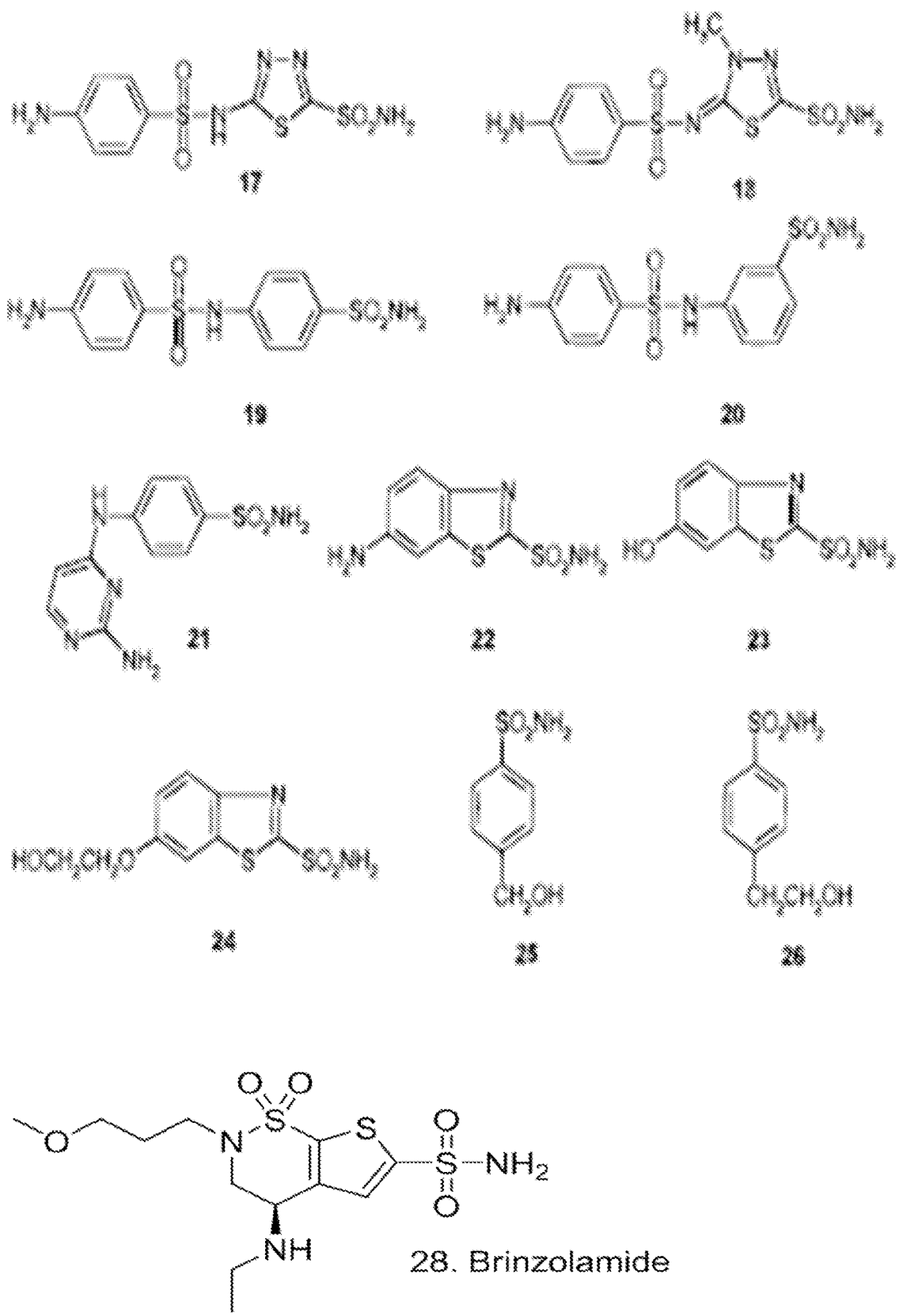

FIG. 17 shows the structures of exemplary carbonic anhydrase inhibitors, including dorzolamide and brinzolamide, among others. In certain aspects, carbonic anhydrase inhibitors can be used in combination with classes of compounds capable of elevating cAMP, cGMP, calcium or other second messengers in apical mucosal cells of the gastrointestinal tract.

N. Phosphodiesterase Inhibitors

In some embodiments, the compound is a phosphodiesterase inhibitor. Phosphodiesterases (PDEs) are a family of related phosphohydrolyases that selectively catalyze the hydrolysis of 3' cyclic phosphate bonds in adenosine and/or guanine 3',5' cyclic monophosphate (cAMP and/or cGMP). They regulate the cellular levels, localization and duration of action of these second messengers by controlling the rate of their degradation.

Figure 18:
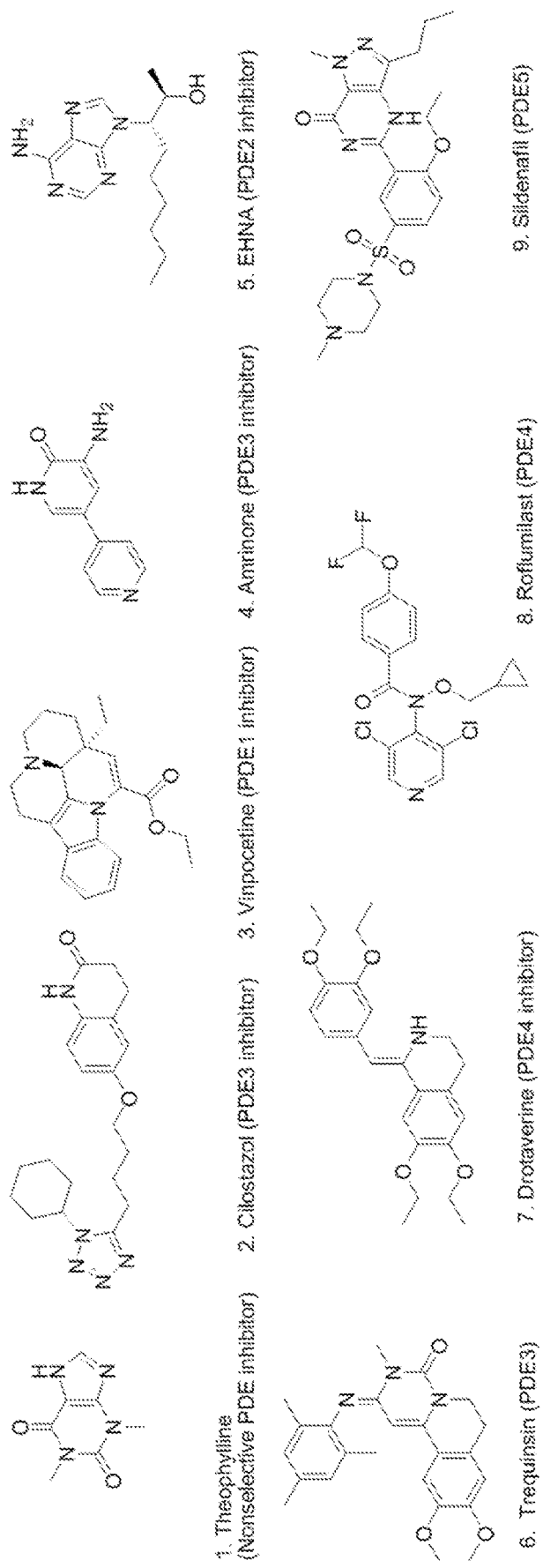
FIG. 18 shows exemplary phosphodiesterase inhibitors.

There are 11 subtypes of PDEs, named PDE1-11; PDE4, 7 and 8 selectively degrade cAMP, PDE5, 6 and 9 selectively degrade cGMP and PDE1, 2, 3, 10 and 11 degrade both cyclic nucleotides. PDEs are expressed ubiquitously, with each subtype having a specific tissue distribution. FIG. 18 shows the structures of exemplary phosphodiesterase inhibitors with varied subtype specificity, including theophylline, cilostazol, vinpocetine, amrinone, EHNA, trequinsin, drotaverine, roflumilast, and sildenafil.

According to one non-limiting theory, phosphodiesterase inhibitors are capable of modulating duodenal bicarbonate secretion (DBS) alone and in combination with agents that increase cytosolic cAMP and cGMP by maintaining the level of these second messengers in enterocytes. PDE1 and PDE3 inhibitors are specifically implicated in modulating DBS. See, e.g., Hayashi, *Biochem. Pharmacol.* 74:1507-1513, 2007. Without being bound by any one mechanism, in certain embodiments a phosphodiesterase inhibitor inhibits or reduces phosphate uptake in the gastrointestinal tract by stimulating bicarbonate secretion into the small intestine or DBS.

In some embodiments, and without being bound by any one mechanism, a phosphodiesterase inhibitor inhibits or reduces phosphate uptake in the gastrointestinal tract by decreasing water absorption in the small intestine.

In certain embodiments, PDE inhibitors slow the degradation of cyclic AMP (cAMP) and/or cyclic GMP (cGMP), which can then lead to a relative increase in the intracellular concentration of cAMP and/or cGMP. General examples include PDE1 inhibitors, PDE3 inhibitors, PDE4 inhibitors, PDE5 inhibitors, PDE3/4 inhibitors, and PDE3/4/5 inhibitors. Merely by way of non-limiting example, PDE inhibitors may include those disclosed in the following patent applications and patents: DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, DE3142982, DE1116676, DE2162096, EP000718, EP0008408, EP0010759, EP0059948, EP0075436, EP0096517, EP0112987, EP0116948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, EP0293063, EP0463756, EP0482208, EP0579496, EP0667345, EP0163965, EP0393500, EP0510562, EP0553174, JP92234389, JP94329652, JP95010875, U.S. Pat. Nos. 4,963,561; 5,141,931; and 6,331,543; International Patent Application Publication Nos. WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, WO9307124, WO9501338 and WO9603399; and U.S. Application No. 2005/0004222 (including those disclosed in formulas I-XIII and paragraphs 37-39, 85-0545 and 557-577), each of which is incorporated by reference in its entirety.

Examples of PDE5 inhibitors include RX-RA-69, SCH-51866, KT-734, vesnarinone, zaprinast, SKF-96231, ER-21355, BF/GP-385, NM-702 and sildenafil (Viagra®). Examples of PDE4 inhibitors include RO-20-1724, MEM 1414 (R1533/R1500; Pharmacia Roche), DENBUFYLLINE, ROLIPRAM, OXAGRELATE, NITRAQUAZONE, Y-590, DH-6471, SKF-94120, MOTAPIZONE, LIXAZINONE, INDOLIDAN, OLPRINONE, ATIZORAM, KS-506-G, DIPAMFYLLINE, BMY-43351, ATIZORAM, AROFYLLINE, FILAMINAST, PDB-093, UCB-29646, CDP-840, SKF-107806, PICLAMILAST, RS-17597, RS-25344-000, SB-207499, TIBENELAST, SB-210667, SB-211572, SB-211600, SB-212066, SB-212179, GW-3600, CDP-840, MOPIDAMOL, ANAGRELIDE, IBUDILAST, AMRINONE, PIMOBENDAN, CILOSTAZOL, QUAZINONE, and N-(3,5-dichloropyrid-4-yl)-3-cyclopropylmethoxy4-difluoromethoxybenzamide. Examples of PDE3 inhibitors include SULMAZOLE, AMPIZONE, CILOSTAMIDE, CARBAZERAN, PIROXIMONE, IMAZODAN, CI-930, SIGUAZODAN, ADIBENDAN, SATERINONE, SKF-95654, SDZ-MKS-492, 349-U-85, EMORADAN, EMD-53998, EMD-57033, NSP-306, NSP-307, REVIZINONE, NM-702, WIN-62582 and WIN-63291, ENOXIMONE, and MILRINONE. Examples of PDE3/4 inhibitors include BENAFENTRINE, TREQUINSIN, ORG-30029, ZARDAVERINE, L-686398, SDZ-ISQ-844, ORG-20241, EMD-54622, and TOLAFENTRINE. Other examples of PDE inhibitors include cilomilast, pentoxifylline, roflumilast, tadalafil (Cialis®), theophylline, vardenafil (Levitra®), and zaprinast (PDE5 specific).

In certain aspects, phosphodiesterase inhibitors can be used in combination with classes of compounds capable of elevating cAMP, cGMP, calcium or other second messengers in apical mucosal cells of the gastrointestinal tract.

O. Agonists of DRA (SLC26A3)

In certain embodiments, the compound is an agonist of the chloride/bicarbonate antiporter SLC26A3, also referred to as Down-Regulated in Adenoma (DRA). One non-limiting function of DRA in the gut is to absorb luminal chloride and secrete bicarbonate ions. Pharmacological stimulation of DRA is expected reduce pHi, for instance, by increasing the pH of the UWL, and provide a phosphate lowering effect as described herein.

Examples of DRA agonists include lysophosphatic acid (LPA) and structurally related compounds. This class of compounds is thought to be acting on DRA activity via stimulation of LPA receptor (for instance LPA2) signaling through the Pi3K/AKT pathway, which is thought to not only activate DRA gene transcription but also increase DRA surface accumulation (Singla et al. *Am. J. Physiol Gastrointest. Liver Physiol.* 298: G182-G189, 2010; Singla et al. *Am. J. Physiol. Gastrointest. Liver Physiol.* 302: G618-G627, 2012). Examples of LPA related compounds with potential role in DRA stimulation are described in Jiang et al., *Bioorg. Med. Chem. Lett.* 23:1865-1869, 2013; Kiss et al., *Molecular Pharmacology* 82:1162-1173, 2012; Kozian et al., *Bioorg. Med. Chem. Lett.* 22: 5239-5243, 2012; Parrill, *Expert. Opin. Ther. Pat.* 21:281-286, 2011; Gupte et al., *Bioorg. Med. Chem. Lett.* 20: 7525-7528, 2010; Liliom et al., *Biochim. Biophys. Acta* 1761:1506-1514, 2006; and Durgam et al., *Journal of Medicinal Chemistry* 48: 4919-4930, 2005.

According to one non-limiting theory, protein Kinase C inhibitors may also increase DRA activity and similarly create a cross-epithelial pH gradient. For example, phorbol 12-myristate 13-acetate (PMA), an in vitro PKC agonist, was shown to directly inhibit the apical membrane $Cl^-$/$HCO_3^-$ activity (Gill et al., *Physiology of the Gastrointestinal Tract*, Chapter 67, 2012). Without being bound by any one mechanism, inhibition of the appropriate PKC isoforms could conversely increase $Cl^-$/$HCO_3^-$ activity and thereby inhibit phosphate uptake via the mechanisms described in the disclosure.

FIGS. 21A-B (Mochly-Rosen et al., *Nature Reviews Drug Discovery* 11, 937-957, 2012) depict representative examples of subtype selective PKC inhibitors with the potential to increase $Cl^-/HCO_3^-$ activity, among other potential mechanisms of action. Other potential DRA agonists include All-trans-retinoic acid (ATRA) and related compounds, more generally compounds activating the retinoic acid receptors (RAR's) α, β and γ, preferably the RAR-β. RAR-β agonists are believed to induce DRA at the transcriptional level (All-Trans-Retinoic Acid Increases SLC26A3 (DRA) Expression via HNF-1 (Priyamvada et al., DDW 2013, Orlando). Another exemplary compound is S20787, which was shown to stimulate the activity of human DRA expressed in oocytes (Chernova et al., *J Physiol.*, 549,1, 3-19, 2003). Agonists of neuropeptide Y1 and Y2 receptor stimulate DRA activity in caco2 monolayers. Stimulation DRA by NPY was found to be independent of membrane trafficking and associated with localization of DRA to lipid rafts (Saksena et al. *Am. J. Physiol Gastrointest Liver Physiol.* 299: G1334-G1343, 2010). Examples of representative NPY1 and NPY2 agonists include NPY, [Leu31, Pro34]-NPY, NPY 13-36, Peptide YY (3-36) and GR 231118.

II. Substantially Systemically Non-Bioavailable Compounds

A. Physical and Performance Properties of Compounds Localizable to the GI Tract

Certain of the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound remains in the gastrointestinal lumen. For example, in accordance with one or more embodiments of the present disclosure, preferably at least about 60%, about 70%, about 75%, about 80%, about 85%, about 90%, about 95%, about 96%, about 97%, about 98%, about 99%, or even about 99.5%, of the compound remains in the gastrointestinal lumen. In such cases, localization to the gastrointestinal lumen refers to reducing net movement of a compound across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" includes embodiments where no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.); stated another way, "substantially impermeable" or "substantially systemically non-bioavailable" may refer to compounds that exhibit some detectable permeability to an epithelial layer of cells in the GI tract of less than about 20% of the administered compound (e.g., less than about 15%, about 10%, or even about 5%, 4%, 3%, or 2%, and for example greater than about 0.5%, or 1%), but then are cleared by the liver (i.e., hepatic extraction) and/or the kidney (i.e., renal excretion).

In this regard it is to be further noted, that in certain embodiments, due to the substantial impermeability and/or substantial systemic non-bioavailability of the compounds of the present invention, greater than about 50%, 60%, 70%, 80%, 90%, or 95% of a compound of the invention is recoverable from the feces over, for example, a 24, 36, 48, 60, 72, 84, or 96 hour period following administration to a subject in need thereof. In this respect, it is understood that a recovered compound can include the sum of the parent compound and its metabolites derived from the parent compound, e.g., by means of hydrolysis, conjugation, reduction, oxidation, N-alkylation, glucuronidation, acetylation, methylation, sulfation, phosphorylation, or any other modification that adds atoms to or removes atoms from the parent compound, where the metabolites are generated via the action of any enzyme or exposure to any physiological environment including, pH, temperature, pressure, or interactions with foodstuffs as they exist in the digestive milieu.

Measurement of fecal recovery of compound and metabolites can be carried out using standard methodology. For example, a compound can be administered orally at a suitable dose (e.g., 10 mg/kg) and feces are then collected at predetermined times after dosing (e.g., 24 hours, 36 hours, 48 hours, 60 hours, 72 hours, 96 hours). Parent compound and metabolites can be extracted with organic solvent and analyzed quantitatively using mass spectrometry. A mass balance analysis of the parent compound and metabolites (including, parent=M, metabolite 1 [M+16], and metabolite 2 [M+32]) can be used to determine the percent recovery in the feces.

(i) Permeability

In this regard it is to be noted that, in various embodiments, the ability of the compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacokinetics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews,* 46:3-26, 2001 incorporated herein by reference.) Accordingly, substantially systemically non-bioavailable compounds can be designed to have molecular structures exceeding one or more of Lipinski's threshold values. (See also Lipinski et al., Experimental and Computational Approaches to Estimate Solubility and Permeability in Drug Discovery and Development Settings, *Adv. Drug Delivery Reviews,* 46:3-26, 2001; and Lipinski, Drug-like Properties and the Causes of Poor Solubility and Poor Permeability, *J. Pharm. & Toxicol. Methods,* 44:235-249, 2000, which are incorporated by reference in their entireties.

In some embodiments, for example, a substantially impermeable or substantially systemically non-bioavailable compound of the present disclosure can be constructed to feature one or more of the following characteristics: (i) a MW greater than about 500 Da, about 600 Da, about 700 Da, about 800 Da, about 900 Da, about 1000 Da, about 1200 Da, about 1300 Da, about 1400 Da, about 1500 Da, about 1600 Da, about 1800 Da, about 2000 Da, about 2500 Da, about 3000 Da, about 4000 Da, about 5000 Da, about 7500 Da, about 10,000 Da or more (in the non-salt form of the compound); (ii) a total number of NH and/or OH and/or other potential hydrogen bond donors greater than about 5, about 6, about 7, about 8, about 9, about 10, about 11, about 12, about 13, about 14, about 15, about 20 or more; (iii) a total number of O atoms and/or N atoms and/or other potential hydrogen bond acceptors greater than about 5, about 6, about 7, about 8, about 9, about 10, about 11, about 12, about 13, about 14, about 15, about 20 or more; (iv) a Moriguchi partition coefficient greater than about $10^5$ (i.e., Log P greater than about 5, about 6, about 7, about 8, about 9, about 10 etc.), or alternatively less than about 10 (i.e., a Log P of less than 1, or even 0); and/or (v) a total number of rotatable bonds greater than about 5, about 10 or about 15, or more. In specific embodiments, the compound has a Log P that is not 14 or is less than about 14, for instance, a Log P that is in the range of about 6-7, 6-8, 6-9, 6-10, 6-11, 6-12, 6-13, 7-8, 7-9, 7-10, 7-11, 7-12, 7-13, 8-9, 8-10, 8-11, 8-12, 8-13, 9-10, 9-11, 9-12, 9-13, 10-11, 10-12, 10-13, 11-12, 11-13, or 12-13.

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. For exemplary Caco2 cell monolayer penetration test details, see for example the description of the Caco2 Model provided in U.S. Pat. No. 6,737,423, incorporated by reference, particularly the text describing the Caco2 Model, which may be applied for example to the evaluation or testing of the compounds of the present invention. PSA is expressed in $Å^2$ (squared angstroms) and is computed from a three-dimensional molecular representation. A fast calculation method is also available (see, e.g., Ertl et al., *Journal of Medicinal Chem.* 43:3714-3717, 2000 the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see Table 1, from Ertl et al., *J. Med. Chem..* 43:3714-3717, 2000):

TABLE 1

| name | % FA[a] | TPSA[b] |
|---|---|---|
| metoprolol | 102 | 50.7 |
| nordiazepam | 99 | 41.5 |
| diazepam | 97 | 32.7 |
| axprenolol | 97 | 50.7 |
| phenazone | 97 | 26.9 |
| axazepam | 97 | 61.7 |
| alprenolol | 96 | 41.9 |
| practolol | 95 | 70.6 |
| pindolol | 92 | 57.3 |
| ciproflaxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

Accordingly, in some embodiments, the compounds of the present disclosure may be constructed to exhibit a tPSA value greater than about 100 $Å^2$, about 116 $Å^2$, about 120 $Å^2$, about 130 $Å^2$, or about 140 $Å^2$, and in some instances about 150 $Å^2$, about 160 $Å^2$, about 170 $Å^2$, about 180 $Å^2$, about 190 $Å^2$, about 200 $Å^2$, about 225 $Å^2$, about 250 $Å^2$, about 270 $Å^2$, about 300 $Å^2$, about 350 $Å^2$, about 400 $Å^2$, about 450 $Å^2$, about 500 $Å^2$, about 750 $Å^2$, or even about 1000 $Å^2$, or in the range of about 100-120 $Å^2$, 100-130 $Å^2$, 100-140 $Å^2$, 100-150 $Å^2$, 100-160 $Å^2$, 100-170 $Å^2$, 100-170 $Å^2$, 100-190 $Å^2$, 100-200 $Å^2$, 100-225 $Å^2$, 100-250 $Å^2$, 100-300 $Å^2$, 100-400 $Å^2$, 100-500 $Å^2$, 100-750 $Å^2$, 100-1000 $Å^2$, 116-120 $Å^2$, 116-130 $Å^2$, 116-140 $Å^2$, 116-150 $Å^2$, 116-160 $Å^2$, 116-170 $Å^2$, 116-170 $Å^2$, 116-190 $Å^2$, 116-200 $Å^2$, 116-225 $Å^2$, 116-250 $Å^2$, 116-300 $Å^2$, 116-400 $Å^2$, 116-500 $Å^2$, 116-750 $Å^2$, 116-1000 $Å^2$, 120-130 $Å^2$, 120-140 $Å^2$, 120-150 $Å^2$, 120-160 $Å^2$, 120-170 $Å^2$, 120-170 $Å^2$, 120-190 $Å^2$, 120-200 $Å^2$, 120-225 $Å^2$, 120-250 $Å^2$, 120-300 $Å^2$, 120-400 $Å^2$, 120-500 $Å^2$, 120-750 $Å^2$, 120-1000 $Å^2$, 130-140 $Å^2$, 130-150 $Å^2$, 130-160 $Å^2$, 130-170 $Å^2$, 130-170 $Å^2$, 130-190 $Å^2$, 130-200 $Å^2$, 130-225 $Å^2$, 130-250 $Å^2$, 130-300 $Å^2$, 130-400 $Å^2$, 130-500 $Å^2$, 130-750 $Å^2$, 130-1000 $Å^2$, 140-150 $Å^2$, 140-160 $Å^2$, 140-170 $Å^2$, 140-170 $Å^2$, 140-190 $Å^2$, 140-200 $Å^2$, 140-225 $Å^2$, 140-250 $Å^2$, 140-300 $Å^2$, 140-400 $Å^2$, 140-500 $Å^2$, 140-750 $Å^2$, 140-1000 $Å^2$, 150-160 $Å^2$, 150-170 $Å^2$, 150-170 $Å^2$, 150-190 $Å^2$, 150-200 $Å^2$, 150-225 $Å^2$, or 150-250 $Å^2$, 150-300 $Å^2$, 150-400 $Å^2$, 150-500 $Å^2$, 150-750 $Å^2$, 150-1000 $Å^2$, 200-250 $Å^2$, 200-300 $Å^2$, 200-400 $Å^2$, 200-500 $Å^2$, 200-750 $Å^2$, 200-1000 $Å^2$, 250-250 $Å^2$, 250-300 $Å^2$, 250-400 $Å^2$, 20-500 $Å^2$, 250-750 $Å^2$, or 250-1000 $Å^2$, such that the compounds are substantially impermeable (e.g., cell impermeable) or substantially systemically non-bioavailable (as defined elsewhere herein).

Because there are exceptions to Lipinski's "rule," or the tPSA model, the permeability properties of the compounds of the present disclosure may be screened experimentally.

The permeability coefficient can be determined by methods known to those of skill in the art, including for example by Caco-2 cell permeability assay and/or using an artificial membrane as a model of a gastrointestinal epithelial cell. A synthetic membrane impregnated with, for example, lecithin and/or dodecane to mimic the net permeability characteristics of a gastrointestinal mucosa may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo (see Wohnsland et al., *J. Med. Chem.* 44:923-930, 2001; Schmidt et al., Millipore Corp. Application Note, 2002, n AN1725EN00, and n AN1728EN00, incorporated herein by reference).

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., 2001, supra).

As previously noted, in accordance with the present disclosure, compounds may be modified to hinder their net absorption through a layer of gut epithelial cells, rendering them substantially systemically non-bioavailable. In some particular embodiments, the compounds of the present disclosure comprise a compound that is linked, coupled or otherwise attached to a non-absorbable moiety, which may be an oligomer moiety, a polymer moiety, a hydrophobic moiety, a hydrophilic moiety, and/or a charged moiety, which renders the overall compound substantially impermeable or substantially systemically non-bioavailable. In some preferred embodiments, the compound is coupled to a multimer or polymer portion or moiety, such that the resulting molecule is substantially impermeable or substantially systemically non-bioavailable. The multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound. In these or other particular embodiments, the compound is modified to substantially hinder its net absorption through a layer of gut epithelial cells.

(ii) $C_{max}$ and $IC_{50}$ or $EC_{50}$ In some embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than the phosphate ion (Pi) transport or uptake inhibitory concentration $IC_{50}$ of the compound. In some embodiments, for instance, the $C_{max}$ is about or at least about 5%, 10%, 20%, 30%, 40%, 50%, 60%, 70%, 80%, 90%, or 100% less than the $IC_{50}$ for inhibiting Pi transport or uptake. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $IC_{50}$ for inhibiting Pi transport or uptake.

In certain embodiments, one or more of the substantially systemically non-bioavailable compounds detailed herein, when administered (e.g., enterally) to a subject in need thereof, may have a ratio of $C_{max}:IC_{50}$ (for inhibiting Pi transport or update), where $C_{max}$ and $IC_{50}$ are expressed in terms of the same units, of at about or less than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0, or a range in between about 0.01-1.0, 0.01-0.9, 0.01-0.8, 0.01-0.7, 0.01-0.6, 0.01-0.5, 0.01-0.4, 0.01-0.3, 0.01-0.2, or 0.01-0.1, or a range in between about 0.1-1.0, 0.1-0.9, 0.1-0.8, 0.1-0.7, 0.1-0.6, 0.1-0.5, 0.1-0.4, 0.1-0.3, or 0.1-0.2.

In some embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than $EC_{50}$ of the compound for increasing fecal output of phosphate, where fecal output is increased by about or at least about 5%, 10%, 20%, 30%, 40%, 50%, 60%, 70%, 80%, 90%, or 100%. In some embodiments, for instance, the $C_{max}$ is about or at least about 5%, 10%, 20%, 30%, 40%, 50%, 60%, 70%, 80%, 90%, or 100% less than the $EC_{50}$ for increasing fecal output of phosphate. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $EC_{50}$ for increasing fecal output of phosphate.

In some embodiments, one or more of the substantially systemically non-bioavailable compounds detailed herein, when administered (e.g., enterally) either alone or in combination with one or more additional pharmaceutically active compounds or agents to a subject in need thereof, or measured in an animal model or cell-based assay, may have an $EC_{50}$ for increasing fecal output of phosphate of about or less than about 10 µM, 9 µM, 8 µM, 7 µM, 7.5 µM, 6 µM, 5 µM, 4 µM, 3 µM, 2.5 µM, 2 µM, 1 µM, 0.5 µM, 0.1 µM, 0.05 µM, or 0.01 µM, or less, the $IC_{50}$ being, for example, within the range of about 0.01 µM to about 10 µM, or about 0.01 µM to about 7.5 µM, or about 0.01 µM to about 5 µM, or about 0.01 µM to about 2.5 µM, or about 0.01 µM to about 1.0, or about 0.1 µM to about 10 µM, or about 0.1 µM to about 7.5 µM, or about 0.1 µM to about 5 µM, or about 0.1 µM to about 2.5 µM, or about 0.1 µM to about 1.0, or about M 0.5 µM to about 10 µM, or about 0.5 µM to about 7.5 µM, or about 0.5 µM to about 5 µM, or about 0.5 µM to about 2.5 µM, or about 0.5 µM to about 1.0 µM.

In particular embodiments, the substantially systemically non-bioavailable compounds detailed herein, when administered (e.g., enterally) either alone or in combination with one or more additional pharmaceutically active compounds or agents to a subject in need thereof, exhibit a maximum concentration detected in the serum, defined as $C_{max}$, that is about the same as or less than $EC_{50}$ of the compound for reducing urinary output of phosphate, where urinary output is reduced by about or at least about 5%, 10%, 20%, 30%, 40%, 50%, 60%, 70%, 80%, 90%, or 100%. In some embodiments, for instance, the $C_{max}$ is about or at least about 5%, 10%, 20%, 30%, 40%, 50%, 60%, 70%, 80%, 90%, or 100% less than the $EC_{50}$ for reducing urinary output of phosphate. In some embodiments, the $C_{max}$ is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9× (0.9 times) the $EC_{50}$ for reducing urinary output of phosphate.

In some embodiments, one or more of the substantially systemically non-bioavailable compounds detailed herein, when administered (e.g., enterally) either alone or in combination with one or more additional pharmaceutically active compounds or agents to a subject in need thereof, or measured in an animal model or cell-based assay, may have an $EC_{50}$ for reducing urinary output of phosphate of about or less than about 10 µM, 9 µM, 8 µM, 7 µM, 7.5 µM, 6 µM, 5 µM, 4 µM, 3 µM, 2.5 µM, 2 µM, 1 µM, 0.5 µM, 0.1 µM, 0.05 µM, or 0.01 µM, or less, the $IC_{50}$ being, for example, within the range of about 0.01 µM to about 10 µM, or about 0.01 µM to about 7.5 µM, or about 0.01 µM to about 5 µM, or about 0.01 µM to about 2.5 µM, or about 0.01 µM to about 1.0, or about 0.1 µM to about 10 µM, or about 0.1 µM to about 7.5 µM, or about 0.1 µM to about 5 µM, or about 0.1 µM to about 2.5 µM, or about 0.1 µM to about 1.0, or about M 0.5 µM to about 10 µM, or about 0.5 µM to about 7.5 µM, or about 0.5 µM to about 5 µM, or about 0.5 µM to about 2.5 µM, or about 0.5 µM to about 1.0 µM.

In certain embodiments, one or more of the substantially systemically non-bioavailable compounds detailed herein, when administered (e.g., enterally) to a subject in need thereof, may have a ratio of $C_{max}:EC_{50}$ (e.g., for increasing fecal output of phosphate, for decreasing urinary output of phosphate), where $C_{max}$ and $EC_{50}$ are expressed in terms of the same units, of at about or less than about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0, or a range in between about 0.01-1.0, 0.01-0.9, 0.01-0.8, 0.01-0.7, 0.01-0.6, 0.01-0.5, 0.01-0.4, 0.01-0.3, 0.01-0.2, or 0.01-0.1, or a range in between about 0.1-1.0, 0.1-0.9, 0.1-0.8, 0.1-0.7, 0.1-0.6, 0.1-0.5, 0.1-0.4, 0.1-0.3, or 0.1-0.2.

Additionally, or alternatively, one or more of the substantially systemically non-bioavailable compounds detailed herein, when administered (e.g., enterally) either alone or in combination with one or more additional pharmaceutically active compounds or agents to a subject in need thereof, may have a $C_{max}$ of about or less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

III. Pharmaceutical Compositions and Methods of Treatment

For the purposes of administration, the compounds of the present invention may be administered to a patient or subject as a raw chemical or may be formulated as pharmaceutical compositions. Pharmaceutical compositions of the present invention generally comprise a compound of the invention and a pharmaceutically acceptable carrier, diluent, or excipient. The compound is present in the composition in an amount which is effective to treat a particular disease or condition of interest, as described herein, and preferably with acceptable toxicity to the subject. The activity of compound(s) can be determined by one skilled in the art, for example, as described herein and in the Examples below. Appropriate concentrations and dosages can be readily determined by one skilled in the art.

A compound or composition of the invention may be used in a method for treating essentially any disease or other condition in a subject which would benefit from phosphate uptake inhibition in the gastrointestinal tract.

For example, by way of explanation, but not limitation, kidney damage reduces the production and activity of renal 1-alpha hydroxylase, leading to lower 1,25-dihydroxy vitamin D. Decreased vitamin D levels limit gastrointestinal calcium absorption, leading to a decline in serum calcium levels. The combination of lower 1,25-dihydroxy vitamin D and lower serum calcium levels synergistically stimulate parathyroid tissue to produce and secrete PTH. A loss of nephrons also impairs Pi excretion, but serum P levels are actively defended by the actions of PTH and FGF-23, and by higher serum P levels, which considerably enhance urinary $PO_4$ excretion. However, tubular actions of PTH and FGF-23 cannot maintain serum P levels in the face of continual nephron loss. Once renal insufficiency progresses to the loss of about 40-50% of renal function, the decrease in the amount of functioning renal tissue does not allow excretion of the full amount of ingested phosphate required to maintain homeostasis. As a result, hyperphosphatemia develops. In addition, a rise in serum P levels impedes renal 1-alpha hydroxylase activity, further suppressing activated vitamin D levels, and further stimulating PTH, leading to secondary hyperparathyroidism (sHPTH).

Phosphorus imbalance, however, does not necessarily equate with hyperphosphatemia. Rather, the vast majority of CKD patients not yet on dialysis are normophosphatemic but their phosphorus balance is positive with the excess phosphorus being disposed in the vasculature in the form of ectopic calcification, e.g. intima-localized vascular calcification. Clinically, patients with CKD have elevated levels of FGF-23 that are significantly associated with deteriorating renal function and with decreased calcitriol levels, and it has been hypothesized that the synthesis of FGF-23 is induced by the presence of excess P in the body consecutive to renal failure.

Furthermore, an unrecognized effect on cardiovascular disease is post-prandial phosphatemia, i.e. serum P excursion secondary to meal intake. Further still, studies have investigated the acute effect of phosphorus loading on endothelial function in vitro and in vivo. Exposing bovine aortic endothelial cells to a phosphorus load increased production of reactive oxygen species and decreased nitric oxide, a known vasodilator agent. In the acute P loading study in healthy volunteers described above, it was found that the flow mediated dilation correlated inversely with postprandial serum P (see, e.g., Shuto et al., *J. Am. Soc. Nephrol.* 20:1504-12, 2009).

Accordingly, in certain embodiments, a compound or composition of the invention can be used in a method selected from one or more of the following: a method for treating hyperphosphatemia, optionally postprandial hyperphosphatemia; a method for treating a renal disease (e.g., chronic kidney disease (CKD), end stage renal disease (ESRD)); a method for reducing serum creatinine levels; a method for treating proteinuria; a method for delaying time to renal replacement therapy (RRT) such as dialysis; a method for reducing FGF23 levels; a method for reducing the hyperphosphatemic effect of active vitamin D; a method for attenuating hyperparathyroidism such as secondary hyperparathyroidism; a method for reducing serum parathyroid hormone (PTH or iPTH); a method for improving endothelial dysfunction optionally induced by postprandial serum phosphorus; a method for reducing vascular calcification or attenuating intima-localized vascular calcification; a method for reducing urinary phosphorus; a method for normalizing serum phosphorus levels; a method for reducing phosphate burden in an elderly patient; a method for decreasing dietary phosphate uptake; a method for reducing postprandial calcium absorption; a method for reducing renal hypertrophy; and a method for reducing heart hypertrophy. In certain embodiments, the subject in need of phosphate lowering has one or more of the foregoing conditions. In some embodiments, the method comprises selecting or identifying such a subject prior to treatment, optionally based on one or more of the clinical or diagnostic parameters described herein.

Hyperphosphatemia refers to a condition in which there is an elevated level of phosphate in the blood. Average serum phosphorus mass in a human adult typically range from about 2.5-4.5 mg/dL (about 0.81-1.45 mmol/L). Levels are often about 50% higher in infants and about 30% higher in children because of growth hormone effects. Hence, certain methods include treating an adult human patient having hyperphosphatemia, where the patient has serum phosphorus mass of about or at least about 4.5, 4.6, 4.7, 4.8, 4.9, 5.0, 5.1, 5.2, 5.3, 5.4, or 5.5 mg/dL. In some aspects, the treatment reduces serum phosphorus concentrations or levels in a hyperphosphatemic subject to about 150%, 145%, 140%, 135%, 130%, 125%, 120%, 115%, 110%, 105%, or 100% (normalized) of the normal serum phosphorus levels (e.g., 2.5-4.5 mg/dL or 0.81-1.45 mmol/L for an adult). In some aspects, the treatment regimen results in and/or includes monitoring phosphate levels so that they remain within the range of about 2.5-4.5 mg/dL (about 0.81-1.45 mmol/L). In some aspects, the treatment shifts the external phosphorus balance towards net excretion, for example, by increasing net excretion of phosphorous by about or at least about 5%, 10%, 20%, 30%, 40%, 50%, 60%, 70%, 80%, 90%, or 100% or more relative to an untreated state, with or without reducing serum phosphorus concentrations or levels.

Also included are methods of treating a child or adolescent human patient, where the patient has serum phosphorus mass of about or at least about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 mg/dL. As noted herein, in these and related embodiments, administration of a compound or composition described herein may reduce serum phosphorus mass in the subject by about or at least about 5%, 10%, 20%, 30%, 40%, 50%, 60%, 70%, 80%, 90%, 100%, 200% or more.

Certain embodiments relate to methods of treating chronic kidney disease (CKD), a condition characterized by the progressive loss of renal function. Common causes of CKD include diabetes mellitus, hypertension, and glomerulonephritis. Hence, certain methods include treating a subject with CKD, where the subject optionally also has one or more of the foregoing conditions.

In some aspects, a subject is classified as having CKD if they have a glomerular filtration rate (GFR) of less than 60 mL/min/1.73 m$^2$ for about 3 months, whether or not they also present with kidney damage. Certain methods thus include treating a subject with a GFR (e.g., an initial GFR, prior to treatment) of about or less than about 60, 55, 50, 45, 40, 30, 35, 20, 25, 20, 15, or 10 mL/min/1.73 m$^2$ or so. In certain embodiments, administration of a compound or composition described herein may result in an increase in GFR of about or at least about 5%, 10%, 20%, 30%, 40%, 50%, 60%, 70%, 80%, 90%, 100%, 200% or more.

CKD is most often characterized according to the stage of disease: Stage 1, Stage 2, Stage, 3, Stage 4, and Stage 5. Stage 1 CKD includes subjects with kidney damage and a normal or relatively high GFR of about or greater than about 90 mL/min/1.73 m$^2$. Stage 2 CKD includes subjects with kidney damage and a GFR of about 60-89 mL/min/1.73 m$^2$. Stage 3 CKD includes subjects with kidney damage and a GFR of about 30-59 mL/min/1.73 m$^2$. Stage 4 CKD includes subjects with kidney damage and a GFR of about 15-29 mL/min/1.73 m$^2$. Stage 5 CKD includes subjects with established kidney failure and a GFR of less than about 15 mL/min/1.73 m$^2$. Stage 5 CKD is also referred to as end-stage renal disease (ESRD). Accordingly, in certain methods, a subject has Stage 1, 2, 3, 4, or 5, CKD and one or more of its associated clinical characteristics (e.g., defined GFR, kidney damage). In some embodiments, the subject has ESRD and any one or more of its associated clinical characteristics, as described herein and known in the art.

CKD can be characterized according to the affected parts of the kidney. For instance, in certain aspects, CKD includes vascular-associated CKD, including large vessel disease such as bilateral renal artery stenosis, and small vessel disease such as ischemic nephropathy, hemolytic-uremic syndrome and vasculitis. In certain aspects, CKD includes glomerular-associated CKD, including primary glomerular disease such as focal segmental glomerulosclerosis and IgA nephritis, and secondary Glomerular diseases such as diabetic nephropathy and lupus nephritis. Also included is tubulointerstitial-associated CKD, including polycystic kidney disease, drug and toxin-induced chronic tubulointerstitial nephritis, and reflux nephropathy. Certain subjects being treated for CKD may thus have one or more foregoing CKD-associated characteristics.

Certain aspects relate to methods of treating a subject with kidney damage or one or more symptoms/clinical signs of kidney damage. Examples of kidney damage (e.g., CKD-associated kidney damage) and its related symptoms include pathological abnormalities and markers of damage, including abnormalities identified in blood testing (e.g., high blood or serum levels of creatinine, creatinine clearance), urine testing (e.g., proteinuria), and/or imaging studies.

Creatinine is a break-down product of creatine phosphate in muscle, and provides an easily-measured and useful indicator of renal health. Normal human reference ranges for blood or serum creatinine range from about 0.5 to 1.0 mg/dL (about 45-90 μmol/1) for women and about 0.7 to 1.2 mg/dL (about 60-110 μmol/L) for men. Hence, certain subjects for treatment according to the methods described herein (e.g., initially, prior to treatment) may have blood or serum creatine levels that are about or greater than about 1.0, 1.1, 1.2, 1.3, 1.4, 1.5, 1.6, 1.7, 1.8, 1.9, 2.0 mg/dL. In these and related embodiments, administration of a compound or composition described herein may reduce overall blood or serum creatinine levels in a subject by about or at least about 5%, 10%, 20%, 30%, 40%, 50%, 60%, 70%, 80%, 90%, 100%, or 200% or more.

Creatinine clearance rate ($C_{Cr}$ or CrCl) refers to the volume of blood plasma that is cleared of creatinine per unit time; it is measured by comparing the levels of creatinine in blood relative to urine over a period of time (e.g., 24 hours). Creatine clearance is often measured as milliliters/minute (ml/min) or as a function of body mass (ml/min/kg). Depending on the test performed, normal values range from about 97-137 ml/min for males and about 88-128 ml/min for females. Reduced creatinine clearance provides a useful sign of kidney damage. Hence, certain male subjects for treatment according to the methods described herein (e.g., initially, prior to treatment) may have a $C_{Cr}$ of about or less than about 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50 or less. Certain female subjects for treatment according to the methods described herein (e.g., initially, prior to treatment) may have a Cc, of about or less than about 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 47, 46, 45, 44, 43, 42, 41, 40 or less. In some embodiments, administration of a compound or composition described herein may maintain or increase the Cc, in a subject by about or at least about 5%, 10%, 20%, 30%, 40%, 50%, 60%, 70%, 80%, 90%, 100%, or 200% or more.

Proteinuria refers to a condition of excess protein in the urine. It is associated with variety of disease conditions including kidney damage. Proteinuria is often characterized as a urine protein/creatinine ratio of greater than about 45 mg/mmol, or in specific tests an albumin/creatine ratio of greater than about 30 mg/mmol. Certain subjects for treatment according to the methods provided herein (e.g., prior to treatment) have proteinuria, alone or in combination with CKD or other kidney damage, including subjects with a urine protein/creatinine ratio of about or greater than about 45, 50, 55, 60, 65, 70, 75, 80, 85, 90, 95, 100, 105, 110, 115, or 120 mg/mmol and/or a urine albumin/creatinine ratio of about or greater than about 30, 35, 40, 50, 55, 60, 65, 70, 75, 80, 85, 90, 95, 100, 105, 110, 115, or 120 mg/mmol. In these and related embodiments, administration of a compound or composition described herein may treat proteinuria, for instance, by reducing the urine protein/creatinine ratio and/or the urine albumin/creatinine ratio by about or at least about 5%, 10%, 20%, 30%, 40%, 50%, 60%, 70%, 80%, 90%, 100%, or 200% or more.

CKD is associated with a variety of clinical symptoms. Examples include high blood pressure (hypertension), urea accumulation, hyperkalemia, anemia, hyperphosphatemia, hypocalcemia, metabolic acidosis, and atherosclerosis. Thus, in certain methods, a subject with CKD may also have or be at risk for having one or more of the foregoing clinical symptoms. In specific aspects, the subject with CKD has or is at risk for having hyperphosphatemia, as described herein.

Renal replacement therapy (RRT) relates to the various life-supporting treatments for renal failure, including those initiated in the later stages of CKD and ESRD. Examples of RRT include dialysis, hemodialysis, hemofiltration, and renal transplantation. In certain embodiments, a subject for treatment according to the methods provided herein is about to undergo, is undergoing, or has undergone one or more types of RRT. In some embodiments, the subject is not yet undergoing RRT, and administration of a compound described herein delays the time to initiating RRT (e.g., relative to an untreated state) by about or at least about 1, 2, 3, 4, 5, 6, 7, 8, 9, 10, 11, 12 weeks, or by about or at least about 1, 2, 3, 4, 5, 6, 7, 8, 9, 10, 11, 12 months, or by about or at least about 1, 2, 3, 4, 5, 6, 7, 8, 9, 10, 11, 12 years or more.

Fibroblast growth factor 23 (FGF23) regulates phosphorus and vitamin D metabolism. It also promotes phosphaturia and decreases production of calcitriol. Increased FGF23 levels associate with mortality, left ventricular hypertrophy (or left ventricular mass index), myocardial performance, endothelial dysfunction, and progression of CKD. Indeed, FGF23 levels increase progressively in early CKD, presumably as a physiological adaptation to maintain normal serum phosphorus levels or normal phosphorus balance. FGF23 levels might also contribute directly to tissue injury in the heart, vessels, and kidneys. Certain embodiments thus relate to the treatment of subjects having increased FGF23 levels in blood or serum (see, e.g., Kirkpantur et al., *Nephrol Dial Transplant.* 26:1346-54, 2011), including subjects with CKD and subjects undergoing dialysis/hemodialysis. In some aspects, administration of a compound or composition described herein reduces the logarithm of FGF23 levels in blood or serum by about or at least about 5%, 10%, 20%, 30%, 40%, 50%, 60%, 70%, 80%, 90%, 100%, or 200% or more.

Vitamin D stimulates, inter alia, the absorption of phosphate ions in the small intestine. Hence, excess levels or activity of Vitamin D can lead to increased phosphate levels and hyperphosphatemia. Certain embodiments thus relate to methods for reducing the hyperphosphatemic effect of active vitamin D, for instance, in a subject having elevated levels or activity of Vitamin D. In some aspects, the subject has Vitamin D toxicity due to over-ingestion of Vitamin D.

Hyperparathyroidism is a disorder in which the parathyroid glands produce too much parathyroid hormone (PTH). Secondary hyperparathyroidism is characterized by the excessive secretion of PTH in response to hypocalcemia and associated hypertrophy of the parathyroid glands. CKD is the most common cause of secondary hyperparathyroidism, generally because the kidneys fail to convert sufficient vitamin D into its active form and to excrete sufficient phosphate. Insoluble calcium phosphate forms in the body and thus removes calcium from the circulation, leading to hypocalcemia. The parathyroid glands then further increase the secretion of PTH in an attempt to increase serum calcium levels. Certain subjects for treatment according to the methods provided herein may thus present (e.g., initially, prior to treatment) with hyperparathyroidism and/or increased PTH levels, optionally in combination with CKD, hyperphosphatemia, hypocalcemia, or other condition or symptom described herein. In some aspects, administration of a compound or composition described herein may reduce hyperparathyroidism including secondary hyperparathyroidism in a subject in need thereof. In some aspects, administration of a compound or composition described herein may reduce PTH levels by about or at least about 5%, 10%, 20%, 30%, 40%, 50%, 60%, 70%, 80%, 90%, 100%, or 200% or more, for instance, by reducing serum phosphorus levels and the associated formation of insoluble calcium phosphate, increasing available calcium, and thereby reducing the hypocalcemia-induced production of PTH.

In certain embodiments, the administration of a compound described herein can provide multiple therapeutic effects to a subject with CKD. In some instances, the administration of a compound reduces FGF23 levels and serum parathyroid hormone (PTH) levels by about or at least about 5%, 10%, 20%, 30%, 40%, 50%, 60%, 70%, 80%, 90%, 100%, or 200% or more relative to an untreated state, reduces blood pressure, and reduces proteinuria by at least about 5%, 10%, 20%, 30%, 40%, 50%, 60%, 70%, 80%, 90%, 100%, or 200% or more relative to an untreated state.

In particular embodiments, the administration of a compound described herein can provide multiple therapeutic effects to a subject with ESRD (or Stage 5 CKD). In specific instances, the administration of a compound reduces serum phosphorus concentrations or levels by about or at least about 5%, 10%, 20%, 30%, 40%, 50%, 60%, 70%, 80%, 90%, 100%, or 200% or more relative to an untreated state.

Hyperphosphatemia can lead to endothelial dysfunction in both healthy subjects and those with kidney disease, independently of vascular calcification (see, e.g., Di Marco et al., *Kidney International.* 83:213-222, 2013). Management of serum phosphorus level by dietary phosphate restriction or phosphate binders can prevent such subjects from developing cardiovascular disease.

Studies have also shown that dietary phosphate restriction can improve aortic endothelial dysfunction (e.g., in CKD with hyperphosphatemia) by increasing the activatory phosphorylation of endothelial nitric oxide synthase and Akt (see, e.g., Van et al., *J Clin Biochem Nutr.* 51:27-32, 2012).

Certain subjects for treatment according to the methods provided herein may have or be at risk for having endothelial dysfunction, optionally combined with hyperphosphatemia, kidney disease, or any other condition described herein. By reducing postprandial or dietary phosphate uptake, alone or in combination with dietary phosphate restriction, administration of a compound or composition described herein may reduce the risk of developing endothelial dysfunction, or may improve already-existing endothelial dysfunction, including endothelial dysfunction induced by postprandial serum phosphorus.

Hyperphosphatemia is a primary inducer of vascular calcification (see Giachelli, *Kidney Int.* 75:890-897, 2009). Calcium phosphate deposition, mostly in the form of apatite, is the hallmark of vascular calcification and can occur in the blood vessels, myocardium, and cardiac valves. Together with passive deposition of calcium-phosphate in extra-skeletal tissues, inorganic phosphate can also induce arterial calcification directly through "ossification" of the tunica media in the vasculature. Moreover, vascular smooth muscle cells respond to elevated phosphate levels by undergoing an osteochondrogenic phenotype change and mineralizing their extracellular matrix through a mechanism requiring sodium-dependent phosphate cotransporters.

Intimal calcification is usually found in atherosclerotic lesions. Medial calcification is commonly observed in age-associated arteriosclerosis and diabetes, and is the major form of calcification observed in ESRD. Indeed, extensive calcification of the arterial wall and soft tissues is a frequent feature of patients with CKD, including those with ESRD. In valves, calcification is a defining feature of aortic valve stenosis, and occurs in both the leaflets and ring, predominantly at sites of inflammation and mechanical stress. These mechanical changes are associated with increased arterial pulse wave velocity and pulse pressure, and lead to impaired arterial distensibility, increased afterload favoring left ventricular hypertrophy, and compromised coronary perfusion (see Guerin et al., *Circulation.* 103:987-992, 2001). Both intimal and medial calcifications may thus contribute to the morbidity and mortality associated with cardiovascular disease, and are likely to be major contributors to the significant increase in cardiovascular mortality risk observed in CKD and ESRD patients. Control of serum phosphorus may thus reduce the formation of calcium/phosphate products and thereby reduce vascular calcification. Accordingly, certain of the subjects for treatment according to the methods provided herein may have or be at risk for developing vascular calcification, including intimal and/or medial calcification, optionally combined with any of hyperphosphatemia, CKD, and ESRD. In some embodiments, administration of a compound or composition described herein reduces the risk of developing or reduces the formation or levels of vascular calcification in a subject in need thereof. In particular embodiments, administration of a compound or composition described herein may reduce vascular calcification by about or at least about 5%, 10%, 20%, 30%, 40%, 50%, 60%, 70%, 80%, 90%, 100%, or 200% or more, for example, relative to an untreated state.

Elderly patients can be especially susceptible to increased phosphate. For instance, dietary and genetic manipulation studies provide in vivo evidence that phosphate toxicity accelerates the aging process and suggest a novel role for phosphate in mammalian aging (see, e.g., Ohnishi and Razzaque, *FASEB J.* 24:3562-71, 2010). These studies show that excess phosphate associates with many signs of premature aging, including kyphosis, uncoordinated movement, hypogonadism, infertility, skeletal muscle wasting, emphysema, and osteopenia, as well as generalized atrophy of the skin, intestine, thymus, and spleen. Certain embodiments thus relate to reducing phosphate burden in an elderly patient, for instance, to reduce any one or more signs of premature aging, comprising administering to the elderly patient a compound described herein. In some instances, an elderly patient is about or at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years of age.

Hypertrophy refers to the increase in the volume of an organ or tissue due to the enlargement of its component cells. Hyperphosphatemia associates with myocardial hypertrophy including left ventricular hypertrophy (see Neves et al., *Kidney Int.* 66:2237-44, 2004; and Achinger and Ayus, *Am Soc Nephrol.* 17(12 Suppl 3):S255-61, 2006) and compensatory renal hypertrophy including glomerular hypertrophy, the latter being often-observed in CKD. Certain subjects for treatment according to the methods provided herein may have (e.g., initially, prior to treatment) myocardial hypertrophy, renal hypertrophy, or both, alone or in combination with CKD or kidney damage. In some embodiments, administration of a compound described herein may reduce myocardial hypertrophy and/or renal hypertrophy by about or at least about 5%, 10%, 20%, 30%, 40%, 50%, 60%, 70%, 80%, 90%, 100%, 200% or more relative to an untreated state.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In certain embodiments, a typical dosage of the substantially impermeable or substantially systemically non-bioavailable, compound may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

Compounds of the invention, or pharmaceutically acceptable derivatives thereof, may also be administered simultaneously with, prior to, or after administration of one or more other therapeutic or biologically active agents, dietary supplements, or any combination thereof. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For example, in certain embodiments, the additional biologically active agent included in a pharmaceutical composition (or method) of the invention is selected, for example, from vitamin $D_2$ (ergocalciferol), vitamin $D_3$ (cholecalciferol), active vitamin D (calcitriol) and active vitamin D analogs (e.g. doxercalciferol, paricalcitol).

In other specific embodiments, the additional biologically active agent included in a pharmaceutical composition (or method) of the invention is a phosphate binder, such as sevelamer (e.g., Renvela® (sevelamer carbonate), Renagel® (sevelamer hydrochloride)), lanthanum carbonate (e.g., Fosrenol®), calcium carbonate (e.g., Calcichew®, Titralac®), calcium acetate (e.g. PhosLo®, Phosex®), calcium acetate/magnesium carbonate (e.g., Renepho®, OsvaRen®), MCI-196, ferric citrate (e.g., Zerenex™), magnesium iron hydroxycarbonate (e.g., Fermagate™), aluminum hydroxide (e.g., Alucaps®, Basaljel®), APS1585, SBR-759, PA-21, and the like.

In some embodiments, the additional biologically active agent is an inhibitor of the intestinal sodium-dependent phosphate transporter (*NaPi*2b inhibitor). Examples of *NaPi*2b inhibitors can be found, for instance, in International Application Nos. PCT/US2011/043267; PCT/US2011/043261; PCT/US2011/043232; PCT/US2011/043266; and PCT/US2011/043263; and U.S. Pat. No. 8,134,015, each of which is incorporated by reference in its entirety.

In certain embodiments, the additional biologically active agent is niacin or nicotinamide.

In some embodiments, the subject has or being treated for CKD, and the additional biologically active agent is a compound used in the treatment or management of CKD. Examples of such compounds include high blood pressure medications such as ACE inhibitors, antiogensin II receptor blockers, beta-blockers, calcium channel blockers, direct renin inhibitors, diuretics, and vasodilators; medications to treat symptoms and complications of CKD such as erythropoietin therapy and/or iron replacement therapy for anemia, electrolytes for electrolyte imbalances, diuretics, ACE inhibitors, and antiogensin II receptor blockers, inhibitors of advanced glycation end products (e.g., aminoguanidine, pyridoxamine) and vitamin D; lipid-lowering agents such as HMG-CoA (3-hydroxy-3-methyl-glutaryl-CoA) reductase inhibitors or statins (e.g., atorvastatin, fluvastatin, lovastatin, pitavastatin, pravastatin, rosuvastatin, simvastatin).

It is understood that in the present description, combinations of substituents and/or variables of the depicted formulae are permissible only if such contributions result in stable or reasonably stable compounds.

It will also be appreciated by those skilled in the art that in the process described herein the functional groups of intermediate compounds may need to be protected by suitable protecting groups. Such functional groups include hydroxy, amino, mercapto, and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

IV. Drug Discovery

Also included are methods relating to the discovery of compounds that can inhibit phosphate uptake in the gastrointestinal tract. Particular embodiments include in vitro methods of drug screening which employ cell cultures such as intestinal cell cultures or cell lines, including mammalian cell lines.

Certain embodiments therefore relate to methods of screening for an inhibitor of phosphate uptake, comprising culturing cells, contacting the cultured cells with a test compound, and measuring one or more of the following: the pH at the apical surface of the cells, the intracellular pH of the cells, bicarbonate secretion by the cells, acid secretion by the cells, water absorption, and/or phosphate uptake by the cells.

Also included is the step of identifying the test compound as an inhibitor of phosphate uptake, where one or more of the following occurs: the pH at the apical surface of the cells increases relative to a control, the intracellular pH of the cells decreases relative to a control, bicarbonate secretion by the cells increases relative to a control, acid secretion by the cells decreases relative to a control, water absorption decreases relative to a control, and/or phosphate uptake by the cells decreases relative to a control. In some aspects, the increase or decrease is statistically significant. The terms "increase" and "decrease" and "statistically significant" are described elsewhere herein. A control can include no compound (e.g., vehicle only) or compound that is known not to possess any of the above-described activities. A control can also include a pre-determined reference value.

In certain embodiments, the cells are intestinal cells. Non-limiting examples of intestinal cell cultures include intestinal cell monolayers, enteroids, and intestinal cell organoids. Intestinal cell monolayers can be prepared according to routine techniques in the art. Non-limiting examples of intestinal cell monolayers include cell lines such as Caco-2, HCT-8, and T84 cell lines (see, e.g., Watson et al., *Am J Physiol Cell Physiol.* 281:C388-9, 2001; Shah et al., *Biotechnol Prog.* 22:186-9, 2006) and neonatal piglet jejunal IPEC-J2 cell monolayers (see, e.g., Chapman et al., *Pediatr Res.* 72:576-82, 2012).

The term "enteroid" includes intestinal cell cultures obtained from intestinal crypts from segment(s) of intestinal tissue, which optionally maintain the structural integrity (e.g., three-dimensional structure of intestinal epithelium) and cell types of intestinal tissue, and replicate the genotypic and phenotypic profiles of primary intestinal tissue. Enteroid cell cultures can be prepared according to techniques known in the art. (see, e.g., U.S. Application No. 2010/0047853; WO 2010/090513; US Application No. 2012/0196312; and WO 2012/168930).

The term "organoid" or "intestinal organoid" includes intestinal cell cultures made primarily from precursor cell such as isolated embryonic stem cells, endoderm cells, or other pluripotent stem cells. Organoids can be prepared, for instance, by the step-wise differentiation of precursor cells into complex, three-dimensional intestinal tissues (see, e.g., WO 2011/140441), including intestinal tissues which can comprise a polarized, columnar epithelium surrounded by mesenchyme that includes a smooth muscle-like layer. In some aspects, the epithelium is patterned into crypt-like proliferative zones and villus-like structures having most if not all of the major functional cell types of the intestine. In some aspects, the precursor cells are first selected or enriched for the expression of markers such as LGR5 and/or LGR6.

Also included are cultures that comprise whole-thickness intestinal preparations (see, e.g., Binder et al., *Am J Physiol.* 225:1232-1239, 1973) and those prepared by pharmacological treatment and seromusculature "stripping" to minimize the influence of the intrinsic neuromuscular system (see, e.g., Clarke, *Am. J. Physiol. Gastrointestin. Liver Physiol.* 296:G1151-66, 2009). Seromusculature stripping removes the serosa (visceral peritoneum) and the longitudinal/circular muscle layers of the intestinal wall, leaving only the underlying submucosal elements, remnants of muscle, and the epithelium. These cultures can be particularly useful when employing a Ussing chamber.

Certain embodiments may employ an Ussing Chamber. The Ussing chamber provides a physiological system to measure the transport of ions, nutrients, and drugs across various epithelial tissues such as intestinal tissues (see, e.g., Clarke et al., supra). For instance, some methods can employ pH stat techniques to measure transepithelial bicarbonate secretion and/or isotopic flux methods to measure net secretion or absorption of substrates. In particular embodiments, the Ussing Chamber is adapted for use with a mouse or rat intestines, including whole-thickness intestinal preparations and those prepared by seromusculature stripping (see, e.g., Clarke et al., supra).

Certain screening methods may employ various non-intestinal cell lines, including mammalian cell lines. Exemplary mammalian cell lines include human embryonic kidney cell lines (e.g., HEK 293-cells), monkey kidney CV1 line transformed by SV40 (COS-7, ATCC CRL 1651); baby hamster kidney cells (BHK, ATCC CCL 10); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells; MRC 5 cells; FS4 cells; and a human hepatoma line (Hep G2). Other useful mammalian cell lines include Chinese hamster ovary (CHO) cells, including DHFR-CHO cells and myeloma cell lines such as NSO and Sp2/0.

Techniques for measuring changes in pH, bicarbonate secretion, acid secretion, water absorption, and phosphate uptake are known in the art. For example, changes in intracellular pH can be measured by contacting cells or tissues with a pH-sensitive fluorescent dye or probe and measuring fluorescence of the dye or probe. Examples of pH-sensitive dyes include 2",7"-Bis-(2-carboxyethyl)-5-(and-6-)carboxyfluorescein 4 (BCECF), 2",7"-bis-(2-carboxypropyl)-5-(and-6-)-carboxyfluorescein (BCPCF 11), 5-(and 6)-carboxynaphthofluorescein, and others (see, e.g., FIGS. 8A and 8B; Han and Burgess, Chem Rev. 110:2709-28, 2010). Techniques for measuring bicarbonate transport (in vitro) through single ion channels, individual cells, and intact epithelial layers are described, for example, in Hug et al., *Methods Mol Biol.* 741:489-509, 2011; Feldman et al., *Am. J. Physiol.* 254:C383-90, 1988. As noted above, changes in pH, bicarbonate secretion, and/or acid secretion can also be measured in an Ussing chamber, for example, using pH stat or isotopic flux methods. Phosphate uptake can be measured, for instance, by contacting cells or tissues with $^{33}$P-labeled phosphate ions and measuring uptake of the labeled phosphate ions (see the Examples; Matsuo et al., *Eur. J. Pharmacol.* 517:111-19, 2005). Other techniques for measuring pH, bicarbonate secretion, acid secretion, and phosphate uptake will be apparent to persons skilled in the art.

In certain aspects, the test compound is a small molecule or peptide that is known or suspected to stimulate bicarbonate secretion (e.g., DBS), inhibit acid secretion, and/or decrease water absorption in the gastrointestinal tract, including the small intestine. Examples of such compounds include, without limitation, P2Y agonists, adenosine A2b receptor agonists, guanylate cyclase C receptor agonists (e.g., peptide agonists), soluble guanylate cyclase agonists, adenylate cyclase receptor agonists, imidazoline-1 receptor agonists, cholinergic agonists, prostaglandin EP4 receptor agonists, dopamine D1 agonists, melatonin receptor agonists, 5HT4 agonists, atrial natriuretic peptide receptor agonists, carbonic anyhdrase inhibitors, and phosphodiesterase inhibitors. Non-limiting examples of such compounds are described elsewhere herein. In some embodiments, the compound is a derivative or analog of one or more of such compounds. Such derivatives or analogs can include modifications, for instance, to increase the system non-bioavailability of the compound, as described herein.

Also included are any of the above methods, or other screening methods known in the art, which are adapted for high-throughput screening (HTS). HTS typically uses automation to run a screen of an assay against a library of candidate agents, for instance, an assay that measures an increase or a decrease in binding and/or activity, as described herein.

Any of the screening methods provided herein may utilize small molecule libraries or libraries generated by combinatorial chemistry. As one example, such libraries can be used to screen for small molecules that associate or interact with a target molecule or elicit the desired physiological response (e.g., decrease intracellular pH of intestinal cells, inhibit phosphate uptake). Libraries of chemical and/or biological mixtures, such as fungal, bacterial, or algal extracts, are known in the art. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

Libraries of agents may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or on phage (Cwirla et al., 1990; Devlin et al., 1990; Felici et al., 1991; Ladner et al., U.S. Pat. No. 5,223,409, 1993; Scott and Smith, 1990). Libraries useful for the purposes of the invention include, but are not limited to, (1) chemical libraries, (2) natural product libraries, and (3) combinatorial libraries comprised of random peptides, oligonucleotides and/or organic molecules.

Chemical libraries consist of structural analogs of known agents or agents that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. See, e.g., Cane et al., Science 282:63-68, 1998. Combinatorial libraries may be composed of large numbers of peptides or organic compounds as a mixture. They are relatively easy to prepare by traditional automated synthesis methods, PCR, cloning or proprietary synthetic methods.

More specifically, a combinatorial chemical library is a collection of diverse chemical agents generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide agent). Millions of chemical agents can be synthesized through such combinatorial mixing of chemical building blocks.

For a review of combinatorial chemistry and libraries created therefrom, see, e.g., Huc and Nguyen, (2001) *Comb. Chem. High Throughput Screen.* 4:53-74; Lepre, (2001) *Drug Discov. Today* 6:133-140; Peng, (2000) *Biomed. Chromatogr.* 14:430-441; Bohm, H. J. and Stahl, M. (2000) *Curr. Opin. Chem. Biol.* 4:283-286; Barnes and Balasubramanian, (2000) *Curr. Opin. Chem. Biol.* 4:346-350; Lepre et al., (2000) *Mass Spectrom Rev.* 19:139-161; Hall, (2000) *Nat. Biotechnol.* 18:262-262; Lazo and Wipf, (2000) *J. Pharmacol. Exp. Ther.* 293:705-709; Houghten, (2000) *Ann. Rev. Pharmacol. Toxicol.* 40:273-282; Kobayashi (2000) *Curr. Opin. Chem. Biol.* (2000) 4:338-345; Kopylov Spiridonova, (2000) *Mol. Biol.* (Mosk) 34:1097-1113; Weber, (2000) *Curr. Opin. Chem. Biol.* 4:295-302; Dolle, (2000) *J. Comb. Chem.* 2:383-433; Floyd et al., (1999) *Prog. Med. Chem.* 36:91-168; Kundu et al., (1999) *Prog. Drug Res.* 53:89-156; Cabilly, (1999) *Mol. Biotechnol.* 12:143-148; Lowe, (1999) *Nat. Prod. Rep.* 16:641-651; Dolle and Nelson, (1999) *J. Comb. Chem.* 1:235-282; Czarnick and Keene, (1998) *Curr. Biol.* 8:R705-R707; Dolle, (1998) *Mol. Divers.* 4:233-256; Myers, (1997) *Curr. Opin. Biotechnol.* 8:701-707; and Pluckthun and Cortese, (1997) *Biol. Chem.* 378:443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

Definitions and Terminology

"Amino" refers to the —NH$_2$ radical.

"Aminocarbonyl" refers to the —C(=O)NH$_2$ radical.

"Carboxy" refers to the —CO$_2$H radical. "Carboxylate" refers to a salt or ester thereof.

"Cyano" refers to the —CN radical.

"Hydroxy" or "hydroxyl" refers to the —OH radical.

"Imino" refers to the =NH radical.

"Nitro" refers to the —NO$_2$ radical.

"Oxo" or "carbonyl" refers to the =O radical.

"Thioxo" refers to the =S radical.

"Guanidinyl" (or "guanidine") refers to the —NHC(=NH)NH$_2$ radical.

"Amidinyl" (or "amidine") refers to the —C(=NH)NH$_2$ radical.

"Phosphate" refers to the —OP(=O)(OH)$_2$ radical.

"Phosphonate" refers to the —P(=O)(OH)$_2$ radical.

"Phosphinate" refers to the —PH(=O)OH radical, where each R$^a$ is independently an alkyl group as defined herein.

"Sulfate" refers to the —OS(=O)$_2$OH radical.

"Sulfonate" or "hydroxysulfonyl" refers to the —S(=O)$_2$OH radical.

"Sulfinate" refers to the —S(=O)OH radical.

"Sulfonyl" refers to a moiety comprising a —SO$_2$— group. For example, "alkylsulfonyl" or "alkylsulfone" refers to the —SO$_2$—R$^a$ group, where R$^a$ is an alkyl group as defined herein.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms (C$_{1-12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) where at least one hydrogen atom is replaced by a bond to a non-hydrogen atoms such as, but not limited to: a halogen atom such as F, Cl, Br, and I; an oxygen atom in groups such as hydroxyl groups, carboxyl groups, phosphate groups, sulfate groups, alkoxy groups, and ester groups; a sulfur atom in groups such as thiol groups, thioalkyl groups, sulfinate groups, sulfone groups, sulfonyl groups, and sulfoxide groups; a phosphorus atom in groups such as phosphinate groups and phosphonate groups; a nitrogen atom in groups such as guanidine groups, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH2SO2NR_gR_h$, —$(CH_2CH_2O)_{1-10}R_g$, —$(CH_2CH_2O)_{2-10}R_g$, —$(OCH_2CH_2)_{1-10}R_g$ and —$(OCH_2CH_2)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents" or "non-hydrogen substituents". In addition, each of the foregoing substituents may also be optionally substituted with one or more of the above substituents.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight, length, or other unit described herein.

The term "activate" refers to the application of physical, chemical, or biochemical conditions, substances or processes that a receptor (e.g, pore receptor) to structurally change in a way that allows passage of ions, molecules, or other substances.

The term "active state" refers to the state or condition of a receptor in its non-resting condition.

"EffMux" refers to the movement or flux of ions, molecules, or other substances from an intracellular space to an extracellular space.

"Enteral" or "enteric" administration refers to administration via the gastrointestinal tract, including oral, sublingual, sublabial, buccal, and rectal administration, and including administration via a gastric or duodenal feeding tube.

The term "inactive state" refers to the state of a receptor in its original endogenous state, that is, its resting state.

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10, 15, 20, 30, 40, 50 or more times (e.g., 100, 200, 500, 1000 times) (including all integers and decimal points and ranges in between and above 1, e.g., 5.5, 5.6, 5.7. 5.8, etc.) the amount produced by a control (e.g., the absence or lesser amount of a compound, a different compound or treatment), or the amount of an earlier time-point (e.g., prior to treatment with a compound). A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and decimal points and ranges in between) in the amount or activity produced by a control (e.g., the absence or lesser amount of a compound, a different compound or treatment), or the amount of an earlier time-point (e.g., prior to treatment with a compound).

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethyl aminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

"Stable compound" and "stable structure" are meant to indicate a compound that is sufficiently robust to survive isolation to a useful degree of purity from a reaction mixture, and formulation into an efficacious therapeutic agent.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" includes nearly totally or completely, for instance, 80%, 85%, 90%, 95%, 96%, 97%, 98%, 99% or greater of some given quantity.

The term "secondary" refers to a condition or state that can occur with another disease state, condition, or treatment, can follow on from another disease state, condition, or treatment, or can result from another disease state, condition or treatment. The term also refers to situations where a disease state, condition, or treatment can play only a minor role in creating symptoms or a response in a patient's final diseased state, symptoms or condition.

"Subjects" or "patients" (the terms are used interchangeably herein) in need of treatment with a compound of the present disclosure include, for instance, subjects "in need of phosphate lowering," which can include subjects in need of "phosphate management," e.g., prophylactic management of phosphate or phosphorus levels. Included are mammals having or at risk for having the diseases and/or conditions described herein, particularly diseases and/or conditions that can be treated with the compounds of the invention, with or without other active agents, to achieve a beneficial therapeutic and/or prophylactic result. A beneficial outcome includes a decrease in the severity of symptoms, a delay in the onset of symptoms, maintenance of normophosphatemia, reduction in the risk of developing hyperphosphatemia, modulation of one or more indications described herein (e.g., reduced phosphorus levels in serum or blood of patients with or at risk for hyperphosphatemia, increased fecal output of phosphate ions in patients with or at risk for hyperphosphatemia), increased longevity, and/or more rapid or more complete resolution of the disease or condition.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

A "therapeutically effective amount" or "effective amount" includes an amount of a compound of the invention which, when administered to a mammal, preferably a human, is sufficient to inhibit or otherwise reduce the transport of phosphate ions from the gastrointestinal lumen, increase fecal output of phosphate ions, reduce serum levels of phosphate ions, treat hyperphosphatemia in the mammal, preferably a human, and/or treat any one or more other conditions described herein. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, where a more or less specific set of symptoms have been identified by clinicians.

EXAMPLES

Example 1

Increased Intracellular pH Results in Decreased Phosphate Uptake in Cells

Experiments were performed to test the relationship between alterations in intracellular pH and the uptake of phosphate ions (Pi) in human embryonic kidney cells (HEK-293 cells).

HEK-293 cells were seeded into 96-well plates at 25,000 cells/well and cultured overnight. Cells were then transfected with either rat or human NaP2b cDNA, or were mock transfected (no DNA) using Lipofectamine 2000 (Invitrogen). Cells were allowed to approach confluence during a second overnight incubation.

An ammonium pulse procedure was used to reduce the intracellular pH from ~7.4 to ~6.8. Medium was aspirated from the wells, cells were washed twice with NaCl-HEPES buffer (100 mM NaCl, 50 mM HEPES, 10 mM glucose, 5 mM KCl, 2 mM $CaCl_2$, 1 mM $MgCl_2$, pH 7.4), then incubated for 30 min at room temperature with $NH_4Cl$-HEPES buffer (20 mM $NH_4Cl$, 80 mM NaCl, 50 mM HEPES, 5 mM KCl, 2 mM $CaCl_2$, 1 mM $MgCl_2$, pH 7.4) containing 5 µM BCECF-AM. Cells were washed twice with ammonium free, $Na^+$-free HEPES (100 mM choline, 50 mM HEPES, 10 mM glucose, 5 mM KCl, 2 mM $CaCl_2$, 1 mM $MgCl_2$, pH 7.4) and incubated in the same buffer for 10 minutes at room temperature to lower intracellular pH. The reduction in intracellular pH to approximately pH 6.8 was verified by monitoring the pH sensitive changes in BCECF fluorescence ($\lambda$ex 505 nm, $\lambda$em 538 nm) normalized to the pH insensitive BCECF fluorescence ($\lambda$ex 439 nm, $\lambda$em 538 nm). A control was included which omitted the ammonium pulse procedure, and BCECF was used to show a normal intracellular pH of 7.4.

Cells were then washed with sodium free uptake buffer (14 mM Tris, 137 mM choline chloride, 5.4 mM KCl, 2.8 mM CaCl2, 1.2 mM $MgSO_4$, 100 µM $KH_2PO_4$, 1 mg/mL Bovine Serum Albumin, pH 7.4), and $^{33}P$ uptake was initiated by overlaying the cells with sodium-containing uptake buffer (14 mM Tris, 137 mM sodium chloride, 5.4 mM KCl, 2.8 mM $CaCl_2$, 1.2 mM $MgSO_4$, 100 µM $KH_2PO_4$, 1 mg/mL Bovine Serum Albumin, pH 7.4). For cell lines transfected with rat or human NaP2b, the endogenous PiT activity was suppressed with a PiT silencing agent, so that the only sodium-dependent $^{33}P$ uptake is due to NaP2b. The PiT silencing agent was not used on the mock transfected cells, so sodium-dependent $^{33}P$ is only due to PiT.

Uptake of $^{33}P$ was measured in the presence and absence of 5 µM EIPA, a specific inhibitor of NHE1. After 23 minutes at room temperature, assay mixtures were removed, and the cells were washed twice with ice cold sodium free uptake buffer. Cells were lysed by addition of 20 µL 0.1% Tween 80 followed by 100 µL scintillation fluid, and counted using a TopCount (Perkin Elmer).

Figure 22C:
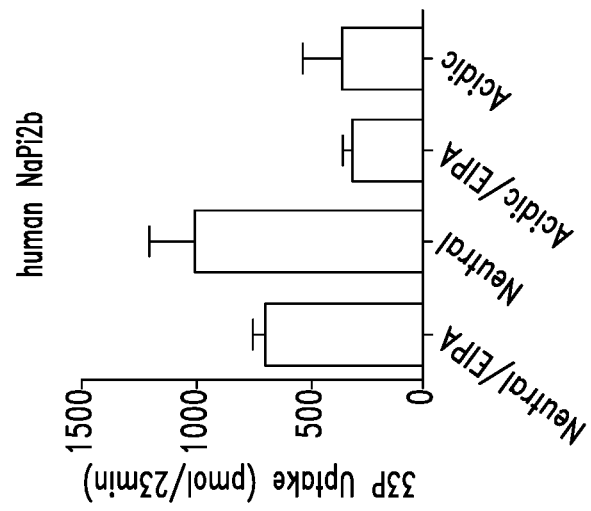
FIGS. 22A-22C show that acidification of the interior of HEK-293 cells led to a significant reduction in phosphate uptake, as measured by uptake of $^{33}P$ labeled Pi.
Figure 22B:
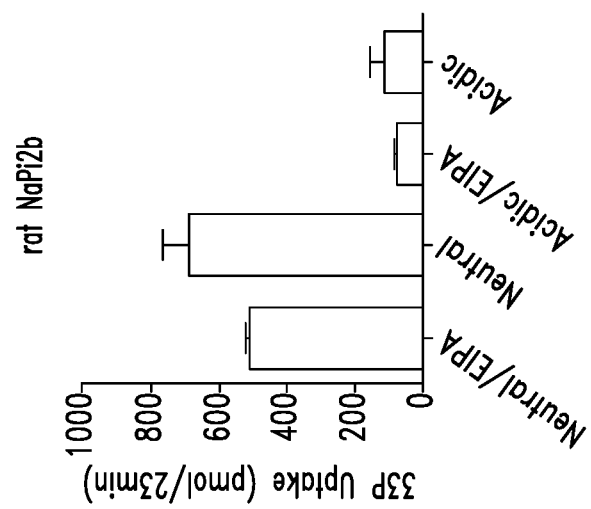
Figure 22A:
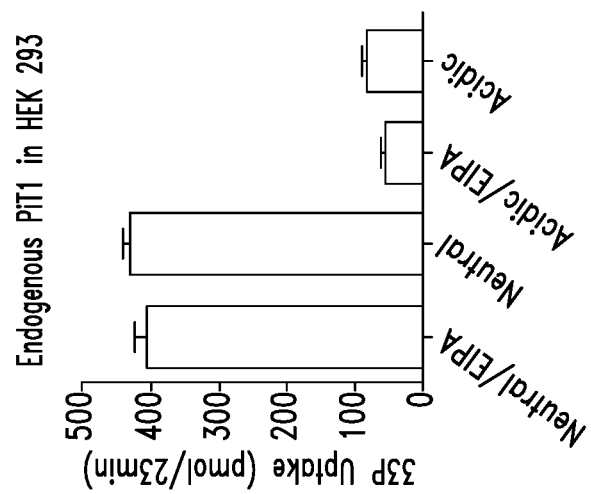

As shown in FIGS. 22A-22C, intracellular acidification caused a >75% decrease in either PiT (22A) or NaPi2b (22B-22C) mediated $^{33}P$ uptake. EIPA, which blocks NHE1-mediated proton export from the cytoplasm, also caused a small yet significant decrease in Pi uptake in cells that were not pretreated to lower their intracellular pH.

Example 2

Guanylate Cyclase C (GC-C) Receptor Agonist Decreases Phosphate Absorption

Experiments were performed to determine whether guanylate cyclase C (GC-C) receptor agonists can decrease phosphate absorption/uptake in the small intestine as measured by $^{33}P$ uptake. Rats were simultaneously dosed with $^{33}P$ and linaclotide as shown below:
1. Vehicle (N=5/group)
2. Linaclotide at 0.1 mg/kg (N=6/group)
3. Linaclotide at 0.3 mg/kg (N=4/group)

Figure 1A:
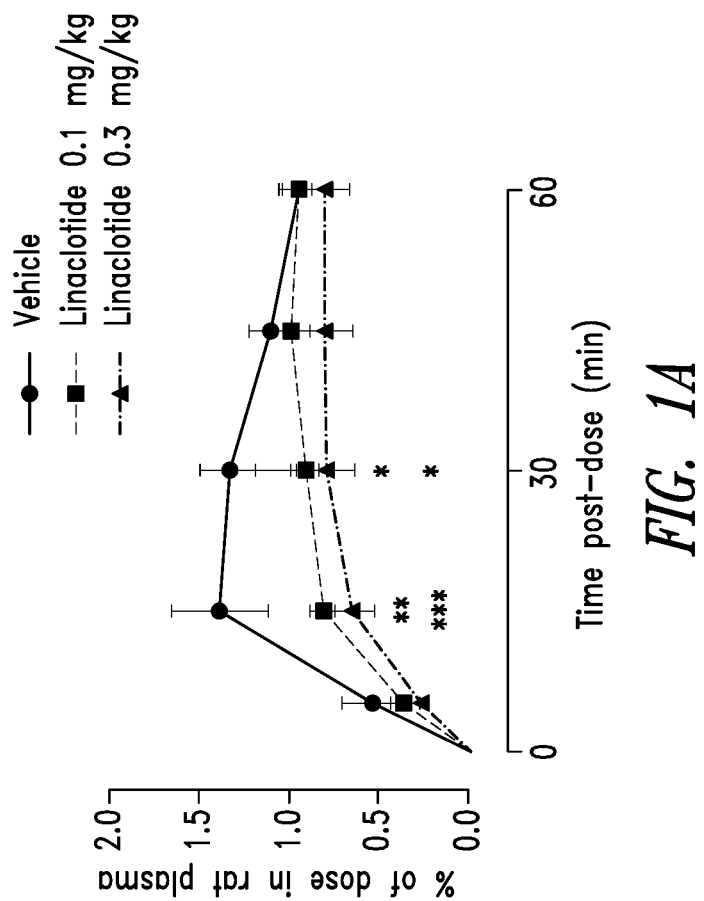

Blood was collected at 5, 15, 30, 45, and 60 minutes post-$^{33}P$ administration and plasma scintillation counting was performed. The results are shown in FIGS. 1A-1B. FIG. 1A shows the results of two-way ANOVA with repeated measures followed by Dunnett's multiple comparison test, and FIG. 1B shows the results of one-way ANOVA followed by Dunnett's multiple comparison test. These results show that both doses of linaclotide decreased the absorption of phosphate in the gastrointestinal tract.

Example 3

I1 Receptor Agonist and Adenylate Cyclase Agonist Decrease Phosphate Absorption

Figures 2A, 2B:
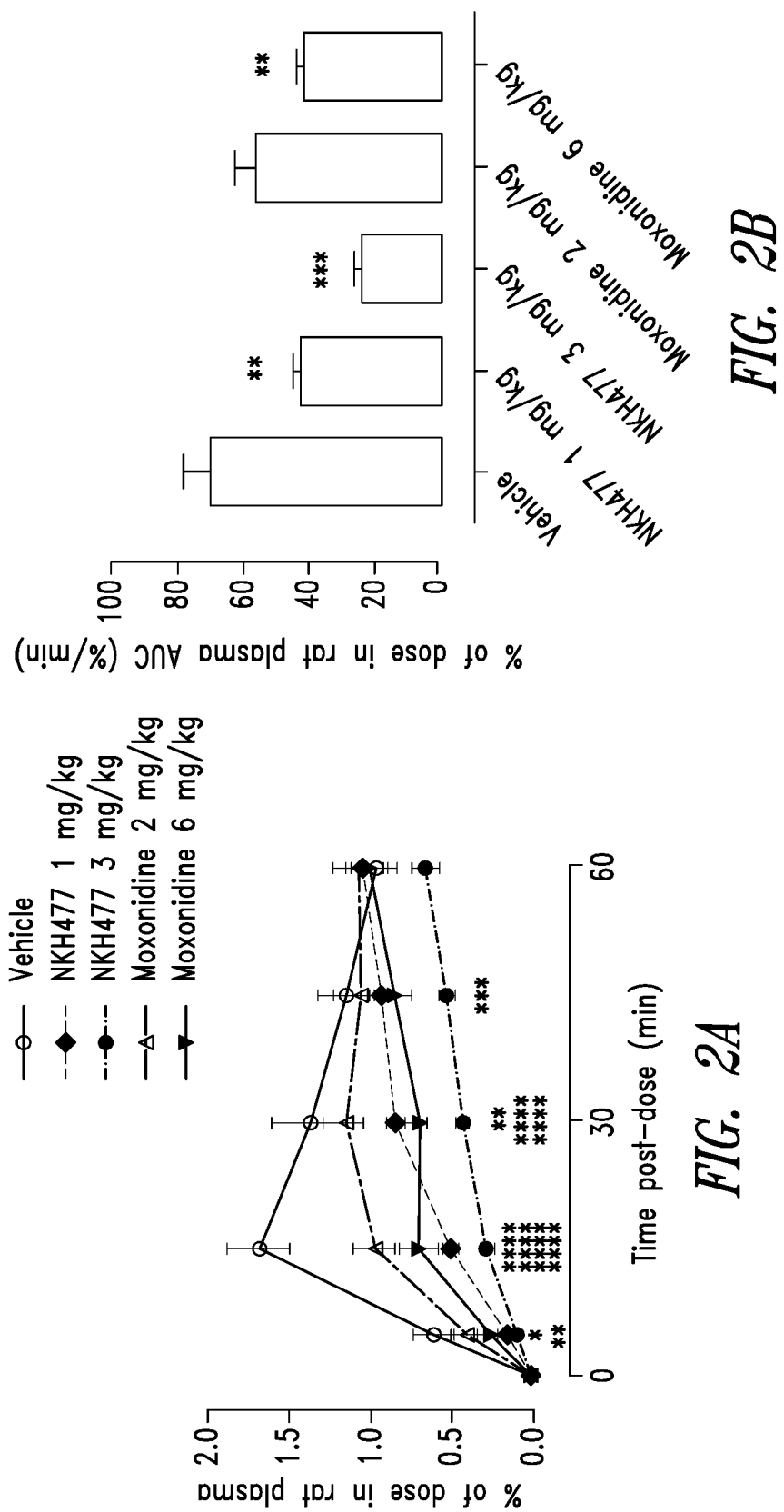
FIGS. 2A-2B show that moxonidine (an imidazoline subtype 1 ($I_1$) receptor agonist) and the water soluble-forskolin analog colforsin (an adenylate cyclase agonist) reduce the uptake of phosphate uptake in the gastrointestinal tract of rats.

Experiments were performed to determine whether other classes of drugs can decrease phosphate absorption/uptake in the small intestine as measured by $^{33}P$ uptake. Rats were simultaneously dosed with $^{33}P$ and either an imidazoline subtype 1 ($I_1$) receptor agonist (moxonidine) or an adenylate cyclase agonist (the water-soluble forskolin analog NKH477) as shown below:
1. Vehicle
2. Moxonidine at 2 mg/kg
3. Moxonidine at 6 mg/kg
4. NKH477 at 1 mg/kg
5. NKH477 at 3 mg/kg Blood was collected at 5, 15, 30, 45, and 60 minutes post-$^{33}P$ administration and plasma scintillation counting was performed. The results are shown in FIGS. 2A-2B. FIG. 2A shows the results of two-way ANOVA with repeated measures followed by Dunnett's multiple comparison test, and FIG. 2B shows the results of one-way ANOVA followed by Dunnett's multiple comparison test. These results show that all test compounds significantly decreased $^{33}P$ uptake/absorption at 15 minutes.

Example 4

A2B Agonist and P2Y2 Agonist Decrease Phosphate Absorption

Experiments were performed to determine whether increasing intracellular calcium ($Ca^{++}$) by different mechanisms can also decrease phosphate absorption in the small intestine as measured by $^{33}P$ uptake. Rats were simultaneously dosed with $^{33}P$ and test compounds as shown below:
1. Vehicle, n=6
2. BAY 60-6583 at 10 mg/kg (adenosine A2B agonist)
3. $Up_4U$ at 15 mg/kg (P2Y2 receptor agonist)

Figure 3:
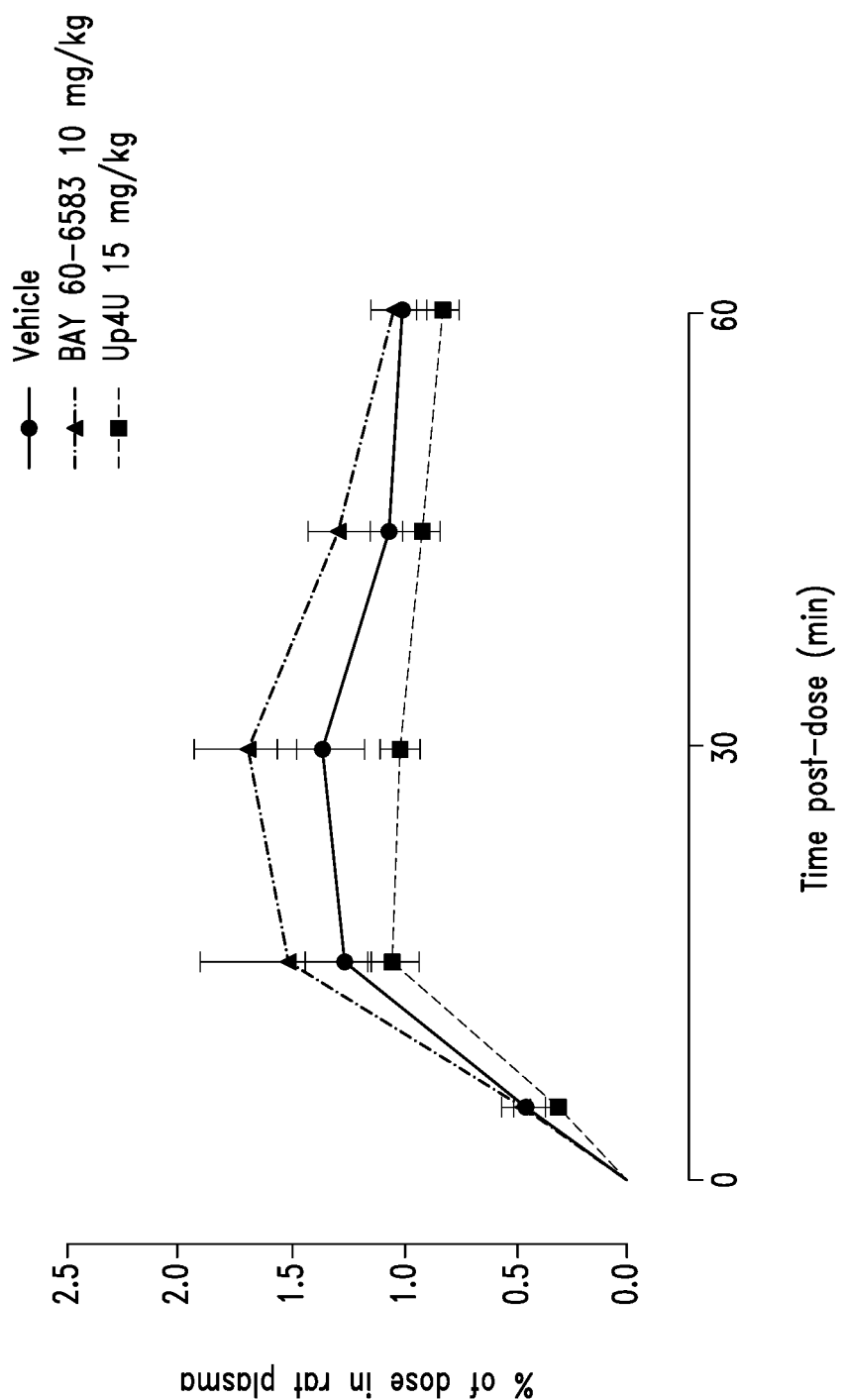
FIG. 3 shows that the P2Y2 receptor agonist $Up_4U$ reduces the uptake of phosphate uptake in the gastrointestinal tract of rats.
Figure 4:
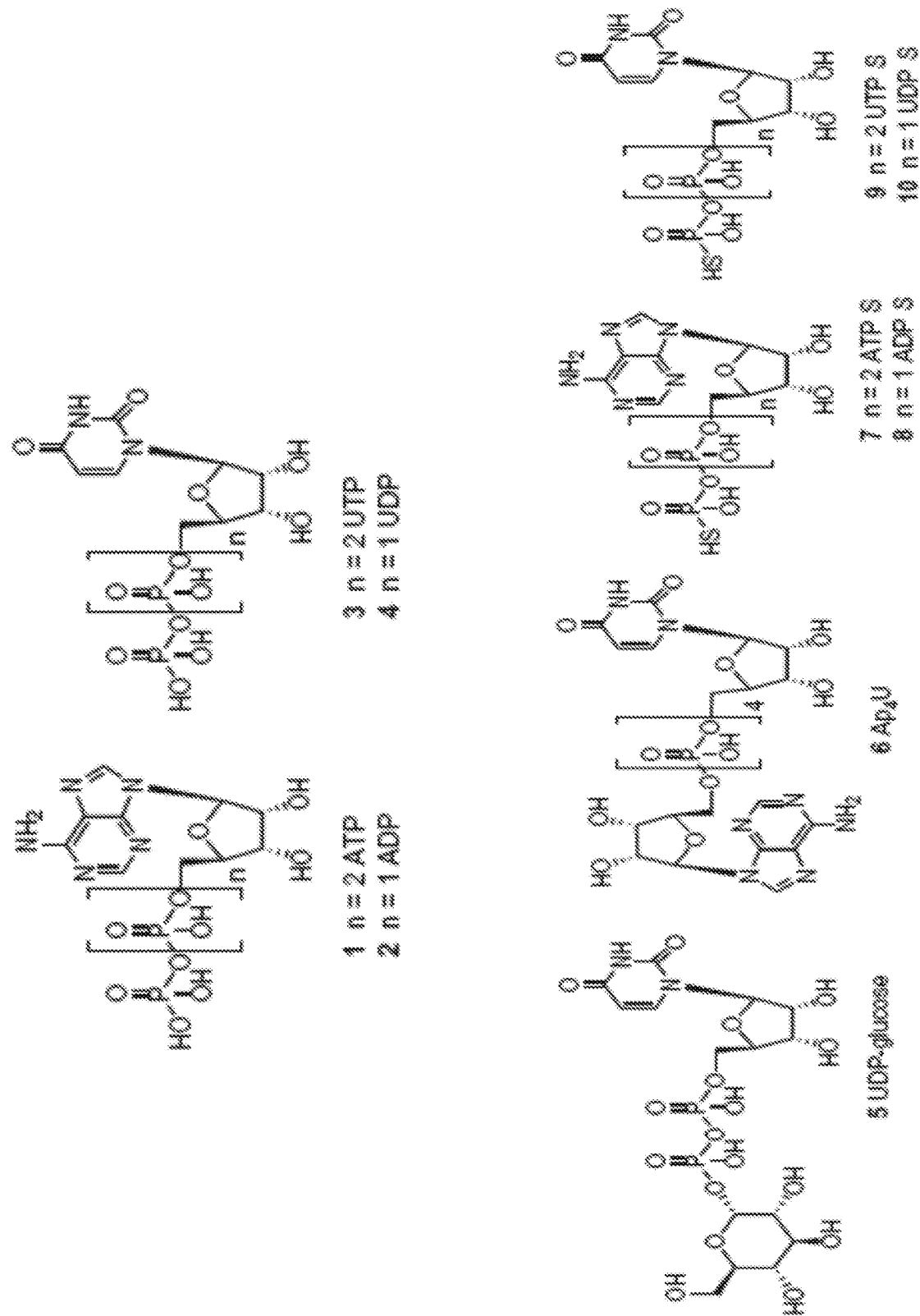
FIG. 4 shows exemplary small molecule P2Y receptor agonists.
Figure 4:
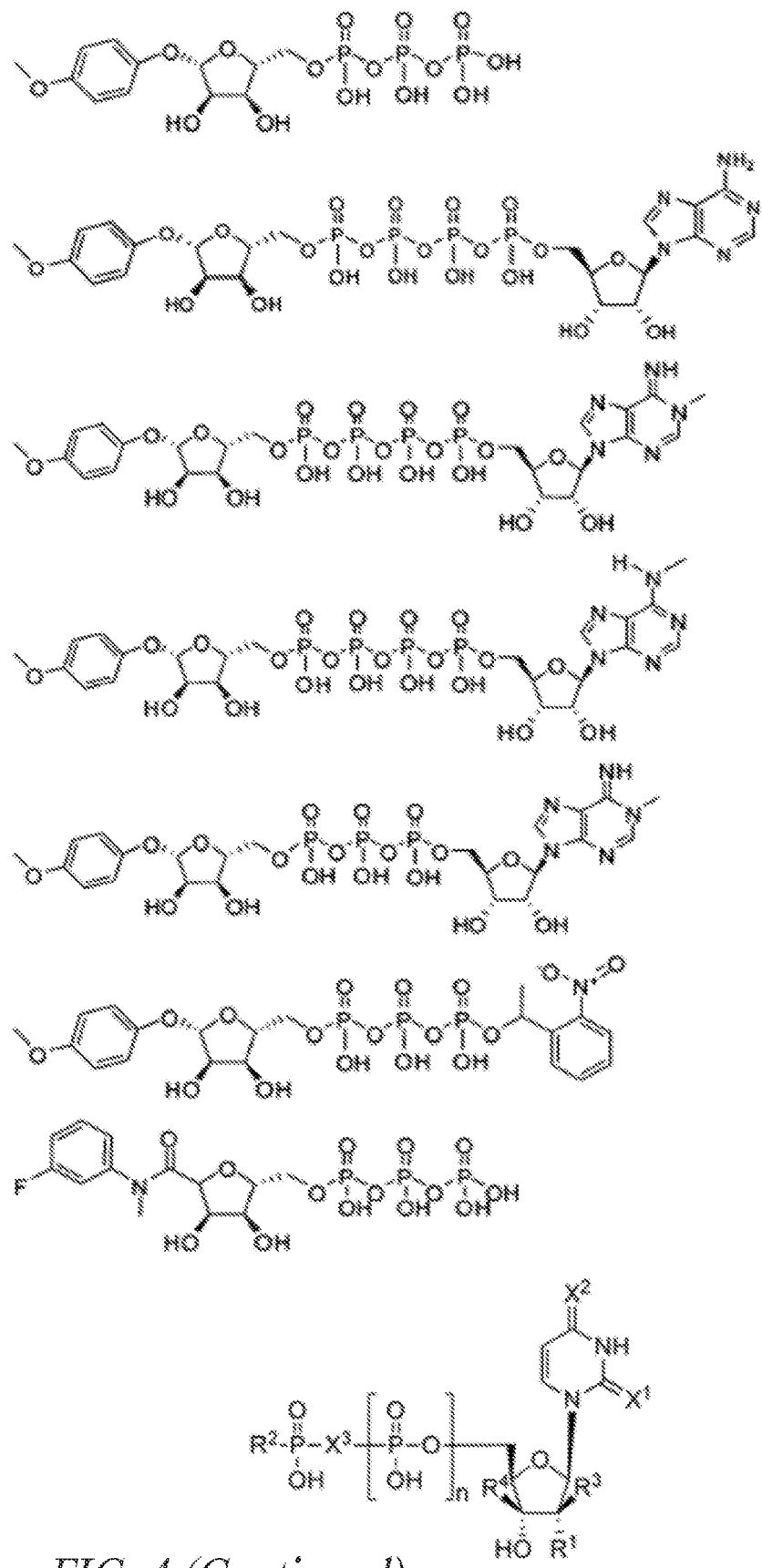
Figure 5A:
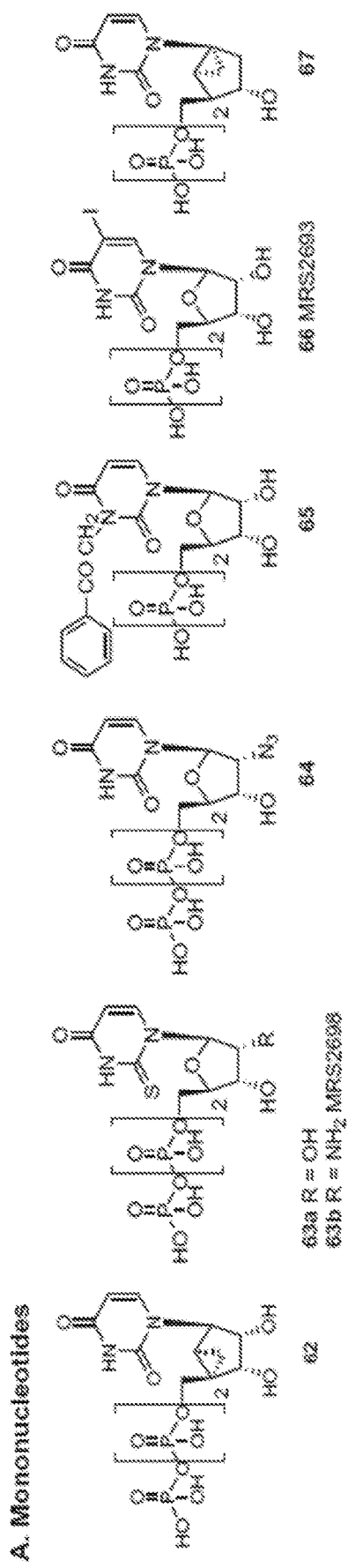
FIGS. 5A-5C show exemplary small molecule P2Y receptor agonists.
Figure 5B:
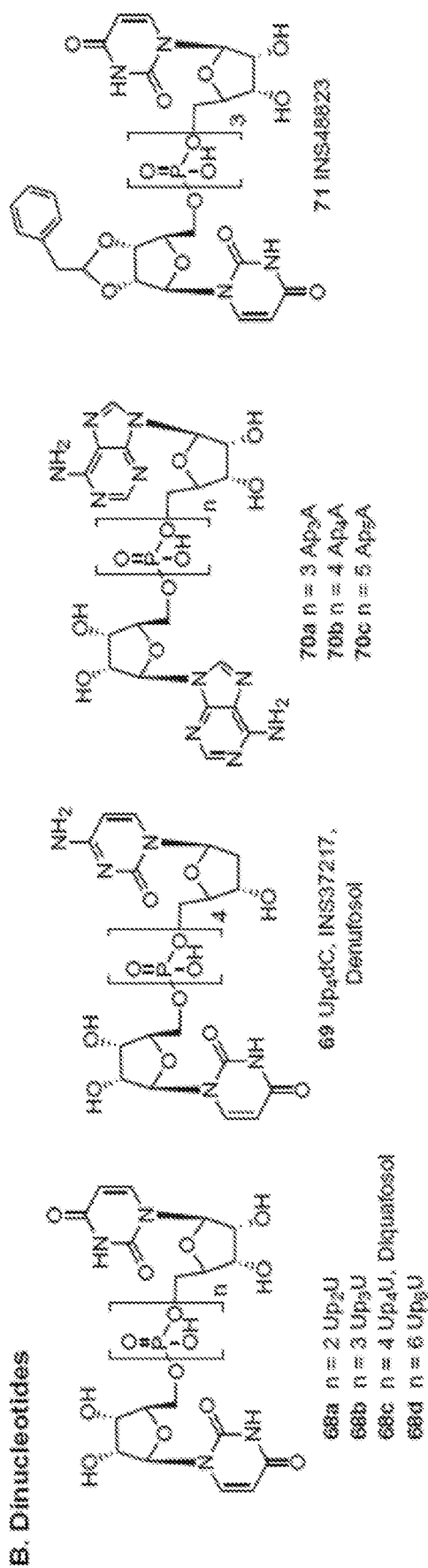
Figure 5C:
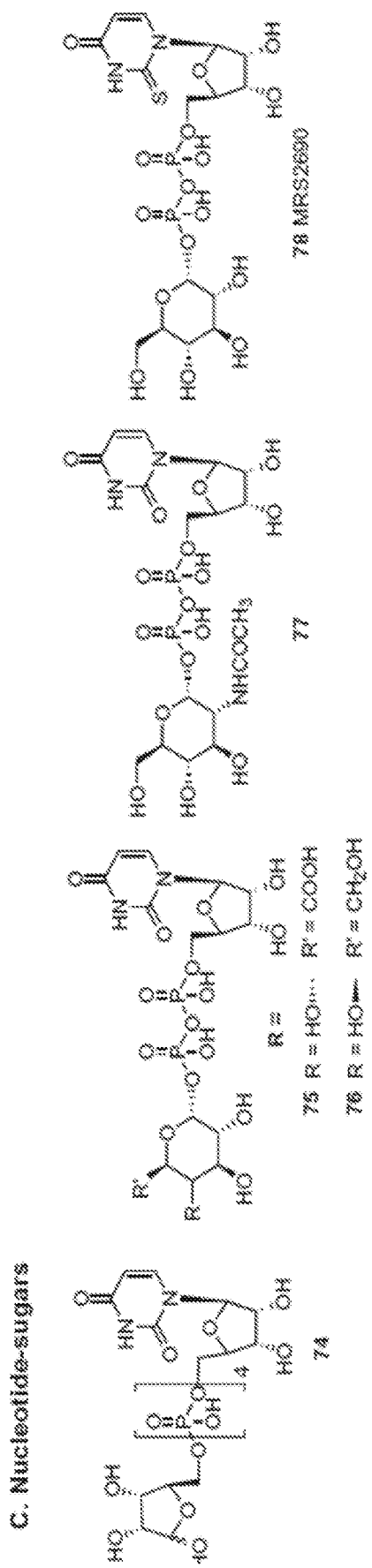

Blood was collected at 5, 15, 30, 45, and 60 minutes post-$^{33}P$ administration and plasma scintillation counting was performed. FIG. 3 shows that the P2Y2 receptor agonist $Up_4U$ (15 mg/kg) significantly decreased $^{33}P$ uptake/absorption.

Example 5

Pharmacodynamic Effects on Acute Phosphate Uptake in Rats

Compounds were tested for the ability to reduce the appearance of circulating radiolabeled phosphate subsequent to administration to the alimentary canal in rats. The rate of radiolabeled phosphate tracer accumulation in the blood of rats was taken as a surrogate for the intestinal absorption rate of a phosphate meal from the gastrointestinal tract. To this end, circulating radiolabeled phosphate was monitored after intragastric co-administration to rats of a phosphate tracer meal along with example compounds. However, since some of the compounds tested potentially had properties that may hinder this assay, such as having putative gastrointestinal motility effects (e.g., delaying gastric emptying) or being purposefully chemically unstable in the gastrointestinal tract, direct intraduodenal administrations of the phosphate tracer bolus was also performed at times.

Male Sprague-Dawley rats that were 8-weeks of age were purchased from Charles River Laboratories (Hollister, Calif.). To enable blood sampling, rats were purchased with catheters surgically implanted in the jugular vein by the vendor. For studies requiring intraduodenal administration, an additional catheter was surgically implanted by the vendor to allow for direct infusion to the lumen of the duodenum. Rats were fed a normal, grain-based chow (Harlan Teklad, Madison, Wis.; 2018 Teklad Global 18% Protein Rodent Diet) containing 0.65% P, 1% Ca, and 1.5 iu/g Vitamin $D_3$ and given water ad libitum leading up to the study.

Following an overnight fast, rats were administered a phosphate solution containing [$^{33}$P]orthophosphate (PerkinElmer, Waltham, Mass.) as a tracer with or without test articles dispersed in the solution at the indicated dosage. This dosing solution typically contained 8 mM monobasic sodium phosphate (1.25 µCi [$^{33}$P]orthophosphate/µmol), 4 mM calcium chloride, 0.4% hydroxypropyl methocellulose (w/v), and 2% dimethylsulfoxide (w/v). The dosing solutions were prepared in water for intragastric gavage at 10 ml/kg and in saline if administered intraduodenally using a previously implanted catheter at 5 ml/kg as a bolus.

Blood was sampled from the jugular vein via implanted catheters from conscious rats following dosing and the radioisotope associated with the resulting plasma was determined by scintillation counting. The relative amount of phosphate uptake from the administered dose to the plasma was assessed using body weight estimation of total circulating plasma. See Bijsterbosch et al., *Experientia*. 37: 381-382, 1981 (The plasma volume of the Wistar rat in relation to the body weight). The comparative amount of phosphate uptake at 15 min post-dose for each group (n=6) was expressed as a percentage relative to the study vehicle group (n=6) as mean±SEM. Statistical comparisons of the means of each test group compared to the mean of the vehicle group were determined by one-way analysis of variance followed by the Dunnett's posthoc test and P<0.05 was accepted as statistically significant (ns, not significant; *, P<0.05; , P<0.01; and *, P <0.001).

The results of the studies testing example compounds with intragastric dosing are summarized in Table E1 below.

TABLE E1

Uptake of phosphate tracer to plasma 15 min after intragastric co-administration of a phosphate test meal and compounds in rats

| Compound Name | Primary Target/Compound Class | Dose | % of study vehicle |
|---|---|---|---|
| Prucalopride | 5-HT$_4$ receptor agonist | 10 mg/kg | >75% |
| BAY 60-6583 | A2B receptor agonist | 10 mg/kg | >75% |
| 6-guanyl NECA | A2B receptor agonist | 10 mg/kg | >75% |
| FIG. 6C. Structure 1 | A2B receptor agonist | 10 mg/kg | 50-75% |
| FIG. 6C. Structure 2 | A2B receptor agonist | 10 mg/kg | 50-75% |
| Dorzolamide | Carbonic anhydrase inhibitor | 20 mg/kg | 50-75% |
| A68930 | Dopamine D1 receptor agonist | 10 mg/kg | 50-75% |
| Rilmenidine | Imidazoline I1 receptor agonist | 3 mg/kg | >75% |
| Moxonidine | Imidazoline I1 receptor agonist | 2 mg/kg | 50-75% |
| | | 6 mg/kg | 25-50% |
| FIG. 11. Structure 4 | Imidazoline I1 receptor agonist | 6 mg/kg | >75% |
| Linaclotide | Guanylate Cyclase 2C agonist | 0.03 mg/kg | 50-75% |
| | | 0.1 mg/kg | 50-75% |
| | | 0.3 mg/kg | 25-50% |
| Bethanechol | Muscarinic receptor agonist | 10 mg/kg | >75% |
| Melatonin | MT2 melatonin receptor agonist | 10 mg/kg | 50-75% |
| Sodium nitroprusside | NO release | 10 mg/kg | 25-50% |
| UTP-γ-s | Agonist of P2Y$_2$/$_4$ receptors | 4 mg/kg | >75% |
| Up$_4$U | P2Y2 receptor agonist | 5 mg/kg | >75% |
| | | 15 mg/kg | >75% |
| | | 50 mg/kg | >75% |
| 16,16-dimethyl-PGE2 | Agonist of EP receptors | 3 µg/kg | >75% |
| Bay 41-2271 | Soluble guanylyl cyclase activator | 10 mg/kg | >75% |
| Bay 58-2667 | Soluble guanylyl cyclase activator | 10 mg/kg | 50-75% |
| Vinpocetine | PDE1 inhibitor | 1 mg/kg | >75% |
| | | 10 mg/kg | >75% |
| | | 1 mg/kg + 0.03 mg/kg Linacolitde | 50-75% |
| | | 10 mg/kg + 0.03 mg/kg Linacolitde | 25-50% |
| NKH 477 | Water-soluble analog of forskolin | 0.3 mg/kg | 50-75% |
| | | 1 mg/kg | 25-50% |
| | | 3 mg/kg | 0-25% |
| | | 10 mg/kg | 0-25% |

The results of the studies testing example compounds with intraduodenal dosing in Table E2 below.

TABLE E2

Uptake of phosphate tracer to plasma 15 min after intraduodenal co-administration of a phosphate test meal and compounds in rats.

| Compound Name | Primary Target/Compound Class | Dose | % of study vehicle |
|---|---|---|---|
| 2-methylthio-ADP | P2Y$_1$ receptor agonist | 10 mg/kg | >75% |
| PSB1114 | P2Y$_2$ receptor agonist | 15 mg/kg | >75% |
| NKH477 | Water-soluble analog of forskolin | 1 mg/kg | 25-50% |
| FIG. 11. Structure 4 | Imidazoline I1 receptor agonist | 6 mg/kg | >75% |
| Sodium nitroprusside | NO release | 10 mg/kg | >75% |
| Atrial natriuretic peptide | Atrial natriuretic peptide receptor agonist | 0.2 mg/kg | >75% |

Test compounds that were examples of an A2B receptor agonist, a carbonic anhydrase inhibitor, a dopamine D1 receptor agonist, an imidazoline 11 receptor agonist, a guanylate Cyclase 2C agonist, an MT2 melatonin receptor agonist, an NO releasing agent, a soluble guanylyl cyclase activator, and a soluble analog of forskolin all individually significantly reduced the acute uptake of phosphate from a gastrically delivered meal. Additionally, it was determined that a soluble analog of forskolin dosed directly to the duodenum of the small intestine inhibited the phosphate uptake from a co-administered test bolus.

Example 6

Ussing Chamber

Segments of duodenum and jejunum are immediately removed from anesthetized animals and opened along the mesenteric line and fixed on a Pyrex plate with the mucosal surface uppermost. Epithelial tissues are stripped off the muscle layers and mounted in computer-controlled Ussing chambers (National Physiology Instrument, California) with an exposed area of 100 mm$^2$. The tissues are incubated on both sides with 13 mL of an isotonic buffer solution (pH 6.0 or pH7.4) containing (mmol/L) NaCl 125.4, KCl 5.4, CaCl$_2$, 1.2, NaHCO$_3$, 21, NaHPO, 0.3, NaH$_2$PO$_4$, 1.2. The functional viability and the integrity of the tissues at the start and the end of flux measurements will be ensured with the measurement of short-circuit current ($I_{sc}$) in response to either theophylline (10 mM serosal) or glucose (10 mM mucosal) or L-alanine (5 mM mucosal).

For calculations of unidirectional Pi flux rates ($J_{ms}$: flux from mucosal to serosal side, $J_{sm}$: flux in the opposite direction), 185 KBq [$^{33}$P]-orthophosphate (370 MBq/mL, Perkin-Elmer) and test compounds are added to one side of the tissue. Samples (0.1 ml) are taken from the labeled side 20 minutes later and subsequently in at least three 10 min intervals from the unlabeled side (0.5 mL) of the Ussing chamber. All samples taken from the unlabeled side are replaced by equal volumes of isosmotic bathing fluid. Net fluxes ($J_{net}$) are calculated as differences between $J_{ms}$ and $J_{sm}$ of paired tissues whose conductances do not differ by more than 25%. In another series of experiments flux measurements are done before and after the addition of arsenate (mucosal) or ouabain (serosal) to the bathing solution. Radioactivity measurements are measured in a TopCount (Perkin Elmer) liquid scintillation counter.

Example 7

In Vitro—Ex Vivo Assays

Segments of duodenum and jejunum (5 cm) are removed from animals anesthetized with pentobarbitone sodium, flushed with ice-cold 0.9% saline and everted on glass rods. Samples are securely mounted on the rod and then preincubated for 5 min at 37° C. in oxygenated buffer, pH 7.4 or 6.0, containing in mM: hydroxyethylpiperazine-N'-2-ethanesulfonic acid 16, glucose 10, KCl 3 0.5, MgSO$_4$ 10, CaCl$_2$ 1, NaCl 125, followed by 2 min incubation in the same buffer containing 100 mM $^{33}$Pi ($^{33}$Pi-specific activity 1.85 MBq/mL) and test compounds. The buffer is rapidly stirred using a magnetic flea to minimize the effects of static water layers at the mucosal surface.

Uptake is terminated by exposing the tissue for 10 minutes at room temperature to phosphate-buffered saline containing a 10-fold excess of nonradioactive phosphate. This procedure is followed by a further 10 minute wash in phosphate-buffered saline at room temperature and samples are then blotted dry and the weight recorded. Samples are digested overnight in Protosol (PerkinElmer). Scintillation counting of the digested sample and initial uptake solution permits calculation of phosphate retention of tissue (in nmol/g).

Example 8

Target-Based Screening Assays

Activation of gut receptors can result in signaling that causes in either direct or indirect inhibition of phosphate absorption (e.g. by changing the local pH of the luminal membranes of the gut). Measurement of a compound's ability to interact with these targets may be accomplished using commercial cell lines that heterologously express the target of interest. These cell lines are commonly available from companies such as Perkin Elmer or Multispan. Alternatively, primary cells expressing the target of interest are also commonly used.

Measurement of the interaction of a putative ligand may be accomplished by either of two approaches (see Table E3 below): (1) displacement of a radioisotopically labeled standard ligand from either intact cells or membranes prepared from such cells, or (2) measurement of a secondary messenger production upon treatment with the test compound. For measurement of secondary messengers, numerous commercial kits are available to measure intracellular cAMP, cGMP (e.g. from Cis Bio) and Calcium (e.g. Calcium 6 dye from Molecular Devices).

TABLE E3

| Target | Radioligand probe | 2$^{nd}$ messenger assay |
|---|---|---|
| Purinergic receptor P2Y2 | $^{33}$P-γ-S-ATP or $^{33}$P-ATP | Ca$^{2+}$ |
| Purinergic receptor P2Y1 | [$^3$H]Diquafosol | Ca$^{2+}$ |
| Adenosine receptor A2B | [$^3$H]MRS 1754 | cAMP |
| Acetylcholine receptors | [$^3$H]AF-DX 116 | Ca$^{2+}$ |
| Prostaglandin EP4 receptor | [$^3$H] Prostaglandin E2 | cAMP |
| Dopamine D1 receptor | [$^3$H]SCH23390 | cAMP or Ca$^{2+}$ |
| Melatonin M2 receptor | [$^{125}$I]melatonin | Ca$^{2+}$ |

TABLE E3-continued

| Target | Radioligand probe | 2$^{nd}$ messenger assay |
|---|---|---|
| Seratonin 5H4 receptor | [$^3$H] GR112808 | Ca$^{2+}$ |
| Guanylin receptor | $^{125}$I-ST1 (NSSNYCCELCCNPACTGCY) (SEQ ID NO: 529) | cGMP |
| Atrial Natriuretic Peptide receptor | $^{125}$I-Tyr28ANP(1-28) | cGMP |
| Adenylate cyclase | $^{33}$P-ATP or $^{33}$P-γ-S-ATP | cAMP |
| Imidazoline 1 receptor | [$^3$H]Clonidine | NO |

In cases where the activity of a soluble enzyme is directly affected, an enzyme assay may be employed in which a purified enzyme preparation is used, and the product of the enzymatic reaction is monitored (see Table E4 below).

TABLE E4

| Enzyme | Product |
|---|---|
| soluble guanylate cyclase | cGMP |
| Carbonic anhydrase | H+ (lower pH) |
| PDE inhibitors | cAMP and/or cGMP |

Example 9

Inhibition of Intestinal Sodium and Phosphate Absorption

To assess the ability of selected example compounds to inhibit the absorption of phosphate from the intestinal lumen, the intake and excretion balance of phosphate is measured in rats. Eight week old Sprague Dawley rats are purchased from Charles River Laboratories (Hollister, Calif.) and acclimated for at least 6 days with free access to food and water. During this time and throughout the study, rats may be fed a standard diet (Harlan Teklad, Madison, Wis.; 2018 Teklad Global 18% Protein Rodent Diet) or a purified egg white synthetic diet consisting of 0.6% Ca and 0.35 or 0.6% phosphorus (Harlan Teklad; TD.84122 and TD.130318, respectively).

A day prior to the initiation of the study, rats are acclimated to individual metabolic cages with free access to water and a powdered version of the diets listed above. Animals are dosed approximately 1 hour prior to the commencement to the dark phase either PO at 10 ml/kg with an effective dose of the test article or via drug-admixed food) based on the daily mass of chow rats have been determined to consume. With both dosing paradigms, each rat is given free access to water and an aliquot of powdered chow for each day they are housed in the metabolic cage that is the daily average of ad libitum consumption for that type of chow, for the same type of rats (i.e., male rats at 8 weeks of age consume an average of 18 g/d of the purified diets listed above). This is done to reduce variability and streamline subsequent 24 hour consumption and excretion measurements. Daily water and chow consumption measurements as well as daily urine and fecal collections follow from 1 to 4 consecutive days.

The phosphate, sodium, and potassium content of urine samples are determined by ion chromatography. Urine samples are processed by gravimetric volume determinations followed by acidification with 6 N HCl. Acidified samples are briefly centrifuged (3,600×g) and the supernatants are then diluted with 10 mM HCl. The diluted samples, calibration standards (Sigma/Fluka Analytical), and QC samples (standards prepared in-house) are filtered prior to injection on an ion exchange chromatography system (Dionex ICS-3000). Sodium and potassium are resolved using an isocratic method consisting of a 25 mM methanesulfonic acid mobile phase and a Dionex CS12A cation exchange analytical column. Phosphate is resolved using an isocratic method consisting of a 35 mM potassium hydroxide mobile phase and a Dionex AS18 anion exchange analytical column. Quantitative analysis is performed using Dionex Chromeleon software. All sample concentrations are interpolated from a calibration curve based on chromatographic peak areas.

The phosphate, sodium, calcium, and potassium content of each 24 hour fecal sample are determined by atomic emission spectroscopy. Dried fecal pellets or a representative sample from dried homogenized feces are digested with repeated additions of concentrated nitric acid and hydrogen peroxide over 2-3 hours at 65-95° C. The sample solutions are then diluted with 1% nitric acid prior to analysis with an atomic emission spectrometer (Agilent 4100 MP-AES) at the following element emission wavelengths: calcium (422.673 nm), sodium (588.995 nm), potassium (766.491 nm), and phosphorus (214.915 or 213.618 nm). A cesium solution is used as both an ionization buffer and an internal standard. Data analysis is performed using Agilent MP Expert software.

Daily urinary and fecal phosphate output relative to the P consumed in the diet for each animal on each day measured is calculated. The percentage inhibition of phosphorus absorption is expressed by determining the reduction of these ratios compared to the control group (animals with no drug in chow). This may also be done with other ions of interest. If there are multiple days tested, these may represent replicates for steady-state measurement of phosphate balance for each rat, in which case regular daily consumption by the animals is a prerequisite. Increased fecal phosphate with an approximate concomitant decrease in urinary P to maintain neutral balance in the rats is an indication of overall decreased phosphate absorption in rats treated with example compounds.

Example 10

Effects in a Rat Chronic Kidney Disease (CKD) Model

To assess the ability of selected example compounds to impact soft tissue calcification often associated with later stages of CKD, the 5/6 nephrectomy (5/6Nx) rat model is utilized to examine mineral homeostasis in a diseased state. A commonly used model to study various aspects of CKD, the 5/6Nx rat is not normally hyperphosphatemic unless challenged with dietary phosphate (see Shobeiri et. al., *Am J Nephrol*. 31:471-481, 2010, Vascular Calcification in Animal Models of CKD: A Review). Therefore, to ensure efficient and steady phosphatemic vascular calcification progression in these animals, a combination of enhanced bioavailable phosphate in the diet and Vitamin D$_3$ treatment is implemented as adapted from the protocol developed by the Lopez group (see Lopez et al., *J Am Soc Nephrol*. 17: 795-804, 2006. Calcimimetic R-568 Decreases Extraosseous Calcifications in Uremic Rats Treated with Calcitriol).

Male Sprague-Dawley 5/6th nephrectomized rats are purchased from Charles River Laboratories (Hollister, Calif.) with surgical procedures performed by the vendor. Reduction in functional renal mass is achieved by two surgeries:

sub-total nephrectomy of the left kidney followed by a 1-week recovery prior to uninephrectomy of the right kidney. After a 3 day recovery period from the second surgery, the rats are transported to the testing facility at 9 weeks of age.

Upon arrival and throughout the study, rats are fed a purified powdered diet consisting of 0.9% inorganic P (phosphorus) and 0.6% Ca (TD.10809, Harlan-Teklad, Madison, Wis.). Matinal serum is obtained by retroorbital or tail vein bleeding and only animals with serum creatinine levels of 0.9 to 1.2 mg/dl are enrolled to the study with groups (n=12) stratified based on serum creatinine and body weight. Enrolled rats in treatment groups are dosed drug-in-chow using the same diet as the vehicle group described above. Additionally, a regimen of calcitriol (active Vitamin $D_3$ 80 ng/kg i.p.) administration 3 times per week is initiated.

Kidney function, phosphatemic state as well as other parameters are monitored weekly with appropriate serum marker measurements via standard clinical chemistry or ELISA analysis. Rats with serum creatinine greater than 2 mg/dL or with a body weight of 80% or less of the mean cohort body weight are removed form study due to advanced diseased state. Urine markers for kidney function may also be measured by placing rats in metabolic cages to allow for the collection of excretions.

After 4 weeks, rats are euthanized and organs are collected and weighed. The mineralization of the aortic arch, heart, stomach and kidney remnant are determined. Whole tissue samples are digested with repeated additions of concentrated nitric acid and hydrogen peroxide over 2-3 hours at 65-95° C. The sample solutions are then diluted with 1% nitric acid prior to analysis with an atomic emission spectrometer (Agilent 4100 MP-AES) at the following element emission wavelengths: calcium (422.673 nm), sodium (588.995 nm), potassium (766.491 nm), and phosphorus (214.915 or 213.618 nm). A cesium solution is used as an ionization buffer and internal standard. Data analysis is performed using Agilent MP Expert software.

A reduction in vascular calcification in animals treated with test articles compared to their untreated counterparts is consistent with the reported inhibition of dietary phosphate absorption that is needed to drive the disease state in this CKD rat model.

The invention claimed is:

1. A method for inhibiting phosphate uptake in the gastrointestinal tract of a patient in need of phosphate lowering, comprising administering to the patient a guanylate cyclase C receptor (GC-C) agonist compound that comprises the amino acid sequence Cys Cys Glu Tyr Cys Cys Asn Pro Ala Cys Thr Gly Cys Tyr (SEQ ID NO:4);

Asn Asp Glu Cys Glu Leu Cys Val Asn Val Ala Cys Thr Gly Cys Leu (SEQ ID NO:6);

Cys Cys Glu Trp Cys Cys Asn Pro Ala Cys Thr Gly Cys Tyr (SEQ ID NO:72); or

Cys Cys Glu Phe Cys Cys Asn Pro Ala Cys Thr Gly Cys Tyr (SEQ ID NO:70)

where the GC-C agonist compound is active in the gastrointestinal tract to inhibit transport of phosphate ions (Pi) therein upon administration to the patient in need thereof.

2. The method of claim 1, wherein the (GC-C) agonist compound comprises amino acid sequence: Cys Cys Glu Tyr Cys Cys Asn Pro Ala Cys Thr Gly Cys Tyr (SEQ ID NO:4).

3. The method of claim 1, wherein the (GC-C) agonist compound comprises amino acid sequence: Asn Asp Glu Cys Glu Leu Cys Val Asn Val Ala Cys Thr Gly Cys Leu (SEQ ID NO:6).

4. The method of claim 1, wherein the (GC-C) agonist compound comprises amino acid sequence: Cys Cys Glu Trp Cys Cys Asn Pro Ala Cys Thr Gly Cys Tyr (SEQ ID NO:72).

5. The method of claim 1, wherein the (GC-C) agonist compound comprises amino acid sequence: Cys Cys Glu Phe Cys Cys Asn Pro Ala Cys Thr Gly Cys Tyr (SEQ ID NO:70).

6. The method of claim 2, wherein the (GC-C) agonist compound is linaclotide.

7. The method of claim 3, wherein the (GC-C) agonist compound is plecanatide.

8. The method of claim 1, wherein the patient in need of phosphate lowering has hyperphosphatemia.

9. The method of claim 6, wherein the patient in need of phosphate lowering has hyperphosphatemia.

10. The method of claim 7, wherein the patient in need of phosphate lowering has hyperphosphatemia.

11. The method of claim 1, where the patient has end-stage renal disease (ESRD).

12. The method of claim 1, where the patient has chronic kidney disease (CKD).

13. The method of claim 6, wherein the patient has end-stage renal disease (ESRD).

14. The method of claim 7, wherein the patient has chronic kidney disease (CKD).

* * * * *

SEQUENCE LISTING

```
<160> NUMBER OF SEQ ID NOS: 760

<210> SEQ ID NO 1
<211> LENGTH: 21
<212> TYPE: PRT
<213> ORGANISM: Artificial Sequence
<220> FEATURE:
<223> OTHER INFORMATION: guanylate cyclase C receptor (GC-C) agonist
<220> FEATURE:
<221> NAME/KEY: MISC_FEATURE
<222> LOCATION: (1)..(1)
<223> OTHER INFORMATION: Xaa = Asn or is absent
<220> FEATURE:
<221> NAME/KEY: MISC_FEATURE
<222> LOCATION: (2)..(3)
<223> OTHER INFORMATION: Xaa = Ser or is absent
<220> FEATURE:
<221> NAME/KEY: MISC_FEATURE
<222> LOCATION: (4)..(4)
<223> OTHER INFORMATION: Xaa = Asn or is absent
<220> FEATURE:
<221> NAME/KEY: MISC_FEATURE
<222> LOCATION: (8)..(9)
<223> OTHER INFORMATION: Xaa = Any amino acid
<220> FEATURE:
<221> NAME/KEY: MISC_FEATURE
<222> LOCATION: (12)..(14)
<223> OTHER INFORMATION: Xaa = Any amino acid
<220> FEATURE:
<221> NAME/KEY: MISC_FEATURE
<222> LOCATION: (16)..(17)
<223> OTHER INFORMATION: Xaa = Any amino acid
<220> FEATURE:
<221> NAME/KEY: MISC_FEATURE
<222> LOCATION: (19)..(21)
<223> OTHER INFORMATION: Xaa = Any amino acid

<400> SEQUENCE: 1

Xaa Xaa Xaa Xaa Tyr Cys Cys Xaa Xaa Cys Cys Xaa Xaa Xaa Cys Xaa
1               5                   10                  15

Xaa Cys Xaa Xaa Xaa
            20

<210> SEQ ID NO 2
<211> LENGTH: 5
<212> TYPE: PRT
<213> ORGANISM: Artificial Sequence
```

```
<220> FEATURE:
<223> OTHER INFORMATION: Fragment of guanylate cyclase C receptor
      (GC-C) agonist

<400> SEQUENCE: 2

Asn Ser Ser Asn Tyr
1               5

<210> SEQ ID NO 3
<211> LENGTH: 19
<212> TYPE: PRT
<213> ORGANISM: Artificial Sequence
<220> FEATURE:
<223> OTHER INFORMATION: Guanylate cyclase C receptor (GC-C) agonist

<400> SEQUENCE: 3

Asn Ser Ser Asn Tyr Cys Cys Glu Tyr Cys Cys Asn Pro Ala Cys Thr
1               5                   10                  15

Gly Cys Tyr

<210> SEQ ID NO 4
<211> LENGTH: 14
<212> TYPE: PRT
<213> ORGANISM: Artificial Sequence
<220> FEATURE:
<223> OTHER INFORMATION: Guanylate cyclase C receptor (GC-C) agonist

<400> SEQUENCE: 4

Cys Cys Glu Tyr Cys Cys Asn Pro Ala Cys Thr Gly Cys Tyr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Guanylate cyclase C receptor (GC-C) agonist
<220> FEATURE:
<221> NAME/KEY: MISC_FEATURE
<222> LOCATION: (1)..(1)
<223> OTHER INFORMATION: Xaa = Ser, Asn, Tyr, Ala, Gln, Pro, Lys, Gly,
      or Thr, or is absent
<220> FEATURE:
<221> NAME/KEY: MISC_FEATURE
<222> LOCATION: (2)..(2)
<223> OTHER INFORMATION: Xaa = His, Asp, Glu, Ala, Ser, Asn, Gly, or is
      absent
<220> FEATURE:
<221> NAME/KEY: MISC_FEATURE
<222> LOCATION: (3)..(3)
<223> OTHER INFORMATION: Xaa = Thr, Asp, Ser, Glu, Pro, Val or Leu
<220> FEATURE:
<221> NAME/KEY: MISC_FEATURE
<222> LOCATION: (5)..(5)
<223> OTHER INFORMATION: Xaa = Asp, Ile or Glu
<220> FEATURE:
<221> NAME/KEY: MISC_FEATURE
<222> LOCATION: (6)..(6)
<223> OTHER INFORMATION: Xaa = Ile, Trp or Leu
<220> FEATURE:
<221> NAME/KEY: MISC_FEATURE
<222> LOCATION: (7)..(7)
<223> OTHER INFORMATION: Xaa = Cys, Ser, or Tyr
<220> FEATURE:
<221> NAME/KEY: MISC_FEATURE
<222> LOCATION: (8)..(8)
<223> OTHER INFORMATION: Xaa = Ala, Val, Thr, Ile, Met or is absent
<220> FEATURE:
<221> NAME/KEY: MISC_FEATURE
<222> LOCATION: (9)..(9)
<223> OTHER INFORMATION: Xaa = Phe, Tyr, Asn, or Trp
<220> FEATURE:
```

```
<221> NAME/KEY: MISC_FEATURE
<222> LOCATION: (10)..(10)
<223> OTHER INFORMATION: Xaa = Ala, Val, Met, Thr or Ile
<220> FEATURE:
<221> NAME/KEY: MISC_FEATURE
<222> LOCATION: (11)..(11)
<223> OTHER INFORMATION: Xaa = Ala or Val
<220> FEATURE:
<221> NAME/KEY: MISC_FEATURE
<222> LOCATION: (13)..(13)
<223> OTHER INFORMATION: Xaa = Thr or Ala
<220> FEATURE:
<221> NAME/KEY: MISC_FEATURE
<222> LOCATION: (14)..(14)
<223> OTHER INFORMATION: Xaa = Gly, Ala or Ser
<220> FEATURE:
<221> NAME/KEY: MISC_FEATURE
<222> LOCATION: (15)..(15)
<223> OTHER INFORMATION: Xaa = Cys, Tyr or is absent
<220> FEATURE:
<221> NAME/KEY: MISC_FEATURE
<222> LOCATION: (16)..(16)
<223> OTHER INFORMATION: Xaa = His, Leu or Ser

<400> SEQUENCE: 5

Xaa Xaa Xaa Cys Xaa Xaa Xaa Xaa Xaa Xaa Xaa Cys Xaa Xaa Xaa Xaa
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Guanylate cyclase C receptor (GC-C) agonist

<400> SEQUENCE: 6

Asn Asp Glu Cys Glu Leu Cys Val Asn Val Ala Cys Thr Gly Cys Leu
1               5                   10                  15

<210> SEQ ID NO 7
<211> LENGTH: 28
<212> TYPE: PRT
<213> ORGANISM: Artificial Sequence
<220> FEATURE:
<223> OTHER INFORMATION: Atrial natriuretic peptide receptor agonist

<400> SEQUENCE: 7

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 8
<211> LENGTH: 17
<212> TYPE: PRT
<213> ORGANISM: Artificial Sequence
<220> FEATURE:
<223> OTHER INFORMATION: Atrial natriuretic peptide receptor agonist

<400> SEQUENCE: 8

Cys Phe Gly Gly Arg Ile Asp Arg Ile Gly Ala Gln Ser Gly Leu Gly
1               5                   10                  15

Cys

<210> SEQ ID NO 9
<211> LENGTH: 23
<212> TYPE: PRT
<213> ORGANISM: Artificial Sequence
<220> FEATURE:
```

<223> OTHER INFORMATION: Atrial natriuretic peptide receptor agonist

<400> SEQUENCE: 9

Ser Ser Cys Phe Gly Gly Arg Ile Asp Arg Ile Gly Ala Gln Ser Gly
1               5                   10                  15

Leu Gly Cys Asn Ser Phe Arg
            20

<210> SEQ ID NO 10
<211> LENGTH: 19
<212> TYPE: PRT
<213> ORGANISM: Escherichia coli

<400> SEQUENCE: 10

Asn Ser Ser Asn Tyr Cys Cys Glu Leu Cys Cys Asn Pro Ala Cys Thr
1               5                   10                  15

Gly Cys Tyr

<210> SEQ ID NO 11
<211> LENGTH: 18
<212> TYPE: PRT
<213> ORGANISM: Escherichia coli

<400> SEQUENCE: 11

Asn Thr Phe Tyr Cys Cys Glu Leu Cys Cys Asn Pro Ala Cys Ala Gly
1               5                   10                  15

Cys Tyr

<210> SEQ ID NO 12
<211> LENGTH: 18
<212> TYPE: PRT
<213> ORGANISM: Escherichia coli

<400> SEQUENCE: 12

Asn Thr Phe Tyr Cys Cys Glu Leu Cys Cys Tyr Pro Ala Cys Ala Gly
1               5                   10                  15

Cys Asn

<210> SEQ ID NO 13
<211> LENGTH: 18
<212> TYPE: PRT
<213> ORGANISM: Citrobacter freundii

<400> SEQUENCE: 13

Asn Thr Phe Tyr Cys Cys Glu Leu Cys Cys Asn Pro Ala Cys Ala Gly
1               5                   10                  15

Cys Tyr

<210> SEQ ID NO 14
<211> LENGTH: 30
<212> TYPE: PRT
<213> ORGANISM: Yersinia enterocolitica

<400> SEQUENCE: 14

Gln Ala Cys Asp Pro Pro Ser Pro Ala Glu Val Ser Ser Asp Trp
1               5                   10                  15

Asp Cys Cys Asp Val Cys Cys Asn Pro Ala Cys Ala Gly Cys
            20                  25                  30

<210> SEQ ID NO 15
<211> LENGTH: 30

```
<212> TYPE: PRT
<213> ORGANISM: Yersinia enterocolitica

<400> SEQUENCE: 15

Gln Ala Cys Asp Pro Pro Leu Pro Ala Glu Val Ser Ser Asp Trp
1               5                   10                  15

Asp Cys Cys Asp Val Cys Cys Asn Pro Ala Cys Ala Gly Cys
            20                  25                  30

<210> SEQ ID NO 16
<211> LENGTH: 30
<212> TYPE: PRT
<213> ORGANISM: Yersinia enterocolitica

<400> SEQUENCE: 16

Lys Ala Cys Asp Thr Gln Thr Pro Ser Pro Ser Glu Glu Asn Asp Asp
1               5                   10                  15

Trp Cys Cys Glu Val Cys Cys Asn Pro Ala Cys Ala Gly Cys
            20                  25                  30

<210> SEQ ID NO 17
<211> LENGTH: 53
<212> TYPE: PRT
<213> ORGANISM: Yersinia enterocolitica

<400> SEQUENCE: 17

Gln Glu Thr Ala Ser Gly Gln Val Gly Asp Val Ser Ser Thr Ile
1               5                   10                  15

Ala Thr Glu Val Ser Glu Ala Glu Cys Gly Thr Gln Ser Ala Thr Thr
            20                  25                  30

Gln Gly Glu Asn Asp Trp Asp Trp Cys Cys Glu Leu Cys Cys Asn Pro
        35                  40                  45

Ala Cys Phe Gly Cys
    50

<210> SEQ ID NO 18
<211> LENGTH: 16
<212> TYPE: PRT
<213> ORGANISM: Yersinia kristensenii

<400> SEQUENCE: 18

Ser Asp Trp Cys Cys Glu Val Cys Cys Asn Pro Ala Cys Ala Gly Cys
1               5                   10                  15

<210> SEQ ID NO 19
<211> LENGTH: 17
<212> TYPE: PRT
<213> ORGANISM: Vibrio cholerae

<400> SEQUENCE: 19

Ile Asp Cys Cys Glu Ile Cys Cys Asn Pro Ala Cys Phe Gly Cys Leu
1               5                   10                  15

Asn

<210> SEQ ID NO 20
<211> LENGTH: 17
<212> TYPE: PRT
<213> ORGANISM: Vibrio mimicus

<400> SEQUENCE: 20

Ile Asp Cys Cys Glu Ile Cys Cys Asn Pro Ala Cys Phe Gly Cys Leu
1               5                   10                  15
```

Asn

<210> SEQ ID NO 21
<211> LENGTH: 18
<212> TYPE: PRT
<213> ORGANISM: Escherichia coli

<400> SEQUENCE: 21

Asn Thr Phe Tyr Cys Cys Glu Leu Cys Cys Asn Pro Ala Cys Ala Pro
1               5                   10                  15

Cys Tyr

<210> SEQ ID NO 22
<211> LENGTH: 13
<212> TYPE: PRT
<213> ORGANISM: Vibrio cholerae

<400> SEQUENCE: 22

Ile Asp Cys Cys Glu Ile Cys Cys Asn Pro Ala Cys Phe
1               5                   10

<210> SEQ ID NO 23
<211> LENGTH: 14
<212> TYPE: PRT
<213> ORGANISM: Vibrio cholerae

<400> SEQUENCE: 23

Ile Asp Cys Cys Glu Ile Cys Cys Asn Pro Ala Cys Phe Gly
1               5                   10

<210> SEQ ID NO 24
<211> LENGTH: 17
<212> TYPE: PRT
<213> ORGANISM: Vibrio mimicus

<400> SEQUENCE: 24

Ile Asp Arg Cys Glu Ile Cys Cys Asn Pro Ala Cys Phe Gly Cys Leu
1               5                   10                  15

Asn

<210> SEQ ID NO 25
<211> LENGTH: 16
<212> TYPE: PRT
<213> ORGANISM: Yersinia enterocolitica

<400> SEQUENCE: 25

Asp Trp Asp Cys Cys Asp Val Cys Cys Asn Pro Ala Cys Ala Gly Cys
1               5                   10                  15

<210> SEQ ID NO 26
<211> LENGTH: 16
<212> TYPE: PRT
<213> ORGANISM: Yersinia enterocolitica

<400> SEQUENCE: 26

Asp Trp Asp Cys Cys Asp Val Cys Cys Asn Pro Ala Cys Ala Gly Cys
1               5                   10                  15

<210> SEQ ID NO 27
<211> LENGTH: 17
<212> TYPE: PRT
<213> ORGANISM: Yersinia enterocolitica

```
<400> SEQUENCE: 27

Asn Asp Asp Trp Cys Cys Glu Val Cys Asn Pro Ala Cys Ala Gly
1               5                   10                  15

Cys

<210> SEQ ID NO 28
<211> LENGTH: 16
<212> TYPE: PRT
<213> ORGANISM: Yersinia enterocolitica

<400> SEQUENCE: 28

Trp Asp Trp Cys Cys Glu Leu Cys Cys Asn Pro Ala Cys Phe Gly Cys
1               5                   10                  15

<210> SEQ ID NO 29
<211> LENGTH: 30
<212> TYPE: PRT
<213> ORGANISM: Yersinia enterocolitica

<400> SEQUENCE: 29

Gln Ala Cys Asp Pro Ser Pro Ala Glu Val Ser Ser Asp Trp
1               5                   10                  15

Asp Cys Cys Asp Val Cys Cys Asp Pro Ala

```
<400> SEQUENCE: 33

Ser Lys Glu Lys Ile Thr Leu Glu Thr Lys Cys Asp Val Val Lys
1               5                   10                  15

Asn Asn Ser Glu Lys Lys Ser Glu Asn
            20                  25

<210> SEQ ID NO 34
<211> LENGTH: 20
<212> TYPE: PRT
<213> ORGANISM: Escherichia coli

<400> SEQUENCE: 34

Met Asn Asn Thr Phe Tyr Cys Cys Glu Leu Cys Cys Asn Pro Ala Cys
1               5                   10                  15

Ala Gly Cys Tyr
            20

<210> SEQ ID NO 35
<211> LENGTH: 27
<212> TYPE: PRT
<213> ORGANISM: Escherichia coli

<400> SEQUENCE: 35

Met Lys Lys Ser Ile Leu Phe Ile Phe Leu Ser Val Leu Ser Phe Ser
1               5                   10                  15

Pro Phe Ala Gln Asp Ala Lys Pro Val Glu Ser
            20                  25

<210> SEQ ID NO 36
<211> LENGTH: 26
<212> TYPE: PRT
<213> ORGANISM: Escherichia coli

<400> SEQUENCE: 36

Ser Lys Glu Lys Ile Thr Leu Glu Ser Lys Lys Cys Asn Ile Ala Lys
1               5                   10                  15

Lys Ser Asn Lys Ser Gly Pro Glu Ser Met
            20                  25

<210> SEQ ID NO 37
<211> LENGTH: 19
<212> TYPE: PRT
<213> ORGANISM: Escherichia coli

<400> SEQUENCE: 37

Asn Ser Ser Asn Tyr Cys Cys Glu Leu Cys Cys Asn Pro Ala Cys Thr
1               5                   10                  15

Gly Cys Tyr

<210> SEQ ID NO 38
<211> LENGTH: 25
<212> TYPE: PRT
<213> ORGANISM: Yersinia enterocolitica

<400> SEQUENCE: 38

Met Lys Lys Ile Val Phe Val Leu Val Leu Met Leu Ser Ser Phe Gly
1               5                   10                  15

Ala Phe Gly Gln Glu Thr Val Ser Gly
            20                  25
```

-continued

<210> SEQ ID NO 39
<211> LENGTH: 26
<212> TYPE: PRT
<213> ORGANISM: Yersinia enterocolitica

<400> SEQUENCE: 39

Gln Phe Ser Asp Ala Leu Ser Thr Pro Ile Thr Ala Glu Val Tyr Lys
1               5                   10                  15

Gln Ala Cys Asp Pro Pro Leu Pro Pro Ala
            20                  25

<210> SEQ ID NO 40
<211> LENGTH: 20
<212> TYPE: PRT
<213> ORGANISM: Yersinia enterocolitica

<400> SEQUENCE: 40

Glu Val Ser Ser Asp Trp Asp Cys Cys Asp Val Cys Cys Asn Pro Ala
1               5                   10                  15

Cys Ala Gly Cys
            20

<210> SEQ ID NO 41
<211> LENGTH: 72
<212> TYPE: PRT
<213> ORGANISM: Escherichia coli

<400> SEQUENCE: 41

Met Lys Lys Leu Met Leu Ala Ile Phe Ile Ser Val Leu Ser Phe Pro
1               5                   10                  15

Ser Phe Ser Gln Ser Thr Glu Ser Leu Asp Ser Ser Lys Glu Lys Ile
            20                  25                  30

Thr Leu Glu Thr Lys Lys Cys Asp Val Val Lys Asn Asn Ser Glu Lys
        35                  40                  45

Lys Ser Glu Asn Met Asn Asn Thr Phe Tyr Cys Cys Glu Leu Cys Cys
    50                  55                  60

Asn Pro Ala Cys Ala Gly Cys Tyr
65                  70

<210> SEQ ID NO 42
<211> LENGTH: 72
<212> TYPE: PRT
<213> ORGANISM: Escherichia coli

<400> SEQUENCE: 42

Met Lys Lys Ser Ile Leu Phe Ile Phe Leu Ser Val Leu Ser Phe Ser
1               5                   10                  15

Pro Phe Ala Gln Asp Ala Lys Pro Val Glu Ser Ser Lys Glu Lys Ile
            20                  25                  30

Thr Leu Glu Ser Lys Lys Cys Asn Ile Ala Lys Lys Ser Asn Lys Ser
        35                  40                  45

Gly Pro Glu Ser Met Asn Ser Ser Asn Tyr Cys Cys Glu Leu Cys Cys
    50                  55                  60

Asn Pro Ala Cys Thr Gly Cys Tyr
65                  70

<210> SEQ ID NO 43
<211> LENGTH: 71
<212> TYPE: PRT
<213> ORGANISM: Yersinia enterocolitica

<400> SEQUENCE: 43

```
Met Lys Lys Ile Val Phe Val Leu Tyr Leu Met Leu Ser Ser Phe Gly
1               5                   10                  15

Ala Phe Gly Gln Glu Thr Val Ser Gly Gln Phe Ser Asp Ala Leu Ser
            20                  25                  30

Thr Pro Ile Thr Ala Glu Val Tyr Lys Gln Ala Cys Asp Pro Pro Leu
        35                  40                  45

Pro Pro Ala Glu Val Ser Ser Asp Trp Asp Cys Cys Asp Val Cys Cys
50                  55                  60

Asn Pro Ala Cys Ala Gly Cys
65                  70
```

<210> SEQ ID NO 44
<211> LENGTH: 6
<212> TYPE: PRT
<213> ORGANISM: Artificial Sequence
<220> FEATURE:
<223> OTHER INFORMATION: Carboxy terminus fragments of peptide

<400> SEQUENCE: 44

```
Lys Lys Lys Lys Lys Lys
1               5
```

<210> SEQ ID NO 45
<211> LENGTH: 7
<212> TYPE: PRT
<213> ORGANISM: Artificial Sequence
<220> FEATURE:
<223> OTHER INFORMATION: Carboxy terminus fragments of peptide

<400> SEQUENCE: 45

```
Asp Lys Lys Lys Lys Lys Lys
1               5
```

<210> SEQ ID NO 46
<211> LENGTH: 21
<212> TYPE: PRT
<213> ORGANISM: Artificial Sequence
<220> FEATURE:
<223> OTHER INFORMATION: GC-C agonist peptide (bacterial STanalog)
<220> FEATURE:
<221> NAME/KEY: MISC_FEATURE
<222> LOCATION: (1)..(5)
<223> OTHER INFORMATION: Xaa = Any amino acid
<220> FEATURE:
<221> NAME/KEY: MISC_FEATURE
<222> LOCATION: (8)..(9)
<223> OTHER INFORMATION: Xaa = Any amino acid
<220> FEATURE:
<221> NAME/KEY: MISC_FEATURE
<222> LOCATION: (12)..(14)
<223> OTHER INFORMATION: Xaa = Any amino acid
<220> FEATURE:
<221> NAME/KEY: MISC_FEATURE
<222> LOCATION: (16)..(17)
<223> OTHER INFORMATION: Xaa = Any amino acid
<220> FEATURE:
<221> NAME/KEY: MISC_FEATURE
<222> LOCATION: (19)..(21)
<223> OTHER INFORMATION: Xaa = Any amino acid

<400> SEQUENCE: 46

```
Xaa Xaa Xaa Xaa Xaa Cys Cys Xaa Xaa Cys Cys Xaa Xaa Xaa Cys Xaa
1               5                   10                  15

Xaa Cys Xaa Xaa Xaa
            20
```

```
<210> SEQ ID NO 47
<211> LENGTH: 21
<212> TYPE: PRT
<213> ORGANISM: Artificial Sequence
<220> FEATURE:
<223> OTHER INFORMATION: GC-C agonist peptide
<220> FEATURE:
<221> NAME/KEY: MISC_FEATURE
<222> LOCATION: (1)..(1)
<223> OTHER INFORMATION: Xaa = Asn or is absent
<220> FEATURE:
<221> NAME/KEY: MISC_FEATURE
<222> LOCATION: (2)..(2)
<223> OTHER INFORMATION: Xaa = Ser or is absent
<220> FEATURE:
<221> NAME/KEY: MISC_FEATURE
<222> LOCATION: (3)..(3)
<223> OTHER INFORMATION: Xaa = Ser or is absent
<220> FEATURE:
<221> NAME/KEY: MISC_FEATURE
<222> LOCATION: (4)..(4)
<223> OTHER INFORMATION: Xaa = Asn or is absent
<220> FEATURE:
<221> NAME/KEY: MISC_FEATURE
<222> LOCATION: (5)..(5)
<223> OTHER INFORMATION: Xaa = Tyr or Asn or is absent
<220> FEATURE:
<221> NAME/KEY: MISC_FEATURE
<222> LOCATION: (8)..(8)
<223> OTHER INFORMATION: Xaa = Glu or Asp
<220> FEATURE:
<221> NAME/KEY: MISC_FEATURE
<222> LOCATION: (9)..(9)
<223> OTHER INFORMATION: Xaa = Leu, Ile, Val, Trp, Tyr or Phe
<220> FEATURE:
<221> NAME/KEY: MISC_FEATURE
<222> LOCATION: (16)..(16)
<223> OTHER INFORMATION: Xaa = Thr, Ala or Trp
<220> FEATURE:
<221> NAME/KEY: MISC_FEATURE
<222> LOCATION: (19)..(19)
<223> OTHER INFORMATION: Xaa = Trp, Tyr, Phe or Leu or is missing
<220> FEATURE:
<221> NAME/KEY: MISC_FEATURE
<222> LOCATION: (20)..(20)
<223> OTHER INFORMATION: Xaa = Asp
<220> FEATURE:
<221> NAME/KEY: MISC_FEATURE
<222> LOCATION: (21)..(21)
<223> OTHER INFORMATION: Xaa = Phe

<400> SEQUENCE: 47

Xaa Xaa Xaa Xaa Xaa Cys Cys Xaa Xaa Cys Cys Asn Pro Ala Cys Xaa
1               5                   10                  15

Gly Cys Xaa Xaa Xaa
            20

<210> SEQ ID NO 48
<211> LENGTH: 21
<212> TYPE: PRT
<213> ORGANISM: Artificial sequence
<220> FEATURE:
<223> OTHER INFORMATION: GC-C agonist peptide
<220> FEATURE:
<221> NAME/KEY: MISC_FEATURE
<222> LOCATION: (1)..(4)
<223> OTHER INFORMATION: Xaa is absent
<220> FEATURE:
<221> NAME/KEY: MISC_FEATURE
<222> LOCATION: (5)..(5)
<223> OTHER INFORMATION: Xaa = Asn
<220> FEATURE:
<221> NAME/KEY: MISC_FEATURE
<222> LOCATION: (8)..(8)
<223> OTHER INFORMATION: Xaa = Any amino acid
```

```
<220> FEATURE:
<221> NAME/KEY: MISC_FEATURE
<222> LOCATION: (9)..(9)
<223> OTHER INFORMATION: Xaa = Leu, Ile, Val, Trp, Tyr or Phe
<220> FEATURE:
<221> NAME/KEY: MISC_FEATURE
<222> LOCATION: (16)..(16)
<223> OTHER INFORMATION: Xaa = Trp, Tyr, Phe, Thr or Ala
<220> FEATURE:
<221> NAME/KEY: MISC_FEATURE
<222> LOCATION: (19)..(19)
<223> OTHER INFORMATION: Xaa = Trp, Tyr or Phe
<220> FEATURE:
<221> NAME/KEY: MISC_FEATURE
<222> LOCATION: (20)..(20)
<223> OTHER INFORMATION: Xaa = Asp
<220> FEATURE:
<221> NAME/KEY: MISC_FEATURE
<222> LOCATION: (21)..(21)
<223> OTHER INFORMATION: Xaa = Phe

<400> SEQUENCE: 48

Xaa Xaa Xaa Xaa Xaa Cys Cys Xaa Xaa Cys Cys Asn Pro Ala Cys Xaa
1               5                   10                  15

Gly Cys Xaa Xaa Xaa
            20

<210> SEQ ID NO 49
<211> LENGTH: 21
<212> TYPE: PRT
<213> ORGANISM: Artificial Sequence
<220> FEATURE:
<223> OTHER INFORMATION: GC-C agonist peptide
<220> FEATURE:
<221> NAME/KEY: MISC_FEATURE
<222> LOCATION: (1)..(1)
<223> OTHER INFORMATION: Xaa = Asn or is absent
<220> FEATURE:
<221> NAME/KEY: MISC_FEATURE
<222> LOCATION: (2)..(2)
<223> OTHER INFORMATION: Xaa = Ser or is absent
<220> FEATURE:
<221> NAME/KEY: MISC_FEATURE
<222> LOCATION: (3)..(3)
<223> OTHER INFORMATION: Xaa = Ser or is absent
<220> FEATURE:
<221> NAME/KEY: MISC_FEATURE
<222> LOCATION: (4)..(4)
<223> OTHER INFORMATION: Xaa = Asn or is absent
<220> FEATURE:
<221> NAME/KEY: MISC_FEATURE
<222> LOCATION: (5)..(5)
<223> OTHER INFORMATION: Xaa = Tyr or is absent
<220> FEATURE:
<221> NAME/KEY: MISC_FEATURE
<222> LOCATION: (9)..(9)
<223> OTHER INFORMATION: Xaa = Any amino acid
<220> FEATURE:
<221> NAME/KEY: MISC_FEATURE
<222> LOCATION: (19)..(19)
<223> OTHER INFORMATION: Xaa = Tyr or is absent
<220> FEATURE:
<221> NAME/KEY: MISC_FEATURE
<222> LOCATION: (20)..(20)
<223> OTHER INFORMATION: Xaa = Asp, Asn or Glu or is absent
<220> FEATURE:
<221> NAME/KEY: MISC_FEATURE
<222> LOCATION: (21)..(21)
<223> OTHER INFORMATION: Xaa = Phe or is absent

<400> SEQUENCE: 49

Xaa Xaa Xaa Xaa Xaa Cys Cys Glu Xaa Cys Cys Asn Pro Ala Cys Thr
1               5                   10                  15

Gly Cys Xaa Xaa Xaa
```

-continued

```
<210> SEQ ID NO 50
<211> LENGTH: 21
<212> TYPE: PRT
<213> ORGANISM: Artificial Sequence
<220> FEATURE:
<223> OTHER INFORMATION: GC-C agonist peptide
<220> FEATURE:
<221> NAME/KEY: MISC_FEATURE
<222> LOCATION: (1)..(5)
<223> OTHER INFORMATION: Xaa = Any amino acid or is absent
<220> FEATURE:
<221> NAME/KEY: MISC_FEATURE
<222> LOCATION: (8)..(9)
<223> OTHER INFORMATION: Xaa = Any amino acid
<220> FEATURE:
<221> NAME/KEY: MISC_FEATURE
<222> LOCATION: (12)..(14)
<223> OTHER INFORMATION: Xaa = Any amino acid
<220> FEATURE:
<221> NAME/KEY: MISC_FEATURE
<222> LOCATION: (16)..(17)
<223> OTHER INFORMATION: Xaa = Any amino acid
<220> FEATURE:
<221> NAME/KEY: MISC_FEATURE
<222> LOCATION: (19)..(21)
<223> OTHER INFORMATION: Xaa = Any amino acid or is absent

<400> SEQUENCE: 50

Xaa Xaa Xaa Xaa Xaa Cys Cys Xaa Xaa Cys Cys Xaa Xaa Xaa Cys Xaa
1               5                  10                  15

Xaa Cys Xaa Xaa Xaa
            20

<210> SEQ ID NO 51
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 51

Gln Ser Ser Asn Tyr Cys Cys Glu Tyr Cys Cys Asn Pro Ala Cys Thr
1               5                  10                  15

Gly Cys Tyr

<210> SEQ ID NO 52
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 52

Asn Leu Ser Asn Tyr Cys Cys Glu Tyr Cys Cys Asn Pro Ala Cys Thr
1               5                  10                  15

Gly Cys Tyr

<210> SEQ ID NO 53
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 53

Asn Ser Ser Gln Tyr Cys Cys Glu Tyr Cys Cys Asn Pro Ala Cys Thr
```

```
1               5                  10                  15

Gly Cys Tyr

<210> SEQ ID NO 54
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 54

Gln Ser Ser Gln Tyr Cys Cys Glu Tyr Cys Cys Asn Pro Ala Cys Thr
1               5                  10                  15

Gly Cys Tyr

<210> SEQ ID NO 55
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 55

Asn Ser Ser Asn Tyr Cys Cys Glu Ala Cys Cys Asn Pro Ala Cys Thr
1               5                  10                  15

Gly Cys Tyr

<210> SEQ ID NO 56
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 56

Asn Ser Ser Asn Tyr Cys Cys Glu Asn Cys Cys Asn Pro Ala Cys Thr
1               5                  10                  15

Gly Cys Tyr

<210> SEQ ID NO 57
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 57

Asn Ser Ser Asn Tyr Cys Cys Glu Cys Cys Cys Asn Pro Ala Cys Thr
1               5                  10                  15

Gly Cys Tyr

<210> SEQ ID NO 58
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 58

Asn Ser Ser Asn Tyr Cys Cys Glu Glu Cys Cys Asn Pro Ala Cys Thr
1               5                  10                  15

Gly Cys Tyr
```

<210> SEQ ID NO 59
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 59

Asn Ser Ser Asn Tyr Cys Cys Glu His Cys Cys Asn Pro Ala Cys Thr
1               5                   10                  15

Gly Cys Tyr

<210> SEQ ID NO 60
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 60

Asn Ser Ser Asn Tyr Cys Cys Glu Lys Cys Cys Asn Pro Ala Cys Thr
1               5                   10                  15

Gly Cys Tyr

<210> SEQ ID NO 61
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 61

Asn Ser Ser Asn Tyr Cys Cys Glu Phe Cys Cys Asn Pro Ala Cys Thr
1               5                   10                  15

Gly Cys Tyr

<210> SEQ ID NO 62
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 62

Asn Ser Ser Asn Tyr Cys Cys Glu Ser Cys Cys Asn Pro Ala Cys Thr
1               5                   10                  15

Gly Cys Tyr

<210> SEQ ID NO 63
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 63

Asn Ser Ser Asn Tyr Cys Cys Glu Trp Cys Cys Asn Pro Ala Cys Thr
1               5                   10                  15

Gly Cys Tyr

<210> SEQ ID NO 64
<211> LENGTH: 14
<212> TYPE: PRT

```
<213> ORGANISM: Artificial Sequence
<220> FEATURE:
<223> OTHER INFORMATION: GC-C agonist peptide

<400> SEQUENCE: 64

Cys Cys Glu Ala Cys Cys Asn Pro Ala Cys Thr Gly Cys Tyr
1               5                   10

<210> SEQ ID NO 65
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 65

Cys Cys Glu Asn Cys Cys Asn Pro Ala Cys Thr Gly Cys Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 66

Cys Cys Glu Cys Cys Cys Asn Pro Ala Cys Thr Gly Cys Tyr
1               5                   10

<210> SEQ ID NO 67
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 67

Cys Cys Glu Glu Cys Cys Asn Pro Ala Cys Thr Gly Cys Tyr
1               5                   10

<210> SEQ ID NO 68
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 68

Cys Cys Glu His Cys Cys Asn Pro Ala Cys Thr Gly Cys Tyr
1               5                   10

<210> SEQ ID NO 69
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 69

Cys Cys Glu Lys Cys Cys Asn Pro Ala Cys Thr Gly Cys Tyr
1               5                   10

<210> SEQ ID NO 70
<211> LENGTH: 14
<212> TYPE: PRT
<213> ORGANISM: Artificial Sequence
```

```
<220> FEATURE:
<223> OTHER INFORMATION: GC-C agonist peptide

<400> SEQUENCE: 70

Cys Cys Glu Phe Cys Cys Asn Pro Ala Cys Thr Gly Cys Tyr
1               5                   10

<210> SEQ ID NO 71
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 71

Cys Cys Glu Ser Cys Cys Asn Pro Ala Cys Thr Gly Cys Tyr
1               5                   10

<210> SEQ ID NO 72
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 72

Cys Cys Glu Trp Cys Cys Asn Pro Ala Cys Thr Gly Cys Tyr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 73

Cys Cys Glu Tyr Cys Cys Asn Pro Ala Cys Thr Gly Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 74

Cys Cys Glu Arg Cys Cys Asn Pro Ala Cys Thr Gly Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 75

Cys Cys Glu Asp Cys Cys Asn Pro Ala Cys Thr Gly Cys
1               5                   10

<210> SEQ ID NO 76
<211> LENGTH: 13
<212> TYPE: PRT
<213> ORGANISM: Artificial Sequence
<220> FEATURE:
```

<223> OTHER INFORMATION: GC-C agonist peptide

<400> SEQUENCE: 76

Cys Cys Glu Gln Cys Cys Asn Pro Ala Cys Thr Gly Cys
1               5                   10

<210> SEQ ID NO 77
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 77

Cys Cys Glu Gly Cys Cys Asn Pro Ala Cys Thr Gly Cys
1               5                   10

<210> SEQ ID NO 78
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 78

Cys Cys Glu Ile Cys Cys Asn Pro Ala Cys Thr Gly Cys
1               5                   10

<210> SEQ ID NO 79
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 79

Cys Cys Glu Met Cys Cys Asn Pro Ala Cys Thr Gly Cys
1               5                   10

<210> SEQ ID NO 80
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 80

Cys Cys Glu Pro Cys Cys Asn Pro Ala Cys Thr Gly Cys
1               5                   10

<210> SEQ ID NO 81
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 81

Cys Cys Glu Thr Cys Cys Asn Pro Ala Cys Thr Gly Cys
1               5                   10

<210> SEQ ID NO 82
<211> LENGTH: 13
<212> TYPE: PRT
<213> ORGANISM: Artificial Sequence
<220> FEATURE:
<223> OTHER INFORMATION: GC-C agonist peptide

```
<400> SEQUENCE: 82

Cys Cys Glu Val Cys Cys Asn Pro Ala Cys Thr Gly Cys
1               5                   10

<210> SEQ ID NO 83
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 83

Asn Thr Ser Asn Tyr Cys Cys Glu Tyr Cys Cys Asn Pro Ala Cys Thr
1               5                   10                  15

Gly Cys Tyr

<210> SEQ ID NO 84
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 84

Asn Ile Ser Asn Tyr Cys Cys Glu Tyr Cys Cys Asn Pro Ala Cys Thr
1               5                   10                  15

Gly Cys Tyr

<210> SEQ ID NO 85
<211> LENGTH: 18
<212> TYPE: PRT
<213> ORGANISM: Artificial Sequence
<220> FEATURE:
<223> OTHER INFORMATION: GC-C agonist peptide

<400> SEQUENCE: 85

Ser Ser Asn Tyr Cys Cys Glu Tyr Cys Cys Asn Pro Ala Cys Thr Gly
1               5                   10                  15

Cys Tyr

<210> SEQ ID NO 86
<211> LENGTH: 18
<212> TYPE: PRT
<213> ORGANISM: Artificial Sequence
<220> FEATURE:
<223> OTHER INFORMATION: GC-C agonist peptide

<400> SEQUENCE: 86

Ser Ser Gln Tyr Cys Cys Glu Tyr Cys Cys Asn Pro Ala Cys Thr Gly
1               5                   10                  15

Cys Tyr

<210> SEQ ID NO 87
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 87

Asn Ser Ser Asn Tyr Cys Cys Glu Arg Cys Cys Asn Pro Ala Cys Thr
1               5                   10                  15
```

Gly Cys Tyr

<210> SEQ ID NO 88
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 88

Asn Ser Ser Asn Tyr Cys Cys Glu Asp Cys Cys Asn Pro Ala Cys Thr
1               5                   10                  15

Gly Cys Tyr

<210> SEQ ID NO 89
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 89

Asn Ser Ser Asn Tyr Cys Cys Glu Gln Cys Cys Asn Pro Ala Cys Thr
1               5                   10                  15

Gly Cys Tyr

<210> SEQ ID NO 90
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 90

Asn Ser Ser Asn Tyr Cys Cys Glu Gly Cys Cys Asn Pro Ala Cys Thr
1               5                   10                  15

Gly Cys Tyr

<210> SEQ ID NO 91
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 91

Asn Ser Ser Asn Tyr Cys Cys Glu Ile Cys Cys Asn Pro Ala Cys Thr
1               5                   10                  15

Gly Cys Tyr

<210> SEQ ID NO 92
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 92

Asn Ser Ser Asn Tyr Cys Cys Glu Met Cys Cys Asn Pro Ala Cys Thr
1               5                   10                  15

Gly Cys Tyr

<210> SEQ ID NO 93

<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 93

Asn Ser Ser Asn Tyr Cys Cys Glu Pro Cys Cys Asn Pro Ala Cys Thr
1               5                   10                  15

Gly Cys Tyr

<210> SEQ ID NO 94
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 94

Asn Ser Ser Asn Tyr Cys Cys Glu Thr Cys Cys Asn Pro Ala Cys Thr
1               5                   10                  15

Gly Cys Tyr

<210> SEQ ID NO 95
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 95

Asn Ser Ser Asn Tyr Cys Cys Glu Val Cys Cys Asn Pro Ala Cys Thr
1               5                   10                  15

Gly Cys Tyr

<210> SEQ ID NO 96
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 96

Cys Cys Glu Arg Cys Cys Asn Pro Ala Cys Thr Gly Cys Tyr
1               5                   10

<210> SEQ ID NO 97
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 97

Cys Cys Glu Asp Cys Cys Asn Pro Ala Cys Thr Gly Cys Tyr
1               5                   10

<210> SEQ ID NO 98
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 98

```
Cys Cys Glu Gln Cys Cys Asn Pro Ala Cys Thr Gly Cys Tyr
1               5                   10
```

<210> SEQ ID NO 99
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 99

```
Cys Cys Glu Gly Cys Cys Asn Pro Ala Cys Thr Gly Cys Tyr
1               5                   10
```

<210> SEQ ID NO 100
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 100

```
Cys Cys Glu Ile Cys Cys Asn Pro Ala Cys Thr Gly Cys Tyr
1               5                   10
```

<210> SEQ ID NO 101
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 101

```
Cys Cys Glu Met Cys Cys Asn Pro Ala Cys Thr Gly Cys Tyr
1               5                   10
```

<210> SEQ ID NO 102
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 102

```
Cys Cys Glu Pro Cys Cys Asn Pro Ala Cys Thr Gly Cys Tyr
1               5                   10
```

<210> SEQ ID NO 103
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 103

```
Cys Cys Glu Thr Cys Cys Asn Pro Ala Cys Thr Gly Cys Tyr
1               5                   10
```

<210> SEQ ID NO 104
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 104

```
Cys Cys Glu Val Cys Cys Asn Pro Ala Cys Thr Gly Cys Tyr
```

```
1               5                   10
```

<210> SEQ ID NO 105
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 105

```
Cys Cys Glu Ala Cys Cys Asn Pro Ala Cys Thr Gly Cys
1               5                   10
```

<210> SEQ ID NO 106
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 106

```
Cys Cys Glu Asn Cys Cys Asn Pro Ala Cys Thr Gly Cys
1               5                   10
```

<210> SEQ ID NO 107
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 107

```
Cys Cys Glu Cys Cys Cys Asn Pro Ala Cys Thr Gly Cys
1               5                   10
```

<210> SEQ ID NO 108
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 108

```
Cys Cys Glu Glu Cys Cys Asn Pro Ala Cys Thr Gly Cys
1               5                   10
```

<210> SEQ ID NO 109
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 109

```
Cys Cys Gln His Cys Cys Asn Pro Ala Cys Thr Gly Cys
1               5                   10
```

<210> SEQ ID NO 110
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 110

```
Cys Cys Glu Lys Cys Cys Asn Pro Ala Cys Thr Gly Cys
1               5                   10
```

<210> SEQ ID NO 111
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 111

Cys Cys Glu Phe Cys Cys Asn Pro Ala Cys Thr Gly Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 112

Cys Cys Glu Ser Cys Cys Asn Pro Ala Cys Thr Gly Cys
1               5                   10

<210> SEQ ID NO 113
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 113

Cys Cys Glu Trp Cys Cys Asn Pro Ala Cys Thr Gly Cys
1               5                   10

<210> SEQ ID NO 114
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 114

Cys Cys Glu Leu Cys Cys Ala Pro Ala Cys Thr Gly Cys Tyr
1               5                   10

<210> SEQ ID NO 115
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 115

Cys Cys Glu Leu Cys Cys Leu Pro Ala Cys Thr Gly Cys Tyr
1               5                   10

<210> SEQ ID NO 116
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 116

Cys Cys Glu Leu Cys Cys Pro Pro Ala Cys Thr Gly Cys Tyr
1               5                   10

```
<210> SEQ ID NO 117
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 117

Cys Cys Glu Leu Cys Cys Phe Pro Ala Cys Thr Gly Cys Tyr
1               5                   10

<210> SEQ ID NO 118
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 118

Cys Cys Glu Leu Cys Cys Gly Pro Ala Cys Thr Gly Cys Tyr
1               5                   10

<210> SEQ ID NO 119
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 119

Cys Cys Glu Leu Cys Cys Thr Pro Ala Cys Thr Gly Cys Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 120

Cys Cys Glu Leu Cys Cys Gln Pro Ala Cys Thr Gly Cys Tyr
1               5                   10

<210> SEQ ID NO 121
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 121

Cys Cys Glu Leu Cys Cys Asp Pro Ala Cys Thr Gly Cys Tyr
1               5                   10

<210> SEQ ID NO 122
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 122

Cys Cys Glu Leu Cys Cys Lys Pro Ala Cys Thr Gly Cys Tyr
1               5                   10
```

```
<210> SEQ ID NO 123
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 123

Cys Cys Glu Leu Cys Cys His Pro Ala Cys Thr Gly Cys Tyr
1               5                   10

<210> SEQ ID NO 124
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 124

Cys Cys Glu Tyr Cys Cys Val Pro Ala Cys Thr Gly Cys Tyr
1               5                   10

<210> SEQ ID NO 125
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 125

Cys Cys Glu Tyr Cys Cys Ile Pro Ala Cys Thr Gly Cys Tyr
1               5                   10

<210> SEQ ID NO 126
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 126

Cys Cys Glu Tyr Cys Cys Met Pro Ala Cys Thr Gly Cys Tyr
1               5                   10

<210> SEQ ID NO 127
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 127

Cys Cys Glu Tyr Cys Cys Trp Pro Ala Cys Thr Gly Cys Tyr
1               5                   10

<210> SEQ ID NO 128
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 128

Cys Cys Glu Tyr Cys Cys Ser Pro Ala Cys Thr Gly Cys Tyr
1               5                   10

<210> SEQ ID NO 129
```

```
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 129

Cys Cys Glu Tyr Cys Cys Pro Ala Cys Thr Gly Cys Tyr
1               5                   10

<210> SEQ ID NO 130
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 130

Cys Cys Glu Tyr Cys Cys Tyr Pro Ala Cys Thr Gly Cys Tyr
1               5                   10

<210> SEQ ID NO 131
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 131

Cys Cys Glu Tyr Cys Cys Glu Pro Ala Cys Thr Gly Cys Tyr
1               5                   10

<210> SEQ ID NO 132
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 132

Cys Cys Glu Tyr Cys Cys Arg Pro Ala Cys Thr Gly Cys Tyr
1               5                   10

<210> SEQ ID NO 133
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 133

Cys Cys Glu Leu Cys Cys Ala Pro Ala Cys Thr Gly Cys
1               5                   10

<210> SEQ ID NO 134
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 134

Cys Cys Glu Leu Cys Cys Leu Pro Ala Cys Thr Gly Cys
1               5                   10

<210> SEQ ID NO 135
<211> LENGTH: 13
```

```
<212> TYPE: PRT
<213> ORGANISM: Artificial Sequence
<220> FEATURE:
<223> OTHER INFORMATION: GC-C agonist peptide

<400> SEQUENCE: 135

Cys Cys Glu Leu Cys Cys Pro Pro Ala Cys Thr Gly Cys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 136

Cys Cys Glu Leu Cys Cys Phe Pro Ala Cys Thr Gly Cys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 137

Cys Cys Glu Leu Cys Cys Gly Pro Ala Cys Thr Gly Cys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 138

Cys Cys Glu Leu Cys Cys Thr Pro Ala Cys Thr Gly Cys
1               5                   10

<210> SEQ ID NO 139
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 139

Cys Cys Glu Leu Cys Cys Gln Pro Ala Cys Thr Gly Cys
1               5                   10

<210> SEQ ID NO 140
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 140

Cys Cys Glu Leu Cys Cys Asp Pro Ala Cys Thr Gly Cys
1               5                   10

<210> SEQ ID NO 141
<211> LENGTH: 13
<212> TYPE: PRT
```

```
<213> ORGANISM: Artificial Sequence
<220> FEATURE:
<223> OTHER INFORMATION: GC-C agonist peptide

<400> SEQUENCE: 141

Cys Cys Glu Leu Cys Cys Lys Pro Ala Cys Thr Gly Cys
1               5                   10

<210> SEQ ID NO 142
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 142

Cys Cys Glu Leu Cys Cys His Pro Ala Cys Thr Gly Cys
1               5                   10

<210> SEQ ID NO 143
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 143

Cys Cys Glu Tyr Cys Cys Val Pro Ala Cys Thr Gly Cys
1               5                   10

<210> SEQ ID NO 144
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 144

Cys Cys Glu Tyr Cys Cys Ile Pro Ala Cys Thr Gly Cys
1               5                   10

<210> SEQ ID NO 145
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 145

Cys Cys Glu Tyr Cys Cys Met Pro Ala Cys Thr Gly Cys
1               5                   10

<210> SEQ ID NO 146
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 146

Cys Cys Glu Tyr Cys Cys Trp Pro Ala Cys Thr Gly Cys
1               5                   10

<210> SEQ ID NO 147
<211> LENGTH: 13
<212> TYPE: PRT
<213> ORGANISM: Artificial Sequence
```

```
<220> FEATURE:
<223> OTHER INFORMATION: GC-C agonist peptide

<400> SEQUENCE: 147

Cys Cys Glu Tyr Cys Cys Ser Pro Ala Cys Thr Gly Cys
1               5                   10

<210> SEQ ID NO 148
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 148

Cys Cys Glu Tyr Cys Cys Cys Pro Ala Cys Thr Gly Cys
1               5                   10

<210> SEQ ID NO 149
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 149

Cys Cys Glu Tyr Cys Cys Tyr Pro Ala Cys Thr Gly Cys
1               5                   10

<210> SEQ ID NO 150
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 150

Cys Cys Glu Tyr Cys Cys Glu Pro Ala Cys Thr Gly Cys
1               5                   10

<210> SEQ ID NO 151
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 151

Cys Cys Glu Tyr Cys Cys Arg Pro Ala Cys Thr Gly Cys
1               5                   10

<210> SEQ ID NO 152
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 152

Cys Cys Glu Leu Cys Cys Asn Pro Thr Cys Thr Gly Cys Tyr
1               5                   10

<210> SEQ ID NO 153
<211> LENGTH: 13
<212> TYPE: PRT
<213> ORGANISM: Artificial Sequence
<220> FEATURE:
```

```
<223> OTHER INFORMATION: GC-C agonist peptide

<400> SEQUENCE: 153

Cys Cys Glu Leu Cys Cys Asn Pro Thr Cys Thr Gly Cys
1               5                   10

<210> SEQ ID NO 154
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 154

Cys Cys Glu Phe Cys Cys Asn Pro Thr Cys Thr Gly Cys Tyr
1               5                   10

<210> SEQ ID NO 155
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 155

Cys Cys Glu Trp Cys Cys Asn Pro Thr Cys Thr Gly Cys Tyr
1               5                   10

<210> SEQ ID NO 156
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 156

Cys Cys Glu Leu Cys Cys Asn Gly Ala Cys Thr Gly Cys Tyr
1               5                   10

<210> SEQ ID NO 157
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 157

Cys Cys Glu Leu Cys Cys Asn Gly Ala Cys Thr Gly Cys
1               5                   10

<210> SEQ ID NO 158
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 158

Cys Cys Glu Phe Cys Cys Asn Gly Ala Cys Thr Gly Cys Tyr
1               5                   10

<210> SEQ ID NO 159
<211> LENGTH: 14
<212> TYPE: PRT
<213> ORGANISM: Artificial Sequence
<220> FEATURE:
<223> OTHER INFORMATION: GC-C agonist peptide
```

<400> SEQUENCE: 159

Cys Cys Glu Trp Cys Cys Asn Gly Ala Cys Thr Gly Cys Tyr
1               5                   10

<210> SEQ ID NO 160
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 160

Cys Cys Glu Leu Cys Cys Asn Pro Ala Cys Val Gly Cys Tyr
1               5                   10

<210> SEQ ID NO 161
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 161

Cys Cys Glu Leu Cys Cys Asn Pro Ala Cys Val Gly Cys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 162

Cys Cys Glu Phe Cys Cys Asn Pro Ala Cys Val Gly Cys Tyr
1               5                   10

<210> SEQ ID NO 163
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 163

Cys Cys Glu Trp Cys Cys Asn Pro Ala Cys Val Gly Cys Tyr
1               5                   10

<210> SEQ ID NO 164
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 164

Cys Cys Glu Leu Cys Cys Asn Pro Ala Cys Gly Gly Cys Tyr
1               5                   10

<210> SEQ ID NO 165
<211> LENGTH: 13
<212> TYPE: PRT
<213> ORGANISM: Artificial Sequence
<220> FEATURE:
<223> OTHER INFORMATION: GC-C agonist peptide

```
<400> SEQUENCE: 165

Cys Cys Glu Leu Cys Cys Asn Pro Ala Cys Gly Gly Cys
1               5                   10

<210> SEQ ID NO 166
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 166

Cys Cys Glu Phe Cys Cys Asn Pro Ala Cys Gly Gly Cys Tyr
1               5                   10

<210> SEQ ID NO 167
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 167

Cys Cys Glu Trp Cys Cys Asn Pro Ala Cys Gly Gly Cys Tyr
1               5                   10

<210> SEQ ID NO 168
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 168

Cys Cys Glu Leu Cys Cys Asn Pro Ala Cys Thr Ala Cys Tyr
1               5                   10

<210> SEQ ID NO 169
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 169

Cys Cys Glu Leu Cys Cys Asn Pro Ala Cys Thr Ala Cys
1               5                   10

<210> SEQ ID NO 170
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 170

Cys Cys Glu Trp Cys Cys Asn Pro Ala Cys Thr Ala Cys Tyr
1               5                   10

<210> SEQ ID NO 171
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 171
```

```
Cys Cys Glu Phe Cys Cys Asn Pro Ala Cys Thr Ala Cys Tyr
1               5                   10
```

<210> SEQ ID NO 172
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 172

```
Cys Cys Glu Leu Cys Cys Asn Pro Ala Cys Thr Gly Cys Ala
1               5                   10
```

<210> SEQ ID NO 173
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 173

```
Cys Cys Glu Leu Cys Cys Asn Pro Ala Cys Thr Gly Cys Leu
1               5                   10
```

<210> SEQ ID NO 174
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 174

```
Cys Cys Glu Leu Cys Cys Asn Pro Ala Cys Thr Gly Cys Pro
1               5                   10
```

<210> SEQ ID NO 175
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 175

```
Cys Cys Glu Leu Cys Cys Asn Pro Ala Cys Thr Gly Cys Phe
1               5                   10
```

<210> SEQ ID NO 176
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 176

```
Cys Cys Glu Leu Cys Cys Asn Pro Ala Cys Thr Gly Cys Gly
1               5                   10
```

<210> SEQ ID NO 177
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 177

Cys Cys Glu Leu Cys Cys Asn Pro Ala Cys Thr Gly Cys Thr
1               5                   10

<210> SEQ ID NO 178
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 178

Cys Cys Glu Leu Cys Cys Asn Pro Ala Cys Thr Gly Cys Asn
1               5                   10

<210> SEQ ID NO 179
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 179

Cys Cys Glu Leu Cys Cys Asn Pro Ala Cys Thr Gly Cys Asp
1               5                   10

<210> SEQ ID NO 180
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 180

Cys Cys Glu Leu Cys Cys Asn Pro Ala Cys Thr Gly Cys Lys
1               5                   10

<210> SEQ ID NO 181
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 181

Cys Cys Glu Leu Cys Cys Asn Pro Ala Cys Thr Gly Cys His
1               5                   10

<210> SEQ ID NO 182
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 182

Cys Cys Glu Tyr Cys Cys Asn Pro Ala Cys Thr Gly Cys Val
1               5                   10

<210> SEQ ID NO 183
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 183

Cys Cys Glu Tyr Cys Cys Asn Pro Ala Cys Thr Gly Cys Ile

```
1               5                  10
```

<210> SEQ ID NO 184
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 184

```
Cys Cys Glu Tyr Cys Cys Asn Pro Ala Cys Thr Gly Cys Met
1               5                  10
```

<210> SEQ ID NO 185
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 185

```
Cys Cys Glu Tyr Cys Cys Asn Pro Ala Cys Thr Gly Cys Trp
1               5                  10
```

<210> SEQ ID NO 186
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 186

```
Cys Cys Glu Tyr Cys Cys Asn Pro Ala Cys Thr Gly Cys Ser
1               5                  10
```

<210> SEQ ID NO 187
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 187

```
Cys Cys Glu Tyr Cys Cys Asn Pro Ala Cys Thr Gly Cys Cys
1               5                  10
```

<210> SEQ ID NO 188
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 188

```
Cys Cys Glu Tyr Cys Cys Asn Pro Ala Cys Thr Gly Cys Gln
1               5                  10
```

<210> SEQ ID NO 189
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 189

```
Cys Cys Glu Tyr Cys Cys Asn Pro Ala Cys Thr Gly Cys Glu
1               5                  10
```

<210> SEQ ID NO 190
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 190

Cys Cys Glu Tyr Cys Cys Asn Pro Ala Cys Thr Gly Cys Arg
1               5                   10

<210> SEQ ID NO 191
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 191

Cys Cys Ala Leu Cys Cys Asn Pro Ala Cys Thr Gly Cys Tyr
1               5                   10

<210> SEQ ID NO 192
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 192

Cys Cys Leu Leu Cys Cys Asn Pro Ala Cys Thr Gly Cys Tyr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 193

Cys Cys Met Leu Cys Cys Asn Pro Ala Cys Thr Gly Cys Tyr
1               5                   10

<210> SEQ ID NO 194
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 194

Cys Cys Trp Leu Cys Cys Asn Pro Ala Cys Thr Gly Cys Tyr
1               5                   10

<210> SEQ ID NO 195
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 195

Cys Cys Ser Leu Cys Cys Asn Pro Ala Cys Thr Gly Cys Tyr
1               5                   10

```
<210> SEQ ID NO 196
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 196

Cys Cys Cys Leu Cys Cys Asn Pro Ala Cys Thr Gly Cys Tyr
1               5                   10

<210> SEQ ID NO 197
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 197

Cys Cys Gln Leu Cys Cys Asn Pro Ala Cys Thr Gly Cys Tyr
1               5                   10

<210> SEQ ID NO 198
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 198

Cys Cys Asp Leu Cys Cys Asn Pro Ala Cys Thr Gly Cys Tyr
1               5                   10

<210> SEQ ID NO 199
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 199

Cys Cys Arg Leu Cys Cys Asn Pro Ala Cys Thr Gly Cys Tyr
1               5                   10

<210> SEQ ID NO 200
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 200

Cys Cys Ala Leu Cys Cys Asn Pro Ala Cys Thr Gly Cys
1               5                   10

<210> SEQ ID NO 201
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 201

Cys Cys Leu Leu Cys Cys Asn Pro Ala Cys Thr Gly Cys
1               5                   10
```

```
<210> SEQ ID NO 202
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 202

Cys Cys Met Leu Cys Cys Asn Pro Ala Cys Thr Gly Cys
1               5                   10

<210> SEQ ID NO 203
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 203

Cys Cys Trp Leu Cys Cys Asn Pro Ala Cys Thr Gly Cys
1               5                   10

<210> SEQ ID NO 204
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 204

Cys Cys Ser Leu Cys Cys Asn Pro Ala Cys Thr Gly Cys
1               5                   10

<210> SEQ ID NO 205
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 205

Cys Cys Cys Leu Cys Cys Asn Pro Ala Cys Thr Gly Cys
1               5                   10

<210> SEQ ID NO 206
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 206

Cys Cys Gln Leu Cys Cys Asn Pro Ala Cys Thr Gly Cys
1               5                   10

<210> SEQ ID NO 207
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 207

Cys Cys Asp Leu Cys Cys Asn Pro Ala Cys Thr Gly Cys
1               5                   10

<210> SEQ ID NO 208
```

```
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 208

Cys Cys Arg Leu Cys Cys Asn Pro Ala Cys Thr Gly Cys
1               5                   10

<210> SEQ ID NO 209
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 209

Cys Cys Ala Tyr Cys Cys Asn Pro Ala Cys Thr Gly Cys Tyr
1               5                   10

<210> SEQ ID NO 210
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 210

Cys Cys Leu Tyr Cys Cys Asn Pro Ala Cys Thr Gly Cys Tyr
1               5                   10

<210> SEQ ID NO 211
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 211

Cys Cys Met Tyr Cys Cys Asn Pro Ala Cys Thr Gly Cys Tyr
1               5                   10

<210> SEQ ID NO 212
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 212

Cys Cys Trp Tyr Cys Cys Asn Pro Ala Cys Thr Gly Cys Tyr
1               5                   10

<210> SEQ ID NO 213
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 213

Cys Cys Ser Tyr Cys Cys Asn Pro Ala Cys Thr Gly Cys Tyr
1               5                   10

<210> SEQ ID NO 214
<211> LENGTH: 14
```

```
<212> TYPE: PRT
<213> ORGANISM: Artificial Sequence
<220> FEATURE:
<223> OTHER INFORMATION: GC-C agonist peptide

<400> SEQUENCE: 214

Cys Cys Cys Tyr Cys Cys Asn Pro Ala Cys Thr Gly Cys Tyr
1               5                   10

<210> SEQ ID NO 215
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 215

Cys Cys Gln Tyr Cys Cys Asn Pro Ala Cys Thr Gly Cys Tyr
1               5                   10

<210> SEQ ID NO 216
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 216

Cys Cys Asp Tyr Cys Cys Asn Pro Ala Cys Thr Gly Cys Tyr
1               5                   10

<210> SEQ ID NO 217
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 217

Cys Cys Arg Tyr Cys Cys Asn Pro Ala Cys Thr Gly Cys Tyr
1               5                   10

<210> SEQ ID NO 218
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 218

Cys Cys Ala Tyr Cys Cys Asn Pro Ala Cys Thr Gly Cys
1               5                   10

<210> SEQ ID NO 219
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 219

Cys Cys Leu Tyr Cys Cys Asn Pro Ala Cys Thr Gly Cys
1               5                   10

<210> SEQ ID NO 220
<211> LENGTH: 13
<212> TYPE: PRT
```

```
<213> ORGANISM: Artificial Sequence
<220> FEATURE:
<223> OTHER INFORMATION: GC-C agonist peptide

<400> SEQUENCE: 220

Cys Cys Met Tyr Cys Cys Asn Pro Ala Cys Thr Gly Cys
1               5                   10

<210> SEQ ID NO 221
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 221

Cys Cys Trp Tyr Cys Cys Asn Pro Ala Cys Thr Gly Cys
1               5                   10

<210> SEQ ID NO 222
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 222

Cys Cys Ser Tyr Cys Cys Asn Pro Ala Cys Thr Gly Cys
1               5                   10

<210> SEQ ID NO 223
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 223

Cys Cys Cys Tyr Cys Cys Asn Pro Ala Cys Thr Gly Cys
1               5                   10

<210> SEQ ID NO 224
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 224

Cys Cys Gln Tyr Cys Cys Asn Pro Ala Cys Thr Gly Cys
1               5                   10

<210> SEQ ID NO 225
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 225

Cys Cys Asp Tyr Cys Cys Asn Pro Ala Cys Thr Gly Cys
1               5                   10

<210> SEQ ID NO 226
<211> LENGTH: 13
<212> TYPE: PRT
<213> ORGANISM: Artificial Sequence
```

```
<220> FEATURE:
<223> OTHER INFORMATION: GC-C agonist peptide

<400> SEQUENCE: 226

Cys Cys Arg Tyr Cys Cys Asn Pro Ala Cys Thr Gly Cys
1               5                   10

<210> SEQ ID NO 227
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 227

Cys Cys Glu Phe Cys Cys Ala Pro Ala Cys Thr Gly Cys Tyr
1               5                   10

<210> SEQ ID NO 228
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 228

Cys Cys Glu Phe Cys Cys Leu Pro Ala Cys Thr Gly Cys Tyr
1               5                   10

<210> SEQ ID NO 229
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 229

Cys Cys Glu Phe Cys Cys Pro Pro Ala Cys Thr Gly Cys Tyr
1               5                   10

<210> SEQ ID NO 230
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 230

Cys Cys Glu Phe Cys Cys Phe Pro Ala Cys Thr Gly Cys Tyr
1               5                   10

<210> SEQ ID NO 231
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 231

Cys Cys Glu Phe Cys Cys Gly Pro Ala Cys Thr Gly Cys Tyr
1               5                   10

<210> SEQ ID NO 232
<211> LENGTH: 14
<212> TYPE: PRT
<213> ORGANISM: Artificial Sequence
<220> FEATURE:
```

```
<223> OTHER INFORMATION: GC-C agonist peptide

<400> SEQUENCE: 232

Cys Cys Glu Phe Cys Cys Thr Pro Ala Cys Thr Gly Cys Tyr
1               5                   10

<210> SEQ ID NO 233
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 233

Cys Cys Glu Phe Cys Cys Gln Pro Ala Cys Thr Gly Cys Tyr
1               5                   10

<210> SEQ ID NO 234
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 234

Cys Cys Glu Phe Cys Cys Asp Pro Ala Cys Thr Gly Cys Tyr
1               5                   10

<210> SEQ ID NO 235
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 235

Cys Cys Glu Phe Cys Cys Lys Pro Ala Cys Thr Gly Cys Tyr
1               5                   10

<210> SEQ ID NO 236
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 236

Cys Cys Glu Phe Cys Cys His Pro Ala Cys Thr Gly Cys Tyr
1               5                   10

<210> SEQ ID NO 237
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 237

Cys Cys Glu Phe Cys Cys Val Pro Ala Cys Thr Gly Cys
1               5                   10

<210> SEQ ID NO 238
<211> LENGTH: 13
<212> TYPE: PRT
<213> ORGANISM: Artificial Sequence
<220> FEATURE:
<223> OTHER INFORMATION: GC-C agonist peptide
```

<400> SEQUENCE: 238

Cys Cys Glu Phe Cys Cys Ile Pro Ala Cys Thr Gly Cys
1               5                   10

<210> SEQ ID NO 239
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 239

Cys Cys Glu Phe Cys Cys Met Pro Ala Cys Thr Gly Cys
1               5                   10

<210> SEQ ID NO 240
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 240

Cys Cys Glu Phe Cys Cys Trp Pro Ala Cys Thr Gly Cys
1               5                   10

<210> SEQ ID NO 241
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 241

Cys Cys Glu Phe Cys Cys Ser Pro Ala Cys Thr Gly Cys
1               5                   10

<210> SEQ ID NO 242
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 242

Cys Cys Glu Phe Cys Cys Cys Pro Ala Cys Thr Gly Cys
1               5                   10

<210> SEQ ID NO 243
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 243

Cys Cys Glu Phe Cys Cys Tyr Pro Ala Cys Thr Gly Cys
1               5                   10

<210> SEQ ID NO 244
<211> LENGTH: 13
<212> TYPE: PRT
<213> ORGANISM: Artificial Sequence
<220> FEATURE:
<223> OTHER INFORMATION: GC-C agonist peptide

```
<400> SEQUENCE: 244

Cys Cys Glu Phe Cys Cys Glu Pro Ala Cys Thr Gly Cys
1               5                   10

<210> SEQ ID NO 245
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 245

Cys Cys Glu Phe Cys Cys Arg Pro Ala Cys Thr Gly Cys
1               5                   10

<210> SEQ ID NO 246
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 246

Cys Cys Glu Trp Cys Cys Ala Pro Ala Cys Thr Gly Cys Tyr
1               5                   10

<210> SEQ ID NO 247
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 247

Cys Cys Glu Trp Cys Cys Leu Pro Ala Cys Thr Gly Cys Tyr
1               5                   10

<210> SEQ ID NO 248
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 248

Cys Cys Glu Trp Cys Cys Pro Pro Ala Cys Thr Gly Cys Tyr
1               5                   10

<210> SEQ ID NO 249
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 249

Cys Cys Glu Trp Cys Cys Phe Pro Ala Cys Thr Gly Cys Tyr
1               5                   10

<210> SEQ ID NO 250
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 250
```

```
Cys Cys Glu Trp Cys Cys Gly Pro Ala Cys Thr Gly Cys Tyr
1               5                   10
```

<210> SEQ ID NO 251
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 251

```
Cys Cys Glu Trp Cys Cys Thr Pro Ala Cys Thr Gly Cys Tyr
1               5                   10
```

<210> SEQ ID NO 252
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 252

```
Cys Cys Glu Trp Cys Cys Gln Pro Ala Cys Thr Gly Cys Tyr
1               5                   10
```

<210> SEQ ID NO 253
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 253

```
Cys Cys Glu Trp Cys Cys Asp Pro Ala Cys Thr Gly Cys Tyr
1               5                   10
```

<210> SEQ ID NO 254
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 254

```
Cys Cys Glu Trp Cys Cys Lys Pro Ala Cys Thr Gly Cys Tyr
1               5                   10
```

<210> SEQ ID NO 255
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 255

```
Cys Cys Glu Trp Cys Cys His Pro Ala Cys Thr Gly Cys Tyr
1               5                   10
```

<210> SEQ ID NO 256
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 256

```
Cys Cys Glu Trp Cys Cys Val Pro Ala Cys Thr Gly Cys
1               5                   10
```

<210> SEQ ID NO 257
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 257

```
Cys Cys Glu Trp Cys Cys Ile Pro Ala Cys Thr Gly Cys
1               5                   10
```

<210> SEQ ID NO 258
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 258

```
Cys Cys Glu Trp Cys Cys Met Pro Ala Cys Thr Gly Cys
1               5                   10
```

<210> SEQ ID NO 259
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 259

```
Cys Cys Glu Trp Cys Cys Trp Pro Ala Cys Thr Gly Cys
1               5                   10
```

<210> SEQ ID NO 260
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 260

```
Cys Cys Glu Trp Cys Cys Ser Pro Ala Cys Thr Gly Cys
1               5                   10
```

<210> SEQ ID NO 261
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 261

```
Cys Cys Glu Trp Cys Cys Cys Pro Ala Cys Thr Gly Cys
1               5                   10
```

<210> SEQ ID NO 262
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 262

```
Cys Cys Glu Trp Cys Cys Tyr Pro Ala Cys Thr Gly Cys
```

<210> SEQ ID NO 263
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 263

Cys Cys Glu Trp Cys Cys Glu Pro Ala Cys Thr Gly Cys
1               5                   10

<210> SEQ ID NO 264
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 264

Cys Cys Glu Trp Cys Cys Arg Pro Ala Cys Thr Gly Cys
1               5                   10

<210> SEQ ID NO 265
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 265

Cys Cys Glu Trp Cys Cys Asn Pro Ala Cys Thr Gly Cys Ala
1               5                   10

<210> SEQ ID NO 266
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 266

Cys Cys Glu Trp Cys Cys Asn Pro Ala Cys Thr Gly Cys Leu
1               5                   10

<210> SEQ ID NO 267
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 267

Cys Cys Glu Trp Cys Cys Asn Pro Ala Cys Thr Gly Cys Pro
1               5                   10

<210> SEQ ID NO 268
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 268

Cys Cys Glu Trp Cys Cys Asn Pro Ala Cys Thr Gly Cys Phe
1               5                   10

```
<210> SEQ ID NO 269
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 269

Cys Cys Glu Trp Cys Cys Asn Pro Ala Cys Thr Gly Cys Gly
1               5                   10

<210> SEQ ID NO 270
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 270

Cys Cys Glu Trp Cys Cys Asn Pro Ala Cys Thr Gly Cys Thr
1               5                   10

<210> SEQ ID NO 271
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 271

Cys Cys Glu Trp Cys Cys Asn Pro Ala Cys Thr Gly Cys Asn
1               5                   10

<210> SEQ ID NO 272
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 272

Cys Cys Glu Trp Cys Cys Asn Pro Ala Cys Thr Gly Cys Asp
1               5                   10

<210> SEQ ID NO 273
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 273

Cys Cys Glu Trp Cys Cys Asn Pro Ala Cys Thr Gly Cys Lys
1               5                   10

<210> SEQ ID NO 274
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 274

Cys Cys Glu Trp Cys Cys Asn Pro Ala Cys Thr Gly Cys His
1               5                   10
```

```
<210> SEQ ID NO 275
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 275

Cys Cys Glu Phe Cys Cys Asn Pro Ala Cys Thr Gly Cys Val
1               5                   10

<210> SEQ ID NO 276
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 276

Cys Cys Glu Phe Cys Cys Asn Pro Ala Cys Thr Gly Cys Ile
1               5                   10

<210> SEQ ID NO 277
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 277

Cys Cys Glu Phe Cys Cys Asn Pro Ala Cys Thr Gly Cys Met
1               5                   10

<210> SEQ ID NO 278
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 278

Cys Cys Glu Phe Cys Cys Asn Pro Ala Cys Thr Gly Cys Trp
1               5                   10

<210> SEQ ID NO 279
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 279

Cys Cys Glu Phe Cys Cys Asn Pro Ala Cys Thr Gly Cys Ser
1               5                   10

<210> SEQ ID NO 280
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 280

Cys Cys Glu Phe Cys Cys Asn Pro Ala Cys Thr Gly Cys Cys
1               5                   10
```

```
<210> SEQ ID NO 281
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 281

Cys Cys Glu Phe Cys Cys Asn Pro Ala Cys Thr Gly Cys Gln
1               5                   10

<210> SEQ ID NO 282
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 282

Cys Cys Glu Phe Cys Cys Asn Pro Ala Cys Thr Gly Cys Glu
1               5                   10

<210> SEQ ID NO 283
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 283

Cys Cys Glu Phe Cys Cys Asn Pro Ala Cys Thr Gly Cys Arg
1               5                   10

<210> SEQ ID NO 284
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 284

Cys Cys Ala Phe Cys Cys Asn Pro Ala Cys Thr Gly Cys Tyr
1               5                   10

<210> SEQ ID NO 285
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 285

Cys Cys Leu Phe Cys Cys Asn Pro Ala Cys Thr Gly Cys Tyr
1               5                   10

<210> SEQ ID NO 286
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 286

Cys Cys Met Phe Cys Cys Asn Pro Ala Cys Thr Gly Cys Tyr
1               5                   10

<210> SEQ ID NO 287
```

```
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 287

Cys Cys Trp Phe Cys Cys Asn Pro Ala Cys Thr Gly Cys Tyr
1               5                   10

<210> SEQ ID NO 288
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 288

Cys Cys Ser Phe Cys Cys Asn Pro Ala Cys Thr Gly Cys Tyr
1               5                   10

<210> SEQ ID NO 289
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 289

Cys Cys Cys Phe Cys Cys Asn Pro Ala Cys Thr Gly Cys Tyr
1               5                   10

<210> SEQ ID NO 290
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 290

Cys Cys Gln Phe Cys Cys Asn Pro Ala Cys Thr Gly Cys Tyr
1               5                   10

<210> SEQ ID NO 291
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 291

Cys Cys Asp Phe Cys Cys Asn Pro Ala Cys Thr Gly Cys Tyr
1               5                   10

<210> SEQ ID NO 292
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 292

Cys Cys Arg Phe Cys Cys Asn Pro Ala Cys Thr Gly Cys Tyr
1               5                   10

<210> SEQ ID NO 293
<211> LENGTH: 13
```

```
<212> TYPE: PRT
<213> ORGANISM: Artificial Sequence
<220> FEATURE:
<223> OTHER INFORMATION: GC-C agonist peptide

<400> SEQUENCE: 293

Cys Cys Ala Phe Cys Cys Asn Pro Ala Cys Thr Gly Cys
1               5                   10

<210> SEQ ID NO 294
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 294

Cys Cys Leu Phe Cys Cys Asn Pro Ala Cys Thr Gly Cys
1               5                   10

<210> SEQ ID NO 295
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 295

Cys Cys Met Phe Cys Cys Asn Pro Ala Cys Thr Gly Cys
1               5                   10

<210> SEQ ID NO 296
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 296

Cys Cys Trp Phe Cys Cys Asn Pro Ala Cys Thr Gly Cys
1               5                   10

<210> SEQ ID NO 297
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 297

Cys Cys Ser Phe Cys Cys Asn Pro Ala Cys Thr Gly Cys
1               5                   10

<210> SEQ ID NO 298
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 298

Cys Cys Cys Phe Cys Cys Asn Pro Ala Cys Thr Gly Cys
1               5                   10

<210> SEQ ID NO 299
<211> LENGTH: 13
<212> TYPE: PRT
```

```
<213> ORGANISM: Artificial Sequence
<220> FEATURE:
<223> OTHER INFORMATION: GC-C agonist peptide

<400> SEQUENCE: 299

Cys Cys Gln Phe Cys Cys Asn Pro Ala Cys Thr Gly Cys
1               5                   10

<210> SEQ ID NO 300
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 300

Cys Cys Asp Phe Cys Cys Asn Pro Ala Cys Thr Gly Cys
1               5                   10

<210> SEQ ID NO 301
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 301

Cys Cys Arg Phe Cys Cys Asn Pro Ala Cys Thr Gly Cys
1               5                   10

<210> SEQ ID NO 302
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 302

Cys Cys Ala Trp Cys Cys Asn Pro Ala Cys Thr Gly Cys Tyr
1               5                   10

<210> SEQ ID NO 303
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 303

Cys Cys Leu Trp Cys Cys Asn Pro Ala Cys Thr Gly Cys Tyr
1               5                   10

<210> SEQ ID NO 304
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 304

Cys Cys Met Trp Cys Cys Asn Pro Ala Cys Thr Gly Cys Tyr
1               5                   10

<210> SEQ ID NO 305
<211> LENGTH: 14
<212> TYPE: PRT
<213> ORGANISM: Artificial Sequence
```

```
<220> FEATURE:
<223> OTHER INFORMATION: GC-C agonist peptide

<400> SEQUENCE: 305

Cys Cys Trp Trp Cys Cys Asn Pro Ala Cys Thr Gly Cys Tyr
1               5                   10

<210> SEQ ID NO 306
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 306

Cys Cys Ser Trp Cys Cys Asn Pro Ala Cys Thr Gly Cys Tyr
1               5                   10

<210> SEQ ID NO 307
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 307

Cys Cys Cys Trp Cys Cys Asn Pro Ala Cys Thr Gly Cys Tyr
1               5                   10

<210> SEQ ID NO 308
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 308

Cys Cys Gln Trp Cys Cys Asn Pro Ala Cys Thr Gly Cys Tyr
1               5                   10

<210> SEQ ID NO 309
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 309

Cys Cys Asp Trp Cys Cys Asn Pro Ala Cys Thr Gly Cys Tyr
1               5                   10

<210> SEQ ID NO 310
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 310

Cys Cys Arg Trp Cys Cys Asn Pro Ala Cys Thr Gly Cys Tyr
1               5                   10

<210> SEQ ID NO 311
<211> LENGTH: 13
<212> TYPE: PRT
<213> ORGANISM: Artificial Sequence
<220> FEATURE:
```

```
<223> OTHER INFORMATION: GC-C agonist peptide

<400> SEQUENCE: 311

Cys Cys Ala Trp Cys Cys Asn Pro Ala Cys Thr Gly Cys
1               5                   10

<210> SEQ ID NO 312
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 312

Cys Cys Leu Trp Cys Cys Asn Pro Ala Cys Thr Gly Cys
1               5                   10

<210> SEQ ID NO 313
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 313

Cys Cys Met Trp Cys Cys Asn Pro Ala Cys Thr Gly Cys
1               5                   10

<210> SEQ ID NO 314
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 314

Cys Cys Trp Trp Cys Cys Asn Pro Ala Cys Thr Gly Cys
1               5                   10

<210> SEQ ID NO 315
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 315

Cys Cys Ser Trp Cys Cys Asn Pro Ala Cys Thr Gly Cys
1               5                   10

<210> SEQ ID NO 316
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 316

Cys Cys Cys Trp Cys Cys Asn Pro Ala Cys Thr Gly Cys
1               5                   10

<210> SEQ ID NO 317
<211> LENGTH: 13
<212> TYPE: PRT
<213> ORGANISM: Artificial Sequence
<220> FEATURE:
<223> OTHER INFORMATION: GC-C agonist peptide
```

```
<400> SEQUENCE: 317

Cys Cys Gln Trp Cys Cys Asn Pro Ala Cys Thr Gly Cys
1               5                   10

<210> SEQ ID NO 318
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 318

Cys Cys Asp Trp Cys Cys Asn Pro Ala Cys Thr Gly Cys
1               5                   10

<210> SEQ ID NO 319
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 319

Cys Cys Arg Trp Cys Cys Asn Pro Ala Cys Thr Gly Cys
1               5                   10

<210> SEQ ID NO 320
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 320

Cys Cys Glu Leu Cys Cys Val Pro Ala Cys Thr Gly Cys Tyr
1               5                   10

<210> SEQ ID NO 321
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 321

Cys Cys Glu Leu Cys Cys Ile Pro Ala Cys Thr Gly Cys Tyr
1               5                   10

<210> SEQ ID NO 322
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 322

Cys Cys Glu Leu Cys Cys Met Pro Ala Cys Thr Gly Cys Tyr
1               5                   10

<210> SEQ ID NO 323
<211> LENGTH: 14
<212> TYPE: PRT
<213> ORGANISM: Artificial Sequence
<220> FEATURE:
<223> OTHER INFORMATION: GC-C agonist peptide
```

```
<400> SEQUENCE: 323

Cys Cys Glu Leu Cys Cys Trp Pro Ala Cys Thr Gly Cys Tyr
1               5                   10

<210> SEQ ID NO 324
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 324

Cys Cys Glu Leu Cys Cys Ser Pro Ala Cys Thr Gly Cys Tyr
1               5                   10

<210> SEQ ID NO 325
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 325

Cys Cys Glu Leu Cys Cys Cys Pro Ala Cys Thr Gly Cys Tyr
1               5                   10

<210> SEQ ID NO 326
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 326

Cys Cys Glu Leu Cys Cys Tyr Pro Ala Cys Thr Gly Cys Tyr
1               5                   10

<210> SEQ ID NO 327
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 327

Cys Cys Glu Leu Cys Cys Glu Pro Ala Cys Thr Gly Cys Tyr
1               5                   10

<210> SEQ ID NO 328
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 328

Cys Cys Glu Leu Cys Cys Arg Pro Ala Cys Thr Gly Cys Tyr
1               5                   10

<210> SEQ ID NO 329
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 329
```

```
Cys Cys Glu Tyr Cys Cys Ala Pro Ala Cys Thr Gly Cys Tyr
1               5                   10

<210> SEQ ID NO 330
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 330

Cys Cys Glu Tyr Cys Cys Leu Pro Ala Cys Thr Gly Cys Tyr
1               5                   10

<210> SEQ ID NO 331
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 331

Cys Cys Glu Tyr Cys Cys Pro Pro Ala Cys Thr Gly Cys Tyr
1               5                   10

<210> SEQ ID NO 332
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 332

Cys Cys Glu Tyr Cys Cys Phe Pro Ala Cys Thr Gly Cys Tyr
1               5                   10

<210> SEQ ID NO 333
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 333

Cys Cys Glu Tyr Cys Cys Gly Pro Ala Cys Thr Gly Cys Tyr
1               5                   10

<210> SEQ ID NO 334
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 334

Cys Cys Glu Tyr Cys Cys Thr Pro Ala Cys Thr Gly Cys Tyr
1               5                   10

<210> SEQ ID NO 335
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 335
```

```
Cys Cys Glu Tyr Cys Cys Gln Pro Ala Cys Thr Gly Cys Tyr
1               5                   10
```

<210> SEQ ID NO 336
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 336

```
Cys Cys Glu Tyr Cys Cys Asp Pro Ala Cys Thr Gly Cys Tyr
1               5                   10
```

<210> SEQ ID NO 337
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 337

```
Cys Cys Glu Tyr Cys Cys Lys Pro Ala Cys Thr Gly Cys Tyr
1               5                   10
```

<210> SEQ ID NO 338
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 338

```
Cys Cys Glu Tyr Cys Cys His Pro Ala Cys Thr Gly Cys Tyr
1               5                   10
```

<210> SEQ ID NO 339
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 339

```
Cys Cys Glu Leu Cys Cys Val Pro Ala Cys Thr Gly Cys
1               5                   10
```

<210> SEQ ID NO 340
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 340

```
Cys Cys Glu Leu Cys Cys Ile Pro Ala Cys Thr Gly Cys
1               5                   10
```

<210> SEQ ID NO 341
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 341

```
Cys Cys Glu Leu Cys Cys Met Pro Ala Cys Thr Gly Cys
```

```
1               5                   10
```

<210> SEQ ID NO 342
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 342

```
Cys Cys Glu Leu Cys Cys Trp Pro Ala Cys Thr Gly Cys
1               5                   10
```

<210> SEQ ID NO 343
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 343

```
Cys Cys Glu Leu Cys Cys Ser Pro Ala Cys Thr Gly Cys
1               5                   10
```

<210> SEQ ID NO 344
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 344

```
Cys Cys Glu Leu Cys Cys Cys Pro Ala Cys Thr Gly Cys
1               5                   10
```

<210> SEQ ID NO 345
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 345

```
Cys Cys Glu Leu Cys Cys Tyr Pro Ala Cys Thr Gly Cys
1               5                   10
```

<210> SEQ ID NO 346
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 346

```
Cys Cys Glu Leu Cys Cys Glu Pro Ala Cys Thr Gly Cys
1               5                   10
```

<210> SEQ ID NO 347
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 347

```
Cys Cys Glu Leu Cys Cys Arg Pro Ala Cys Thr Gly Cys
1               5                   10
```

```
<210> SEQ ID NO 348
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 348

Cys Cys Glu Tyr Cys Cys Ala Pro Ala Cys Thr Gly Cys
1               5                   10

<210> SEQ ID NO 349
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 349

Cys Cys Glu Tyr Cys Cys Leu Pro Ala Cys Thr Gly Cys
1               5                   10

<210> SEQ ID NO 350
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 350

Cys Cys Glu Tyr Cys Cys Pro Pro Ala Cys Thr Gly Cys
1               5                   10

<210> SEQ ID NO 351
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 351

Cys Cys Glu Tyr Cys Cys Phe Pro Ala Cys Thr Gly Cys
1               5                   10

<210> SEQ ID NO 352
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 352

Cys Cys Glu Tyr Cys Cys Gly Pro Ala Cys Thr Gly Cys
1               5                   10

<210> SEQ ID NO 353
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 353

Cys Cys Glu Tyr Cys Cys Thr Pro Ala Cys Thr Gly Cys
1               5                   10
```

```
<210> SEQ ID NO 354
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 354

Cys Cys Glu Tyr Cys Cys Gln Pro Ala Cys Thr Gly Cys
1               5                   10

<210> SEQ ID NO 355
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 355

Cys Cys Glu Tyr Cys Cys Asp Pro Ala Cys Thr Gly Cys
1               5                   10

<210> SEQ ID NO 356
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 356

Cys Cys Glu Tyr Cys Cys Lys Pro Ala Cys Thr Gly Cys
1               5                   10

<210> SEQ ID NO 357
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 357

Cys Cys Glu Tyr Cys Cys His Pro Ala Cys Thr Gly Cys
1               5                   10

<210> SEQ ID NO 358
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 358

Cys Cys Glu Tyr Cys Cys Asn Pro Thr Cys Thr Gly Cys Tyr
1               5                   10

<210> SEQ ID NO 359
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 359

Cys Cys Glu Tyr Cys Cys Asn Pro Thr Cys Thr Gly Cys
1               5                   10
```

```
<210> SEQ ID NO 360
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 360

Cys Cys Glu Phe Cys Cys Asn Pro Thr Cys Thr Gly Cys
1               5                   10

<210> SEQ ID NO 361
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 361

Cys Cys Glu Trp Cys Cys Asn Pro Thr Cys Thr Gly Cys
1               5                   10

<210> SEQ ID NO 362
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 362

Cys Cys Glu Tyr Cys Cys Asn Gly Ala Cys Thr Gly Cys Tyr
1               5                   10

<210> SEQ ID NO 363
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 363

Cys Cys Glu Tyr Cys Cys Asn Gly Ala Cys Thr Gly Cys
1               5                   10

<210> SEQ ID NO 364
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 364

Cys Cys Glu Phe Cys Cys Asn Gly Ala Cys Thr Gly Cys
1               5                   10

<210> SEQ ID NO 365
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 365

Cys Cys Glu Trp Cys Cys Asn Gly Ala Cys Thr Gly Cys
1               5                   10

<210> SEQ ID NO 366
```

```
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 366

Cys Cys Glu Tyr Cys Cys Asn Pro Ala Cys Val Gly Cys Tyr
1               5                   10

<210> SEQ ID NO 367
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 367

Cys Cys Glu Tyr Cys Cys Asn Pro Ala Cys Val Gly Cys
1               5                   10

<210> SEQ ID NO 368
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 368

Cys Cys Glu Phe Cys Cys Asn Pro Ala Cys Val Gly Cys
1               5                   10

<210> SEQ ID NO 369
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 369

Cys Cys Glu Trp Cys Cys Asn Pro Ala Cys Val Gly Cys
1               5                   10

<210> SEQ ID NO 370
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 370

Cys Cys Glu Tyr Cys Cys Asn Pro Ala Cys Gly Gly Cys Tyr
1               5                   10

<210> SEQ ID NO 371
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 371

Cys Cys Glu Tyr Cys Cys Asn Pro Ala Cys Gly Gly Cys
1               5                   10

<210> SEQ ID NO 372
<211> LENGTH: 13
```

```
<212> TYPE: PRT
<213> ORGANISM: Artificial Sequence
<220> FEATURE:
<223> OTHER INFORMATION: GC-C agonist peptide

<400> SEQUENCE: 372

Cys Cys Glu Phe Cys Cys Asn Pro Ala Cys Gly Gly Cys
1               5                   10

<210> SEQ ID NO 373
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 373

Cys Cys Glu Trp Cys Cys Asn Pro Ala Cys Gly Gly Cys
1               5                   10

<210> SEQ ID NO 374
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 374

Cys Cys Glu Tyr Cys Cys Asn Pro Ala Cys Thr Ala Cys Tyr
1               5                   10

<210> SEQ ID NO 375
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 375

Cys Cys Glu Tyr Cys Cys Asn Pro Ala Cys Thr Ala Cys
1               5                   10

<210> SEQ ID NO 376
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 376

Cys Cys Glu Trp Cys Cys Asn Pro Ala Cys Thr Ala Cys
1               5                   10

<210> SEQ ID NO 377
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 377

Cys Cys Glu Phe Cys Cys Asn Pro Ala Cys Thr Ala Cys
1               5                   10

<210> SEQ ID NO 378
<211> LENGTH: 14
<212> TYPE: PRT
```

```
<213> ORGANISM: Artificial Sequence
<220> FEATURE:
<223> OTHER INFORMATION: GC-C agonist peptide

<400> SEQUENCE: 378

Cys Cys Glu Leu Cys Cys Asn Pro Ala Cys Thr Gly Cys Val
1               5                   10

<210> SEQ ID NO 379
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 379

Cys Cys Glu Leu Cys Cys Asn Pro Ala Cys Thr Gly Cys Ile
1               5                   10

<210> SEQ ID NO 380
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 380

Cys Cys Glu Leu Cys Cys Asn Pro Ala Cys Thr Gly Cys Met
1               5                   10

<210> SEQ ID NO 381
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 381

Cys Cys Glu Leu Cys Cys Asn Pro Ala Cys Thr Gly Cys Trp
1               5                   10

<210> SEQ ID NO 382
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 382

Cys Cys Glu Leu Cys Cys Asn Pro Ala Cys Thr Gly Cys Ser
1               5                   10

<210> SEQ ID NO 383
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 383

Cys Cys Glu Leu Cys Cys Asn Pro Ala Cys Thr Gly Cys Cys
1               5                   10

<210> SEQ ID NO 384
<211> LENGTH: 14
<212> TYPE: PRT
<213> ORGANISM: Artificial Sequence
```

```
<220> FEATURE:
<223> OTHER INFORMATION: GC-C agonist peptide

<400> SEQUENCE: 384

Cys Cys Glu Leu Cys Cys Asn Pro Ala Cys Thr Gly Cys Gln
1               5                   10

<210> SEQ ID NO 385
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 385

Cys Cys Glu Leu Cys Cys Asn Pro Ala Cys Thr Gly Cys Glu
1               5                   10

<210> SEQ ID NO 386
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 386

Cys Cys Glu Leu Cys Cys Asn Pro Ala Cys Thr Gly Cys Arg
1               5                   10

<210> SEQ ID NO 387
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 387

Cys Cys Glu Tyr Cys Cys Asn Pro Ala Cys Thr Gly Cys Ala
1               5                   10

<210> SEQ ID NO 388
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 388

Cys Cys Glu Tyr Cys Cys Asn Pro Ala Cys Thr Gly Cys Leu
1               5                   10

<210> SEQ ID NO 389
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 389

Cys Cys Glu Tyr Cys Cys Asn Pro Ala Cys Thr Gly Cys Pro
1               5                   10

<210> SEQ ID NO 390
<211> LENGTH: 14
<212> TYPE: PRT
<213> ORGANISM: Artificial Sequence
<220> FEATURE:
```

<223> OTHER INFORMATION: GC-C agonist peptide

<400> SEQUENCE: 390

Cys Cys Glu Tyr Cys Cys Asn Pro Ala Cys Thr Gly Cys Phe
1               5                   10

<210> SEQ ID NO 391
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 391

Cys Cys Glu Tyr Cys Cys Asn Pro Ala Cys Thr Gly Cys Gly
1               5                   10

<210> SEQ ID NO 392
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 392

Cys Cys Glu Tyr Cys Cys Asn Pro Ala Cys Thr Gly Cys Thr
1               5                   10

<210> SEQ ID NO 393
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 393

Cys Cys Glu Tyr Cys Cys Asn Pro Ala Cys Thr Gly Cys Asn
1               5                   10

<210> SEQ ID NO 394
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 394

Cys Cys Glu Tyr Cys Cys Asn Pro Ala Cys Thr Gly Cys Asp
1               5                   10

<210> SEQ ID NO 395
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 395

Cys Cys Glu Tyr Cys Cys Asn Pro Ala Cys Thr Gly Cys Lys
1               5                   10

<210> SEQ ID NO 396
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 396

Cys Cys Glu Tyr Cys Cys Asn Pro Ala Cys Thr Gly Cys His
1               5                   10

<210> SEQ ID NO 397
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 397

Cys Cys Val Leu Cys Cys Asn Pro Ala Cys Thr Gly Cys Tyr
1               5                   10

<210> SEQ ID NO 398
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 398

Cys Cys Ile Leu Cys Cys Asn Pro Ala Cys Thr Gly Cys Tyr
1               5                   10

<210> SEQ ID NO 399
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 399

Cys Cys Phe Leu Cys Cys Asn Pro Ala Cys Thr Gly Cys Tyr
1               5                   10

<210> SEQ ID NO 400
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 400

Cys Cys Gly Leu Cys Cys Asn Pro Ala Cys Thr Gly Cys Tyr
1               5                   10

<210> SEQ ID NO 401
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 401

Cys Cys Thr Leu Cys Cys Asn Pro Ala Cys Thr Gly Cys Tyr
1               5                   10

<210> SEQ ID NO 402
<211> LENGTH: 14
<212> TYPE: PRT
<213> ORGANISM: Artificial Sequence
<220> FEATURE:
<223> OTHER INFORMATION: GC-C agonist peptide

```
<400> SEQUENCE: 402

Cys Cys Asn Leu Cys Cys Asn Pro Ala Cys Thr Gly Cys Tyr
1               5                   10

<210> SEQ ID NO 403
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 403

Cys Cys Tyr Leu Cys Cys Asn Pro Ala Cys Thr Gly Cys Tyr
1               5                   10

<210> SEQ ID NO 404
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 404

Cys Cys Lys Leu Cys Cys Asn Pro Ala Cys Thr Gly Cys Tyr
1               5                   10

<210> SEQ ID NO 405
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 405

Cys Cys His Leu Cys Cys Asn Pro Ala Cys Thr Gly Cys Tyr
1               5                   10

<210> SEQ ID NO 406
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 406

Cys Cys Val Leu Cys Cys Asn Pro Ala Cys Thr Gly Cys
1               5                   10

<210> SEQ ID NO 407
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 407

Cys Cys Ile Leu Cys Cys Asn Pro Ala Cys Thr Gly Cys
1               5                   10

<210> SEQ ID NO 408
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 408
```

```
Cys Cys Phe Leu Cys Cys Asn Pro Ala Cys Thr Gly Cys
1               5                   10

<210> SEQ ID NO 409
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 409

Cys Cys Gly Leu Cys Cys Asn Pro Ala Cys Thr Gly Cys
1               5                   10

<210> SEQ ID NO 410
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 410

Cys Cys Thr Leu Cys Cys Asn Pro Ala Cys Thr Gly Cys
1               5                   10

<210> SEQ ID NO 411
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 411

Cys Cys Asn Leu Cys Cys Asn Pro Ala Cys Thr Gly Cys
1               5                   10

<210> SEQ ID NO 412
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 412

Cys Cys Tyr Leu Cys Cys Asn Pro Ala Cys Thr Gly Cys
1               5                   10

<210> SEQ ID NO 413
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 413

Cys Cys Lys Leu Cys Cys Asn Pro Ala Cys Thr Gly Cys
1               5                   10

<210> SEQ ID NO 414
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 414
```

-continued

Cys Cys His Leu Cys Cys Asn Pro Ala Cys Thr Gly Cys
1               5                   10

<210> SEQ ID NO 415
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 415

Cys Cys Val Tyr Cys Cys Asn Pro Ala Cys Thr Gly Cys Tyr
1               5                   10

<210> SEQ ID NO 416
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 416

Cys Cys Ile Tyr Cys Cys Asn Pro Ala Cys Thr Gly Cys Tyr
1               5                   10

<210> SEQ ID NO 417
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 417

Cys Cys Phe Tyr Cys Cys Asn Pro Ala Cys Thr Gly Cys Tyr
1               5                   10

<210> SEQ ID NO 418
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 418

Cys Cys Gly Tyr Cys Cys Asn Pro Ala Cys Thr Gly Cys Tyr
1               5                   10

<210> SEQ ID NO 419
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 419

Cys Cys Thr Tyr Cys Cys Asn Pro Ala Cys Thr Gly Cys Tyr
1               5                   10

<210> SEQ ID NO 420
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 420

Cys Cys Asn Tyr Cys Cys Asn Pro Ala Cys Thr Gly Cys Tyr

```
<210> SEQ ID NO 421
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 421

Cys Cys Tyr Tyr Cys Cys Asn Pro Ala Cys Thr Gly Cys Tyr
1               5                   10

<210> SEQ ID NO 422
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 422

Cys Cys Lys Tyr Cys Cys Asn Pro Ala Cys Thr Gly Cys Tyr
1               5                   10

<210> SEQ ID NO 423
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 423

Cys Cys His Tyr Cys Cys Asn Pro Ala Cys Thr Gly Cys Tyr
1               5                   10

<210> SEQ ID NO 424
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 424

Cys Cys Val Tyr Cys Cys Asn Pro Ala Cys Thr Gly Cys
1               5                   10

<210> SEQ ID NO 425
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 425

Cys Cys Ile Tyr Cys Cys Asn Pro Ala Cys Thr Gly Cys
1               5                   10

<210> SEQ ID NO 426
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 426

Cys Cys Phe Tyr Cys Cys Asn Pro Ala Cys Thr Gly Cys
1               5                   10
```

<210> SEQ ID NO 427
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 427

Cys Cys Gly Tyr Cys Cys Asn Pro Ala Cys Thr Gly Cys
1               5                   10

<210> SEQ ID NO 428
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 428

Cys Cys Thr Tyr Cys Cys Asn Pro Ala Cys Thr Gly Cys
1               5                   10

<210> SEQ ID NO 429
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 429

Cys Cys Asn Tyr Cys Cys Asn Pro Ala Cys Thr Gly Cys
1               5                   10

<210> SEQ ID NO 430
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 430

Cys Cys Tyr Tyr Cys Cys Asn Pro Ala Cys Thr Gly Cys
1               5                   10

<210> SEQ ID NO 431
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 431

Cys Cys Lys Tyr Cys Cys Asn Pro Ala Cys Thr Gly Cys
1               5                   10

<210> SEQ ID NO 432
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 432

Cys Cys His Tyr Cys Cys Asn Pro Ala Cys Thr Gly Cys
1               5                   10

<210> SEQ ID NO 433
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 433

Cys Cys Glu Phe Cys Cys Val Pro Ala Cys Thr Gly Cys Tyr
1               5                   10

<210> SEQ ID NO 434
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 434

Cys Cys Glu Phe Cys Cys Ile Pro Ala Cys Thr Gly Cys Tyr
1               5                   10

<210> SEQ ID NO 435
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 435

Cys Cys Glu Phe Cys Cys Met Pro Ala Cys Thr Gly Cys Tyr
1               5                   10

<210> SEQ ID NO 436
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 436

Cys Cys Glu Phe Cys Cys Trp Pro Ala Cys Thr Gly Cys Tyr
1               5                   10

<210> SEQ ID NO 437
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 437

Cys Cys Glu Phe Cys Cys Ser Pro Ala Cys Thr Gly Cys Tyr
1               5                   10

<210> SEQ ID NO 438
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 438

Cys Cys Glu Phe Cys Cys Cys Pro Ala Cys Thr Gly Cys Tyr
1               5                   10

```
<210> SEQ ID NO 439
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 439

Cys Cys Glu Phe Cys Cys Tyr Pro Ala Cys Thr Gly Cys Tyr
1               5                   10

<210> SEQ ID NO 440
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 440

Cys Cys Glu Phe Cys Cys Glu Pro Ala Cys Thr Gly Cys Tyr
1               5                   10

<210> SEQ ID NO 441
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 441

Cys Cys Glu Phe Cys Cys Arg Pro Ala Cys Thr Gly Cys Tyr
1               5                   10

<210> SEQ ID NO 442
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 442

Cys Cys Glu Phe Cys Cys Ala Pro Ala Cys Thr Gly Cys
1               5                   10

<210> SEQ ID NO 443
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 443

Cys Cys Glu Phe Cys Cys Leu Pro Ala Cys Thr Gly Cys
1               5                   10

<210> SEQ ID NO 444
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 444

Cys Cys Glu Phe Cys Cys Pro Pro Ala Cys Thr Gly Cys
1               5                   10

<210> SEQ ID NO 445
```

```
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 445

Cys Cys Glu Phe Cys Cys Phe Pro Ala Cys Thr Gly Cys
1               5                   10

<210> SEQ ID NO 446
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 446

Cys Cys Glu Phe Cys Cys Gly Pro Ala Cys Thr Gly Cys
1               5                   10

<210> SEQ ID NO 447
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 447

Cys Cys Glu Phe Cys Cys Thr Pro Ala Cys Thr Gly Cys
1               5                   10

<210> SEQ ID NO 448
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 448

Cys Cys Glu Phe Cys Cys Gln Pro Ala Cys Thr Gly Cys
1               5                   10

<210> SEQ ID NO 449
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 449

Cys Cys Glu Phe Cys Cys Asp Pro Ala Cys Thr Gly Cys
1               5                   10

<210> SEQ ID NO 450
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 450

Cys Cys Glu Phe Cys Cys Lys Pro Ala Cys Thr Gly Cys
1               5                   10

<210> SEQ ID NO 451
<211> LENGTH: 13
```

```
<212> TYPE: PRT
<213> ORGANISM: Artificial Sequence
<220> FEATURE:
<223> OTHER INFORMATION: GC-C agonist peptide

<400> SEQUENCE: 451

Cys Cys Glu Phe Cys Cys His Pro Ala Cys Thr Gly Cys
1               5                   10

<210> SEQ ID NO 452
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 452

Cys Cys Glu Trp Cys Cys Val Pro Ala Cys Thr Gly Cys Tyr
1               5                   10

<210> SEQ ID NO 453
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 453

Cys Cys Glu Trp Cys Cys Ile Pro Ala Cys Thr Gly Cys Tyr
1               5                   10

<210> SEQ ID NO 454
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 454

Cys Cys Glu Trp Cys Cys Met Pro Ala Cys Thr Gly Cys Tyr
1               5                   10

<210> SEQ ID NO 455
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 455

Cys Cys Glu Trp Cys Cys Trp Pro Ala Cys Thr Gly Cys Tyr
1               5                   10

<210> SEQ ID NO 456
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 456

Cys Cys Glu Trp Cys Cys Ser Pro Ala Cys Thr Gly Cys Tyr
1               5                   10

<210> SEQ ID NO 457
<211> LENGTH: 14
<212> TYPE: PRT
```

```
<213> ORGANISM: Artificial Sequence
<220> FEATURE:
<223> OTHER INFORMATION: GC-C agonist peptide

<400> SEQUENCE: 457

Cys Cys Glu Trp Cys Cys Cys Pro Ala Cys Thr Gly Cys Tyr
1               5                   10

<210> SEQ ID NO 458
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 458

Cys Cys Glu Trp Cys Cys Tyr Pro Ala Cys Thr Gly Cys Tyr
1               5                   10

<210> SEQ ID NO 459
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 459

Cys Cys Glu Trp Cys Cys Glu Pro Ala Cys Thr Gly Cys Tyr
1               5                   10

<210> SEQ ID NO 460
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 460

Cys Cys Glu Trp Cys Cys Arg Pro Ala Cys Thr Gly Cys Tyr
1               5                   10

<210> SEQ ID NO 461
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 461

Cys Cys Glu Trp Cys Cys Ala Pro Ala Cys Thr Gly Cys
1               5                   10

<210> SEQ ID NO 462
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 462

Cys Cys Glu Trp Cys Cys Leu Pro Ala Cys Thr Gly Cys
1               5                   10

<210> SEQ ID NO 463
<211> LENGTH: 13
<212> TYPE: PRT
<213> ORGANISM: Artificial Sequence
```

```
<220> FEATURE:
<223> OTHER INFORMATION: GC-C agonist peptide

<400> SEQUENCE: 463

Cys Cys Glu Trp Cys Cys Pro Pro Ala Cys Thr Gly Cys
1               5                   10

<210> SEQ ID NO 464
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 464

Cys Cys Glu Trp Cys Cys Phe Pro Ala Cys Thr Gly Cys
1               5                   10

<210> SEQ ID NO 465
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 465

Cys Cys Glu Trp Cys Cys Gly Pro Ala Cys Thr Gly Cys
1               5                   10

<210> SEQ ID NO 466
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 466

Cys Cys Glu Trp Cys Cys Thr Pro Ala Cys Thr Gly Cys
1               5                   10

<210> SEQ ID NO 467
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 467

Cys Cys Glu Trp Cys Cys Gln Pro Ala Cys Thr Gly Cys
1               5                   10

<210> SEQ ID NO 468
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 468

Cys Cys Glu Trp Cys Cys Asp Pro Ala Cys Thr Gly Cys
1               5                   10

<210> SEQ ID NO 469
<211> LENGTH: 13
<212> TYPE: PRT
<213> ORGANISM: Artificial Sequence
<220> FEATURE:
```

```
<223> OTHER INFORMATION: GC-C agonist peptide

<400> SEQUENCE: 469

Cys Cys Glu Trp Cys Cys Lys Pro Ala Cys Thr Gly Cys
1               5                   10

<210> SEQ ID NO 470
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 470

Cys Cys Glu Trp Cys Cys His Pro Ala Cys Thr Gly Cys
1               5                   10

<210> SEQ ID NO 471
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 471

Cys Cys Glu Trp Cys Cys Asn Pro Ala Cys Thr Gly Cys Val
1               5                   10

<210> SEQ ID NO 472
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 472

Cys Cys Glu Trp Cys Cys Asn Pro Ala Cys Thr Gly Cys Ile
1               5                   10

<210> SEQ ID NO 473
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 473

Cys Cys Glu Trp Cys Cys Asn Pro Ala Cys Thr Gly Cys Met
1               5                   10

<210> SEQ ID NO 474
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 474

Cys Cys Glu Trp Cys Cys Asn Pro Ala Cys Thr Gly Cys Trp
1               5                   10

<210> SEQ ID NO 475
<211> LENGTH: 14
<212> TYPE: PRT
<213> ORGANISM: Artificial Sequence
<220> FEATURE:
<223> OTHER INFORMATION: GC-C agonist peptide
```

<400> SEQUENCE: 475

Cys Cys Glu Trp Cys Cys Asn Pro Ala Cys Thr Gly Cys Ser
1               5                   10

<210> SEQ ID NO 476
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 476

Cys Cys Glu Trp Cys Cys Asn Pro Ala Cys Thr Gly Cys Cys
1               5                   10

<210> SEQ ID NO 477
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 477

Cys Cys Glu Trp Cys Cys Asn Pro Ala Cys Thr Gly Cys Gln
1               5                   10

<210> SEQ ID NO 478
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 478

Cys Cys Glu Trp Cys Cys Asn Pro Ala Cys Thr Gly Cys Glu
1               5                   10

<210> SEQ ID NO 479
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 479

Cys Cys Glu Trp Cys Cys Asn Pro Ala Cys Thr Gly Cys Arg
1               5                   10

<210> SEQ ID NO 480
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 480

Cys Cys Glu Phe Cys Cys Asn Pro Ala Cys Thr Gly Cys Ala
1               5                   10

<210> SEQ ID NO 481
<211> LENGTH: 14
<212> TYPE: PRT
<213> ORGANISM: Artificial Sequence
<220> FEATURE:
<223> OTHER INFORMATION: GC-C agonist peptide

```
<400> SEQUENCE: 481

Cys Cys Glu Phe Cys Cys Asn Pro Ala Cys Thr Gly Cys Leu
1               5                   10

<210> SEQ ID NO 482
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 482

Cys Cys Glu Phe Cys Cys Asn Pro Ala Cys Thr Gly Cys Pro
1               5                   10

<210> SEQ ID NO 483
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 483

Cys Cys Glu Phe Cys Cys Asn Pro Ala Cys Thr Gly Cys Phe
1               5                   10

<210> SEQ ID NO 484
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 484

Cys Cys Glu Phe Cys Cys Asn Pro Ala Cys Thr Gly Cys Gly
1               5                   10

<210> SEQ ID NO 485
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 485

Cys Cys Glu Phe Cys Cys Asn Pro Ala Cys Thr Gly Cys Thr
1               5                   10

<210> SEQ ID NO 486
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 486

Cys Cys Glu Phe Cys Cys Asn Pro Ala Cys Thr Gly Cys Asn
1               5                   10

<210> SEQ ID NO 487
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 487
```

```
Cys Cys Glu Phe Cys Cys Asn Pro Ala Cys Thr Gly Cys Asp
1               5                   10
```

<210> SEQ ID NO 488
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 488

```
Cys Cys Glu Phe Cys Cys Asn Pro Ala Cys Thr Gly Cys Lys
1               5                   10
```

<210> SEQ ID NO 489
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 489

```
Cys Cys Glu Phe Cys Cys Asn Pro Ala Cys Thr Gly Cys His
1               5                   10
```

<210> SEQ ID NO 490
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 490

```
Cys Cys Val Phe Cys Cys Asn Pro Ala Cys Thr Gly Cys Tyr
1               5                   10
```

<210> SEQ ID NO 491
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 491

```
Cys Cys Ile Phe Cys Cys Asn Pro Ala Cys Thr Gly Cys Tyr
1               5                   10
```

<210> SEQ ID NO 492
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 492

```
Cys Cys Phe Phe Cys Cys Asn Pro Ala Cys Thr Gly Cys Tyr
1               5                   10
```

<210> SEQ ID NO 493
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 493

Cys Cys Gly Phe Cys Cys Asn Pro Ala Cys Thr Gly Cys Tyr
1               5                   10

<210> SEQ ID NO 494
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 494

Cys Cys Thr Phe Cys Cys Asn Pro Ala Cys Thr Gly Cys Tyr
1               5                   10

<210> SEQ ID NO 495
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 495

Cys Cys Asn Phe Cys Cys Asn Pro Ala Cys Thr Gly Cys Tyr
1               5                   10

<210> SEQ ID NO 496
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 496

Cys Cys Tyr Phe Cys Cys Asn Pro Ala Cys Thr Gly Cys Tyr
1               5                   10

<210> SEQ ID NO 497
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 497

Cys Cys Lys Phe Cys Cys Asn Pro Ala Cys Thr Gly Cys Tyr
1               5                   10

<210> SEQ ID NO 498
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 498

Cys Cys His Phe Cys Cys Asn Pro Ala Cys Thr Gly Cys Tyr
1               5                   10

<210> SEQ ID NO 499
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 499

Cys Cys Val Phe Cys Cys Asn Pro Ala Cys Thr Gly Cys

```
1               5                   10

<210> SEQ ID NO 500
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 500

Cys Cys Ile Phe Cys Cys Asn Pro Ala Cys Thr Gly Cys
1               5                   10

<210> SEQ ID NO 501
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 501

Cys Cys Phe Phe Cys Cys Asn Pro Ala Cys Thr Gly Cys
1               5                   10

<210> SEQ ID NO 502
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 502

Cys Cys Gly Phe Cys Cys Asn Pro Ala Cys Thr Gly Cys
1               5                   10

<210> SEQ ID NO 503
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 503

Cys Cys Thr Phe Cys Cys Asn Pro Ala Cys Thr Gly Cys
1               5                   10

<210> SEQ ID NO 504
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 504

Cys Cys Asn Phe Cys Cys Asn Pro Ala Cys Thr Gly Cys
1               5                   10

<210> SEQ ID NO 505
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 505

Cys Cys Tyr Phe Cys Cys Asn Pro Ala Cys Thr Gly Cys
1               5                   10
```

```
<210> SEQ ID NO 506
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 506

Cys Cys Lys Phe Cys Cys Asn Pro Ala Cys Thr Gly Cys
1               5                   10

<210> SEQ ID NO 507
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 507

Cys Cys His Phe Cys Cys Asn Pro Ala Cys Thr Gly Cys
1               5                   10

<210> SEQ ID NO 508
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 508

Cys Cys Val Trp Cys Cys Asn Pro Ala Cys Thr Gly Cys Tyr
1               5                   10

<210> SEQ ID NO 509
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 509

Cys Cys Ile Trp Cys Cys Asn Pro Ala Cys Thr Gly Cys Tyr
1               5                   10

<210> SEQ ID NO 510
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 510

Cys Cys Phe Trp Cys Cys Asn Pro Ala Cys Thr Gly Cys Tyr
1               5                   10

<210> SEQ ID NO 511
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 511

Cys Cys Gly Trp Cys Cys Asn Pro Ala Cys Thr Gly Cys Tyr
1               5                   10
```

<210> SEQ ID NO 512
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 512

Cys Cys Thr Trp Cys Cys Asn Pro Ala Cys Thr Gly Cys Tyr
1               5                   10

<210> SEQ ID NO 513
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 513

Cys Cys Asn Trp Cys Cys Asn Pro Ala Cys Thr Gly Cys Tyr
1               5                   10

<210> SEQ ID NO 514
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 514

Cys Cys Tyr Trp Cys Cys Asn Pro Ala Cys Thr Gly Cys Tyr
1               5                   10

<210> SEQ ID NO 515
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 515

Cys Cys Lys Trp Cys Cys Asn Pro Ala Cys Thr Gly Cys Tyr
1               5                   10

<210> SEQ ID NO 516
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 516

Cys Cys His Trp Cys Cys Asn Pro Ala Cys Thr Gly Cys Tyr
1               5                   10

<210> SEQ ID NO 517
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 517

Cys Cys Val Trp Cys Cys Asn Pro Ala Cys Thr Gly Cys
1               5                   10

```
<210> SEQ ID NO 518
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 518

Cys Cys Ile Trp Cys Cys Asn Pro Ala Cys Thr Gly Cys
1               5                   10

<210> SEQ ID NO 519
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 519

Cys Cys Phe Trp Cys Cys Asn Pro Ala Cys Thr Gly Cys
1               5                   10

<210> SEQ ID NO 520
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 520

Cys Cys Gly Trp Cys Cys Asn Pro Ala Cys Thr Gly Cys
1               5                   10

<210> SEQ ID NO 521
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 521

Cys Cys Thr Trp Cys Cys Asn Pro Ala Cys Thr Gly Cys
1               5                   10

<210> SEQ ID NO 522
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 522

Cys Cys Asn Trp Cys Cys Asn Pro Ala Cys Thr Gly Cys
1               5                   10

<210> SEQ ID NO 523
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 523

Cys Cys Tyr Trp Cys Cys Asn Pro Ala Cys Thr Gly Cys
1               5                   10

<210> SEQ ID NO 524
```

```
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 524

Cys Cys Lys Trp Cys Cys Asn Pro Ala Cys Thr Gly Cys
1               5                   10

<210> SEQ ID NO 525
<211> LENGTH: 13
<212> TYPE: PRT
<213> ORGANISM: Artificial Sequence
<220> FEATURE:
<223> OTHER INFORMATION: GC-C agonist peptide

<400> SEQUENCE: 525

Cys Cys His Trp Cys Cys Asn Pro Ala Cys Thr Gly Cys
1               5                   10

<210> SEQ ID NO 526
<211> LENGTH: 13
<212> TYPE: PRT
<213> ORGANISM: Artificial Sequence
<220> FEATURE:
<223> OTHER INFORMATION: GC-C agonist peptide
<220> FEATURE:
<221> NAME/KEY: MISC_FEATURE
<222> LOCATION: (3)..(4)
<223> OTHER INFORMATION: Xaa = Any amino acid or is absent
<220> FEATURE:
<221> NAME/KEY: MISC_FEATURE
<222> LOCATION: (7)..(9)
<223> OTHER INFORMATION: Xaa = Any amino acid or is absent
<220> FEATURE:
<221> NAME/KEY: MISC_FEATURE
<222> LOCATION: (11)..(12)
<223> OTHER INFORMATION: Xaa = Any amino acid or is absent

<400> SEQUENCE: 526

Cys Cys Xaa Xaa Cys Cys Xaa Xaa Xaa Cys Xaa Xaa Cys
1               5                   10

<210> SEQ ID NO 527
<211> LENGTH: 70
<212> TYPE: PRT
<213> ORGANISM: Artificial Sequence
<220> FEATURE:
<223> OTHER INFORMATION: GC-C agonist peptide
<220> FEATURE:
<221> NAME/KEY: MISC_FEATURE
<222> LOCATION: (2)..(5)
<223> OTHER INFORMATION: Xaa = Any amino acid or absent
<220> FEATURE:
<221> NAME/KEY: MISC_FEATURE
<222> LOCATION: (7)..(10)
<223> OTHER INFORMATION: Xaa = Any amino acid or absent
<220> FEATURE:
<221> NAME/KEY: MISC_FEATURE
<222> LOCATION: (12)..(15)
<223> OTHER INFORMATION: Xaa = Any amino acid or absent
<220> FEATURE:
<221> NAME/KEY: MISC_FEATURE
<222> LOCATION: (17)..(20)
<223> OTHER INFORMATION: Xaa = Any amino acid or absent
<220> FEATURE:
<221> NAME/KEY: MISC_FEATURE
<222> LOCATION: (22)..(25)
<223> OTHER INFORMATION: Xaa = Any amino acid or absent
<220> FEATURE:
<221> NAME/KEY: MISC_FEATURE
<222> LOCATION: (27)..(30)
```

```
<223> OTHER INFORMATION: Xaa = Any amino acid or absent
<220> FEATURE:
<221> NAME/KEY: MISC_FEATURE
<222> LOCATION: (32)..(35)
<223> OTHER INFORMATION: Xaa = Any amino acid or absent
<220> FEATURE:
<221> NAME/KEY: MISC_FEATURE
<222> LOCATION: (37)..(40)
<223> OTHER INFORMATION: Xaa = Any amino acid or absent
<220> FEATURE:
<221> NAME/KEY: MISC_FEATURE
<222> LOCATION: (42)..(45)
<223> OTHER INFORMATION: Xaa = Any amino acid or absent
<220> FEATURE:
<221> NAME/KEY: MISC_FEATURE
<222> LOCATION: (47)..(50)
<223> OTHER INFORMATION: Xaa = Any amino acid or absent
<220> FEATURE:
<221> NAME/KEY: MISC_FEATURE
<222> LOCATION: (52)..(55)
<223> OTHER INFORMATION: Xaa = Any amino acid or absent
<220> FEATURE:
<221> NAME/KEY: MISC_FEATURE
<222> LOCATION: (57)..(60)
<223> OTHER INFORMATION: Xaa = Any amino acid or absent
<220> FEATURE:
<221> NAME/KEY: MISC_FEATURE
<222> LOCATION: (62)..(65)
<223> OTHER INFORMATION: Xaa = Any amino acid or absent
<220> FEATURE:
<221> NAME/KEY: MISC_FEATURE
<222> LOCATION: (67)..(70)
<223> OTHER INFORMATION: Xaa = Any amino acid or absent

<400> SEQUENCE: 527

Cys Xaa Xaa Xaa Xaa Cys Xaa Xaa Xaa Glu Xaa Xaa Xaa Xaa Tyr
1               5                   10                  15

Xaa Xaa Xaa Xaa Cys Xaa Xaa Xaa Xaa Cys Xaa Xaa Xaa Xaa Asn Xaa
            20                  25                  30

Xaa Xaa Xaa Pro Xaa Xaa Xaa Xaa Ala Xaa Xaa Xaa Xaa Cys Xaa Xaa
        35                  40                  45

Xaa Xaa Thr Xaa Xaa Xaa Xaa Gly Xaa Xaa Xaa Xaa Cys Xaa Xaa Xaa
    50                  55                  60

Xaa Tyr Xaa Xaa Xaa Xaa
65                  70

<210> SEQ ID NO 528
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 528

Cys Cys Glu Leu Cys Cys Asn Pro Ala Cys Thr Gly Cys Tyr
1               5                   10

<210> SEQ ID NO 529
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 529

Asn Ser Ser Asn Tyr Cys Cys Glu Leu Cys Cys Asn Pro Ala Cys Thr
1               5                   10                  15

Gly Cys Tyr
```

<210> SEQ ID NO 530
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 530

Asn Ser Ser Asn Tyr Cys Cys Glu Leu Cys Cys Asn Pro Ala Cys Trp
1               5                   10                  15

Gly Cys Tyr

<210> SEQ ID NO 531
<211> LENGTH: 19
<212> TYPE: PRT
<213> ORGANISM: Artificial Sequence
<220> FEATURE:
<223> OTHER INFORMATION: GC-C agonist peptide

<400> SEQUENCE: 531

Asn Ser Ser Asn Tyr Cys Cys Glu Tyr Cys Cys Asn Pro Ala Cys Thr
1               5                   10                  15

Gly Cys Tyr

<210> SEQ ID NO 532
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 532

Cys Cys Glu Leu Cys Cys Asn Pro Ala Cys Trp Gly Cys Tyr
1               5                   10

<210> SEQ ID NO 533
<211> LENGTH: 14
<212> TYPE: PRT
<213> ORGANISM: Artificial Sequence
<220> FEATURE:
<223> OTHER INFORMATION: GC-C agonist peptide

<400> SEQUENCE: 533

Cys Cys Glu Tyr Cys Cys Asn Pro Ala Cys Thr Gly Cys Tyr
1               5                   10

<210> SEQ ID NO 534
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 534

Asn Cys Cys Glu Leu Cys Cys Asn Pro Ala Cys Thr Gly Cys Tyr
1               5                   10                  15

<210> SEQ ID NO 535
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 535

Asn Cys Cys Glu Leu Cys Cys Asn Pro Ala Cys Trp Gly Cys Tyr
1               5                   10                  15

<210> SEQ ID NO 536
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 536

Asn Cys Cys Glu Phe Cys Cys Asn Pro Ala Cys Thr Gly Cys Tyr
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 537

Asn Cys Cys Glu Tyr Cys Cys Asn Pro Ala Cys Thr Gly Cys Tyr
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 538

Asn Cys Cys Glu Trp Cys Cys Asn Pro Ala Cys Thr Gly Cys Tyr
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 539

Asn Cys Cys Glu Arg Cys Cys Asn Pro Ala Cys Thr Gly Cys Tyr
1               5                   10                  15

<210> SEQ ID NO 540
<211> LENGTH: 15
<212> TYPE: PRT
<213> ORGANISM: Artificial Sequence
<220> FEATURE:
<223> OTHER INFORMATION: GC-C agonist peptide

<400> SEQUENCE: 540

Asn Cys Cys Glu Lys Cys Cys Asn Pro Ala Cys Thr Gly Cys Tyr
1               5                   10                  15

<210> SEQ ID NO 541
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 541

Asn Ser Ser Asn Tyr Cys Cys Glu Leu Cys Cys Asn Pro Ala Cys Thr

Gly Cys Tyr Asp Phe
            20

<210> SEQ ID NO 542
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 542

Asn Ser Ser Asn Tyr Cys Cys Glu Leu Cys Cys Asn Pro Ala Cys Trp
1               5                   10                  15

Gly Cys Tyr Asp Phe
            20

<210> SEQ ID NO 543
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 543

Asn Ser Ser Asn Tyr Cys Cys Glu Phe Cys Cys Asn Pro Ala Cys Thr
1               5                   10                  15

Gly Cys Tyr Asp Phe
            20

<210> SEQ ID NO 544
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 544

Asn Ser Ser Asn Tyr Cys Cys Glu Tyr Cys Cys Asn Pro Ala Cys Thr
1               5                   10                  15

Gly Cys Tyr Asp Phe
            20

<210> SEQ ID NO 545
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 545

Asn Ser Ser Asn Tyr Cys Cys Glu Trp Cys Cys Asn Pro Ala Cys Thr
1               5                   10                  15

Gly Cys Tyr Asp Phe
            20

<210> SEQ ID NO 546
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 546

-continued

Asn Ser Ser Asn Tyr Cys Cys Glu Arg Cys Cys Asn Pro Ala Cys Thr
1               5                   10                  15

Gly Cys Tyr Asp Phe
            20

<210> SEQ ID NO 547
<211> LENGTH: 21
<212> TYPE: PRT
<213> ORGANISM: Artificial Sequence
<220> FEATURE:
<223> OTHER INFORMATION: GC-C agonist peptide

<400> SEQUENCE: 547

Asn Ser Ser Asn Tyr Cys Cys Glu Lys Cys Cys Asn Pro Ala Cys Thr
1               5                   10                  15

Gly Cys Tyr Asp Phe
            20

<210> SEQ ID NO 548
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 548

Cys Cys Glu Leu Cys Cys Asn Pro Ala Cys Thr Gly Cys Tyr Asp Phe
1               5                   10                  15

<210> SEQ ID NO 549
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 549

Cys Cys Glu Leu Cys Cys Asn Pro Ala Cys Trp Gly Cys Tyr Asp Phe
1               5                   10                  15

<210> SEQ ID NO 550
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 550

Cys Cys Glu Phe Cys Cys Asn Pro Ala Cys Thr Gly Cys Tyr Asp Phe
1               5                   10                  15

<210> SEQ ID NO 551
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 551

Cys Cys Glu Tyr Cys Cys Asn Pro Ala Cys Thr Gly Cys Tyr Asp Phe
1               5                   10                  15

<210> SEQ ID NO 552
<211> LENGTH: 16
<212> TYPE: PRT
<213> ORGANISM: Artificial Sequence

```
<220> FEATURE:
<223> OTHER INFORMATION: GC-C agonist peptide

<400> SEQUENCE: 552

Cys Cys Glu Trp Cys Cys Asn Pro Ala Cys Thr Gly Cys Tyr Asp Phe
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 553

Cys Cys Glu Arg Cys Cys Asn Pro Ala Cys Thr Gly Cys Tyr Asp Phe
1               5                   10                  15

<210> SEQ ID NO 554
<211> LENGTH: 16
<212> TYPE: PRT
<213> ORGANISM: Artificial Sequence
<220> FEATURE:
<223> OTHER INFORMATION: GC-C agonist peptide

<400> SEQUENCE: 554

Cys Cys Glu Lys Cys Cys Asn Pro Ala Cys Thr Gly Cys Tyr Asp Phe
1               5                   10                  15

<210> SEQ ID NO 555
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 555

Asn Cys Cys Glu Leu Cys Cys Asn Pro Ala Cys Thr Gly Cys Tyr Asp
1               5                   10                  15

Phe

<210> SEQ ID NO 556
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 556

Asn Cys Cys Glu Leu Cys Cys Asn Pro Ala Cys Trp Gly Cys Tyr Asp
1               5                   10                  15

Phe

<210> SEQ ID NO 557
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 557

Asn Cys Cys Glu Phe Cys Cys Asn Pro Ala Cys Thr Gly Cys Tyr Asp
1               5                   10                  15

Phe
```

<210> SEQ ID NO 558
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 558

Asn Cys Cys Glu Tyr Cys Cys Asn Pro Ala Cys Thr Gly Cys Tyr Asp
1               5                   10                  15
Phe

<210> SEQ ID NO 559
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 559

Asn Cys Cys Glu Trp Cys Cys Asn Pro Ala Cys Thr Gly Cys Tyr Asp
1               5                   10                  15
Phe

<210> SEQ ID NO 560
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 560

Asn Cys Cys Glu Arg Cys Cys Asn Pro Ala Cys Thr Gly Cys Tyr Asp
1               5                   10                  15
Phe

<210> SEQ ID NO 561
<211> LENGTH: 17
<212> TYPE: PRT
<213> ORGANISM: Artificial Sequence
<220> FEATURE:
<223> OTHER INFORMATION: GC-C agonist peptide

<400> SEQUENCE: 561

Asn Cys Cys Glu Lys Cys Cys Asn Pro Ala Cys Thr Gly Cys Tyr Asp
1               5                   10                  15
Phe

<210> SEQ ID NO 562
<211> LENGTH: 15
<212> TYPE: PRT
<213> ORGANISM: Homo sapiens

<400> SEQUENCE: 562

Pro Gly Thr Cys Glu Ile Cys Ala Tyr Ala Ala Cys Thr Gly Cys
1               5                   10                  15

<210> SEQ ID NO 563
<211> LENGTH: 16
<212> TYPE: PRT
<213> ORGANISM: Artificial Sequence
<220> FEATURE:
<223> OTHER INFORMATION: GC-agonist peptide - human guanylin analog

<400> SEQUENCE: 563

Pro Gly Thr Cys Glu Gly Ile Cys Ala Tyr Ala Ala Cys Thr Gly Cys
1               5                   10                  15

<210> SEQ ID NO 564
<211> LENGTH: 16
<212> TYPE: PRT
<213> ORGANISM: Artificial Sequence
<220> FEATURE:
<223> OTHER INFORMATION: GC-agonist peptide - human guanylin analog

<400> SEQUENCE: 564

Pro Gly Thr Cys Glu Ile Gly Cys Ala Tyr Ala Ala Cys Thr Gly Cys
1               5                   10                  15

<210> SEQ ID NO 565
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 565

Pro Gly Thr Cys Glu Ile Gly Cys Gly Ala Tyr Ala Ala Cys Thr Gly
1               5                   10                  15

Cys

<210> SEQ ID NO 566
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 566

Pro Gly Thr Cys Glu Ile Gly Cys Ala Gly Tyr Ala Ala Cys Thr Gly
1               5                   10                  15

Cys

<210> SEQ ID NO 567
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 567

Pro Gly Thr Cys Glu Ile Gly Cys Ala Tyr Gly Ala Ala Cys Thr Gly
1               5                   10                  15

Cys

<210> SEQ ID NO 568
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 568

Pro Gly Thr Cys Glu Ile Gly Cys Ala Tyr Ala Gly Ala Cys Thr Gly
1               5                   10                  15

Cys

<210> SEQ ID NO 569
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 569

Pro Gly Thr Cys Glu Ile Gly Cys Ala Tyr Ala Ala Gly Cys Thr Gly
1               5                   10                  15

Cys

<210> SEQ ID NO 570
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 570

Pro Gly Thr Cys Glu Ile Gly Cys Ala Tyr Ala Ala Cys Gly Thr Gly
1               5                   10                  15

Cys

<210> SEQ ID NO 571
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 571

Pro Gly Thr Cys Glu Ile Gly Cys Ala Tyr Ala Ala Cys Thr Gly Gly
1               5                   10                  15

Cys

<210> SEQ ID NO 572
<211> LENGTH: 16
<212> TYPE: PRT
<213> ORGANISM: Artificial Sequence
<220> FEATURE:
<223> OTHER INFORMATION: GC-agonist peptide - human guanylin analog

<400> SEQUENCE: 572

Pro Gly Thr Cys Ala Glu Ile Cys Ala Tyr Ala Ala Cys Thr Gly Cys
1               5                   10                  15

<210> SEQ ID NO 573
<211> LENGTH: 16
<212> TYPE: PRT
<213> ORGANISM: Artificial Sequence
<220> FEATURE:
<223> OTHER INFORMATION: GC-agonist peptide - human guanylin analog

<400> SEQUENCE: 573

Pro Gly Thr Cys Glu Ala Ile Cys Ala Tyr Ala Ala Cys Thr Gly Cys
1               5                   10                  15

<210> SEQ ID NO 574
<211> LENGTH: 16
<212> TYPE: PRT
<213> ORGANISM: Artificial Sequence
<220> FEATURE:
<223> OTHER INFORMATION: GC-agonist peptide - human guanylin analog

<400> SEQUENCE: 574

```
Pro Gly Thr Cys Glu Ile Ala Cys Ala Tyr Ala Ala Cys Thr Gly Cys
1               5                   10                  15
```

<210> SEQ ID NO 575
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 575

```
Pro Gly Thr Cys Glu Ile Gly Cys Ala Ala Tyr Ala Ala Cys Thr Gly
1               5                   10                  15

Cys
```

<210> SEQ ID NO 576
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 576

```
Pro Gly Thr Cys Glu Ile Gly Cys Ala Tyr Ala Ala Ala Cys Thr Gly
1               5                   10                  15

Cys
```

<210> SEQ ID NO 577
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 577

```
Pro Gly Thr Cys Glu Ile Gly Cys Ala Tyr Ala Ala Cys Ala Thr Gly
1               5                   10                  15

Cys
```

<210> SEQ ID NO 578
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 578

```
Pro Gly Thr Cys Glu Ile Gly Cys Ala Tyr Ala Ala Cys Thr Ala Gly
1               5                   10                  15

Cys
```

<210> SEQ ID NO 579
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 579

```
Pro Gly Thr Cys Glu Ile Gly Cys Ala Tyr Ala Ala Cys Thr Gly Ala
1               5                   10                  15

Cys
```

```
<210> SEQ ID NO 580
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 580

Pro Gly Thr Cys Ala Glu Ile Cys Ala Ala Tyr Ala Ala Cys Thr Gly
1               5                   10                  15

Cys

<210> SEQ ID NO 581
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 581

Pro Gly Thr Cys Glu Ala Ile Cys Ala Ala Tyr Ala Ala Cys Thr Gly
1               5                   10                  15

Cys

<210> SEQ ID NO 582
<211> LENGTH: 17
<212> TYPE: PRT
<213> ORGANISM: Artificial Sequence
<220> FEATURE:
<223> OTHER INFORMATION: GC-agonist peptide - human guanylin analog

<400> SEQUENCE: 582

Pro Gly Thr Cys Glu Ile Ala Cys Ala Ala Tyr Ala Ala Cys Thr Gly
1               5                   10                  15

Cys

<210> SEQ ID NO 583
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 583

Ser His Thr Cys Glu Ile Cys Ala Asn Ala Ala Cys Ala Gly Cys
1               5                   10                  15

<210> SEQ ID NO 584
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 584

Ser His Thr Cys Glu Leu Cys Ala Asn Ala Ala Cys Ala Gly Cys
1               5                   10                  15

<210> SEQ ID NO 585
<211> LENGTH: 15
<212> TYPE: PRT
<213> ORGANISM: Artificial Sequence
<220> FEATURE:
<223> OTHER INFORMATION: GC-agonist peptide - human guanylin analog
```

```
<400> SEQUENCE: 585

Ser His Thr Cys Glu Val Cys Ala Asn Ala Ala Cys Ala Gly Cys
1               5                   10                  15

<210> SEQ ID NO 586
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 586

Ser His Thr Cys Glu Tyr Cys Ala Asn Ala Ala Cys Ala Gly Cys
1               5                   10                  15

<210> SEQ ID NO 587
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 587

Ser His Thr Cys Glu Ile Cys Ala Asn Ala Ala Cys Ala Gly Cys
1               5                   10                  15

<210> SEQ ID NO 588
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 588

Ser His Thr Cys Glu Leu Cys Ala Asn Ala Ala Cys Ala Gly Cys
1               5                   10                  15

<210> SEQ ID NO 589
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 589

Ser His Thr Cys Glu Val Cys Ala Asn Ala Ala Cys Ala Gly Cys
1               5                   10                  15

<210> SEQ ID NO 590
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 590

Ser His Thr Cys Glu Tyr Cys Ala Asn Ala Ala Cys Ala Gly Cys
1               5                   10                  15

<210> SEQ ID NO 591
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 591
```

```
Ser His Thr Cys Glu Ile Cys Ala Asn Ala Ala Cys Ala Gly Cys
1               5                   10                  15

<210> SEQ ID NO 592
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 592

Ser His Thr Cys Glu Leu Cys Ala Asn Ala Ala Cys Ala Gly Cys
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 593

Ser His Thr Cys Glu Val Cys Ala Asn Ala Ala Cys Ala Gly Cys
1               5                   10                  15

<210> SEQ ID NO 594
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 594

Ser His Thr Cys Glu Tyr Cys Ala Asn Ala Ala Cys Ala Gly Cys
1               5                   10                  15

<210> SEQ ID NO 595
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 595

Ser His Thr Cys Glu Ile Cys Ala Asn Ala Ala Cys Ala Gly Cys
1               5                   10                  15

<210> SEQ ID NO 596
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 596

Ser His Thr Cys Glu Leu Cys Ala Asn Ala Ala Cys Ala Gly Cys
1               5                   10                  15

<210> SEQ ID NO 597
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 597
```

```
Ser His Thr Cys Glu Val Cys Ala Asn Ala Ala Cys Ala Gly Cys
1               5                   10                  15

<210> SEQ ID NO 598
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 598

Ser His Thr Cys Glu Tyr Cys Ala Asn Ala Ala Cys Ala Gly Cys
1               5                   10                  15

<210> SEQ ID NO 599
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 599

Asn Asp Glu Cys Glu Ile Cys Ala Asn Ala Ala Cys Ala Gly Cys
1               5                   10                  15

<210> SEQ ID NO 600
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 600

Asn Asp Glu Cys Glu Leu Cys Ala Asn Ala Ala Cys Ala Gly Cys
1               5                   10                  15

<210> SEQ ID NO 601
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 601

Asn Asp Glu Cys Glu Val Cys Ala Asn Ala Ala Cys Ala Gly Cys
1               5                   10                  15

<210> SEQ ID NO 602
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 602

Asn Asp Glu Cys Glu Tyr Cys Ala Asn Ala Ala Cys Ala Gly Cys
1               5                   10                  15

<210> SEQ ID NO 603
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 603

Asn Asp Glu Cys Glu Ile Cys Ala Asn Ala Ala Cys Ala Gly Cys
```

```
1               5                   10                  15
```

<210> SEQ ID NO 604
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 604

```
Asn Asp Glu Cys Glu Leu Cys Ala Asn Ala Ala Cys Ala Gly Cys
1               5                   10                  15
```

<210> SEQ ID NO 605
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 605

```
Asn Asp Glu Cys Glu Val Cys Ala Asn Ala Ala Cys Ala Gly Cys
1               5                   10                  15
```

<210> SEQ ID NO 606
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 606

```
Asn Asp Glu Cys Glu Tyr Cys Ala Asn Ala Ala Cys Ala Gly Cys
1               5                   10                  15
```

<210> SEQ ID NO 607
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 607

```
Asn Asp Glu Cys Glu Ile Cys Ala Asn Ala Ala Cys Ala Gly Cys
1               5                   10                  15
```

<210> SEQ ID NO 608
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 608

```
Asn Asp Glu Cys Glu Leu Cys Ala Asn Ala Ala Cys Ala Gly Cys
1               5                   10                  15
```

<210> SEQ ID NO 609
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 609

```
Asn Asp Glu Cys Glu Val Cys Ala Asn Ala Ala Cys Ala Gly Cys
1               5                   10                  15
```

```
<210> SEQ ID NO 610
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 610

Asn Asp Glu Cys Glu Tyr Cys Ala Asn Ala Ala Cys Ala Gly Cys
1               5                   10                  15

<210> SEQ ID NO 611
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 611

Asn Asp Glu Cys Glu Ile Cys Ala Asn Ala Ala Cys Ala Gly Cys
1               5                   10                  15

<210> SEQ ID NO 612
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 612

Asn Asp Glu Cys Glu Leu Cys Ala Asn Ala Ala Cys Ala Gly Cys
1               5                   10                  15

<210> SEQ ID NO 613
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 613

Asn Asp Glu Cys Glu Val Cys Ala Asn Ala Ala Cys Ala Gly Cys
1               5                   10                  15

<210> SEQ ID NO 614
<211> LENGTH: 15
<212> TYPE: PRT
<213> ORGANISM: Artificial Sequence
<220> FEATURE:
<223> OTHER INFORMATION: GC-agonist peptide - human guanylin analog

<400> SEQUENCE: 614

Asn Asp Glu Cys Glu Tyr Cys Ala Asn Ala Ala Cys Ala Gly Cys
1               5                   10                  15

<210> SEQ ID NO 615
<211> LENGTH: 15
<212> TYPE: PRT
<213> ORGANISM: Homo sapiens

<400> SEQUENCE: 615

Gln Glu Glu Cys Glu Leu Cys Ile Asn Met Ala Cys Thr Gly Tyr
1               5                   10                  15

<210> SEQ ID NO 616
```

```
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 616

Gln Glu Glu Cys Glu Thr Cys Ile Asn Met Ala Cys Thr Gly Tyr
1               5                   10                  15

<210> SEQ ID NO 617
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 617

Gln Asp Glu Cys Glu Thr Cys Ile Asn Met Ala Cys Thr Gly Tyr
1               5                   10                  15

<210> SEQ ID NO 618
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 618

Gln Asp Asp Cys Glu Thr Cys Ile Asn Met Ala Cys Thr Gly Tyr
1               5                   10                  15

<210> SEQ ID NO 619
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 619

Gln Glu Asp Cys Glu Thr Cys Ile Asn Met Ala Cys Thr Gly Tyr
1               5                   10                  15

<210> SEQ ID NO 620
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 620

Gln Glu Glu Cys Glu Glu Cys Ile Asn Met Ala Cys Thr Gly Tyr
1               5                   10                  15

<210> SEQ ID NO 621
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 621
```

```
Gln Asp Glu Cys Glu Glu Cys Ile Asn Met Ala Cys Thr Gly Tyr
1               5                   10                  15

<210> SEQ ID NO 622
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 622

Gln Asp Asp Cys Glu Glu Cys Ile Asn Met Ala Cys Thr Gly Tyr
1               5                   10                  15

<210> SEQ ID NO 623
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 623

Gln Glu Asp Cys Glu Glu Cys Ile Asn Met Ala Cys Thr Gly Tyr
1               5                   10                  15

<210> SEQ ID NO 624
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 624

Gln Glu Glu Cys Glu Tyr Cys Ile Asn Met Ala Cys Thr Gly Tyr
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 625

Gln Asp Glu Cys Glu Tyr Cys Ile Asn Met Ala Cys Thr Gly Tyr
1               5                   10                  15

<210> SEQ ID NO 626
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 626

Gln Asp Asp Cys Glu Tyr Cys Ile Asn Met Ala Cys Thr Gly Tyr
1               5                   10                  15

<210> SEQ ID NO 627
<211> LENGTH: 15
<212> TYPE: PRT
<213> ORGANISM: Artificial Sequence
<220> FEATURE:
```

<223> OTHER INFORMATION: GC-agonist peptide - human lymphoguanylin
      analog

<400> SEQUENCE: 627

Gln Glu Asp Cys Glu Tyr Cys Ile Asn Met Ala Cys Thr Gly Tyr
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 628

Gln Glu Glu Cys Glu Ile Cys Ile Asn Met Ala Cys Thr Gly Tyr
1               5                   10                  15

<210> SEQ ID NO 629
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 629

Gln Asp Glu Cys Glu Ile Cys Ile Asn Met Ala Cys Thr Gly Tyr
1               5                   10                  15

<210> SEQ ID NO 630
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 630

Gln Asp Asp Cys Glu Ile Cys Ile Asn Met Ala Cys Thr Gly Tyr
1               5                   10                  15

<210> SEQ ID NO 631
<211> LENGTH: 15
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 631

Gln Glu Asp Cys Glu Ile Cys Ile Asn Met Ala Cys Thr Gly Tyr
1               5                   10                  15

<210> SEQ ID NO 632
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 632

Gln Glu Glu Cys Glu Thr Cys Ile Asn Met Ala Cys Thr Gly Cys Ser
1               5                   10                  15

```
<210> SEQ ID NO 633
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 633

Gln Asp Glu Cys Glu Thr Cys Ile Asn Met Ala Cys Thr Gly Cys Ser
1               5                   10                  15

<210> SEQ ID NO 634
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 634

Gln Asp Asp Cys Glu Thr Cys Ile Asn Met Ala Cys Thr Gly Cys Ser
1               5                   10                  15

<210> SEQ ID NO 635
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 635

Gln Glu Asp Cys Glu Thr Cys Ile Asn Met Ala Cys Thr Gly Cys Ser
1               5                   10                  15

<210> SEQ ID NO 636
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 636

Gln Glu Glu Cys Glu Glu Cys Ile Asn Met Ala Cys Thr Gly Cys Ser
1               5                   10                  15

<210> SEQ ID NO 637
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 637

Gln Asp Glu Cys Glu Glu Cys Ile Asn Met Ala Cys Thr Gly Cys Ser
1               5                   10                  15

<210> SEQ ID NO 638
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 638
```

Gln Asp Asp Cys Glu Glu Cys Ile Asn Met Ala Cys Thr Gly Cys Ser
1               5                   10                  15

<210> SEQ ID NO 639
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 639

Gln Glu Asp Cys Glu Glu Cys Ile Asn Met Ala Cys Thr Gly Cys Ser
1               5                   10                  15

<210> SEQ ID NO 640
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 640

Gln Glu Glu Cys Glu Tyr Cys Ile Asn Met Ala Cys Thr Gly Cys Ser
1               5                   10                  15

<210> SEQ ID NO 641
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 641

Gln Asp Glu Cys Glu Tyr Cys Ile Asn Met Ala Cys Thr Gly Cys Ser
1               5                   10                  15

<210> SEQ ID NO 642
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 642

Gln Asp Asp Cys Glu Tyr Cys Ile Asn Met Ala Cys Thr Gly Cys Ser
1               5                   10                  15

<210> SEQ ID NO 643
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 643

Gln Glu Asp Cys Glu Tyr Cys Ile Asn Met Ala Cys Thr Gly Cys Ser
1               5                   10                  15

<210> SEQ ID NO 644
<211> LENGTH: 16
<212> TYPE: PRT
<213> ORGANISM: Artificial Sequence

```
<220> FEATURE:
<223> OTHER INFORMATION: GC-agonist peptide - human lymphoguanylin
      analog

<400> SEQUENCE: 644

Gln Glu Glu Cys Glu Ile Cys Ile Asn Met Ala Cys Thr Gly Cys Ser
1               5                   10                  15

<210> SEQ ID NO 645
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 645

Gln Asp Glu Cys Glu Ile Cys Ile Asn Met Ala Cys Thr Gly Cys Ser
1               5                   10                  15

<210> SEQ ID NO 646
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 646

Gln Asp Asp Cys Glu Ile Cys Ile Asn Met Ala Cys Thr Gly Cys Ser
1               5                   10                  15

<210> SEQ ID NO 647
<211> LENGTH: 16
<212> TYPE: PRT
<213> ORGANISM: Artificial Sequence
<220> FEATURE:
<223> OTHER INFORMATION: GC-agonist peptide - human lymphoguanylin
      analog

<400> SEQUENCE: 647

Gln Glu Asp Cys Glu Ile Cys Ile Asn Met Ala Cys Thr Gly Cys Ser
1               5                   10                  15

<210> SEQ ID NO 648
<211> LENGTH: 16
<212> TYPE: PRT
<213> ORGANISM: Homo sapiens

<400> SEQUENCE: 648

Asn Asp Asp Cys Glu Leu Cys Val Asn Val Ala Cys Thr Gly Cys Leu
1               5                   10                  15

<210> SEQ ID NO 649
<211> LENGTH: 15
<212> TYPE: PRT
<213> ORGANISM: Artificial Sequence
<220> FEATURE:
<223> OTHER INFORMATION: GC-agonist peptide - human uroguanylin
      analog

<400> SEQUENCE: 649

Gln Asp Asp Cys Glu Thr Cys Ile Asn Met Ala Cys Thr Gly Tyr
1               5                   10                  15

<210> SEQ ID NO 650
<211> LENGTH: 16
```

```
<212> TYPE: PRT
<213> ORGANISM: Artificial Sequence
<220> FEATURE:
<223> OTHER INFORMATION: Human uroguanylin peptide analog
<220> FEATURE:
<221> NAME/KEY: MISC_FEATURE
<222> LOCATION: (1)..(3)
<223> OTHER INFORMATION: Xaa = Any amino acid or is absent
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(7)
<223> OTHER INFORMATION: Xaa = Any amino acid
<220> FEATURE:
<221> NAME/KEY: MISC_FEATURE
<222> LOCATION: (8)..(8)
<223> OTHER INFORMATION: Xaa = Any amino acid or is absent
<220> FEATURE:
<221> NAME/KEY: MISC_FEATURE
<222> LOCATION: (9)..(11)
<223> OTHER INFORMATION: Xaa = Any amino acid
<220> FEATURE:
<221> NAME/KEY: MISC_FEATURE
<222> LOCATION: (13)..(15)
<223> OTHER INFORMATION: Xaa = Any amino acid
<220> FEATURE:
<221> NAME/KEY: MISC_FEATURE
<222> LOCATION: (16)..(16)
<223> OTHER INFORMATION: Xaa = Any amino acid or is absent

<400> SEQUENCE: 650

Xaa Xaa Xaa Cys Xaa Xaa Xaa Xaa Xaa Xaa Xaa Cys Xaa Xaa Xaa Xaa
1               5                   10                  15

<210> SEQ ID NO 651
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 651

Ile Ala Glu Asp Ser His Thr
1               5

<210> SEQ ID NO 652
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 652

Ile Ala Gln Asp Pro Ser Thr
1               5

<210> SEQ ID NO 653
<211> LENGTH: 4
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 653

Asp Pro Asn Thr
1
```

<210> SEQ ID NO 654
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 654

Ile Ala Gln Asp Pro Asn Thr
1               5

<210> SEQ ID NO 655
<211> LENGTH: 4
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 655

Lys Pro Asn Thr
1

<210> SEQ ID NO 656
<211> LENGTH: 4
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 656

Asp Pro Gly Thr
1

<210> SEQ ID NO 657
<211> LENGTH: 5
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 657

Glu Asp Pro Gly Thr
1               5

<210> SEQ ID NO 658
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 658

Val Ala Ala Arg Ala Asp Leu
1               5

<210> SEQ ID NO 659
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 659

Arg Thr Ile Ala Asn Asp Asp
1               5

<210> SEQ ID NO 660
<211> LENGTH: 6
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 660

Thr Ile Ala Asn Asp Asp
1               5

<210> SEQ ID NO 661
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 661

Arg Thr Met Asp Asn Asp Glu
1               5

<210> SEQ ID NO 662
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 662

Arg Thr Ile Ala Gly Asp Asp
1               5

<210> SEQ ID NO 663
<211> LENGTH: 6
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 663

Arg Thr Ile Ala Asn Asp
1               5

<210> SEQ ID NO 664
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 664

Arg Ser Ile Ser Gln Glu Asp
1               5

<210> SEQ ID NO 665
<211> LENGTH: 7

```
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 665

Arg Thr Ile Ala Thr Asp Glu
1               5

<210> SEQ ID NO 666
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 666

Ile Ile Thr Pro Pro Asp Pro
1               5

<210> SEQ ID NO 667
<211> LENGTH: 7
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 667

Arg Tyr Ile Asn Gln Glu Glu
1               5

<210> SEQ ID NO 668
<211> LENGTH: 6
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 668

Ala Ser Ser Tyr Ala Ser
1               5

<210> SEQ ID NO 669
<211> LENGTH: 6
<212> TYPE: PRT
<213> ORGANISM: Artificial Sequence
<220> FEATURE:
<223> OTHER INFORMATION: Fragment insert into human uroguanylin peptide
      analog

<400> SEQUENCE: 669

Thr Ser Ser Tyr Ala Ser
1               5

<210> SEQ ID NO 670
<211> LENGTH: 16
<212> TYPE: PRT
<213> ORGANISM: Artificial Sequence
<220> FEATURE:
<223> OTHER INFORMATION: Human uroguanylin peptide analog
<220> FEATURE:
<221> NAME/KEY: MISC_FEATURE
<222> LOCATION: (2)..(2)
<223> OTHER INFORMATION: Xaa = Asp or Glu
<220> FEATURE:
```

```
<221> NAME/KEY: MISC_FEATURE
<222> LOCATION: (3)..(3)
<223> OTHER INFORMATION: Xaa = Asp or Glu
<220> FEATURE:
<221> NAME/KEY: MISC_FEATURE
<222> LOCATION: (4)..(4)
<223> OTHER INFORMATION: Xaa = Cys or Mpt (mercaptoproline) or Pen
      (penicillamine) or Dpr (diaminopropionic acid) or Asp or Glu
<220> FEATURE:
<221> NAME/KEY: MISC_FEATURE
<222> LOCATION: (7)..(7)
<223> OTHER INFORMATION: Xaa = Cys or Mpt (mercaptoproline) or Pen
      (penicillamine) or Dpr (diaminopropionic acid) or Asp or Glu
<220> FEATURE:
<221> NAME/KEY: MISC_FEATURE
<222> LOCATION: (10)..(10)
<223> OTHER INFORMATION: Xaa = Val or Pro
<220> FEATURE:
<221> NAME/KEY: MISC_FEATURE
<222> LOCATION: (11)..(11)
<223> OTHER INFORMATION: Xaa = Ala or Aib (alpha-aminoisobutyric acid)
<220> FEATURE:
<221> NAME/KEY: MISC_FEATURE
<222> LOCATION: (12)..(12)
<223> OTHER INFORMATION: Xaa = Cys or Mpt (mercaptoproline) or Pen
      (penicillamine) or Dpr (diaminopropionic acid) or Asp or Glu
<220> FEATURE:
<221> NAME/KEY: MISC_FEATURE
<222> LOCATION: (14)..(14)
<223> OTHER INFORMATION: Xaa = Gly or Ala
<220> FEATURE:
<221> NAME/KEY: MISC_FEATURE
<222> LOCATION: (15)..(15)
<223> OTHER INFORMATION: Xaa = Cys or Mpt (mercaptoproline) or Pen
      (penicillamine) or Dpr (diaminopropionic acid) or Asp or Glu

<400> SEQUENCE: 670

Asn Xaa Xaa Xaa Glu Leu Xaa Val Asn Xaa Xaa Xaa Thr Xaa Xaa Leu
1               5                   10                  15

<210> SEQ ID NO 671
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 671

Asn Asp Glu Cys Glu Leu Cys Val Asn Val Ala Cys Thr Gly Cys Leu
1               5                   10                  15

<210> SEQ ID NO 672
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 672

Glu Asp Asp Cys Glu Leu Cys Val Asn Val Ala Cys Thr Gly Cys Leu
1               5                   10                  15

<210> SEQ ID NO 673
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 673

Glu Asp Glu Cys Glu Leu Cys Val Asn Val Ala Cys Thr Gly Cys Leu
1               5                   10                  15
```

<210> SEQ ID NO 674
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 674

Glu Glu Asp Cys Glu Leu Cys Val Asn Val Ala Cys Thr Gly Cys Leu
1               5                   10                  15

<210> SEQ ID NO 675
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 675

Glu Glu Glu Cys Glu Leu Cys Val Asn Val Ala Cys Thr Gly Cys Leu
1               5                   10                  15

<210> SEQ ID NO 676
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 676

Asp Asp Asp Cys Glu Leu Cys Val Asn Val Ala Cys Thr Gly Cys Leu
1               5                   10                  15

<210> SEQ ID NO 677
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 677

Asp Asp Glu Cys Glu Leu Cys Val Asn Val Ala Cys Thr Gly Cys Leu
1               5                   10                  15

<210> SEQ ID NO 678
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 678

Asp Glu Asp Cys Glu Leu Cys Val Asn Val Ala Cys Thr Gly Cys Leu
1               5                   10                  15

<210> SEQ ID NO 679
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 679

Asp Glu Glu Cys Glu Leu Cys Val Asn Val Ala Cys Thr Gly Cys Leu
1               5                   10                  15

<210> SEQ ID NO 680
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 680

Gln Asp Asp Cys Glu Leu Cys Val Asn Val Ala Cys Thr Gly Cys Leu
1               5                   10                  15

<210> SEQ ID NO 681
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 681

Gln Asp Glu Cys Glu Leu Cys Val Asn Val Ala Cys Thr Gly Cys Leu
1               5                   10                  15

<210> SEQ ID NO 682
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 682

Gln Glu Asp Cys Glu Leu Cys Val Asn Val Ala Cys Thr Gly Cys Leu
1               5                   10                  15

<210> SEQ ID NO 683
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 683

Gln Glu Glu Cys Glu Leu Cys Val Asn Val Ala Cys Thr Gly Cys Leu
1               5                   10                  15

<210> SEQ ID NO 684
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 684

Lys Asp Asp Cys Glu Leu Cys Val Asn Val Ala Cys Thr Gly Cys Leu
1               5                   10                  15

<210> SEQ ID NO 685
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 685

Lys Asp Glu Cys Glu Leu Cys Val Asn Val Ala Cys Thr Gly Cys Leu
1               5                   10                  15

```
<210> SEQ ID NO 686
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 686

Lys Glu Asp Cys Glu Leu Cys Val Asn Val Ala Cys Thr Gly Cys Leu
1               5                   10                  15

<210> SEQ ID NO 687
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 687

Lys Glu Glu Cys Glu Leu Cys Val Asn Val Ala Cys Thr Gly Cys Leu
1               5                   10                  15

<210> SEQ ID NO 688
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 688

Glu Asp Asp Cys Glu Leu Cys Val Asn Val Ala Cys Thr Gly Cys Ser
1               5                   10                  15

<210> SEQ ID NO 689
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 689

Glu Asp Glu Cys Glu Leu Cys Val Asn Val Ala Cys Thr Gly Cys Ser
1               5                   10                  15

<210> SEQ ID NO 690
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 690

Glu Glu Asp Cys Glu Leu Cys Val Asn Val Ala Cys Thr Gly Cys Ser
1               5                   10                  15

<210> SEQ ID NO 691
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 691

Glu Glu Glu Cys Glu Leu Cys Val Asn Val Ala Cys Thr Gly Cys Ser
1               5                   10                  15

<210> SEQ ID NO 692
```

```
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 692

Asp Asp Asp Cys Glu Leu Cys Val Asn Val Ala Cys Thr Gly Cys Ser
1               5                   10                  15

<210> SEQ ID NO 693
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 693

Asp Asp Glu Cys Glu Leu Cys Val Asn Val Ala Cys Thr Gly Cys Ser
1               5                   10                  15

<210> SEQ ID NO 694
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 694

Asp Glu Asp Cys Glu Leu Cys Val Asn Val Ala Cys Thr Gly Cys Ser
1               5                   10                  15

<210> SEQ ID NO 695
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 695

Asp Glu Glu Cys Glu Leu Cys Val Asn Val Ala Cys Thr Gly Cys Ser
1               5                   10                  15

<210> SEQ ID NO 696
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 696

Gln Asp Asp Cys Glu Leu Cys Val Asn Val Ala Cys Thr Gly Cys Ser
1               5                   10                  15

<210> SEQ ID NO 697
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 697

Gln Asp Glu Cys Glu Leu Cys Val Asn Val Ala Cys Thr Gly Cys Ser
1               5                   10                  15

<210> SEQ ID NO 698
<211> LENGTH: 16
```

```
<212> TYPE: PRT
<213> ORGANISM: Artificial Sequence
<220> FEATURE:
<223> OTHER INFORMATION: human uroguanylin analog

<400> SEQUENCE: 698

Gln Glu Asp Cys Glu Leu Cys Val Asn Val Ala Cys Thr Gly Cys Ser
1               5                   10                  15

<210> SEQ ID NO 699
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 699

Gln Glu Glu Cys Glu Leu Cys Val Asn Val Ala Cys Thr Gly Cys Ser
1               5                   10                  15

<210> SEQ ID NO 700
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 700

Lys Asp Asp Cys Glu Leu Cys Val Asn Val Ala Cys Thr Gly Cys Ser
1               5                   10                  15

<210> SEQ ID NO 701
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 701

Lys Asp Glu Cys Glu Leu Cys Val Asn Val Ala Cys Thr Gly Cys Ser
1               5                   10                  15

<210> SEQ ID NO 702
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 702

Lys Glu Asp Cys Glu Leu Cys Val Asn Val Ala Cys Thr Gly Cys Ser
1               5                   10                  15

<210> SEQ ID NO 703
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 703

Lys Glu Glu Cys Glu Leu Cys Val Asn Val Ala Cys Thr Gly Cys Ser
1               5                   10                  15

<210> SEQ ID NO 704
<211> LENGTH: 16
<212> TYPE: PRT
```

```
<213> ORGANISM: Artificial Sequence
<220> FEATURE:
<223> OTHER INFORMATION: human uroguanylin analog

<400> SEQUENCE: 704

Glu Asp Asp Cys Glu Leu Cys Ile Asn Met Ala Cys Thr Gly Cys Leu
1               5                   10                  15

<210> SEQ ID NO 705
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 705

Glu Asp Glu Cys Glu Leu Cys Ile Asn Met Ala Cys Thr Gly Cys Leu
1               5                   10                  15

<210> SEQ ID NO 706
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 706

Glu Glu Asp Cys Glu Leu Cys Ile Asn Met Ala Cys Thr Gly Cys Leu
1               5                   10                  15

<210> SEQ ID NO 707
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 707

Glu Glu Glu Cys Glu Leu Cys Ile Asn Met Ala Cys Thr Gly Cys Leu
1               5                   10                  15

<210> SEQ ID NO 708
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 708

Asp Asp Asp Cys Glu Leu Cys Ile Asn Met Ala Cys Thr Gly Cys Leu
1               5                   10                  15

<210> SEQ ID NO 709
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 709

Asp Asp Glu Cys Glu Leu Cys Ile Asn Met Ala Cys Thr Gly Cys Leu
1               5                   10                  15

<210> SEQ ID NO 710
<211> LENGTH: 16
<212> TYPE: PRT
<213> ORGANISM: Artificial Sequence
```

```
<220> FEATURE:
<223> OTHER INFORMATION: human uroguanylin analog

<400> SEQUENCE: 710

Asp Glu Asp Cys Glu Leu Cys Ile Asn Met Ala Cys Thr Gly Cys Leu
1               5                   10                  15

<210> SEQ ID NO 711
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 711

Asp Glu Glu Cys Glu Leu Cys Ile Asn Met Ala Cys Thr Gly Cys Leu
1               5                   10                  15

<210> SEQ ID NO 712
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 712

Gln Asp Asp Cys Glu Leu Cys Ile Asn Met Ala Cys Thr Gly Cys Leu
1               5                   10                  15

<210> SEQ ID NO 713
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 713

Gln Asp Glu Cys Glu Leu Cys Ile Asn Met Ala Cys Thr Gly Cys Leu
1               5                   10                  15

<210> SEQ ID NO 714
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 714

Gln Glu Asp Cys Glu Leu Cys Ile Asn Met Ala Cys Thr Gly Cys Leu
1               5                   10                  15

<210> SEQ ID NO 715
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 715

Gln Glu Glu Cys Glu Leu Cys Ile Asn Met Ala Cys Thr Gly Cys Leu
1               5                   10                  15

<210> SEQ ID NO 716
<211> LENGTH: 16
<212> TYPE: PRT
<213> ORGANISM: Artificial Sequence
<220> FEATURE:
```

<223> OTHER INFORMATION: human uroguanylin analog

<400> SEQUENCE: 716

Lys Asp Asp Cys Glu Leu Cys Ile Asn Met Ala Cys Thr Gly Cys Leu
1               5                   10                  15

<210> SEQ ID NO 717
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 717

Lys Asp Glu Cys Glu Leu Cys Ile Asn Met Ala Cys Thr Gly Cys Leu
1               5                   10                  15

<210> SEQ ID NO 718
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 718

Lys Glu Asp Cys Glu Leu Cys Ile Asn Met Ala Cys Thr Gly Cys Leu
1               5                   10                  15

<210> SEQ ID NO 719
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 719

Lys Glu Glu Cys Glu Leu Cys Ile Asn Met Ala Cys Thr Gly Cys Leu
1               5                   10                  15

<210> SEQ ID NO 720
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 720

Glu Asp Asp Cys Glu Leu Cys Ile Asn Met Ala Cys Thr Gly Cys Ser
1               5                   10                  15

<210> SEQ ID NO 721
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 721

Glu Asp Glu Cys Glu Leu Cys Ile Asn Met Ala Cys Thr Gly Cys Ser
1               5                   10                  15

<210> SEQ ID NO 722
<211> LENGTH: 16
<212> TYPE: PRT
<213> ORGANISM: Artificial Sequence
<220> FEATURE:
<223> OTHER INFORMATION: human uroguanylin analog

```
<400> SEQUENCE: 722

Glu Glu Asp Cys Glu Leu Cys Ile Asn Met Ala Cys Thr Gly Cys Ser
1               5                   10                  15

<210> SEQ ID NO 723
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 723

Glu Glu Glu Cys Glu Leu Cys Ile Asn Met Ala Cys Thr Gly Cys Ser
1               5                   10                  15

<210> SEQ ID NO 724
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 724

Asp Asp Asp Cys Glu Leu Cys Ile Asn Met Ala Cys Thr Gly Cys Ser
1               5                   10                  15

<210> SEQ ID NO 725
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 725

Asp Asp Glu Cys Glu Leu Cys Ile Asn Met Ala Cys Thr Gly Cys Ser
1               5                   10                  15

<210> SEQ ID NO 726
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 726

Asp Glu Asp Cys Glu Leu Cys Ile Asn Met Ala Cys Thr Gly Cys Ser
1               5                   10                  15

<210> SEQ ID NO 727
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 727

Asp Glu Glu Cys Glu Leu Cys Ile Asn Met Ala Cys Thr Gly Cys Ser
1               5                   10                  15

<210> SEQ ID NO 728
<211> LENGTH: 16
<212> TYPE: PRT
<213> ORGANISM: Artificial Sequence
<220> FEATURE:
<223> OTHER INFORMATION: human uroguanylin analog
```

```
<400> SEQUENCE: 728

Gln Asp Asp Cys Glu Leu Cys Ile Asn Met Ala Cys Thr Gly Cys Ser
1               5                   10                  15

<210> SEQ ID NO 729
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 729

Gln Asp Glu Cys Glu Leu Cys Ile Asn Met Ala Cys Thr Gly Cys Ser
1               5                   10                  15

<210> SEQ ID NO 730
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 730

Gln Glu Asp Cys Glu Leu Cys Ile Asn Met Ala Cys Thr Gly Cys Ser
1               5                   10                  15

<210> SEQ ID NO 731
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 731

Gln Glu Glu Cys Glu Leu Cys Ile Asn Met Ala Cys Thr Gly Cys Ser
1               5                   10                  15

<210> SEQ ID NO 732
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 732

Lys Asp Asp Cys Glu Leu Cys Ile Asn Met Ala Cys Thr Gly Cys Ser
1               5                   10                  15

<210> SEQ ID NO 733
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 733

Lys Asp Glu Cys Glu Leu Cys Ile Asn Met Ala Cys Thr Gly Cys Ser
1               5                   10                  15

<210> SEQ ID NO 734
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 734
```

Lys Glu Asp Cys Glu Leu Cys Ile Asn Met Ala Cys Thr Gly Cys Ser
1               5                   10                  15

<210> SEQ ID NO 735
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 735

Lys Glu Glu Cys Glu Leu Cys Ile Asn Met Ala Cys Thr Gly Cys Ser
1               5                   10                  15

<210> SEQ ID NO 736
<211> LENGTH: 15
<212> TYPE: PRT
<213> ORGANISM: Artificial Sequence
<220> FEATURE:
<223> OTHER INFORMATION: human uroguanylin analog

<400> SEQUENCE: 736

Asn Glu Cys Glu Leu Cys Val Asn Val Ala Cys Thr Gly Cys Leu
1               5                   10                  15

<210> SEQ ID NO 737
<211> LENGTH: 14
<212> TYPE: PRT
<213> ORGANISM: Artificial Sequence
<220> FEATURE:
<223> OTHER INFORMATION: human uroguanylin analog

<400> SEQUENCE: 737

Asp Glu Cys Glu Leu Cys Val Asn Val Ala Cys Thr Gly Cys
1               5                   10

<210> SEQ ID NO 738
<211> LENGTH: 14
<212> TYPE: PRT
<213> ORGANISM: Artificial Sequence
<220> FEATURE:
<223> OTHER INFORMATION: human uroguanylin analog

<400> SEQUENCE: 738

Glu Cys Glu Leu Cys Val Asn Val Ala Cys Thr Gly Cys Leu
1               5                   10

<210> SEQ ID NO 739
<211> LENGTH: 13
<212> TYPE: PRT
<213> ORGANISM: Artificial Sequence
<220> FEATURE:
<223> OTHER INFORMATION: human uroguanylin analog

<400> SEQUENCE: 739

Glu Cys Glu Leu Cys Val Asn Val Ala Cys Thr Gly Cys
1               5                   10

<210> SEQ ID NO 740
<211> LENGTH: 13
<212> TYPE: PRT
<213> ORGANISM: Artificial Sequence
<220> FEATURE:
<223> OTHER INFORMATION: human uroguanylin analog

<400> SEQUENCE: 740

```
Cys Glu Leu Cys Val Asn Val Ala Cys Thr Gly Cys Leu
1               5                   10
```

<210> SEQ ID NO 741
<211> LENGTH: 12
<212> TYPE: PRT
<213> ORGANISM: Artificial Sequence
<220> FEATURE:
<223> OTHER INFORMATION: human uroguanylin analog

<400> SEQUENCE: 741

```
Cys Glu Leu Cys Val Asn Val Ala Cys Thr Gly Cys
1               5                   10
```

<210> SEQ ID NO 742
<211> LENGTH: 15
<212> TYPE: PRT
<213> ORGANISM: Artificial Sequence
<220> FEATURE:
<223> OTHER INFORMATION: human uroguanylin analog

<400> SEQUENCE: 742

```
Asn Asp Glu Cys Glu Leu Cys Val Asn Val Ala Cys Thr Gly Cys
1               5                   10                  15
```

<210> SEQ ID NO 743
<211> LENGTH: 16
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (16)..(16)
<223> OTHER INFORMATION: Xaa = Naphthylalanine

<400> SEQUENCE: 743

```
Asn Asp Glu Cys Glu Leu Cys Val Asn Val Ala Cys Thr Gly Cys Xaa
1               5                   10                  15
```

<210> SEQ ID NO 744
<211> LENGTH: 16
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (8)..(8)
<223> OTHER INFORMATION: Aib
<220> FEATURE:
<221> NAME/KEY: MOD_RES
<222> LOCATION: (10)..(10)
<223> OTHER INFORMATION: Aib

<400> SEQUENCE: 744

```
Asn Asp Glu Cys Glu Leu Cys Xaa Asn Xaa Ala Cys Thr Gly Cys Leu
1               5                   10                  15
```

<210> SEQ ID NO 745
<211> LENGTH: 16
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (15)..(15)
<223> OTHER INFORMATION: Orn

```
<400> SEQUENCE: 745

Asn Asp Glu Cys Glu Leu Asp Val Asn Val Ala Cys Thr Gly Xaa Leu
1               5                   10                  15

<210> SEQ ID NO 746
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 746

Asn Asp Glu Cys Glu Tyr Cys Val Asn Val Ala Cys Thr Gly Cys Leu
1               5                   10                  15

<210> SEQ ID NO 747
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 747

Asn Asp Glu Cys Glu Ser Cys Val Asn Val Ala Cys Thr Gly Cys Leu
1               5                   10                  15

<210> SEQ ID NO 748
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 748

Asn Asp Glu Cys Glu Leu Cys Val Asn Val Ala Cys Thr Gly Cys Ser
1               5                   10                  15

<210> SEQ ID NO 749
<211> LENGTH: 16
<212> TYPE: PRT
<213> ORGANISM: Artificial Sequence
<220> FEATURE:
<223> OTHER INFORMATION: human uroguanylin analog

<400> SEQUENCE: 749

Asn Asp Glu Cys Glu Leu Cys Val Asn Val Ala Cys Thr Gly Cys Tyr
1               5                   10                  15

<210> SEQ ID NO 750
<211> LENGTH: 16
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (1)..(1)
<223> OTHER INFORMATION: Xaa = pyroglutamic acid

<400> SEQUENCE: 750

Xaa Asp Glu Cys Glu Leu Cys Val Asn Val Ala Cys Thr Gly Cys Leu
1               5                   10                  15

<210> SEQ ID NO 751
<211> LENGTH: 14
<212> TYPE: PRT
<213> ORGANISM: Artificial Sequence
```

```
<220> FEATURE:
<223> OTHER INFORMATION: human uroguanylin analog

<400> SEQUENCE: 751

Cys Cys Glu Ser Cys Cys Asn Pro Ala Cys Thr Gly Cys Tyr
1               5                   10

<210> SEQ ID NO 752
<211> LENGTH: 14
<212> TYPE: PRT
<213> ORGANISM: Artificial Sequence
<220> FEATURE:
<223> OTHER INFORMATION: human uroguanylin analog

<400> SEQUENCE: 752

Cys Cys Glu Phe Cys Cys Asn Pro Ala Cys Thr Gly Cys Tyr
1               5                   10

<210> SEQ ID NO 753
<211> LENGTH: 13
<212> TYPE: PRT
<213> ORGANISM: Artificial Sequence
<220> FEATURE:
<223> OTHER INFORMATION: human uroguanylin analog

<400> SEQUENCE: 753

Cys Cys Glu Ser Cys Cys Asn Pro Ala Cys Thr Gly Cys
1               5                   10

<210> SEQ ID NO 754
<211> LENGTH: 13
<212> TYPE: PRT
<213> ORGANISM: Artificial Sequence
<220> FEATURE:
<223> OTHER INFORMATION: human uroguanylin analog

<400> SEQUENCE: 754

Cys Cys Glu Phe Cys Cys Asn Pro Ala Cys Thr Gly Cys
1               5                   10

<210> SEQ ID NO 755
<211> LENGTH: 14
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (1)..(2)
<223> OTHER INFORMATION: Xaa = Penicillamine
<220> FEATURE:
<221> NAME/KEY: MOD_RES
<222> LOCATION: (5)..(6)
<223> OTHER INFORMATION: Xaa = Penicillamine
<220> FEATURE:
<221> NAME/KEY: MOD_RES
<222> LOCATION: (10)..(10)
<223> OTHER INFORMATION: Xaa = Penicillamine
<220> FEATURE:
<221> NAME/KEY: MOD_RES
<222> LOCATION: (13)..(13)
<223> OTHER INFORMATION: Xaa = Penicillamine

<400> SEQUENCE: 755

Xaa Xaa Glu Tyr Xaa Xaa Asn Pro Ala Xaa Thr Gly Xaa Tyr
1               5                   10

<210> SEQ ID NO 756
<211> LENGTH: 13
```

```
<212> TYPE: PRT
<213> ORGANISM: Artificial Sequence
<220> FEATURE:
<223> OTHER INFORMATION: human uroguanylin analog
<220> FEATURE:
<221> NAME/KEY: MOD_RES
<222> LOCATION: (1)..(2)
<223> OTHER INFORMATION: Xaa = Penicillamine
<220> FEATURE:
<221> NAME/KEY: MOD_RES
<222> LOCATION: (5)..(6)
<223> OTHER INFORMATION: Xaa = Penicillamine
<220> FEATURE:
<221> NAME/KEY: MOD_RES
<222> LOCATION: (10)..(10)
<223> OTHER INFORMATION: Xaa = Penicillamine
<220> FEATURE:
<221> NAME/KEY: MOD_RES
<222> LOCATION: (13)..(13)
<223> OTHER INFORMATION: Xaa = Penicillamine

<400> SEQUENCE: 756

Xaa Xaa Glu Tyr Xaa Xaa Asn Pro Ala Xaa Thr Gly Xaa
1               5                   10

<210> SEQ ID NO 757
<211> LENGTH: 10
<212> TYPE: PRT
<213> ORGANISM: Artificial Sequence
<220> FEATURE:
<223> OTHER INFORMATION: Artificial Polypeptide

<400> SEQUENCE: 757

Ser Phe Asn Ser Tyr Glu Leu Gly Ser Leu
1               5                   10

<210> SEQ ID NO 758
<211> LENGTH: 8
<212> TYPE: PRT
<213> ORGANISM: Artificial Sequence
<220> FEATURE:
<223> OTHER INFORMATION: Artificial Polypeptide

<400> SEQUENCE: 758

Glu Ala Val Ser Leu Lys Pro Thr
1               5

<210> SEQ ID NO 759
<211> LENGTH: 11
<212> TYPE: PRT
<213> ORGANISM: Artificial Sequence
<220> FEATURE:
<223> OTHER INFORMATION: Artificial Polypeptide

<400> SEQUENCE: 759

Cys Tyr Gly Arg Lys Lys Arg Gln Arg Arg
1               5                   10

<210> SEQ ID NO 760
<211> LENGTH: 8
<212> TYPE: PRT
<213> ORGANISM: Artificial Sequence
<220> FEATURE:
<223> OTHER INFORMATION: Artificial Polypeptide

<400> SEQUENCE: 760

His Asp Ala Pro Ile Gly Tyr Asp
1               5
```